US011639394B2

(12) United States Patent
Grau-Richards et al.

(10) Patent No.: US 11,639,394 B2
(45) Date of Patent: May 2, 2023

(54) BISPECIFIC ANTIGEN BINDING MOLECULE FOR A COSTIMULATORY TNF RECEPTOR

(71) Applicant: Hoffmann-La Roche Inc., Little Falls, NJ (US)

(72) Inventors: Sandra Grau-Richards, Schlieren (CH); Christian Klein, Schlieren (CH); Pablo Umaña, Schlieren (CH); Maria Amann, Schlieren (CH); Laurene Pousse, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 225 days.

(21) Appl. No.: 16/581,756

(22) Filed: Sep. 25, 2019

(65) Prior Publication Data

US 2020/0231691 A1 Jul. 23, 2020

Related U.S. Application Data

(63) Continuation of application No. PCT/EP2018/057734, filed on Mar. 27, 2018.

(30) Foreign Application Priority Data

Mar. 29, 2017 (EP) ..................................... 17163639

(51) Int. Cl.
*C07K 16/28* (2006.01)
*C07K 16/30* (2006.01)
*A61K 39/00* (2006.01)

(52) U.S. Cl.
CPC .......... *C07K 16/2878* (2013.01); *C07K 16/30* (2013.01); *A61K 2039/505* (2013.01); *C07K 2317/31* (2013.01); *C07K 2317/33* (2013.01); *C07K 2317/35* (2013.01); *C07K 2317/515* (2013.01); *C07K 2317/524* (2013.01); *C07K 2317/526* (2013.01); *C07K 2317/55* (2013.01); *C07K 2317/622* (2013.01); *C07K 2317/64* (2013.01); *C07K 2317/71* (2013.01); *C07K 2317/74* (2013.01); *C07K 2317/92* (2013.01)

(58) Field of Classification Search
CPC ............ C07K 16/2878; C07K 2317/31; C07K 2317/64
USPC .................................................... 424/133.1
See application file for complete search history.

(56) References Cited

U.S. PATENT DOCUMENTS

| 5,731,168 | A | 3/1998 | Carter et al. |
| 7,695,936 | B2 | 4/2010 | Carter et al. |
| 8,637,017 | B2* | 1/2014 | Cicortas Gunnarsson .................. C07K 16/30 424/133.1 |
| 9,011,847 | B2 | 4/2015 | Bacac et al. |
| 10,253,110 | B2 | 4/2019 | Bacac et al. |
| 10,392,445 | B2 | 8/2019 | Amann et al. |
| 10,464,981 | B2 | 11/2019 | Amann et al. |
| 10,526,413 | B2* | 1/2020 | Amann .................. C07K 16/30 |
| 10,577,429 | B2 | 3/2020 | Bacac et al. |
| 10,596,257 | B2* | 3/2020 | Bacac ..................... C07K 16/30 |
| 11,013,801 | B2* | 5/2021 | Bacac ..................... A61P 35/00 |
| 11,149,083 | B2 | 10/2021 | Amann et al. |
| 11,242,396 | B2 | 2/2022 | Bruenker et al. |
| 11,267,903 | B2 | 3/2022 | Amann et al. |
| 11,286,300 | B2 | 3/2022 | Ferrara Koller et al. |
| 11,306,154 | B2 | 4/2022 | Amann et al. |
| 2010/0310463 | A1* | 12/2010 | Cicortas Gunnarsson .................. A61P 35/00 424/9.1 |
| 2015/0010567 | A1 | 1/2015 | Bourquin et al. |
| 2015/0166654 | A1 | 6/2015 | Igawa et al. |
| 2016/0002357 | A1 | 1/2016 | May et al. |
| 2017/0114141 | A1* | 4/2017 | Amann .................. A61P 43/00 |
| 2017/0174786 | A1 | 6/2017 | Bacac et al. |
| 2017/0247467 | A1* | 8/2017 | Amann .................. A61P 37/04 |
| 2018/0171017 | A1 | 6/2018 | Taniguchi et al. |
| 2018/0230215 | A1 | 8/2018 | Hofer et al. |
| 2018/0340030 | A1 | 11/2018 | Bruenker et al. |
| 2019/0016771 | A1 | 1/2019 | Amann et al. |
| 2019/0185566 | A1 | 6/2019 | Koller et al. |
| 2019/0194291 | A1 | 6/2019 | Bruenker et al. |
| 2019/0211113 | A1* | 7/2019 | Amann ............. C07K 16/2878 |
| 2019/0262397 | A1* | 8/2019 | Connolly ......... C07K 14/70521 |
| 2020/0071411 | A1* | 3/2020 | Amann ............. C07K 16/2878 |
| 2020/0190206 | A1 | 6/2020 | Koller et al. |
| 2020/0270321 | A1 | 8/2020 | Amann et al. |
| 2020/0277392 | A1* | 9/2020 | Amann ............. C07K 16/2878 |
| 2020/0317774 | A1 | 10/2020 | Hofer et al. |
| 2020/0325225 | A1 | 10/2020 | Bacac et al. |
| 2020/0325238 | A1 | 10/2020 | Bacac et al. |

(Continued)

FOREIGN PATENT DOCUMENTS

| CN | 102770456 | 11/2012 |
| CN | 104487457 | 11/2012 |

(Continued)

OTHER PUBLICATIONS

Al-Shamkhani, A., et al., "OX40 is differentially expressed on activated rat and mouse T cells and is the sole receptor for the OX40 ligand" Eur J Immunol 26:1695-1699 (Aug. 1, 1996).
Baeuerle, P.A., et al., "EpCAM (CD326) finding its role in cancer" Brit J Cancer 96(3):417-423 (Feb. 12, 2007).
Baudino, L., et al., "Crucial Role of Aspartic Acid at Position 265 in the CH2 Domain for Murine IgG2a and IgG2b Fc-Associated Effector Functions" J. Immunol 181(9):6664-6669 (Nov. 1, 2008).

(Continued)

*Primary Examiner* — Lynn A Bristol
(74) *Attorney, Agent, or Firm* — Yan Qi

(57) ABSTRACT

The invention relates to bispecific antigen binding molecules comprising (a) at least one moiety capable of specific binding to OX40, and (b) at least one moiety capable of specific binding to epithelial cell adhesion molecule (Ep-CAM), and to methods of producing these molecules and to methods of using the same.

9 Claims, 14 Drawing Sheets

Specification includes a Sequence Listing.

(56) References Cited

U.S. PATENT DOCUMENTS

| | | | |
|---|---|---|---|
| 2020/0347115 A1 | 11/2020 | Duerr et al. | |
| 2020/0392237 A1* | 12/2020 | Bacac | C07K 16/2818 |
| 2021/0009656 A1 | 1/2021 | Bruenker et al. | |
| 2021/0024610 A1 | 1/2021 | Koller et al. | |
| 2021/0070882 A1 | 3/2021 | Bacac et al. | |
| 2021/0095002 A1 | 4/2021 | Claus et al. | |
| 2021/0163617 A1 | 6/2021 | Ferrara et al. | |
| 2021/0188992 A1 | 6/2021 | Bruenker et al. | |
| 2021/0252144 A1* | 8/2021 | Bacac | A61P 43/00 |
| 2021/0253724 A1 | 8/2021 | Claus et al. | |
| 2021/0284719 A1* | 9/2021 | Yu | A61K 39/39591 |
| 2021/0292426 A1 | 9/2021 | Duerr et al. | |
| 2021/0315863 A1* | 10/2021 | Klein | A61K 31/4025 |
| 2021/0324108 A1* | 10/2021 | Amann | A61K 45/06 |
| 2022/0025046 A1 | 1/2022 | Amann et al. | |
| 2022/0025069 A1 | 1/2022 | Claus et al. | |
| 2022/0073646 A1 | 3/2022 | Amann et al. | |

FOREIGN PATENT DOCUMENTS

| | | |
|---|---|---|
| JP | 2012/529281 | 11/2012 |
| JP | 2015502373 | 1/2015 |
| JP | 2015/506954 | 3/2015 |
| JP | 2016/514098 | 5/2016 |
| WO | 2010/142990 A1 | 12/2010 |
| WO | 2011/069104 A2 | 6/2011 |
| WO | 2012/130831 A1 | 10/2012 |
| WO | 2013/092001 A1 | 6/2013 |
| WO | 2013/113615 A1 | 8/2013 |
| WO | 2013/123061 A1 | 8/2013 |
| WO | 2014/131694 A1 | 9/2014 |
| WO | 2014/165818 A2 | 10/2014 |
| WO | 2015/052230 A1 | 4/2015 |
| WO | 2016/030350 A1 | 3/2016 |
| WO | 2016/057667 A1 | 4/2016 |
| WO | 2016/194992 A1 | 12/2016 |
| WO | 2020/260329 A1 | 12/2020 |
| WO | 2021/140130 A1 | 7/2021 |
| WO | 2021/198335 A1 | 10/2021 |

OTHER PUBLICATIONS

Baumann, R., et al., "Functional expression of CD134 by neutrophils" Eur J Immunol 34(8):2268-2275 (Aug 1, 2004).

Croft, M. et al., "The significance of OX40 and OX40L to T-cell biology and immune disease" Immunol Rev 229(1):173-191 (May 1, 2009).

Farr, A., et al., "Epithelial heterogeneity in the murine thymus: a cell surface glycoprotein expressed by subcapsular and medullary epithelium" J Histochem Cytochem 39(5):645-653 (May 1, 1991).

Imrich, S., et al., "EpCAM and its potential role in tumor-initiating cells" Cell ADH MIGR 6(1):30-38 (Jan. 1, 2012).

"International Preliminary Report on Patentability—PCT/EP2018/057734":pp. 1-12 (Oct. 10, 2019).

"International Search Report—PCT/EP2018/057734":pp. 1-9 (Jul. 27, 2018).

Maetzel, D., et al., "Nuclear signalling by tumour-associated antigen EpCAM" Nat Cell Biol 11:162-171 (Jan. 11, 2009).

Münz, M., et al., "Side-by-side analysis of five clinically tested anti-EpCAM monoclonal ant" Cancer Cell Int 10(44):1-12 (Nov. 2, 2010).

Schell, U., et al., "EpCAM: Structure and function in health and disease" Biochim Biophys Acta 1828:1989-2001 (Apr. 23, 2013).

Song et al., "Activation of NF-kB1 by OX40 Contributes to Antigen-Driven T Cell Expansion and Survival" J Immunol 180(11):7240-7248 (Jun. 1, 2008).

Trzpis, M., et al., "Epithelial Cell Adhesion Mole: More than a Carcinoma Marker and Adhesion Molecule" Am J Pathol 171(2):386-395 (Aug. 1, 2007).

Watts, T., "TNF/TNFR family members in costimulation of T cell responses" Annu Rev Immunol 23:23-68 (Sep. 2005).

Weinberg, A., et al., "Engagement of the OC-40 Receptor In Vivo Enhances Antitumor Immunity" J Immuol 164(4):2160-2169 (Feb. 15, 2000).

Dong et al., "Expressions of inhibitory receptors PD-1 and LAG-3 on CD4 + T cells in the patients with chronic hepatitis B virus infection and their significance" Chin. J. Clin. Lab. Sci. (Abstract in English), 34(2):100-102 (Feb. 5, 2016).

Everett et al., "Abstract PR06: A LAG-3/PD-L1 bispecific antibody inhibits tumor growth in two syngeneic colon carcinoma models" Cancer Immunology Research 5(3 Suppl PR06):1-4 (Mar. 2017).

Klooster et al., "Abstract B088: Generation of immuno-modulatory receptor binding bispecific antibodies to modulate tumor immunity" Cancer Immunology Research 4( Suppl 11):B088: 1-4 (Nov. 2016).

LaMotte-Mohs et al., "Abstract 3217: MGD013, a bispecific PD-1 x LAG-3 Dual-Affinity Re-Targeting (DART®) protein with T-cell imrnunomodulatory activity for cancer treatment" Cancer Research 76( Suppl 14):3217 (Jul. 2016).

Weiner et al., "Antibody-Based on Immunotherapy for Cancer: New Insights, New Targets" Cell 148(6):1081-1084.

* cited by examiner

</p>

SEQUENCE LISTING

```
<160> NUMBER OF SEQ ID NOS: 193

<210> SEQ ID NO 1
<211> LENGTH: 186
<212> TYPE: PRT
<213> ORGANISM: Homo sapiens

<400> SEQUENCE: 1

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60
```

```
Ser Glu Arg Lys Gln Leu Cys Thr Ala Thr Gln Asp Thr Val Cys Arg
 65                  70                  75                  80

Cys Arg Ala Gly Thr Gln Pro Leu Asp Ser Tyr Lys Pro Gly Val Asp
                 85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala
            180                 185

<210> SEQ ID NO 2
<211> LENGTH: 192
<212> TYPE: PRT
<213> ORGANISM: Mus musculus

<400> SEQUENCE: 2

Val Thr Ala Arg Arg Leu Asn Cys Val Lys His Thr Tyr Pro Ser Gly
 1               5                  10                  15

His Lys Cys Cys Arg Glu Cys Gln Pro Gly His Gly Met Val Ser Arg
                20                  25                  30

Cys Asp His Thr Arg Asp Thr Leu Cys His Pro Cys Glu Thr Gly Phe
            35                  40                  45

Tyr Asn Glu Ala Val Asn Tyr Asp Thr Cys Lys Gln Cys Thr Gln Cys
        50                  55                  60

Asn His Arg Ser Gly Ser Glu Leu Lys Gln Asn Cys Thr Pro Thr Gln
 65                  70                  75                  80

Asp Thr Val Cys Arg Cys Arg Pro Gly Thr Gln Pro Arg Gln Asp Ser
                 85                  90                  95

Gly Tyr Lys Leu Gly Val Asp Cys Val Pro Cys Pro Pro Gly His Phe
            100                 105                 110

Ser Pro Gly Asn Asn Gln Ala Cys Lys Pro Trp Thr Asn Cys Thr Leu
        115                 120                 125

Ser Gly Lys Gln Thr Arg His Pro Ala Ser Asp Ser Leu Asp Ala Val
130                 135                 140

Cys Glu Asp Arg Ser Leu Leu Ala Thr Leu Leu Trp Glu Thr Gln Arg
145                 150                 155                 160

Pro Thr Phe Arg Pro Thr Thr Val Gln Ser Thr Thr Val Trp Pro Arg
                165                 170                 175

Thr Ser Glu Leu Pro Ser Pro Pro Thr Leu Val Thr Pro Glu Gly Pro
            180                 185                 190

<210> SEQ ID NO 3
<211> LENGTH: 186
<212> TYPE: PRT
<213> ORGANISM: cynomolgus

<400> SEQUENCE: 3

Leu His Cys Val Gly Asp Thr Tyr Pro Ser Asn Asp Arg Cys Cys Gln
 1               5                  10                  15
```

```
Glu Cys Arg Pro Gly Asn Gly Met Val Ser Arg Cys Asn Arg Ser Gln
            20                  25                  30

Asn Thr Val Cys Arg Pro Cys Gly Pro Gly Phe Tyr Asn Asp Val Val
        35                  40                  45

Ser Ala Lys Pro Cys Lys Ala Cys Thr Trp Cys Asn Leu Arg Ser Gly
50                  55                  60

Ser Glu Arg Lys Gln Pro Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
130                 135                 140

Pro Thr Gln Pro Gln Glu Thr Gln Gly Pro Pro Ala Arg Pro Thr Thr
145                 150                 155                 160

Val Gln Pro Thr Glu Ala Trp Pro Arg Thr Ser Gln Arg Pro Ser Thr
                165                 170                 175

Arg Pro Val Glu Val Pro Arg Gly Pro Ala
            180                 185

<210> SEQ ID NO 4
<211> LENGTH: 5
<212> TYPE: PRT
<213> ORGANISM: Artificial sequence
<220> FEATURE:
<223> OTHER INFORMATION: OX40(8H9,49B4,1G4, 20B7)   CDR-H1

<400> SEQUENCE: 4

Ser Tyr Ala Ile Ser
1               5

<210> SEQ ID NO 5
<211> LENGTH: 5
<212> TYPE: PRT
<213> ORGANISM: Artificial sequence
<220> FEATURE:
<223> OTHER INFORMATION: OX40(CLC-563, CLC-564, 17A9)   CDR-H1

<400> SEQUENCE: 5

Ser Tyr Ala Met Ser
1               5

<210> SEQ ID NO 6
<211> LENGTH: 17
<212> TYPE: PRT
<213> ORGANISM: Artificial sequence
<220> FEATURE:
<223> OTHER INFORMATION: OX40(8H9,49B4,1G4, 20B7)   CDR-H2

<400> SEQUENCE: 6

Gly Ile Ile Pro Ile Phe Gly Thr Ala Asn Tyr Ala Gln Lys Phe Gln
1               5                   10                  15

Gly

<210> SEQ ID NO 7
<211> LENGTH: 17
<212> TYPE: PRT
```

```
<213> ORGANISM: Artificial sequence
<220> FEATURE:
<223> OTHER INFORMATION: OX40(CLC-563, CLC-564, 17A9) CDR-H2

<400> SEQUENCE: 7

Ala Ile Ser Gly Ser Gly Gly Ser Thr Tyr Tyr Ala Asp Ser Val Lys
1               5                   10                  15

Gly

<210> SEQ ID NO 8
<211> LENGTH: 7
<212> TYPE: PRT
<213> ORGANISM: Artificial sequence
<220> FEATURE:
<223> OTHER INFORMATION: OX40(8H9) CDR-H3

<400> SEQUENCE: 8

Glu Tyr Gly Trp Met Asp Tyr
1               5

<210> SEQ ID NO 9
<211> LENGTH: 9
<212> TYPE: PRT
<213> ORGANISM: Artificial sequence
<220> FEATURE:
<223> OTHER INFORMATION: OX40(49B4) CDR-H3

<400> SEQUENCE: 9

Glu Tyr Tyr Arg Gly Pro Tyr Asp Tyr
1               5

<210> SEQ ID NO 10
<211> LENGTH: 7
<212> TYPE: PRT
<213> ORGANISM: Artificial sequence
<220> FEATURE:
<223> OTHER INFORMATION: OX40(1G4) CDR-H3

<400> SEQUENCE: 10

Glu Tyr Gly Ser Met Asp Tyr
1               5

<210> SEQ ID NO 11
<211> LENGTH: 13
<212> TYPE: PRT
<213> ORGANISM: Artificial sequence
<220> FEATURE:
<223> OTHER INFORMATION: OX40(20B7) CDR-H3

<400> SEQUENCE: 11

Val Asn Tyr Pro Tyr Ser Tyr Trp Gly Asp Phe Asp Tyr
1               5                   10

<210> SEQ ID NO 12
<211> LENGTH: 7
<212> TYPE: PRT
<213> ORGANISM: Artificial sequence
<220> FEATURE:
<223> OTHER INFORMATION: OX40(CLC-563) CDR-H3

<400> SEQUENCE: 12

Asp Val Gly Ala Phe Asp Tyr
1               5

<210> SEQ ID NO 13
<211> LENGTH: 7
```

<212> TYPE: PRT
<213> ORGANISM: Artificial sequence
<220> FEATURE:
<223> OTHER INFORMATION: OX40(CLC-564) CDR-H3

<400> SEQUENCE: 13

Asp Val Gly Pro Phe Asp Tyr
1               5

<210> SEQ ID NO 14
<211> LENGTH: 11
<212> TYPE: PRT
<213> ORGANISM: Artificial sequence
<220> FEATURE:
<223> OTHER INFORMATION: OX40(17A9)-CDR-H3

<400> SEQUENCE: 14

Val Phe Tyr Arg Gly Gly Val Ser Met Asp Tyr
1               5                   10

<210> SEQ ID NO 15
<211> LENGTH: 11
<212> TYPE: PRT
<213> ORGANISM: Artificial sequence
<220> FEATURE:
<223> OTHER INFORMATION: OX40(8H9,49B4,1G4, 20B7) CDR-L1

<400> SEQUENCE: 15

Arg Ala Ser Gln Ser Ile Ser Ser Trp Leu Ala
1               5                   10

<210> SEQ ID NO 16
<211> LENGTH: 12
<212> TYPE: PRT
<213> ORGANISM: Artificial sequence
<220> FEATURE:
<223> OTHER INFORMATION: OX40(CLC-563, CLC564) CDR-L1

<400> SEQUENCE: 16

Arg Ala Ser Gln Ser Val Ser Ser Ser Tyr Leu Ala
1               5                   10

<210> SEQ ID NO 17
<211> LENGTH: 11
<212> TYPE: PRT
<213> ORGANISM: Artificial sequence
<220> FEATURE:
<223> OTHER INFORMATION: OX40(17A9) CDR-L1

<400> SEQUENCE: 17

Gln Gly Asp Ser Leu Arg Ser Tyr Tyr Ala Ser
1               5                   10

<210> SEQ ID NO 18
<211> LENGTH: 7
<212> TYPE: PRT
<213> ORGANISM: Artificial sequence
<220> FEATURE:
<223> OTHER INFORMATION: OX40(8H9,49B4,1G4, 20B7) CDR-L2

<400> SEQUENCE: 18

Asp Ala Ser Ser Leu Glu Ser
1               5

<210> SEQ ID NO 19
<211> LENGTH: 7
<212> TYPE: PRT

```
<213> ORGANISM: Artificial sequence
<220> FEATURE:
<223> OTHER INFORMATION: OX40(CLC-563, CLC564) CDR-L2

<400> SEQUENCE: 19

Gly Ala Ser Ser Arg Ala Thr
1               5

<210> SEQ ID NO 20
<211> LENGTH: 7
<212> TYPE: PRT
<213> ORGANISM: Artificial sequence
<220> FEATURE:
<223> OTHER INFORMATION: OX40(17A9) CDR-L2

<400> SEQUENCE: 20

Gly Lys Asn Asn Arg Pro Ser
1               5

<210> SEQ ID NO 21
<211> LENGTH: 10
<212> TYPE: PRT
<213> ORGANISM: Artificial sequence
<220> FEATURE:
<223> OTHER INFORMATION: OX40(8H9) CDR-L3

<400> SEQUENCE: 21

Gln Gln Tyr Leu Thr Tyr Ser Arg Phe Thr
1               5                   10

<210> SEQ ID NO 22
<211> LENGTH: 9
<212> TYPE: PRT
<213> ORGANISM: Artificial sequence
<220> FEATURE:
<223> OTHER INFORMATION: OX40(49B4) CDR-L3

<400> SEQUENCE: 22

Gln Gln Tyr Ser Ser Gln Pro Tyr Thr
1               5

<210> SEQ ID NO 23
<211> LENGTH: 10
<212> TYPE: PRT
<213> ORGANISM: Artificial sequence
<220> FEATURE:
<223> OTHER INFORMATION: OX40(1G4) CDR-L3

<400> SEQUENCE: 23

Gln Gln Tyr Ile Ser Tyr Ser Met Leu Thr
1               5                   10

<210> SEQ ID NO 24
<211> LENGTH: 9
<212> TYPE: PRT
<213> ORGANISM: Artificial sequence
<220> FEATURE:
<223> OTHER INFORMATION: OX40(20B7) CDR-L3

<400> SEQUENCE: 24

Gln Gln Tyr Gln Ala Phe Ser Leu Thr
1               5

<210> SEQ ID NO 25
<211> LENGTH: 9
<212> TYPE: PRT
<213> ORGANISM: Artificial sequence
```

```
<220> FEATURE:
<223> OTHER INFORMATION: OX40(CLC-563, CLC-164)  CDR-L3

<400> SEQUENCE: 25

Gln Gln Tyr Gly Ser Ser Pro Leu Thr
1               5

<210> SEQ ID NO 26
<211> LENGTH: 10
<212> TYPE: PRT
<213> ORGANISM: Artificial sequence
<220> FEATURE:
<223> OTHER INFORMATION: OX40(17A9) CDR-L3

<400> SEQUENCE: 26

Asn Ser Arg Val Met Pro His Asn Arg Val
1               5                   10

<210> SEQ ID NO 27
<211> LENGTH: 5
<212> TYPE: PRT
<213> ORGANISM: Mus musculus

<400> SEQUENCE: 27

Gly Tyr Asn Leu His
1               5

<210> SEQ ID NO 28
<211> LENGTH: 16
<212> TYPE: PRT
<213> ORGANISM: Mus musculus

<400> SEQUENCE: 28

Arg Met Arg Tyr Asp Gly Asp Thr Tyr Tyr Asn Ser Val Leu Lys Ser
1               5                   10                  15

<210> SEQ ID NO 29
<211> LENGTH: 9
<212> TYPE: PRT
<213> ORGANISM: Mus musculus

<400> SEQUENCE: 29

Asp Gly Arg Gly Asp Ser Phe Asp Tyr
1               5

<210> SEQ ID NO 30
<211> LENGTH: 16
<212> TYPE: PRT
<213> ORGANISM: Mus musculus

<400> SEQUENCE: 30

Arg Ser Ser Gln Ser Leu Val Tyr Lys Asp Gly Gln Thr Tyr Leu Asn
1               5                   10                  15

<210> SEQ ID NO 31
<211> LENGTH: 7
<212> TYPE: PRT
<213> ORGANISM: Mus musculus

<400> SEQUENCE: 31

Trp Met Ser Thr Arg Ala Ser
1               5

<210> SEQ ID NO 32
<211> LENGTH: 9
```

```
<212> TYPE: PRT
<213> ORGANISM: Mus musculus

<400> SEQUENCE: 32

Gln Gln Val Arg Glu Tyr Pro Phe Thr
1               5

<210> SEQ ID NO 33
<211> LENGTH: 116
<212> TYPE: PRT
<213> ORGANISM: Artificial sequence
<220> FEATURE:
<223> OTHER INFORMATION: OX40(8H9) VH

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Gly Trp Met Asp Tyr Trp Gly Gln Gly Thr Thr Val
            100                 105                 110

Thr Val Ser Ser
        115

<210> SEQ ID NO 34
<211> LENGTH: 108
<212> TYPE: PRT
<213> ORGANISM: Artificial sequence
<220> FEATURE:
<223> OTHER INFORMATION: OX40(8H9) VL

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Leu Thr Tyr Ser Arg
                85                  90                  95

Phe Thr Phe Gly Gln Gly Thr Lys Val Glu Ile Lys
            100                 105

<210> SEQ ID NO 35
<211> LENGTH: 118
<212> TYPE: PRT
<213> ORGANISM: Artificial sequence
<220> FEATURE:
```

-continued

<223> OTHER INFORMATION: OX40(49B4) VH

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser
        115

<210> SEQ ID NO 36
<211> LENGTH: 107
<212> TYPE: PRT
<213> ORGANISM: Artificial sequence
<220> FEATURE:
<223> OTHER INFORMATION: OX40(49B4) VL

<400> SEQUENCE: 36

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys
            100                 105

<210> SEQ ID NO 37
<211> LENGTH: 116
<212> TYPE: PRT
<213> ORGANISM: Artificial sequence
<220> FEATURE:
<223> OTHER INFORMATION: OX40(1G4) VH

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
            50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Gly Ser Met Asp Tyr Trp Gly Gln Gly Thr Thr Val
                100                 105                 110

Thr Val Ser Ser
            115

<210> SEQ ID NO 38
<211> LENGTH: 108
<212> TYPE: PRT
<213> ORGANISM: Artificial sequence
<220> FEATURE:
<223> OTHER INFORMATION: OX40(1G4) VL

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ile Ser Tyr Ser Met
                85                  90                  95

Leu Thr Phe Gly Gln Gly Thr Lys Val Glu Ile Lys
            100                 105

<210> SEQ ID NO 39
<211> LENGTH: 122
<212> TYPE: PRT
<213> ORGANISM: Artificial sequence
<220> FEATURE:
<223> OTHER INFORMATION: OX40(20B7) VH

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Tyr Pro Tyr Ser Tyr Trp Gly Asp Phe Asp Tyr Trp
            100                 105                 110

Gly Gln Gly Thr Thr Val Thr Val Ser Ser
            115                 120

<210> SEQ ID NO 40
<211> LENGTH: 107
<212> TYPE: PRT
<213> ORGANISM: Artificial sequence
<220> FEATURE:
<223> OTHER INFORMATION: OX40(20B7)  VL

<400> SEQUENCE: 40

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ala Phe Ser Leu
                85                  90                  95

Thr Phe Gly Gln Gly Thr Lys Val Glu Ile Lys
            100                 105

<210> SEQ ID NO 41
<211> LENGTH: 116
<212> TYPE: PRT
<213> ORGANISM: Artificial sequence
<220> FEATURE:
<223> OTHER INFORMATION: OX40(CLC-563)  VH

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Asp Val Gly Ala Phe Asp Tyr Trp Gly Gln Gly Ala Leu Val
            100                 105                 110

Thr Val Ser Ser
        115

<210> SEQ ID NO 42
<211> LENGTH: 108
<212> TYPE: PRT
<213> ORGANISM: Artificial sequence
<220> FEATURE:
<223> OTHER INFORMATION: OX40(CLC-563)  VL

<400> SEQUENCE: 42

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
            100                 105

<210> SEQ ID NO 43
<211> LENGTH: 116
<212> TYPE: PRT
<213> ORGANISM: Artificial sequence
<220> FEATURE:
<223> OTHER INFORMATION: OX40(CLC-564) VH

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Phe Asp Val Gly Pro Phe Asp Tyr Trp Gly Gln Gly Thr Leu Val
            100                 105                 110

Thr Val Ser Ser
        115

<210> SEQ ID NO 44
<211> LENGTH: 108
<212> TYPE: PRT
<213> ORGANISM: Artificial sequence
<220> FEATURE:
<223> OTHER INFORMATION: OX40(CLC-564) VL

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
            100                 105

<210> SEQ ID NO 45
<211> LENGTH: 120
<212> TYPE: PRT
<213> ORGANISM: Artificial sequence
<220> FEATURE:
<223> OTHER INFORMATION: OX40(17A9) VH

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Phe Tyr Arg Gly Gly Val Ser Met Asp Tyr Trp Gly Gln
            100                 105                 110

Gly Thr Leu Val Thr Val Ser Ser
        115                 120

<210> SEQ ID NO 46
<211> LENGTH: 106
<212> TYPE: PRT
<213> ORGANISM: Artificial sequence
<220> FEATURE:
<223> OTHER INFORMATION: OX40(17A9) VL

<400> SEQUENCE: 46

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Val Met Pro His Asn Arg
                85                  90                  95

Val Phe Gly Gly Gly Thr Lys Leu Thr Val
            100                 105

<210> SEQ ID NO 47
<211> LENGTH: 117
<212> TYPE: PRT

<213> ORGANISM: Artificial Sequence
<220> FEATURE:
<223> OTHER INFORMATION: muOX40(OX86) VH

<400> SEQUENCE: 47

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Gly Tyr
            20                  25                  30

Asn Leu His Trp Val Arg Gln Pro Pro Gly Lys Gly Leu Glu Trp Met
        35                  40                  45

Gly Arg Met Arg Tyr Asp Gly Asp Thr Tyr Tyr Asn Ser Val Leu Lys
50                  55                  60

Ser Arg Leu Ser Ile Ser Arg Asp Thr Ser Lys Asn Gln Val Phe Leu
65                  70                  75                  80

Lys Met Asn Ser Leu Gln Thr Asp Asp Thr Ala Ile Tyr Tyr Cys Thr
                85                  90                  95

Arg Asp Gly Arg Gly Asp Ser Phe Asp Tyr Trp Gly Gln Gly Val Met
            100                 105                 110

Val Thr Val Ser Ser
        115

<210> SEQ ID NO 48
<211> LENGTH: 112
<212> TYPE: PRT
<213> ORGANISM: Artificial Sequence
<220> FEATURE:
<223> OTHER INFORMATION: muOX40(OX86) VL

<400> SEQUENCE: 48

Asp Ile Val Met Thr Gln Gly Ala Leu Pro Asn Pro Val Pro Ser Gly
1               5                   10                  15

Glu Ser Ala Ser Ile Thr Cys Arg Ser Ser Gln Ser Leu Val Tyr Lys
            20                  25                  30

Asp Gly Gln Thr Tyr Leu Asn Trp Phe Leu Gln Arg Pro Gly Gln Ser
        35                  40                  45

Pro Gln Leu Leu Thr Tyr Trp Met Ser Thr Arg Ala Ser Gly Val Ser
    50                  55                  60

Asp Arg Phe Ser Gly Ser Gly Ser Gly Thr Tyr Phe Thr Leu Lys Ile
65                  70                  75                  80

Ser Arg Val Arg Ala Glu Asp Ala Gly Val Tyr Tyr Cys Gln Gln Val
                85                  90                  95

Arg Glu Tyr Pro Phe Thr Phe Gly Ser Gly Thr Lys Leu Glu Ile Lys
            100                 105                 110

<210> SEQ ID NO 49
<211> LENGTH: 242
<212> TYPE: PRT
<213> ORGANISM: Homo sapiens

<400> SEQUENCE: 49

Gln Glu Glu Cys Val Cys Glu Asn Tyr Lys Leu Ala Val Asn Cys Phe
1               5                   10                  15

Val Asn Asn Asn Arg Gln Cys Gln Cys Thr Ser Val Gly Ala Gln Asn
            20                  25                  30

Thr Val Ile Cys Ser Lys Leu Ala Ala Lys Cys Leu Val Met Lys Ala
        35                  40                  45

Glu Met Asn Gly Ser Lys Leu Gly Arg Arg Ala Lys Pro Glu Gly Ala
            50                  55                  60

Leu Gln Asn Asn Asp Gly Leu Tyr Asp Pro Asp Cys Asp Glu Ser Gly
 65                  70                  75                  80

Leu Phe Lys Ala Lys Gln Cys Asn Gly Thr Ser Met Cys Trp Cys Val
                 85                  90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Glu Leu Lys His Lys
            115                 120                 125

Ala Arg Glu Lys Pro Tyr Asp Ser Lys Ser Leu Arg Thr Ala Leu Gln
130                 135                 140

Lys Glu Ile Thr Thr Arg Tyr Gln Leu Asp Pro Lys Phe Ile Thr Ser
145                 150                 155                 160

Ile Leu Tyr Glu Asn Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
            195                 200                 205

Asp Leu Thr Val Asn Gly Glu Gln Leu Asp Leu Asp Pro Gly Gln Thr
210                 215                 220

Leu Ile Tyr Tyr Val Asp Glu Lys Ala Pro Glu Phe Ser Met Gln Gly
225                 230                 235                 240

Leu Lys

<210> SEQ ID NO 50
<211> LENGTH: 243
<212> TYPE: PRT
<213> ORGANISM: Mus musculus

<400> SEQUENCE: 50

Gln Arg Asp Cys Val Cys Asp Asn Tyr Lys Leu Ala Thr Ser Cys Ser
1               5                   10                  15

Leu Asn Glu Tyr Gly Glu Cys Gln Cys Thr Ser Tyr Gly Thr Gln Asn
                20                  25                  30

Thr Val Ile Cys Ser Lys Leu Ala Ser Lys Cys Leu Ala Met Lys Ala
            35                  40                  45

Glu Met Thr His Ser Lys Ser Gly Arg Arg Ile Lys Pro Glu Gly Ala
 50                  55                  60

Ile Gln Asn Asn Asp Gly Leu Tyr Asp Pro Asp Cys Asp Glu Gln Gly
 65                  70                  75                  80

Leu Phe Lys Ala Lys Gln Cys Asn Gly Thr Ala Thr Cys Trp Cys Val
                 85                  90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Glu Leu Lys His Lys
            115                 120                 125

Glu Arg Glu Ser Pro Tyr Asp His Gln Ser Leu Gln Thr Ala Leu Gln
130                 135                 140

Glu Ala Phe Thr Ser Arg Tyr Lys Leu Asn Gln Lys Phe Ile Lys Asn
145                 150                 155                 160

Ile Met Tyr Glu Asn Asn Val Ile Thr Ile Asp Leu Met Gln Asn Ser
                165                 170                 175

Ser Gln Lys Thr Gln Asp Asp Val Asp Ile Ala Asp Val Ala Tyr Tyr
            180                 185                 190

Phe Glu Lys Asp Val Lys Gly Glu Ser Leu Phe His Ser Ser Lys Ser
        195                 200                 205

Met Asp Leu Arg Val Asn Gly Glu Pro Leu Asp Leu Asp Pro Gly Gln
    210                 215                 220

Thr Leu Ile Tyr Tyr Val Asp Glu Lys Ala Pro Glu Phe Ser Met Gln
225                 230                 235                 240

Gly Leu Thr

<210> SEQ ID NO 51
<211> LENGTH: 5
<212> TYPE: PRT
<213> ORGANISM: Artificial Sequence
<220> FEATURE:
<223> OTHER INFORMATION: EpCAM(3-17I) CDR-H1

<400> SEQUENCE: 51

Ser Tyr Ala Ile Ser
1               5

<210> SEQ ID NO 52
<211> LENGTH: 17
<212> TYPE: PRT
<213> ORGANISM: Artificial Sequence
<220> FEATURE:
<223> OTHER INFORMATION: EpCAM(3-17I) CDR-H2

<400> SEQUENCE: 52

Gly Ile Ile Pro Ile Phe Gly Thr Ala Asn Tyr Ala Gln Lys Phe Gln
1               5                   10                  15

Gly

<210> SEQ ID NO 53
<211> LENGTH: 4
<212> TYPE: PRT
<213> ORGANISM: Artificial Sequence
<220> FEATURE:
<223> OTHER INFORMATION: EpCAM(3-17I) CDR-H3

<400> SEQUENCE: 53

Gly Leu Leu Trp
1

<210> SEQ ID NO 54
<211> LENGTH: 11
<212> TYPE: PRT
<213> ORGANISM: Artificial Sequence
<220> FEATURE:
<223> OTHER INFORMATION: EpCAM(3-17I) CDR-L1

<400> SEQUENCE: 54

Arg Ala Ser Gln Ser Val Ser Ser Asn Leu Ala
1               5                   10

<210> SEQ ID NO 55
<211> LENGTH: 7
<212> TYPE: PRT
<213> ORGANISM: Artificial Sequence
<220> FEATURE:
<223> OTHER INFORMATION: EpCAM(3-17I) CDR-L2

```
<400> SEQUENCE: 55

Gly Ala Ser Thr Thr Ala Ser
1               5

<210> SEQ ID NO 56
<211> LENGTH: 11
<212> TYPE: PRT
<213> ORGANISM: Artificial Sequence
<220> FEATURE:
<223> OTHER INFORMATION: EpCAM(3-17I)  CDR-L3

<400> SEQUENCE: 56

Gln Gln Tyr Asn Asn Trp Pro Pro Ala Tyr Thr
1               5                   10

<210> SEQ ID NO 57
<211> LENGTH: 5
<212> TYPE: PRT
<213> ORGANISM: Mus musculus

<400> SEQUENCE: 57

Asn Phe Pro Met Ala
1               5

<210> SEQ ID NO 58
<211> LENGTH: 17
<212> TYPE: PRT
<213> ORGANISM: Mus musculus

<400> SEQUENCE: 58

Thr Ile Ser Thr Ser Gly Gly Ser Thr Tyr Tyr Arg Asp Ser Val Lys
1               5                   10                  15

Gly

<210> SEQ ID NO 59
<211> LENGTH: 10
<212> TYPE: PRT
<213> ORGANISM: Mus musculus

<400> SEQUENCE: 59

Thr Leu Tyr Ile Leu Arg Val Phe Tyr Phe
1               5                   10

<210> SEQ ID NO 60
<211> LENGTH: 11
<212> TYPE: PRT
<213> ORGANISM: Mus musculus

<400> SEQUENCE: 60

Leu Ala Ser Glu Gly Ile Ser Asn Asp Leu Ala
1               5                   10

<210> SEQ ID NO 61
<211> LENGTH: 7
<212> TYPE: PRT
<213> ORGANISM: Mus musculus

<400> SEQUENCE: 61

Ala Thr Ser Arg Leu Gln Asp
1               5

<210> SEQ ID NO 62
<211> LENGTH: 9
```

```
<212> TYPE: PRT
<213> ORGANISM: Mus musculus

<400> SEQUENCE: 62

Gln Gln Ser Tyr Lys Tyr Pro Trp Thr
1               5

<210> SEQ ID NO 63
<211> LENGTH: 115
<212> TYPE: PRT
<213> ORGANISM: Artificial Sequence
<220> FEATURE:
<223> OTHER INFORMATION: EpCAM(3-17I) VH

<400> SEQUENCE: 63

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Leu Trp Asn Tyr Trp Gly Gln Gly Thr Leu Val Thr
            100                 105                 110

Val Ser Ser
        115

<210> SEQ ID NO 64
<211> LENGTH: 109
<212> TYPE: PRT
<213> ORGANISM: Artificial Sequence
<220> FEATURE:
<223> OTHER INFORMATION: EpCAM(3-17I) VL

<400> SEQUENCE: 64

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Ile Ile
        35                  40                  45

Tyr Gly Ala Ser Thr Thr Ala Ser Gly Ile Pro Ala Arg Phe Ser Ala
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Ala Tyr Thr Phe Gly Gln Gly Thr Lys Leu Glu Ile Lys
            100                 105

<210> SEQ ID NO 65
<211> LENGTH: 121
<212> TYPE: PRT
<213> ORGANISM: Artificial Sequence
<220> FEATURE:
```

<223> OTHER INFORMATION: muEpCAM(G8.8) VH

<400> SEQUENCE: 65

Glu Val Gln Leu Ala Glu Ser Gly Gly Gly Leu Val Gln Pro Gly Arg
1               5                   10                  15

Ser Met Lys Leu Ser Cys Ala Ala Ser Gly Phe Thr Phe Ser Asn Phe
            20                  25                  30

Pro Met Ala Trp Val Arg Gln Ala Pro Thr Lys Gly Leu Glu Trp Val
        35                  40                  45

Ala Thr Ile Ser Thr Ser Gly Gly Ser Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg Thr Leu Tyr Ile Leu Arg Val Phe Tyr Phe Asp Tyr Trp Gly
            100                 105                 110

Gln Gly Val Met Val Thr Val Ser Ser
        115                 120

<210> SEQ ID NO 66
<211> LENGTH: 107
<212> TYPE: PRT
<213> ORGANISM: Artificial Sequence
<220> FEATURE:
<223> OTHER INFORMATION: muEpCAM(G8.8) VL

<400> SEQUENCE: 66

Asp Ile Gln Met Thr Gln Ser Pro Ala Ser Leu Ser Ala Ser Leu Gly
1               5                   10                  15

Glu Thr Val Ser Ile Glu Cys Leu Ala Ser Gly Ile Ser Asn Asp
            20                  25                  30

Leu Ala Trp Tyr Gln Gln Lys Ser Gly Lys Ser Pro Gln Leu Leu Ile
        35                  40                  45

Tyr Ala Thr Ser Arg Leu Gln Asp Gly Val Pro Ser Arg Phe Ser Gly
    50                  55                  60

Ser Gly Ser Gly Thr Arg Tyr Ser Leu Lys Ile Ser Gly Met Gln Pro
65                  70                  75                  80

Glu Asp Glu Ala Asp Tyr Phe Cys Gln Gln Ser Tyr Lys Tyr Pro Trp
                85                  90                  95

Thr Phe Gly Gly Gly Thr Lys Leu Glu Leu Lys
            100                 105

<210> SEQ ID NO 67
<211> LENGTH: 277
<212> TYPE: PRT
<213> ORGANISM: Homo sapiens

<400> SEQUENCE: 67

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

```
Arg Pro Cys Gly Pro Gly Phe Tyr Asn Asp Val Ser Ser Lys Pro
 65                  70                  75                  80

Cys Lys Pro Cys Thr Trp Cys Asn Leu Arg Ser Gly Ser Glu Arg Lys
             85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
            130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
            195                 200                 205

Val Pro Gly Gly Arg Ala Val Ala Ala Ile Leu Gly Leu Gly Leu Val
210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 68
<211> LENGTH: 314
<212> TYPE: PRT
<213> ORGANISM: Homo sapiens

<400> SEQUENCE: 68

Met Ala Pro Pro Gln Val Leu Ala Phe Gly Leu Leu Leu Ala Ala Ala
 1                   5                  10                  15

Thr Ala Thr Phe Ala Ala Ala Gln Glu Glu Cys Val Cys Glu Asn Tyr
             20                  25                  30

Lys Leu Ala Val Asn Cys Phe Val Asn Asn Asn Arg Gln Cys Gln Cys
             35                  40                  45

Thr Ser Val Gly Ala Gln Asn Thr Val Ile Cys Ser Lys Leu Ala Ala
 50                  55                  60

Lys Cys Leu Val Met Lys Ala Glu Met Asn Gly Ser Lys Leu Gly Arg
 65                  70                  75                  80

Arg Ala Lys Pro Glu Gly Ala Leu Gln Asn Asn Asp Gly Leu Tyr Asp
             85                  90                  95

Pro Asp Cys Asp Glu Ser Gly Leu Phe Lys Ala Lys Gln Cys Asn Gly
            100                 105                 110

Thr Ser Met Cys Trp Cys Val Asn Thr Ala Gly Val Arg Arg Thr Asp
            115                 120                 125

Lys Asp Thr Glu Ile Thr Cys Ser Glu Arg Val Arg Thr Tyr Trp Ile
            130                 135                 140

Ile Ile Glu Leu Lys His Lys Ala Arg Glu Lys Pro Tyr Asp Ser Lys
145                 150                 155                 160
```

-continued

```
Ser Leu Arg Thr Ala Leu Gln Lys Glu Ile Thr Thr Arg Tyr Gln Leu
            165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
            195                 200                 205

Ile Ala Asp Val Ala Tyr Tyr Phe Glu Lys Asp Val Lys Gly Glu Ser
            210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
            245                 250                 255

Pro Glu Phe Ser Met Gln Gly Leu Lys Ala Gly Val Ile Ala Val Ile
            260                 265                 270

Val Val Val Val Ile Ala Val Val Ala Gly Ile Val Val Leu Val Ile
            275                 280                 285

Ser Arg Lys Lys Arg Met Ala Lys Tyr Glu Lys Ala Glu Ile Lys Glu
            290                 295                 300

Met Gly Glu Met His Arg Glu Leu Asn Ala
305                 310
```

<210> SEQ ID NO 69
<211> LENGTH: 255
<212> TYPE: PRT
<213> ORGANISM: Homo sapiens

<400> SEQUENCE: 69

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Arg Thr Cys Asp Ile
            50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
            85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
            130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
            165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205
```

```
Arg Phe Ser Val Val Lys Arg Gly Arg Lys Leu Leu Tyr Ile Phe
        210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 70
<211> LENGTH: 260
<212> TYPE: PRT
<213> ORGANISM: Homo sapiens

<400> SEQUENCE: 70

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys His Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260

<210> SEQ ID NO 71
<211> LENGTH: 283
<212> TYPE: PRT
<213> ORGANISM: Homo sapiens

<400> SEQUENCE: 71

Met Glu Pro Pro Gly Asp Trp Gly Pro Pro Pro Trp Arg Ser Thr Pro
1               5                   10                  15
```

```
Lys Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
            35                  40                  45

Val Gly Ser Glu Cys Cys Pro Lys Cys Ser Pro Gly Tyr Arg Val Lys
 50                  55                  60

Glu Ala Cys Gly Glu Leu Thr Gly Thr Val Cys Glu Pro Cys Pro Pro
 65                  70                  75                  80

Gly Thr Tyr Ile Ala His Leu Asn Gly Leu Ser Lys Cys Leu Gln Cys
                 85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
            115                 120                 125

Val Gln Asp Gly Asp His Cys Ala Ala Cys Arg Ala Tyr Ala Thr Ser
130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
            195                 200                 205

Ser Leu Val Ile Val Ile Val Cys Ser Thr Val Gly Leu Ile Ile Cys
210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
            245                 250                 255

Ala Leu Gln Ala Pro Pro Asp Val Thr Thr Val Ala Val Glu Glu Thr
            260                 265                 270

Ile Pro Ser Phe Thr Gly Arg Ser Pro Asn His
            275                 280

<210> SEQ ID NO 72
<211> LENGTH: 595
<212> TYPE: PRT
<213> ORGANISM: Homo sapiens

<400> SEQUENCE: 72

Met Arg Val Leu Leu Ala Ala Leu Gly Leu Leu Phe Leu Gly Ala Leu
 1               5                  10                  15

Arg Ala Phe Pro Gln Asp Arg Pro Phe Glu Asp Thr Cys His Gly Asn
            20                  25                  30

Pro Ser His Tyr Tyr Asp Lys Ala Val Arg Arg Cys Cys Tyr Arg Cys
            35                  40                  45

Pro Met Gly Leu Phe Pro Thr Gln Gln Cys Pro Gln Arg Pro Thr Asp
            50                  55                  60

Cys Arg Lys Gln Cys Glu Pro Asp Tyr Tyr Leu Asp Glu Ala Asp Arg
 65                  70                  75                  80

Cys Thr Ala Cys Val Thr Cys Ser Arg Asp Asp Leu Val Glu Lys Thr
                 85                  90                  95
```

```
Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
            115                 120                 125

Ser Val Cys Pro Ala Gly Met Ile Val Lys Phe Pro Gly Thr Ala Gln
130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
            165                 170                 175

Ala Lys Pro Thr Pro Val Ser Pro Ala Thr Ser Ala Ser Thr Met
            180                 185                 190

Pro Val Arg Gly Gly Thr Arg Leu Ala Gln Glu Ala Ala Ser Lys Leu
            195                 200                 205

Thr Arg Ala Pro Asp Ser Pro Ser Ser Val Gly Arg Pro Ser Ser Asp
            210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
            245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
            275                 280                 285

Cys Ala Thr Ser Ala Thr Asn Ser Cys Ala Arg Cys Val Pro Tyr Pro
            290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
            325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
            355                 360                 365

Ser Ala Pro Val Ala Leu Ser Ser Thr Gly Lys Pro Val Leu Asp Ala
370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
            405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
            435                 440                 445

Ser Gly Ala Ser Val Thr Glu Pro Val Ala Glu Glu Arg Gly Leu Met
            450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
            485                 490                 495

Pro Arg Asp Leu Pro Glu Pro Arg Val Ser Thr Glu His Thr Asn Asn
            500                 505                 510
```

```
Lys Ile Glu Lys Ile Tyr Ile Met Lys Ala Asp Thr Val Ile Val Gly
        515                 520                 525

Thr Val Lys Ala Glu Leu Pro Glu Gly Arg Gly Leu Ala Gly Pro Ala
530                 535                 540

Glu Pro Glu Leu Glu Glu Leu Glu Ala Asp His Thr Pro His Tyr
545                 550                 555                 560

Pro Glu Gln Glu Thr Glu Pro Leu Gly Ser Cys Ser Asp Val Met
                565                 570                 575

Leu Ser Val Glu Glu Gly Lys Glu Asp Pro Leu Pro Thr Ala Ala
                580                 585                 590

Ser Gly Lys
        595

<210> SEQ ID NO 73
<211> LENGTH: 241
<212> TYPE: PRT
<213> ORGANISM: Homo sapiens

<400> SEQUENCE: 73

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
                20                  25                  30

Gly Cys Gly Pro Gly Arg Leu Leu Leu Gly Thr Gly Thr Asp Ala Arg
            35                  40                  45

Cys Cys Arg Val His Thr Thr Arg Cys Cys Arg Asp Tyr Pro Gly Glu
        50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val

<210> SEQ ID NO 74
<211> LENGTH: 272
<212> TYPE: PRT
<213> ORGANISM: Mus musculus
```

<400> SEQUENCE: 74

```
Met Tyr Val Trp Val Gln Gln Pro Thr Ala Leu Leu Leu Ala Leu
1               5                   10                  15

Thr Leu Gly Val Thr Ala Arg Arg Leu Asn Cys Val Lys His Thr Tyr
            20                  25                  30

Pro Ser Gly His Lys Cys Cys Arg Glu Cys Gln Pro Gly His Gly Met
            35                  40                  45

Val Ser Arg Cys Asp His Thr Arg Asp Thr Leu Cys His Pro Cys Glu
50                  55                  60

Thr Gly Phe Tyr Asn Glu Ala Val Asn Tyr Asp Thr Cys Lys Gln Cys
65                  70                  75                  80

Thr Gln Cys Asn His Arg Ser Gly Ser Glu Leu Lys Gln Asn Cys Thr
                85                  90                  95

Pro Thr Gln Asp Thr Val Cys Arg Cys Arg Pro Gly Thr Gln Pro Arg
            100                 105                 110

Gln Asp Ser Gly Tyr Lys Leu Gly Val Asp Cys Val Pro Cys Pro Pro
            115                 120                 125

Gly His Phe Ser Pro Gly Asn Asn Gln Ala Cys Lys Pro Trp Thr Asn
130                 135                 140

Cys Thr Leu Ser Gly Lys Gln Thr Arg His Pro Ala Ser Asp Ser Leu
145                 150                 155                 160

Asp Ala Val Cys Glu Asp Arg Ser Leu Leu Ala Thr Leu Leu Trp Glu
                165                 170                 175

Thr Gln Arg Pro Thr Phe Arg Pro Thr Thr Val Gln Ser Thr Thr Val
            180                 185                 190

Trp Pro Arg Thr Ser Glu Leu Pro Ser Pro Thr Leu Val Thr Pro
            195                 200                 205

Glu Gly Pro Ala Phe Ala Val Leu Leu Gly Leu Gly Leu Gly Leu Leu
210                 215                 220

Ala Pro Leu Thr Val Leu Leu Ala Leu Tyr Leu Leu Arg Lys Ala Trp
225                 230                 235                 240

Arg Leu Pro Asn Thr Pro Lys Pro Cys Trp Gly Asn Ser Phe Arg Thr
            245                 250                 255

Pro Ile Gln Glu Glu His Thr Asp Ala His Phe Thr Leu Ala Lys Ile
            260                 265                 270
```

<210> SEQ ID NO 75
<211> LENGTH: 315
<212> TYPE: PRT
<213> ORGANISM: Mus musculus

<400> SEQUENCE: 75

```
Met Ala Gly Pro Gln Ala Leu Ala Phe Gly Leu Leu Leu Ala Val Val
1               5                   10                  15

Thr Ala Thr Leu Ala Ala Ala Gln Arg Asp Cys Val Cys Asp Asn Tyr
            20                  25                  30

Lys Leu Ala Thr Ser Cys Ser Leu Asn Glu Tyr Gly Cys Gln Cys
            35                  40                  45

Thr Ser Tyr Gly Thr Gln Asn Thr Val Ile Cys Ser Lys Leu Ala Ser
50                  55                  60

Lys Cys Leu Ala Met Lys Ala Glu Met Thr His Ser Lys Ser Gly Arg
65                  70                  75                  80

Arg Ile Lys Pro Glu Gly Ala Ile Gln Asn Asn Asp Gly Leu Tyr Asp
                85                  90                  95
```

```
Pro Asp Cys Asp Glu Gln Gly Leu Phe Lys Ala Lys Gln Cys Asn Gly
            100                 105                 110

Thr Ala Thr Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
    130                 135                 140

Ile Ile Glu Leu Lys His Lys Glu Arg Glu Ser Pro Tyr Asp His Gln
145                 150                 155                 160

Ser Leu Gln Thr Ala Leu Gln Glu Ala Phe Thr Ser Arg Tyr Lys Leu
                165                 170                 175

Asn Gln Lys Phe Ile Lys Asn Ile Met Tyr Glu Asn Asn Val Ile Thr
            180                 185                 190

Ile Asp Leu Met Gln Asn Ser Ser Gln Lys Thr Gln Asp Asp Val Asp
        195                 200                 205

Ile Ala Asp Val Ala Tyr Tyr Phe Glu Lys Asp Val Lys Gly Glu Ser
    210                 215                 220

Leu Phe His Ser Ser Lys Ser Met Asp Leu Arg Val Asn Gly Glu Pro
225                 230                 235                 240

Leu Asp Leu Asp Pro Gly Gln Thr Leu Ile Tyr Tyr Val Asp Glu Lys
                245                 250                 255

Ala Pro Glu Phe Ser Met Gln Gly Leu Thr Ala Gly Ile Ile Ala Val
            260                 265                 270

Ile Val Val Val Ser Leu Ala Val Ile Ala Gly Ile Val Val Leu Val
        275                 280                 285

Ile Ser Thr Arg Lys Lys Ser Ala Lys Tyr Glu Lys Ala Glu Ile Lys
    290                 295                 300

Glu Met Gly Glu Ile His Arg Glu Leu Asn Ala
305                 310                 315

<210> SEQ ID NO 76
<211> LENGTH: 5
<212> TYPE: PRT
<213> ORGANISM: Artificial Sequence
<220> FEATURE:
<223> OTHER INFORMATION: Petpide linker G4S

<400> SEQUENCE: 76

Gly Gly Gly Gly Ser
1               5

<210> SEQ ID NO 77
<211> LENGTH: 10
<212> TYPE: PRT
<213> ORGANISM: Artificial Sequence
<220> FEATURE:
<223> OTHER INFORMATION: Peptide linker (G4S)2

<400> SEQUENCE: 77

Gly Gly Gly Gly Ser Gly Gly Gly Gly Ser
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Peptide linker (SG4)2
```

<400> SEQUENCE: 78

Ser Gly Gly Gly Gly Ser Gly Gly Gly Gly
1               5                   10

<210> SEQ ID NO 79
<211> LENGTH: 15
<212> TYPE: PRT
<213> ORGANISM: Artificial Sequence
<220> FEATURE:
<223> OTHER INFORMATION: Peptide linker (G4S)3

<400> SEQUENCE: 79

Gly Gly Gly Gly Ser Gly Gly Gly Gly Ser Gly Gly Gly Gly Ser
1               5                   10                  15

<210> SEQ ID NO 80
<211> LENGTH: 14
<212> TYPE: PRT
<213> ORGANISM: Artificial Sequence
<220> FEATURE:
<223> OTHER INFORMATION: Peptide linker G4(SG4)2

<400> SEQUENCE: 80

Gly Gly Gly Gly Ser Gly Gly Gly Gly Ser Gly Gly Gly Gly
1               5                   10

<210> SEQ ID NO 81
<211> LENGTH: 20
<212> TYPE: PRT
<213> ORGANISM: Artificial Sequence
<220> FEATURE:
<223> OTHER INFORMATION: Peptide linker (G4S)4

<400> SEQUENCE: 81

Gly Gly Gly Gly Ser Gly Gly Gly Gly Ser Gly Gly Gly Gly Ser Gly
1               5                   10                  15

Gly Gly Gly Ser
            20

<210> SEQ ID NO 82
<211> LENGTH: 10
<212> TYPE: PRT
<213> ORGANISM: Artificial Sequence
<220> FEATURE:
<223> OTHER INFORMATION: Peptide linker GSPGSSSSGS

<400> SEQUENCE: 82

Gly Ser Pro Gly Ser Ser Ser Ser Gly Ser
1               5                   10

<210> SEQ ID NO 83
<211> LENGTH: 8
<212> TYPE: PRT
<213> ORGANISM: Artificial Sequence
<220> FEATURE:
<223> OTHER INFORMATION: Peptide linker GSGSGSGS

<400> SEQUENCE: 83

Gly Ser Gly Ser Gly Ser Gly Ser
1               5

<210> SEQ ID NO 84
<211> LENGTH: 8
<212> TYPE: PRT
<213> ORGANISM: Artificial Sequence
<220> FEATURE:
<223> OTHER INFORMATION: Peptide linker GSGSGNGS

<400> SEQUENCE: 84

Gly Ser Gly Ser Gly Asn Gly Ser
1               5

<210> SEQ ID NO 85
<211> LENGTH: 8
<212> TYPE: PRT
<213> ORGANISM: Artificial Sequence
<220> FEATURE:
<223> OTHER INFORMATION: Peptide linker GGSGSGSG

<400> SEQUENCE: 85

Gly Gly Ser Gly Ser Gly Ser Gly
1               5

<210> SEQ ID NO 86
<211> LENGTH: 6
<212> TYPE: PRT
<213> ORGANISM: Artificial Sequence
<220> FEATURE:
<223> OTHER INFORMATION: Peptide linker GGSGSG

<400> SEQUENCE: 86

Gly Gly Ser Gly Ser Gly
1               5

<210> SEQ ID NO 87
<211> LENGTH: 4
<212> TYPE: PRT
<213> ORGANISM: Artificial Sequence
<220> FEATURE:
<223> OTHER INFORMATION: Peptide linkeer GGSG

<400> SEQUENCE: 87

Gly Gly Ser Gly
1

<210> SEQ ID NO 88
<211> LENGTH: 8
<212> TYPE: PRT
<213> ORGANISM: Artificial Sequence
<220> FEATURE:
<223> OTHER INFORMATION: Peptide linker GGSGNGSG

<400> SEQUENCE: 88

Gly Gly Ser Gly Asn Gly Ser Gly
1               5

<210> SEQ ID NO 89
<211> LENGTH: 8
<212> TYPE: PRT
<213> ORGANISM: Artificial Sequence
<220> FEATURE:
<223> OTHER INFORMATION: Peptide linker GGNGSGSG

<400> SEQUENCE: 89

Gly Gly Asn Gly Ser Gly Ser Gly
1               5

<210> SEQ ID NO 90
<211> LENGTH: 6
<212> TYPE: PRT
<213> ORGANISM: Artificial Sequence
<220> FEATURE:

<223> OTHER INFORMATION: Peptide linker GGNGSG

<400> SEQUENCE: 90

Gly Gly Asn Gly Ser Gly
1               5

<210> SEQ ID NO 91
<211> LENGTH: 681
<212> TYPE: DNA
<213> ORGANISM: Artificial Sequence
<220> FEATURE:
<223> OTHER INFORMATION: Nucleotide sequence Fc hole chain

<400> SEQUENCE: 91

| gacaaaactc | acacatgccc | accgtgccca | gcacctgaac | tcctgggggg | accgtcagtc | 60 |
| ttcctcttcc | ccccaaaacc | caaggacacc | ctcatgatct | cccggacccc | tgaggtcaca | 120 |
| tgcgtggtgg | tggacgtgag | ccacgaagac | cctgaggtca | agttcaactg | gtacgtggac | 180 |
| ggcgtggagg | tgcataatgc | caagacaaag | ccgcgggagg | agcagtacaa | cagcacgtac | 240 |
| cgtgtggtca | gcgtcctcac | cgtcctgcac | caggactggc | tgaatggcaa | ggagtacaag | 300 |
| tgcaaggtct | ccaacaaagc | cctcccagcc | cccatcgaga | aaaccatctc | caaagccaaa | 360 |
| gggcagcccc | gagaaccaca | ggtgtgcacc | ctgcccccat | cccgggatga | gctgaccaag | 420 |
| aaccaggtca | gcctctcgtg | cgcagtcaaa | ggcttctatc | cagcgacat | cgccgtggag | 480 |
| tgggagagca | atgggcagcc | ggagaacaac | tacaagacca | cgcctcccgt | gctggactcc | 540 |
| gacggctcct | tcttcctcgt | gagcaagctc | accgtggaca | agagcaggtg | gcagcagggg | 600 |
| aacgtcttct | catgctccgt | gatgcatgag | gctctgcaca | accactacac | gcagaagagc | 660 |
| ctctccctgt | ctccgggtaa | a |  |  |  | 681 |

<210> SEQ ID NO 92
<211> LENGTH: 1335
<212> TYPE: DNA
<213> ORGANISM: Artificial Sequence
<220> FEATURE:
<223> OTHER INFORMATION: nucleotide sequence human OX40 antigen Fc knob
      chain

<400> SEQUENCE: 92

| ctgcactgcg | tgggcgacac | ctaccccagc | aacgaccggt | gctgccacga | gtgcagaccc | 60 |
| ggcaacggca | tggtgtcccg | gtgcagccgg | tcccagaaca | ccgtgtgcag | accttgcggc | 120 |
| cctggcttct | acaacgacgt | ggtgtccagc | aagcccctgca | agccttgtac | ctggtgcaac | 180 |
| ctgcggagcg | gcagcgagcg | gaagcagctg | tgtaccgcca | cccaggatac | cgtgtgccgg | 240 |
| tgtagagccg | gcacccagcc | cctggacagc | tacaaacccg | gcgtggactg | cgccccttgc | 300 |
| cctcctggcc | acttcagccc | tggcgacaac | caggcctgca | agccttggac | caactgcacc | 360 |
| ctggccggca | agcacaccct | gcagcccgcc | agcaatagca | gcgacgccat | ctgcgaggac | 420 |
| cgggatcctc | ctgccaccca | gcctcaggaa | acccagggcc | ctcccgccag | acccatcacc | 480 |
| gtgcagccta | cagaggcctg | gcccagaacc | agccaggggc | ctagcaccag | acccgtggaa | 540 |
| gtgcctggcg | gcagagccgt | cgacgaacag | ttatattttc | agggcggctc | acccaaatct | 600 |
| gcagacaaaa | ctcacacatg | cccaccgtgc | ccagcacctg | aactcctggg | gggaccgtca | 660 |
| gtcttcctct | tccccccaaa | acccaaggac | accctcatga | tctcccggac | ccctgaggtc | 720 |
| acatgcgtgg | tggtggacgt | gagccacgaa | gaccctgagg | tcaagttcaa | ctggtacgtg | 780 |
| gacggcgtgg | aggtgcataa | tgccaagaca | aagccgcggg | aggagcagta | caacagcacg | 840 |

```
taccgtgtgg tcagcgtcct caccgtcctg caccaggact ggctgaatgg caaggagtac      900
aagtgcaagg tctccaacaa agccctccca gcccccatcg agaaaaccat ctccaaagcc      960
aaagggcagc cccgagaacc acaggtgtac accctgcccc catgccggga tgagctgacc     1020
aagaaccagg tcagcctgtg gtgcctggtc aaaggcttct atcccagcga catcgccgtg     1080
gagtgggaga gcaatgggca gccggagaac aactacaaga ccacgcctcc cgtgctggac     1140
tccgacggct ccttcttcct ctacagcaag ctcaccgtgg acaagagcag gtggcagcag     1200
gggaacgtct tctcatgctc cgtgatgcat gaggctctgc acaaccacta cacgcagaag     1260
agcctctccc tgtctccggg taaatccgga ggcctgaacg acatcttcga ggcccagaag     1320
attgaatggc acgag                                                      1335
```

<210> SEQ ID NO 93
<211> LENGTH: 1335
<212> TYPE: DNA
<213> ORGANISM: Artificial Sequence
<220> FEATURE:
<223> OTHER INFORMATION: nucleotide sequence cynomolgus OX40 antigen Fc knob chain

<400> SEQUENCE: 93

```
ctccactgtg tcggggacac ctaccccagc aacgaccggt gctgtcagga gtgcaggcca       60
ggcaacggga tggtgagccg ctgcaaccgc tcccagaaca cggtgtgccg tccgtgcggg      120
cccggcttct acaacgacgt ggtcagcgcc aagccctgca aggcctgcac atggtgcaac      180
ctcagaagtg ggagtgagcg gaaacagccg tgcacggcca cacaggacac agtctgccgc      240 tgccggggcgg gcacccagcc cctggacagc tacaagcctg gagttgactg tgcccccctgc     300 cctccagggc acttctcccc gggcgacaac caggcctgca gccctggac caactgcacc       360 ttggccggga agcacaccct gcagccagcc agcaatagct cggacgccat ctgtgaggac      420
agggaccccc cacccacaca gccccaggag acccagggcc cccggccag cccaccact       480 gtccagccca ctgaagcctg gccagaacct cacagagac cctccacccg gccgtggag       540 gtccccaggg gccctgcggt cgacgaacag ttatattttc agggcggctc acccaaatct      600
gcagacaaaa ctcacacatg cccaccgtgc ccagcacctg aactcctggg gggaccgtca      660
gtcttcctct tcccccccaaa acccaaggac accctcatga tctcccggac ccctgaggtc     720
acatgcgtgg tggtggacgt gagccacgaa gaccctgagg tcaagttcaa ctggtacgtg     780
gacggcgtgg aggtgcataa tgccaagaca aagccgcggg aggagcagta caacagcacg     840
taccgtgtgg tcagcgtcct caccgtcctg caccaggact ggctgaatgg caaggagtac     900
aagtgcaagg tctccaacaa agccctccca gcccccatcg agaaaaccat ctccaaagcc     960
aaagggcagc cccgagaacc acaggtgtac accctgcccc catgccggga tgagctgacc    1020
aagaaccagg tcagcctgtg gtgcctggtc aaaggcttct atcccagcga catcgccgtg    1080
gagtgggaga gcaatgggca gccggagaac aactacaaga ccacgcctcc cgtgctggac    1140
tccgacggct ccttcttcct ctacagcaag ctcaccgtgg acaagagcag gtggcagcag    1200
gggaacgtct tctcatgctc cgtgatgcat gaggctctgc acaaccacta cacgcagaag    1260
agcctctccc tgtctccggg taaatccgga ggcctgaacg acatcttcga ggcccagaag    1320
attgaatggc acgag                                                     1335
```

<210> SEQ ID NO 94
<211> LENGTH: 1353

<212> TYPE: DNA
<213> ORGANISM: Artificial Sequence
<220> FEATURE:
<223> OTHER INFORMATION: nucleotide sequence murine OX40 antigen Fc knob chain

<400> SEQUENCE: 94

```
gtgaccgcca gacggctgaa ctgcgtgaag cacacctacc ccagcggcca caagtgctgc    60
agagagtgcc agcccggcca cggcatggtg tccagatgcg accacacacg ggacaccctg   120
tgccaccctt gcgagacagg cttctacaac gaggccgtga actacgatac ctgcaagcag   180
tgcacccagt gcaaccacag aagcggcagc gagctgaagc agaactgcac ccccacccag   240
gataccgtgt gcagatgcag acccggcacc cagcccagac aggacagcgg ctacaagctg   300
ggcgtggact gcgtgccctg ccctcctggc cacttcagcc ccggcaacaa ccaggcctgc   360
aagccctgga ccaactgcac cctgagcggc aagcagacca gacaccccgc cagcgacagc   420
ctggatgccg tgtgcgagga cagaagcctg ctggccaccc tgctgtggga cacagcgg    480
cccaccttca gacccaccac cgtgcagagc accaccgtgt ggcccagaac cagcgagctg   540
cccagtcctc ctaccctcgt gacacctgag ggcccgtcg acgaacagtt atattttcag   600
ggcggctcac ccaaatctgc agacaaaact cacacatgcc caccgtgccc agcacctgaa   660
ctcctggggg gaccgtcagt cttcctcttc cccccaaaac ccaaggacac cctcatgatc   720
tcccggaccc ctgaggtcac atgcgtggtg gtggacgtga gccacgaaga ccctgaggtc   780
aagttcaact ggtacgtgga cggcgtggag gtgcataatg ccaagacaaa gccgcgggag   840
gagcagtaca acagcacgta ccgtgtggtc agcgtcctca ccgtcctgca ccaggactgg   900
ctgaatggca aggagtacaa gtgcaaggtc tccaacaaag ccctcccagc ccccatcgag   960
aaaaccatct ccaaagccaa agggcagccc cgagaaccac aggtgtacac cctgccccca  1020
tgccgggatg agctgaccaa gaaccaggtc agcctgtggt gcctggtcaa aggcttctat  1080
cccagcgaca tcgccgtgga gtgggagagc aatgggcagc cggagaacaa ctacaagacc  1140
acgcctcccg tgctggactc cgacggctcc ttcttcctct acagcaagct caccgtggac  1200
aagagcaggt ggcagcaggg gaacgtcttc tcatgctccg tgatgcatga ggctctgcac  1260
aaccactaca cgcagaagag cctctccctg tctccgggta aatccggagg cctgaacgac  1320
atcttcgagg cccagaagat tgaatggcac gag                               1353
```

<210> SEQ ID NO 95
<211> LENGTH: 227
<212> TYPE: PRT
<213> ORGANISM: Artificial Sequence
<220> FEATURE:
<223> OTHER INFORMATION: Fc hole chain

<400> SEQUENCE: 95

```
Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
        50                  55                  60
His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 96
<211> LENGTH: 445
<212> TYPE: PRT
<213> ORGANISM: Artificial Sequence
<220> FEATURE:
<223> OTHER INFORMATION: human OX40 antigen Fc knob chain

<400> SEQUENCE: 96

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Asp Glu Gln Leu Tyr
            180                 185                 190

Phe Gln Gly Gly Ser Pro Lys Ser Ala Asp Lys Thr His Thr Cys Pro
        195                 200                 205
```

```
Pro Cys Pro Ala Pro Glu Leu Leu Gly Gly Pro Ser Val Phe Leu Phe
    210                 215                 220

Pro Pro Lys Pro Lys Asp Thr Leu Met Ile Ser Arg Thr Pro Glu Val
225                 230                 235                 240

Thr Cys Val Val Val Asp Val Ser His Glu Asp Pro Glu Val Lys Phe
                245                 250                 255

Asn Trp Tyr Val Asp Gly Val Glu Val His Asn Ala Lys Thr Lys Pro
            260                 265                 270

Arg Glu Glu Gln Tyr Asn Ser Thr Tyr Arg Val Val Ser Val Leu Thr
        275                 280                 285

Val Leu His Gln Asp Trp Leu Asn Gly Lys Glu Tyr Lys Cys Lys Val
    290                 295                 300

Ser Asn Lys Ala Leu Pro Ala Pro Ile Glu Lys Thr Ile Ser Lys Ala
305                 310                 315                 320

Lys Gly Gln Pro Arg Glu Pro Gln Val Tyr Thr Leu Pro Pro Cys Arg
                325                 330                 335

Asp Glu Leu Thr Lys Asn Gln Val Ser Leu Trp Cys Leu Val Lys Gly
            340                 345                 350

Phe Tyr Pro Ser Asp Ile Ala Val Glu Trp Glu Ser Asn Gly Gln Pro
        355                 360                 365

Glu Asn Asn Tyr Lys Thr Thr Pro Pro Val Leu Asp Ser Asp Gly Ser
    370                 375                 380

Phe Phe Leu Tyr Ser Lys Leu Thr Val Asp Lys Ser Arg Trp Gln Gln
385                 390                 395                 400

Gly Asn Val Phe Ser Cys Ser Val Met His Glu Ala Leu His Asn His
                405                 410                 415

Tyr Thr Gln Lys Ser Leu Ser Leu Ser Pro Gly Lys Ser Gly Gly Leu
            420                 425                 430

Asn Asp Ile Phe Glu Ala Gln Lys Ile Glu Trp His Glu
        435                 440                 445

<210> SEQ ID NO 97
<211> LENGTH: 445
<212> TYPE: PRT
<213> ORGANISM: Artificial Sequence
<220> FEATURE:
<223> OTHER INFORMATION: cynomolgus OX40 antigen Fc knob chain

<400> SEQUENCE: 97

Leu His Cys Val Gly Asp Thr Tyr Pro Ser Asn Asp Arg Cys Cys Gln
1               5                   10                  15

Glu Cys Arg Pro Gly Asn Gly Met Val Ser Arg Cys Asn Arg Ser Gln
            20                  25                  30

Asn Thr Val Cys Arg Pro Cys Gly Pro Gly Phe Tyr Asn Asp Val Val
        35                  40                  45

Ser Ala Lys Pro Cys Lys Ala Cys Thr Trp Cys Asn Leu Arg Ser Gly
    50                  55                  60

Ser Glu Arg Lys Gln Pro Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125
```

```
Pro Ala Ser Asn Ser Ser Asp Ala Ile Cys Glu Asp Arg Asp Pro Pro
            130                 135                 140
Pro Thr Gln Pro Gln Glu Thr Gln Gly Pro Pro Ala Arg Pro Thr Thr
145                 150                 155                 160
Val Gln Pro Thr Glu Ala Trp Pro Arg Thr Ser Gln Arg Pro Ser Thr
                165                 170                 175
Arg Pro Val Glu Val Pro Arg Gly Pro Ala Val Asp Glu Gln Leu Tyr
            180                 185                 190
Phe Gln Gly Gly Ser Pro Lys Ser Ala Asp Lys Thr His Thr Cys Pro
            195                 200                 205
Pro Cys Pro Ala Pro Glu Leu Leu Gly Gly Pro Ser Val Phe Leu Phe
210                 215                 220
Pro Pro Lys Pro Lys Asp Thr Leu Met Ile Ser Arg Thr Pro Glu Val
225                 230                 235                 240
Thr Cys Val Val Val Asp Val Ser His Glu Asp Pro Glu Val Lys Phe
                245                 250                 255
Asn Trp Tyr Val Asp Gly Val Glu Val His Asn Ala Lys Thr Lys Pro
            260                 265                 270
Arg Glu Glu Gln Tyr Asn Ser Thr Tyr Arg Val Val Ser Val Leu Thr
            275                 280                 285
Val Leu His Gln Asp Trp Leu Asn Gly Lys Glu Tyr Lys Cys Lys Val
290                 295                 300
Ser Asn Lys Ala Leu Pro Ala Pro Ile Glu Lys Thr Ile Ser Lys Ala
305                 310                 315                 320
Lys Gly Gln Pro Arg Glu Pro Gln Val Tyr Thr Leu Pro Pro Cys Arg
                325                 330                 335
Asp Glu Leu Thr Lys Asn Gln Val Ser Leu Trp Cys Leu Val Lys Gly
            340                 345                 350
Phe Tyr Pro Ser Asp Ile Ala Val Glu Trp Glu Ser Asn Gly Gln Pro
            355                 360                 365
Glu Asn Asn Tyr Lys Thr Thr Pro Pro Val Leu Asp Ser Asp Gly Ser
            370                 375                 380
Phe Phe Leu Tyr Ser Lys Leu Thr Val Asp Lys Ser Arg Trp Gln Gln
385                 390                 395                 400
Gly Asn Val Phe Ser Cys Ser Val Met His Glu Ala Leu His Asn His
                405                 410                 415
Tyr Thr Gln Lys Ser Leu Ser Leu Ser Pro Gly Lys Ser Gly Gly Leu
            420                 425                 430
Asn Asp Ile Phe Glu Ala Gln Lys Ile Glu Trp His Glu
            435                 440                 445
```

<210> SEQ ID NO 98
<211> LENGTH: 451
<212> TYPE: PRT
<213> ORGANISM: Artificial Sequence
<220> FEATURE:
<223> OTHER INFORMATION: murine OX40 antigen Fc knob chain

<400> SEQUENCE: 98

```
Val Thr Ala Arg Arg Leu Asn Cys Val Lys His Thr Tyr Pro Ser Gly
1               5                   10                  15
His Lys Cys Cys Arg Glu Cys Gln Pro Gly His Gly Met Val Ser Arg
            20                  25                  30
Cys Asp His Thr Arg Asp Thr Leu Cys His Pro Cys Glu Thr Gly Phe
        35                  40                  45
```

```
Tyr Asn Glu Ala Val Asn Tyr Asp Thr Cys Lys Gln Cys Thr Gln Cys
 50                  55                  60
Asn His Arg Ser Gly Ser Glu Leu Lys Gln Asn Cys Thr Pro Thr Gln
 65                  70                  75                  80
Asp Thr Val Cys Arg Cys Arg Pro Gly Thr Gln Pro Arg Gln Asp Ser
                 85                  90                  95
Gly Tyr Lys Leu Gly Val Asp Cys Val Pro Cys Pro Pro Gly His Phe
                100                 105                 110
Ser Pro Gly Asn Asn Gln Ala Cys Lys Pro Trp Thr Asn Cys Thr Leu
                115                 120                 125
Ser Gly Lys Gln Thr Arg His Pro Ala Ser Asp Ser Leu Asp Ala Val
                130                 135                 140
Cys Glu Asp Arg Ser Leu Leu Ala Thr Leu Leu Trp Glu Thr Gln Arg
145                 150                 155                 160
Pro Thr Phe Arg Pro Thr Thr Val Gln Ser Thr Thr Val Trp Pro Arg
                165                 170                 175
Thr Ser Glu Leu Pro Ser Pro Pro Thr Leu Val Thr Pro Glu Gly Pro
                180                 185                 190
Val Asp Glu Gln Leu Tyr Phe Gln Gly Gly Ser Pro Lys Ser Ala Asp
                195                 200                 205
Lys Thr His Thr Cys Pro Pro Cys Pro Ala Pro Glu Leu Leu Gly Gly
                210                 215                 220
Pro Ser Val Phe Leu Phe Pro Pro Lys Pro Lys Asp Thr Leu Met Ile
225                 230                 235                 240
Ser Arg Thr Pro Glu Val Thr Cys Val Val Val Asp Val Ser His Glu
                245                 250                 255
Asp Pro Glu Val Lys Phe Asn Trp Tyr Val Asp Gly Val Glu Val His
                260                 265                 270
Asn Ala Lys Thr Lys Pro Arg Glu Glu Gln Tyr Asn Ser Thr Tyr Arg
                275                 280                 285
Val Val Ser Val Leu Thr Val Leu His Gln Asp Trp Leu Asn Gly Lys
                290                 295                 300
Glu Tyr Lys Cys Lys Val Ser Asn Lys Ala Leu Pro Ala Pro Ile Glu
305                 310                 315                 320
Lys Thr Ile Ser Lys Ala Lys Gly Gln Pro Arg Glu Pro Gln Val Tyr
                325                 330                 335
Thr Leu Pro Pro Cys Arg Asp Glu Leu Thr Lys Asn Gln Val Ser Leu
                340                 345                 350
Trp Cys Leu Val Lys Gly Phe Tyr Pro Ser Asp Ile Ala Val Glu Trp
                355                 360                 365
Glu Ser Asn Gly Gln Pro Glu Asn Asn Tyr Lys Thr Thr Pro Pro Val
                370                 375                 380
Leu Asp Ser Asp Gly Ser Phe Phe Leu Tyr Ser Lys Leu Thr Val Asp
385                 390                 395                 400
Lys Ser Arg Trp Gln Gln Gly Asn Val Phe Ser Cys Ser Val Met His
                405                 410                 415
Glu Ala Leu His Asn His Tyr Thr Gln Lys Ser Leu Ser Leu Ser Pro
                420                 425                 430
Gly Lys Ser Gly Gly Leu Asn Asp Ile Phe Glu Ala Gln Lys Ile Glu
                435                 440                 445
Trp His Glu
450
```

<210> SEQ ID NO 99
<211> LENGTH: 1613
<212> TYPE: DNA
<213> ORGANISM: Artificial Sequence
<220> FEATURE:
<223> OTHER INFORMATION: nucleotide sequence of library DP88-4

<400> SEQUENCE: 99

```
tgaaatacct attgcctacg gcagccgctg gattgttatt actcgcggcc cagccggcca      60
tggccgacat ccagatgacc cagtctcctt ccaccctgtc tgcatctgta ggagaccgtg     120
tcaccatcac ttgccgtgcc agtcagagta ttagtagctg gttggcctgg tatcagcaga     180
aaccagggaa agcccctaag ctcctgatct atgatgcctc cagtttggaa agtggggtcc     240
catcacgttt cagcggcagt ggatccggga cagaattcac tctcaccatc agcagcttgc     300
agcctgatga ttttgcaact tattactgcc aacagtataa tagttattct acgtttggcc     360
agggcaccaa agtcgagatc aagcgtacgg tggctgcacc atctgtcttc atcttcccgc     420
catctgatga gcagttgaaa tctggaactg cctctgttgt gtgcctgctg aataacttct     480
atcccagaga ggccaaagta cagtggaagg tggataacgc cctccaatcg gtaactccc    540
aggagagtgt cacagagcag gacagcaagg acagcaccta cagcctcagc agcaccctga     600
cgctgagcaa agcagactac gagaaacaca agtctacgc ctgcgaagtc acccatcagg     660
gcctgagctc gcccgtcaca aagagcttca cagggggaga gtgtggagcc gcagaacaaa     720
aactcatctc agaagaggat ctgaatggag ccgcagacta caaggacgac gacgacaagg     780
gtgccgcata taaggcgcg ccaattctat ttcaaggaga cagtcatatg aaatacctgc     840
tgccgaccgc tgctgctggt ctgctgctcc tcgctgccca gccggcgatg gcccaggtgc     900
aattggtgca gtctggggct gaggtgaaga gcctgggtc ctcggtgaag gtctcctgca     960
aggcctccgg aggcacattc agcagctacg ctataagctg ggtgcgacag gcccctggac    1020
aagggctcga gtggatggga gggatcatcc ctatctttgg tacagcaaac tacgcacaga    1080
agttccaggg cagggtcacc attactgcag acaaatccac gagcacagcc tacatggagc    1140
tgagcagcct gagatctgag gacaccgccg tgtattactg tgcgagacta tcccaggcg    1200
gttactatgt tatggatgcc tggggccaag ggaccaccgt gaccgtctcc tcagctagca    1260
ccaaaggccc atcggtcttc cccctggcac cctcctccaa gagcacctct ggggcacag    1320
cggccctggg ctgcctggtc aaggactact tccccgaacc ggtgacggtg tcgtggaact    1380
caggcgccct gaccagcggc gtgcacacct tcccggctgt cctacagtcc tcaggactct    1440
actccctcag cagcgtggtg accgtgccct ccagcagctt gggcacccag acctacatct    1500
gcaacgtgaa tcacaagccc agcaacacca agtggacaa gaaagttgag cccaaatctt    1560
gtgacgcggc cgcaagcact agtgcccatc accatcacca tcacgccgcg gca           1613
```

<210> SEQ ID NO 100
<211> LENGTH: 723
<212> TYPE: DNA
<213> ORGANISM: Artificial Sequence
<220> FEATURE:
<223> OTHER INFORMATION: nucleotide sequence of Fab light chain Vk1_5

<400> SEQUENCE: 100

```
gacatccaga tgacccagtc tccttccacc ctgtctgcat ctgtaggaga ccgtgtcacc      60
atcacttgcc gtgccagtca gagtattagt agctggttgg cctggtatca gcagaaacca     120
gggaaagccc ctaagctcct gatctatgat gcctccagtt tggaaagtgg ggtcccatca     180
```

-continued

```
cgtttcagcg gcagtggatc cgggacagaa ttcactctca ccatcagcag cttgcagcct      240
gatgattttg caacttatta ctgccaacag tataatagtt attctacgtt tggccagggc      300
accaaagtcg agatcaagcg tacggtggct gcaccatctg tcttcatctt cccgccatct      360
gatgagcagt tgaaatctgg aactgcctct gttgtgtgcc tgctgaataa cttctatccc      420
agagaggcca agtacagtg gaaggtggat aacgccctcc aatcgggtaa ctcccaggag       480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgtg agccgcaga acaaaaactc       660 atctcagaag aggatctgaa tggagccgca gactacaagg acgacgacga caagggtgcc      720
gca                                                                   723
```

<210> SEQ ID NO 101
<211> LENGTH: 241
<212> TYPE: PRT
<213> ORGANISM: Artificial Sequence
<220> FEATURE:
<223> OTHER INFORMATION: Fab light chain Vk1_5

<400> SEQUENCE: 101

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Ala Ala Glu Gln Lys Leu Ile Ser Glu Glu
    210                 215                 220

Asp Leu Asn Gly Ala Ala Asp Tyr Lys Asp Asp Asp Lys Gly Ala
225                 230                 235                 240

Ala
```

<210> SEQ ID NO 102

<211> LENGTH: 720
<212> TYPE: DNA
<213> ORGANISM: Artificial Sequence
<220> FEATURE:
<223> OTHER INFORMATION: nucleotide sequence of Fab heavy chain VH1_69

<400> SEQUENCE: 102

```
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag ggctcgagtg gatgggaggg atcatccctg tctttggtac agcaaactac     180
gcacagaagt tccagggcag ggtcaccatt actgcagaca aatccacgag cacagcctac     240
atggagctga gcagcctgag atctgaggac accgccgtgt attactgtgc gagactatcc     300
ccaggcggtt actatgttat ggatgcctgg ggccaaggga ccaccgtgac cgtctcctca     360
gctagcacca aaggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaaag tggacaagaa agttgagccc     660
aaatcttgtg acgcggccgc aagcactagt gcccatcacc atcaccatca cgccgcggca     720
```

<210> SEQ ID NO 103
<211> LENGTH: 240
<212> TYPE: PRT
<213> ORGANISM: Artificial Sequence
<220> FEATURE:
<223> OTHER INFORMATION: Fab heavy chain VH1_69

<400> SEQUENCE: 103

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Ala Ala Ala Ser Thr Ser Ala His His His His His His Ala Ala Ala
225                 230                 235                 240
```

<210> SEQ ID NO 104
<211> LENGTH: 26
<212> TYPE: DNA
<213> ORGANISM: Artificial Sequence
<220> FEATURE:
<223> OTHER INFORMATION: LMB3 Primer

<400> SEQUENCE: 104
caggaaacag ctatgaccat gattac                                    26

<210> SEQ ID NO 105
<211> LENGTH: 71
<212> TYPE: DNA
<213> ORGANISM: Artificial Sequence
<220> FEATURE:
<223> OTHER INFORMATION: Vk1_5_L3r_S Primer

<400> SEQUENCE: 105
ctcgactttg gtgccctggc caaacgtsba atacgaatta tactgttggc agtaataagt   60
tgcaaaatca t                                                      71

<210> SEQ ID NO 106
<211> LENGTH: 74
<212> TYPE: DNA
<213> ORGANISM: Artificial Sequence
<220> FEATURE:
<223> OTHER INFORMATION: Vk1_5_L3r_SY Primer

<400> SEQUENCE: 106
ctcgactttg gtgccctggc caaacgtmhr sgratacgaa ttatactgtt ggcagtaata   60
agttgcaaaa tcat                                                   74

<210> SEQ ID NO 107
<211> LENGTH: 77
<212> TYPE: DNA
<213> ORGANISM: Artificial Sequence
<220> FEATURE:
<223> OTHER INFORMATION: Vk1_5_L3r_SPY

<400> SEQUENCE: 107
ctcgactttg gtgccctggc caaacgtmhh msssgratac gaattatact gttggcagta   60
ataagttgca aaatcat                                                77

<210> SEQ ID NO 108
<211> LENGTH: 27
<212> TYPE: DNA
<213> ORGANISM: Artificial Sequence
<220> FEATURE:
<223> OTHER INFORMATION: RJH31 Primer

<400> SEQUENCE: 108
acgtttggcc agggcaccaa agtcgag                                     27

<210> SEQ ID NO 109
<211> LENGTH: 28

```
<212> TYPE: DNA
<213> ORGANISM: Artificial Sequence
<220> FEATURE:
<223> OTHER INFORMATION: RJH32 Primer

<400> SEQUENCE: 109
tctcgcacag taatacacgg cggtgtcc                                    28

<210> SEQ ID NO 110
<211> LENGTH: 64
<212> TYPE: DNA
<213> ORGANISM: Artificial Sequence
<220> FEATURE:
<223> OTHER INFORMATION: DP88-v4-4

<400> SEQUENCE: 110
ggacaccgcc gtgtattact gtgcgagaga ctactggggc caagggacca ccgtgaccgt    60
ctcc                                                                64

<210> SEQ ID NO 111
<211> LENGTH: 64
<212> TYPE: DNA
<213> ORGANISM: Artificial Sequence
<220> FEATURE:
<223> OTHER INFORMATION: DP88-v4-6

<400> SEQUENCE: 111
ggacaccgcc gtgtattact gtgcgagaga ctactggggc caagggacca ccgtgaccgt    60
ctcc                                                                64

<210> SEQ ID NO 112
<211> LENGTH: 64
<212> TYPE: DNA
<213> ORGANISM: Artificial Sequence
<220> FEATURE:
<223> OTHER INFORMATION: DP88-v4-8

<400> SEQUENCE: 112
ggacaccgcc gtgtattact gtgcgagaga ctactggggc caagggacca ccgtgaccgt    60
ctcc                                                                64

<210> SEQ ID NO 113
<211> LENGTH: 30
<212> TYPE: DNA
<213> ORGANISM: Artificial Sequence
<220> FEATURE:
<223> OTHER INFORMATION: fdseqlong Primer

<400> SEQUENCE: 113
gacgttagta aatgaatttt ctgtatgagg                                     30

<210> SEQ ID NO 114
<211> LENGTH: 1596
<212> TYPE: DNA
<213> ORGANISM: Artificial Sequence
<220> FEATURE:
<223> OTHER INFORMATION: (Vk3_20/VH3_23) template

<400> SEQUENCE: 114
atgaaatacc tattgcctac ggcagccgct ggattgttat tactcgcggc ccagccggcc    60
atggccgaaa tcgtgttaac gcagtctcca ggcaccctgt ctttgtctcc agggaaaga   120 gccaccctct cttgcagggc cagtcagagt gttagcagca gctacttagc ctggtaccag   180
```

| | |
|---|---|
| cagaaacctg gccaggctcc caggctcctc atctatggag catccagcag ggccactggc | 240 |
| atcccagaca ggttcagtgg cagtggatcc gggacagact tcactctcac catcagcaga | 300 |
| ctggagcctg aagattttgc agtgtattac tgtcagcagt atggtagctc accgctgacg | 360 |
| ttcggccagg ggaccaaagt ggaaatcaaa cgtacggtgg ctgcaccatc tgtcttcatc | 420 |
| ttcccgccat ctgatgagca gttgaaatct ggaactgcct ctgttgtgtg cctgctgaat | 480 |
| aacttctatc ccagagaggc caaagtacag tggaaggtgg ataacgccct ccaatcgggt | 540 |
| aactcccagg agagtgtcac agagcaggac agcaaggaca gcacctacag cctcagcagc | 600 |
| accctgacgc tgagcaaagc agactacgag aaacacaaag tctacgcctg cgaagtcacc | 660 |
| catcagggcc tgagctcgcc cgtcacaaag agcttcaaca ggggagagtg tggagccgca | 720 |
| catcaccatc accatcacgg agccgcagac tacaaggacg acgacgacaa gggtgccgca | 780 |
| taataaggcg cgccaattct atttcaagga cacagtcata tgaaatacct gctgccgacc | 840 |
| gctgctgctg gtctgctgct cctcgctgcc cagccggcga tggccgaggt gcaattgctg | 900 |
| gagtctgggg gaggcttggt acagcctggg gggtccctga ctctcctg tgcagcctcc | 960 |
| ggattcacct ttagcagtta tgccatgagc tgggtccgcc aggctccagg aaggggctg | 1020 |
| gagtgggtct cagctattag tggtagtggt ggtagcacat actacgcaga ctccgtgaag | 1080 |
| ggccggttca ccatctccag agacaattcc aagaacacgc tgtatctgca gatgaacagc | 1140 |
| ctgagagccg aggacacggc cgtatattac tgtgcgaaac cgtttccgta ttttgactac | 1200 |
| tggggccaag gaaccctggt caccgtctcg agtgctagca ccaaaggccc atcggtcttc | 1260 |
| cccctggcac cctcctccaa gagcacctct gggggcacag cggccctggg ctgcctggtc | 1320 |
| aaggactact tccccgaacc ggtgacggtg tcgtggaact caggcgccct gaccagcggc | 1380 |
| gtgcacacct tcccggctgt cctacagtcc tcaggactct actccctcag cagcgtggtg | 1440 |
| accgtgccct ccagcagctt gggcacccag acctacatct gcaacgtgaa tcacaagccc | 1500 |
| agcaacacca agtggacaa gaaagttgag cccaaatctt gtgacgcggc cgcagaacaa | 1560 |
| aaactcatct cagaagagga tctgaatgcc gcggca | 1596 |

<210> SEQ ID NO 115
<211> LENGTH: 714
<212> TYPE: DNA
<213> ORGANISM: Artificial Sequence
<220> FEATURE:
<223> OTHER INFORMATION: Fab light chain Vk3_20

<400> SEQUENCE: 115

| | |
|---|---|
| gaaatcgtgt taacgcagtc tccaggcacc ctgtctttgt ctccagggga aagagccacc | 60 |
| ctctcttgca gggccagtca gagtgttagc agcagctact tagcctggta ccagcagaaa | 120 |
| cctggccagg ctcccaggct cctcatctat ggagcatcca gcagggccac tggcatccca | 180 |
| gacaggttca gtggcagtgg atccgggaca gacttcactc tcaccatcag cagactggag | 240 |
| cctgaagatt ttgcagtgta ttactgtcag cagtatggta gctcaccgct gacgttcggc | 300 |
| caggggacca agtggaaat caaacgtacg gtggctgcac catctgtctt catcttcccg | 360 |
| ccatctgatg agcagttgaa atctggaact gcctctgttg tgtgcctgct gaataacttc | 420 |
| tatcccagag aggccaaagt acagtggaag gtggataacg ccctccaatc gggtaactcc | 480 |
| caggagagtg tcacagagca ggacagcaag gacagcacct acagcctcag cagcaccctg | 540 |
| acgctgagca aagcagacta cgagaaacac aaagtctacg cctgcgaagt cacccatcag | 600 |

```
ggcctgagct cgcccgtcac aaagagcttc aacaggggag agtgtggagc cgcacatcac    660
catcaccatc acggagccgc agactacaag gacgacgacg acaagggtgc cgca           714
```

<210> SEQ ID NO 116
<211> LENGTH: 238
<212> TYPE: PRT
<213> ORGANISM: Artificial Sequence
<220> FEATURE:
<223> OTHER INFORMATION: Fab light chain Vk3_20

<400> SEQUENCE: 116

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Ala Ala His His His His His His
    210                 215                 220

Gly Ala Ala Asp Tyr Lys Asp Asp Asp Lys Gly Ala Ala
225                 230                 235
```

<210> SEQ ID NO 117
<211> LENGTH: 711
<212> TYPE: DNA
<213> ORGANISM: Artificial Sequence
<220> FEATURE:
<223> OTHER INFORMATION: Fab heavy chain VH3_23

<400> SEQUENCE: 117

```
gaggtgcaat tgctggagtc tgggggaggc ttggtacagc ctgggggtc cctgagactc      60 tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaccgttt    300
```

```
ccgtattttg actactgggg ccaaggaacc ctggtcaccg tctcgagtgc tagcaccaaa      360
ggcccatcgg tcttcccct ggcacctcc tccaagagca cctctggggg cacagcggcc       420
ctgggctgcc tggtcaagga ctacttcccc gaaccggtga cggtgtcgtg gaactcaggc     480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaagtg gacaagaaag ttgagcccaa atcttgtgac    660
gcggccgcag aacaaaaact catctcagaa gaggatctga atgccgcggc a              711
```

<210> SEQ ID NO 118
<211> LENGTH: 237
<212> TYPE: PRT
<213> ORGANISM: Artificial Sequence
<220> FEATURE:
<223> OTHER INFORMATION: Fab heavy chain VH3_23 (DP47)

<400> SEQUENCE: 118

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Ala Ala Ala Glu
    210                 215                 220

Gln Lys Leu Ile Ser Glu Glu Asp Leu Asn Ala Ala Ala
225                 230                 235
```

<210> SEQ ID NO 119
<211> LENGTH: 25
<212> TYPE: DNA
<213> ORGANISM: Artificial Sequence
<220> FEATURE:
<223> OTHER INFORMATION: MS64 Primer

```
<400> SEQUENCE: 119
acgttcggcc aggggaccaa agtgg                                          25

<210> SEQ ID NO 120
<211> LENGTH: 25
<212> TYPE: DNA
<213> ORGANISM: Artificial Sequence
<220> FEATURE:
<223> OTHER INFORMATION: DP47CDR3_ba Primer

<400> SEQUENCE: 120
cgcacagtaa tatacggccg tgtcc                                          25

<210> SEQ ID NO 121
<211> LENGTH: 64
<212> TYPE: DNA
<213> ORGANISM: Artificial Sequence
<220> FEATURE:
<223> OTHER INFORMATION: DP47-v4-4

<400> SEQUENCE: 121
cgaggacacg gccgtatatt actgtgcgga ctactggggc caaggaaccc tggtcaccgt    60
ctcg                                                                 64

<210> SEQ ID NO 122
<211> LENGTH: 64
<212> TYPE: DNA
<213> ORGANISM: Artificial Sequence
<220> FEATURE:
<223> OTHER INFORMATION: DP47-v4-6

<400> SEQUENCE: 122
cgaggacacg gccgtatatt actgtgcgga ctactggggc caaggaaccc tggtcaccgt    60
ctcg                                                                 64

<210> SEQ ID NO 123
<211> LENGTH: 64
<212> TYPE: DNA
<213> ORGANISM: Artificial Sequence
<220> FEATURE:
<223> OTHER INFORMATION: DP47-v4-8

<400> SEQUENCE: 123
cgaggacacg gccgtatatt actgtgcgga ctactggggc caaggaaccc tggtcaccgt    60
ctcg                                                                 64

<210> SEQ ID NO 124
<211> LENGTH: 30
<212> TYPE: DNA
<213> ORGANISM: Artificial Sequence
<220> FEATURE:
<223> OTHER INFORMATION: fdseqlong

<400> SEQUENCE: 124
gacgttagta aatgaattt tctgtatgagg                                     30

<210> SEQ ID NO 125
<211> LENGTH: 1605
<212> TYPE: DNA
<213> ORGANISM: Artificial Sequence
<220> FEATURE:
<223> OTHER INFORMATION: Vl3_19/VH3_23 library template
```

<400> SEQUENCE: 125

```
atgaaatacc tattgcctac ggcagccgct ggattgttat tactcgcggc ccagccggcc      60
atggcctcgt ctgagctgac tcaggaccct gctgtgtctg tggccttggg acagacagtc     120
aggatcacat gccaaggaga cagcctcaga agttattatg caagctggta ccagcagaag     180
ccaggacagg cccctgtact tgtcatctat ggtaaaaaca accggccctc agggatccca     240
gaccgattct ctggctccag ctcaggaaac acagcttcct tgaccatcac tggggctcag     300
gcggaagatg aggctgacta ttactgtaac tcccgtgata gtagcggtaa tcatgtggta     360
ttcggcggag ggaccaagct gaccgtccta ggacaaccca aggctgcccc cagcgtgacc     420
ctgttccccc cagcagcga ggaattgcag gccaacaagg ccaccctggt ctgcctgatc     480
agcgacttct acccaggcgc cgtgaccgtg gcctggaagg ccgacagcag ccccgtgaag     540
gccggcgtgg agaccaccac ccccagcaag cagagcaaca acaagtacgc cgccagcagc     600
tacctgagcc tgacccccga gcagtggaag agccacaggt cctacagctg ccaggtgacc     660
cacgagggca gcaccgtgga aaaaccgtg gcccccaccg agtgcagcgg agccgcagaa     720
caaaaactca tctcagaaga ggatctgaat ggagccgcag actacaagga cgacgacgac     780
aagggtgccg cataataagg cgcgccaatt ctatttcaag agacagtca tatgaaatac      840
ctgctgccga ccgctgctgc tggtctgctg ctcctcgctg cccagccggc gatggccgag     900
gtgcaattgc tggagtctgg gggaggcttg gtacagcctg gggggtccct gagactctcc     960
tgtgcagcct ccggattcac ctttagcagt tatgccatga gctgggtccg ccaggctcca    1020
gggaaggggc tggagtgggt ctcagctatt agtggtagtg gtggtagcac atactacgca    1080
gactccgtga agggccggtt caccatctcc agagacaatt ccaagaacac gctgtatctg    1140
cagatgaaca gcctgagagc cgaggacacg gccgtatatt actgtgcgaa accgtttccg    1200
tattttgact actggggcca aggaaccctg gtcaccgtct cgagtgctag caccaaaggc    1260
ccatcggtct tccccctggc accctcctcc aagagcacct ctgggggcac agcggccctg    1320
ggctgcctgg tcaaggacta cttccccgaa ccggtgacgg tgtcgtggaa ctcaggcgcc    1380
ctgaccagcg gcgtgcacac cttcccggct gtcctacagt cctcaggact ctactccctc    1440
agcagcgtgg tgaccgtgcc ctccagcagc ttgggcaccc agacctacat ctgcaacgtg    1500
aatcacaagc ccagcaacac caaagtggac aagaaagttg agcccaaatc ttgtgacgcg    1560
gccgcaagca ctagtgccca tcaccatcac catcacgccg cggca                    1605
```

<210> SEQ ID NO 126
<211> LENGTH: 726
<212> TYPE: DNA
<213> ORGANISM: Artificial Sequence
<220> FEATURE:
<223> OTHER INFORMATION: Fab light chain Vl3_19

<400> SEQUENCE: 126

```
tcgtctgagc tgactcagga ccctgctgtg tctgtggcct tgggacagac agtcaggatc      60
acatgccaag gagacagcct cagaagttat tatgcaagct ggtaccagca gaagccagga     120
caggcccctg tacttgtcat ctatggtaaa aacaaccggc cctcagggat cccagaccga     180
ttctctggct ccagctcagg aaacacagct tccttgacca tcactggggc tcaggcggaa     240
gatgaggctg actattactg taactcccgt gatagtagcg gtaatcatgt ggtattcggc     300
ggagggacca agctgaccgt cctaggacaa cccaaggctg cccccagcgt gaccctgttc     360
cccccagca gcgaggaatt gcaggccaac aaggccaccc tggtctgcct gatcagcgac     420
```

```
ttctacccag cgccgtgac cgtggcctgg aaggccgaca gcagccccgt gaaggccggc      480
gtggagacca ccaccccag caagcagagc aacaacaagt acgccgccag cagctacctg       540
agcctgaccc ccgagcagtg gaagagccac aggtcctaca gctgccaggt gacccacgag      600
ggcagcaccg tggagaaaac cgtggccccc accgagtgca gcggagccgc agaacaaaaa      660
ctcatctcag aagaggatct gaatggagcc gcagactaca aggacgacga cgacaagggt      720
gccgca                                                                 726
```

<210> SEQ ID NO 127
<211> LENGTH: 242
<212> TYPE: PRT
<213> ORGANISM: Artificial Sequence
<220> FEATURE:
<223> OTHER INFORMATION: Fab light chain Vl3_19

<400> SEQUENCE: 127

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Ala Ala Glu Gln Lys Leu Ile Ser Glu
    210                 215                 220

Glu Asp Leu Asn Gly Ala Ala Asp Tyr Lys Asp Asp Asp Lys Gly
225                 230                 235                 240

Ala Ala

<210> SEQ ID NO 128
<211> LENGTH: 26
<212> TYPE: DNA
<213> ORGANISM: Artificial Sequence
<220> FEATURE:
<223> OTHER INFORMATION: LMB3 lambda-DP47 library

```
<400> SEQUENCE: 128
caggaaacag ctatgaccat gattac                                              26

<210> SEQ ID NO 129
<211> LENGTH: 85
<212> TYPE: DNA
<213> ORGANISM: Artificial Sequence
<220> FEATURE:
<223> OTHER INFORMATION: Vl_3_19_L3r_V lambda-DP47 library

<400> SEQUENCE: 129
ggacggtcag cttggtccct ccgccgaata cvhvattacc gctactatca cgggagttac         60
agtaatagtc agcctcatct ccgc                                                85

<210> SEQ ID NO 130
<211> LENGTH: 88
<212> TYPE: DNA
<213> ORGANISM: Artificial Sequence
<220> FEATURE:
<223> OTHER INFORMATION: Vl_3_19_L3r_HV lambda-DP47

<400> SEQUENCE: 130
ggacggtcag cttggtccct ccgccgaata ccmmatgatt accgctacta tcacgggagt         60
tacagtaata gtcagcctca tcttccgc                                            88

<210> SEQ ID NO 131
<211> LENGTH: 91
<212> TYPE: DNA
<213> ORGANISM: Artificial Sequence
<220> FEATURE:
<223> OTHER INFORMATION: Vl_3_19_L3r_HLV lambda-DP47

<400> SEQUENCE: 131
ggacggtcag cttggtccct ccgccgaata crhmvwgatg attaccgcta ctatcacggg         60
agttacagta atagtcagcc tcatcttccg c                                        91

<210> SEQ ID NO 132
<211> LENGTH: 28
<212> TYPE: DNA
<213> ORGANISM: Artificial Sequence
<220> FEATURE:
<223> OTHER INFORMATION: RJH80 lambda-DP47

<400> SEQUENCE: 132
ttcggcggag ggaccaagct gaccgtcc                                            28

<210> SEQ ID NO 133
<211> LENGTH: 28
<212> TYPE: DNA
<213> ORGANISM: Artificial Sequence
<220> FEATURE:
<223> OTHER INFORMATION: MS63

<400> SEQUENCE: 133
tttcgcacag taatatacgg ccgtgtcc                                            28

<210> SEQ ID NO 134
<211> LENGTH: 318
<212> TYPE: DNA
<213> ORGANISM: Artificial Sequence
<220> FEATURE:
<223> OTHER INFORMATION: DNA (8H9 ) VL
```

<400> SEQUENCE: 134

```
tcgtctgagc tgactcagga ccctgctgtg tctgtggcct tgggacagac agtcaggatc    60
acatgccaag agacagcct cagaagttat tatgcaagct ggtaccagca gaagccagga   120
caggcccctg tacttgtcat ctatggtaaa acaaccggc cctcagggat cccagaccga   180
ttctctggct ccagctcagg aaacacagct tccttgacca tcactggggc tcaggcggaa   240
gatgaggctg actattactg taactcccgt gttatgcctc ataatcgcgt attcggcgga   300
gggaccaagc tgaccgtc                                                 318
```

<210> SEQ ID NO 135
<211> LENGTH: 360
<212> TYPE: DNA
<213> ORGANISM: Artificial Sequence
<220> FEATURE:
<223> OTHER INFORMATION: DNA (8H9) VH

<400> SEQUENCE: 135

```
gaggtgcaat tgttggagtc tgggggaggc ttggtacagc ctggggggtc cctgagactc    60
tcctgtgcag cctccggatt cacctttagc agttatgcca tgagctgggt ccgccaggct   120
ccagggaagg gctggagtg gtctcagct attagtggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gcgtgttttc   300
taccgtggtg gtgtttctat ggactactgg ggccaaggaa ccctggtcac cgtctcgagt   360
```

<210> SEQ ID NO 136
<211> LENGTH: 321
<212> TYPE: DNA
<213> ORGANISM: Artificial  Sequence
<220> FEATURE:
<223> OTHER INFORMATION: DNA (49B4) VL

<400> SEQUENCE: 136

```
gacatccaga tgacccagtc tccttccacc ctgtctgcat ctgtaggaga ccgtgtcacc    60
atcacttgcc gtgccagtca gagtattagt agctggttgg cctggtatca gcagaaacca   120
gggaaagccc ctaagctcct gatctatgat gcctccagtt tggaaagtgg ggtcccatca   180
cgtttcagcg gcagtggatc cgggacagaa ttcactctca ccatcagcag cttgcagcct   240
gatgattttg caacttatta ctgccaacag tatagttcgc agccgtatac gtttggccag   300
ggcaccaaag tcgagatcaa g                                             321
```

<210> SEQ ID NO 137
<211> LENGTH: 354
<212> TYPE: DNA
<213> ORGANISM: Artificial Sequence
<220> FEATURE:
<223> OTHER INFORMATION: DNA (49B4) VH

<400> SEQUENCE: 137

```
caggtgcaat tggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag ggctcgagtg gatgggaggg atcatcccta tctttggtac agcaaactac   180
gcacagaagt tccagggcag ggtcaccatt actgcagaca aatccacgag cacagcctac   240
atggagctga gcagcctgag atctgaggac accgccgtgt attactgtgc gagagaatac   300
taccgtggtc cgtacgacta ctggggccaa gggaccaccg tgaccgtctc ctca         354
```

<210> SEQ ID NO 138
<211> LENGTH: 324
<212> TYPE: DNA
<213> ORGANISM: Artificial Sequence
<220> FEATURE:
<223> OTHER INFORMATION: DNA (1G4) VL

<400> SEQUENCE: 138

```
gacatccaga tgacccagtc tccttccacc ctgtctgcat ctgtaggaga ccgtgtcacc    60
atcacttgcc gtgccagtca gagtattagt agctggttgg cctggtatca gcagaaacca   120
gggaaagccc ctaagctcct gatctatgat gcctccagtt tggaaagtgg ggtcccatca   180
cgtttcagcg gcagtggatc cgggacagaa ttcactctca ccatcagcag cttgcagcct   240
gatgattttg caacttatta ctgccaacag tatatttcgt attccatgtt gacgtttggc   300
cagggcacca agtcgagatc aag                                           324
```

<210> SEQ ID NO 139
<211> LENGTH: 348
<212> TYPE: DNA
<213> ORGANISM: Artificial Sequence
<220> FEATURE:
<223> OTHER INFORMATION: DNA (1G4) VH

<400> SEQUENCE: 139

```
caggtgcaat ggtgcagtc tggggctgag gtgaagaagc ctgggtcctc ggtgaaggtc     60
tcctgcaagg cctccggagg cacattcagc agctacgcta taagctgggt gcgacaggcc   120
cctggacaag gctcgagtg gatgggaggg atcatcccta tctttggtac agcaaactac   180
gcacagaagt tccagggcag ggtcaccatt actgcagaca atccacgag cacagcctac   240
atggagctga gcagcctgag atctgaggac accgccgtgt attactgtgc gagagaatac   300
ggttctatgg actactgggg ccaagggacc accgtgaccg tctcctca               348
```

<210> SEQ ID NO 140
<211> LENGTH: 321
<212> TYPE: DNA
<213> ORGANISM: Artificial Sequence
<220> FEATURE:
<223> OTHER INFORMATION: DNA (20B7) VL

<400> SEQUENCE: 140

```
gacatccaga tgacccagtc tccttccacc ctgtctgcat ctgtaggaga ccgtgtcacc    60
atcacttgcc gtgccagtca gagtattagt agctggttgg cctggtatca gcagaaacca   120
gggaaagccc ctaagctcct gatctatgat gcctccagtt tggaaagtgg ggtcccatca   180
cgtttcagcg gcagtggatc cgggacagaa ttcactctca ccatcagcag cttgcagcct   240
gatgattttg caacttatta ctgccaacag tatcaggctt tttcgcttac gtttggccag   300
ggcaccaaag tcgagatcaa g                                             321
```

<210> SEQ ID NO 141
<211> LENGTH: 366
<212> TYPE: DNA
<213> ORGANISM: Artificial Sequence
<220> FEATURE:
<223> OTHER INFORMATION: DNA (20B7) VH

<400> SEQUENCE: 141

```
caggtgcaat tggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag gctcgagtg gatgggaggg atcatcccta tctttggtac agcaaactac   180
gcacagaagt tccagggcag ggtcaccatt actgcagaca atccacgag cacagcctac   240 atggagctga gcagcctgag atctgaggac accgccgtgt attactgtgc gagagttaac   300
tacccgtact cttactgggg tgacttcgac tactggggcc aagggaccac cgtgaccgtc   360
tcctca                                                              366
```

<210> SEQ ID NO 142
<211> LENGTH: 324
<212> TYPE: DNA
<213> ORGANISM: Artificial Sequence
<220> FEATURE:
<223> OTHER INFORMATION: DNA (CLC-563) VL

<400> SEQUENCE: 142

```
gagatcgtgc tgacccagag ccccggcaca ctctccctgt ctcctgggga aagggccacc    60
ctttcatgca gagccagcca gtccgtctct agtagctacc tggcatggta tcagcagaag   120
ccaggacaag ccccccgcct cctgatttac ggcgcttcct ctcgggcaac tggtatccct   180
gacaggttct cagggagcgg aagcggaaca gattttacct tgactatttc tagactggag   240
ccagaggact tcgccgtgta ttactgtcag cagtacggta gtagccccct cacctttggc   300
caggggacaa aagtcgaaat caag                                          324
```

<210> SEQ ID NO 143
<211> LENGTH: 348
<212> TYPE: DNA
<213> ORGANISM: Artificial Sequence
<220> FEATURE:
<223> OTHER INFORMATION: DNA (CLC-563) VH

<400> SEQUENCE: 143

```
gaggtgcaat tgttggagtc tgggggaggc ttggtacagc ctgggggtc cctgagactc    60 tcctgtgcag cctccggatt caccttagc agttatgcca tgagctgggt ccgccaggct   120
ccagggaagg gctggagtg gtctcagct attagtggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gcttgacgtt   300
ggtgctttcg actactgggg ccaaggagcc ctggtcaccg tctcgagt                348
```

<210> SEQ ID NO 144
<211> LENGTH: 324
<212> TYPE: DNA
<213> ORGANISM: Artificial Sequence
<220> FEATURE:
<223> OTHER INFORMATION: DNA (CLC-564) VL

<400> SEQUENCE: 144

```
gagatcgtgc tgacccagag ccccggcaca ctctccctgt ctcctgggga aagggccacc    60
ctttcatgca gagccagcca gtccgtctct agtagctacc tggcatggta tcagcagaag   120
ccaggacaag ccccccgcct cctgatttac ggcgcttcct ctcgggcaac tggtatccct   180
gacaggttct cagggagcgg aagcggaaca gattttacct tgactatttc tagactggag   240
```

```
ccagaggact cgccgtgta ttactgtcag cagtacggta gtagccccct cacctttggc      300 cagggacaa aagtcgaaat caag                                             324
```

<210> SEQ ID NO 145
<211> LENGTH: 348
<212> TYPE: DNA
<213> ORGANISM: Artificial Sequence
<220> FEATURE:
<223> OTHER INFORMATION: DNA (CLC-564) VH

<400> SEQUENCE: 145

```
gaggtgcaat tgttggagtc tggggaggc ttggtacagc ctgggggtc cctgagactc       60 tcctgtgcag cctccggatt caccttagc agttatgcca tgagctgggt ccgccaggct     120
ccagggaagg gctggagtg ggtctcagct attagtggta gtggtggtag cacatactac     180
gcagactccg tgaagggccg gttcaccatc tccagagaca attccaagaa cacgctgtat    240
ctgcagatga acagcctgag agccgaggac acggccgtat attactgtgc gttcgacgtt    300
ggtccgttcg actactgggg ccaaggaacc ctggtcaccg tctcgagt                 348
```

<210> SEQ ID NO 146
<211> LENGTH: 318
<212> TYPE: DNA
<213> ORGANISM: Artificial Sequence
<220> FEATURE:
<223> OTHER INFORMATION: DNA (17A9) VL

<400> SEQUENCE: 146

```
tcgtctgagc tgactcagga ccctgctgtg tctgtggcct tgggacagac agtcaggatc     60
acatgccaag agacagcct cagaagttat tatgcaagct ggtaccagca gaagccagga   120
caggcccctg tacttgtcat ctatggtaaa acaaccggc cctcagggat cccagaccga    180
ttctctggct ccagctcagg aaacacagct tccttgacca tcactggggc tcaggcggaa   240
gatgaggctg actattactg taactcccgt gttatgcctc ataatcgcgt attcggcgga   300
gggaccaagc tgaccgtc                                                  318
```

<210> SEQ ID NO 147
<211> LENGTH: 360
<212> TYPE: DNA
<213> ORGANISM: Artificial Sequence
<220> FEATURE:
<223> OTHER INFORMATION: DNA (17A9) VH

<400> SEQUENCE: 147

```
gaggtgcaat tgttggagtc tggggaggc ttggtacagc ctgggggtc cctgagactc       60 tcctgtgcag cctccggatt caccttagc agttatgcca tgagctgggt ccgccaggct     120
ccagggaagg gctggagtg ggtctcagct attagtggta gtggtggtag cacatactac     180
gcagactccg tgaagggccg gttcaccatc tccagagaca attccaagaa cacgctgtat    240
ctgcagatga acagcctgag agccgaggac acggccgtat attactgtgc gcgtgttttc    300
taccgtggtg gtgtttctat ggactactgg ggccaaggaa ccctggtcac cgtctcgagt   360
```

<210> SEQ ID NO 148
<211> LENGTH: 645
<212> TYPE: DNA
<213> ORGANISM: Artificial Sequence
<220> FEATURE:
<223> OTHER INFORMATION: DNA 8H9 P329GLALA IgG1 light chain

<400> SEQUENCE: 148

```
gacatccaga tgacccagtc tccttccacc ctgtctgcat ctgtaggaga ccgtgtcacc    60
atcacttgcc gtgccagtca gagtattagt agctggttgg cctggtatca gcagaaacca   120
gggaaagccc ctaagctcct gatctatgat gcctccagtt tggaaagtgg ggtcccatca   180
cgtttcagcg gcagtggatc cgggacagaa ttcactctca ccatcagcag cttgcagcct   240
gatgattttg caacttatta ctgccaacag tatttgacgt attcgcggtt tacgtttggc   300
cagggcacca agtcgagat caagcgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgt              645
```

<210> SEQ ID NO 149
<211> LENGTH: 1338
<212> TYPE: DNA
<213> ORGANISM: Artificial Sequence
<220> FEATURE:
<223> OTHER INFORMATION: DNA 8H9 P329GLALA IgG1 heavy chain

<400> SEQUENCE: 149

```
caggtgcaat tggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag ggctcgagtg gatgggaggg atcatcccta tctttggtac agcaaactac   180
gcacagaagt tccagggcag ggtcaccatt actgcagaca atccacgag cacagcctac   240
atggagctga gcagcctgag atctgaggac accgccgtgt attactgtgc gagagaatac   300
ggttggatgg actactgggg ccaagggacc accgtgaccg tctcctcagc tagcaccaag   360
ggcccatcgg tcttccccct ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca caccttcccg gctgtcctac agtcctcagg actctactcc   540
ctcagcagcg tggtgaccgt gccctccagc agcttgggca cccagaccta catctgcaac   600
gtgaatcaca agcccagcaa caccaaggtg gacaagaaag ttgagcccaa atcttgtgac   660
aaaactcaca catgcccacc gtgcccagca cctgaagctg caggggggacc gtcagtcttc   720
ctcttcccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaacag cacgtaccgt   900
gtggtcagcg tcctcaccgt cctgcaccag gactggctga atggcaagga gtacaagtgc   960
aaggtctcca acaaagccct cggcgccccc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg gcagccggga gaacaactac aagaccacgc ctcccgtgct ggactccgac  1200
ggctccttct tcctctacag caagctcacc gtggacaaga gcaggtggca gcaggggaac  1260
```

```
gtcttctcat gctccgtgat gcatgaggct ctgcacaacc actacacgca gaagagcctc    1320
tccctgtctc cgggtaaa                                                   1338
```

<210> SEQ ID NO 150
<211> LENGTH: 215
<212> TYPE: PRT
<213> ORGANISM: Artificial Sequence
<220> FEATURE:
<223> OTHER INFORMATION: 8H9 P329GLALA IgG1 light chain

<400> SEQUENCE: 150

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Leu Thr Tyr Ser Arg
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 151
<211> LENGTH: 446
<212> TYPE: PRT
<213> ORGANISM: Artificial Sequence
<220> FEATURE:
<223> OTHER INFORMATION: 8H9 P329GLALA IgG1 Heavy chain

<400> SEQUENCE: 151

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Glu Tyr Gly Trp Met Asp Tyr Trp Gly Gln Gly Thr Thr Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 152
<211> LENGTH: 642
<212> TYPE: DNA
<213> ORGANISM: Artificial Sequence
<220> FEATURE:
<223> OTHER INFORMATION: DNA 49B4 P329GLALA IgG1 light chain

<400> SEQUENCE: 152

```
gacatccaga tgacccagtc tccttccacc ctgtctgcat ctgtaggaga ccgtgtcacc    60
atcacttgcc gtgccagtca gagtattagt agctggttgg cctggtatca gcagaaacca   120
gggaaagccc ctaagctcct gatctatgat gcctccagtt tggaaagtgg ggtcccatca   180
cgtttcagcg gcagtggatc cgggacagaa ttcactctca ccatcagcag cttgcagcct   240
gatgattttg caacttatta ctgccaacag tatagttcgc agccgtatac gtttggccag   300
ggcaccaaag tcgagatcaa gcgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga aaacacaaa gtctacgcct gcgaagtcac ccatcagggc   600
ctgagctcgc ccgtcacaaa gagcttcaac aggggagagt gt                     642
```

<210> SEQ ID NO 153
<211> LENGTH: 1344
<212> TYPE: DNA
<213> ORGANISM: Artificial Sequence
<220> FEATURE:
<223> OTHER INFORMATION: DNA 49B4 P329GLALA IgG1 heavy chain

<400> SEQUENCE: 153

```
caggtgcaat tggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag gctcgagtg gatgggaggg atcatcccta tctttggtac agcaaactac   180
gcacagaagt tccagggcag ggtcaccatt actgcagaca aatccacgag cacagcctac   240
atggagctga gcagcctgag atctgaggac accgccgtgt attactgtgc gagagaatac   300
taccgtggtc cgtacgacta ctggggccaa gggaccaccg tgaccgtctc ctcagctagc   360
accaagggcc catcggtctt ccccctggca ccctcctcca agagcacctc tgggggcaca   420
gcggccctgg gctgcctggt caaggactac ttccccgaac cggtgacggt gtcgtggaac   480
tcaggcgccc tgaccagcgg cgtgcacacc ttcccggctg tcctacagtc ctcaggactc   540
tactccctca gcagcgtggt gaccgtgccc tccagcagct tgggcaccca gacctacatc   600
tgcaacgtga atcacaagcc cagcaacacc aaggtggaca agaaagttga gcccaaatct   660
tgtgacaaaa ctcacacatg cccaccgtgc ccagcacctg aagctgcagg ggaccgtca    720
gtcttcctct tccccccaaa acccaaggac accctcatga tctcccggac ccctgaggtc   780
acatgcgtgg tggtggacgt gagccacgaa gaccctgagg tcaagttcaa ctggtacgtg   840
gacggcgtgg aggtgcataa tgccaagaca aagccgcggg aggagcagta caacagcacg   900
taccgtgtgg tcagcgtcct caccgtcctg caccaggact ggctgaatgg caaggagtac   960
aagtgcaagg tctccaacaa agccctcggc gcccccatcg agaaaaccat ctccaaagcc  1020
aaagggcagc cccgagaacc acaggtgtac accctgcccc catcccggga tgagctgacc  1080
aagaaccagg tcagcctgac ctgcctggtc aaaggcttct atcccagcga catcgccgtg  1140
gagtgggaga gcaatgggca gccggagaac aactacaaga ccacgcctcc cgtgctggac  1200
tccgacggct ccttcttcct ctacagcaag ctcaccgtgg acaagagcag gtggcagcag  1260
```
gggaacgtct tctcatgctc cgtgatgcat gaggctctgc acaaccacta cacgcagaag    1320
agcctctccc tgtctccggg taaa                                            1344

<210> SEQ ID NO 154
<211> LENGTH: 214
<212> TYPE: PRT
<213> ORGANISM: Artificial Sequence
<220> FEATURE:
<223> OTHER INFORMATION: 49B4 P329GLALA IgG1 light chain

<400> SEQUENCE: 154

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 155
<211> LENGTH: 448
<212> TYPE: PRT
<213> ORGANISM: Artificial Sequence
<220> FEATURE:
<223> OTHER INFORMATION: 49B4 heavy chain

<400> SEQUENCE: 155

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Glu Tyr Tyr Arg Gly Pro Tyr Asp Tyr Trp Gly Gln Gly Thr
        100                 105                 110

Thr Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 156
<211> LENGTH: 645
<212> TYPE: DNA
<213> ORGANISM: Artificial Sequence
<220> FEATURE:
<223> OTHER INFORMATION: DNA 1G4 P329GLALA IgG1 light chain

<400> SEQUENCE: 156

```
gacatccaga tgacccagtc tccttccacc ctgtctgcat ctgtaggaga ccgtgtcacc    60
atcacttgcc gtgccagtca gagtattagt agctggttgg cctggtatca gcagaaacca   120
gggaaagccc ctaagctcct gatctatgat gcctccagtt tggaaagtgg ggtcccatca   180
cgtttcagcg gcagtggatc cgggacagaa ttcactctca ccatcagcag cttgcagcct   240
gatgattttg caacttatta ctgccaacag tatatttcgt attccatgtt gacgtttggc   300
cagggcacca agtcgagat caagcgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag acagcacct acagcctcag cagcaccctg    540
acgctgagca agcagacta cgagaaacac aaagtctacg cctgcgaagt cacccatcag    600
ggcctgagct cgcccgtcac aaagagcttc aacaggggag agtgt                   645
```

<210> SEQ ID NO 157
<211> LENGTH: 1338
<212> TYPE: DNA
<213> ORGANISM: Artificial Sequence
<220> FEATURE:
<223> OTHER INFORMATION: DNA 1G4 P329GLALA IgG1 heavy chain

<400> SEQUENCE: 157

```
caggtgcaat ggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag gctcgagtg gatgggaggg atcatcccta tctttggtac agcaaactac   180
gcacagaagt tccagggcag ggtcaccatt actgcagaca atccacgag cacagcctac   240
atggagctga gcagcctgag atctgaggac accgccgtgt attactgtgc gagagaatac   300
ggttctatgg actactgggg ccaagggacc accgtgaccg tctcctcagc tagcaccaag   360
ggcccatcgg tcttccccct ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca caccttcccg gctgtcctac agtcctcagg actctactcc   540
ctcagcagcg tggtgaccgt gccctccagc agcttgggca cccagaccta catctgcaac   600
gtgaatcaca agcccagcaa caccaaggtg gacaagaaag ttgagcccaa atcttgtgac   660
aaaactcaca catgcccacc gtgcccagca cctgaagctg caggggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaacag cacgtaccgt   900
gtggtcagcg tcctcaccgt cctgcaccag gactggctga atggcaagga gtacaagtgc   960
aaggtctcca acaaagccct cggcgccccc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
```

```
gtcttctcat gctccgtgat gcatgaggct ctgcacaacc actacacgca gaagagcctc    1320
tccctgtctc cgggtaaa                                                  1338
```

<210> SEQ ID NO 158
<211> LENGTH: 215
<212> TYPE: PRT
<213> ORGANISM: Artificial Sequence
<220> FEATURE:
<223> OTHER INFORMATION: 1G4 P329GLALA IgG1 light chain

<400> SEQUENCE: 158

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ile Ser Tyr Ser Met
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 159
<211> LENGTH: 446
<212> TYPE: PRT
<213> ORGANISM: Artificial Sequence
<220> FEATURE:
<223> OTHER INFORMATION: 1G4 P329GLALA IgG1 heavy chain

<400> SEQUENCE: 159

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

```
Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Tyr Gly Ser Met Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 160
<211> LENGTH: 642
<212> TYPE: DNA
<213> ORGANISM: Artificial sequence
<220> FEATURE:
<223> OTHER INFORMATION: DNA 20B7 P329GLALA IgG1 light chain
```

<400> SEQUENCE: 160

```
gacatccaga tgacccagtc tccttccacc ctgtctgcat ctgtaggaga ccgtgtcacc    60
atcacttgcc gtgccagtca gagtattagt agctggttgg cctggtatca gcagaaacca   120
gggaaagccc ctaagctcct gatctatgat gcctccagtt tggaaagtgg ggtcccatca   180
cgtttcagcg gcagtggatc cgggacagaa ttcactctca ccatcagcag cttgcagcct   240
gatgattttg caacttatta ctgccaacag tatcaggctt ttcgcttac gtttggccag    300
ggcaccaaag tcgagatcaa gcgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga aaacacaaa gtctacgcct gcgaagtcac ccatcagggc    600
ctgagctcgc ccgtcacaaa gagcttcaac aggggagagt gt                      642
```

<210> SEQ ID NO 161
<211> LENGTH: 1356
<212> TYPE: DNA
<213> ORGANISM: Artificial Sequence
<220> FEATURE:
<223> OTHER INFORMATION: DNA 20B7 P329GLALA IgG1 heavy chain

<400> SEQUENCE: 161

```
caggtgcaat tggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag ggctcgagtg gatgggaggg atcatcccta tctttggtac agcaaactac   180
gcacagaagt tccagggcag ggtcaccatt actgcagaca aatccacgag cacagcctac   240
atggagctga gcagcctgag atctgaggac accgccgtgt attactgtgc gagagttaac   300
tacccgtact cttactgggg tgacttcgac tactggggcc aagggaccac cgtgaccgtc   360
tcctcagcta gcaccaaggg cccatcggtc ttccccctgg caccctcctc caagagcacc   420
tctgggggca gcggcccct gggctgcctg gtcaaggact acttccccga accggtgacg    480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacc   600
cagacctaca tctgcaacgt gaatcacaag cccagcaaca ccaaggtgga caagaaagtt   660
gagcccaaat cttgtgacaa aactcacaca tgcccaccgt gcccagcacc tgaagctgca   720
gggggaccgt cagtcttcct cttccccca aaacccaagg acaccctcat gatctcccgg    780
acccctgagg tcacatgcgt ggtggtggac gtgagccacg aagaccctga ggtcaagttc   840
aactggtacg tggacggcgt ggaggtgcat aatgccaaga caaagccgcg ggaggagcag   900
tacaacagca cgtaccgtgt ggtcagcgtc ctcaccgtcc tgcaccagga ctggctgaat   960
ggcaaggagt acaagtgcaa ggtctccaac aaagccctcg cgcccccat cgagaaaacc    1020
atctccaaag ccaaagggca gccccgagaa ccacaggtgt acaccctgcc cccatcccgg   1080
gatgagctga ccaagaacca ggtcagcctg acctgcctgg tcaaaggctt ctatcccagc   1140
gacatcgccg tggagtggga gagcaatggg cagccggaga acaactacaa gaccacgcct   1200
cccgtgctgg actccgacgg ctccttcttc ctctacagca agctcaccgt ggacaagagc   1260
```

-continued

```
aggtggcagc agggggaacgt cttctcatgc tccgtgatgc atgaggctct gcacaaccac    1320
tacacgcaga agagcctctc cctgtctccg ggtaaa                              1356
```

<210> SEQ ID NO 162
<211> LENGTH: 214
<212> TYPE: PRT
<213> ORGANISM: Artificial
<220> FEATURE:
<223> OTHER INFORMATION: 20B7 P329GLALA IgG1 Light chain

<400> SEQUENCE: 162

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ala Phe Ser Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 163
<211> LENGTH: 452
<212> TYPE: PRT
<213> ORGANISM: Artificial
<220> FEATURE:
<223> OTHER INFORMATION: 20B7 P329GLALA IgG1 heavy chain

<400> SEQUENCE: 163

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Val Asn Tyr Pro Tyr Ser Tyr Trp Gly Asp Phe Asp Tyr Trp
        100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Gly Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 164
<211> LENGTH: 645
<212> TYPE: DNA

<213> ORGANISM: Artificial
<220> FEATURE:
<223> OTHER INFORMATION: DNA CLC-563 P329GLALA IgG1 light chain

<400> SEQUENCE: 164

```
gagatcgtgc tgacccagag ccccggcaca ctctccctgt ctcctgggga aagggccacc      60
ctttcatgca gagccagcca gtccgtctct agtagctacc tggcatggta tcagcagaag     120
ccaggacaag ccccccgcct cctgatttac ggcgcttcct ctcgggcaac tggtatccct     180
gacaggttct cagggagcgg aagcggaaca gattttacct tgactatttc tagactggag     240
ccagaggact cgccgtgta ttactgtcag cagtacggta gtagcccct cacctttggc       300
caggggacaa aagtcgaaat caagcgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactta cgagaaacac aaagtctacg cctgcgaagt cacccatcag     600
ggcctgagct cgcccgtcac aaagagcttc aacaggggag agtgt                     645
```

<210> SEQ ID NO 165
<211> LENGTH: 1338
<212> TYPE: DNA
<213> ORGANISM: Artificial
<220> FEATURE:
<223> OTHER INFORMATION: DNA CLC-563 P329GLALA IgG1 heavy chain

<400> SEQUENCE: 165

```
gaggtgcaat tgttggagtc tgggggaggc ttggtacagc ctgggggtc cctgagactc       60
tcctgtgcag cctccggatt caccttagc agttatgcca tgagctgggt ccgccaggct      120
ccagggaagg gctggagtg gtctcagct attagtggta gtggtggtag cacatactac       180
gcagactccg tgaagggccg gttcaccatc tccagagaca attccaagaa cacgctgtat     240
ctgcagatga acagcctgag agccgaggac acggccgtat attactgtgc gcttgacgtt     300
ggtgcttcg actactgggg ccaaggagcc ctggtcaccg tctcgagtgc tagcaccaag      360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagctg caggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cggcgccccc atcgagaaaa ccatctccaa agccaaaggg    1020
cagccccgag aaccacaggt gtacaccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
```

```
gtcttctcat gctccgtgat gcatgaggct ctgcacaacc actacacgca gaagagcctc   1320
tccctgtctc cgggtaaa                                                  1338
```

<210> SEQ ID NO 166
<211> LENGTH: 215
<212> TYPE: PRT
<213> ORGANISM: Artificial
<220> FEATURE:
<223> OTHER INFORMATION: CLC-563 P329GLALA IgG1 light chain

<400> SEQUENCE: 166

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 167
<211> LENGTH: 446
<212> TYPE: PRT
<213> ORGANISM: Artificial
<220> FEATURE:
<223> OTHER INFORMATION: CLC-563 P329GLALA IgG1 heavy chain

<400> SEQUENCE: 167

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Leu Asp Val Gly Ala Phe Asp Tyr Trp Gly Gln Gly Ala Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 168
<211> LENGTH: 645
<212> TYPE: DNA
<213> ORGANISM: Artificial
<220> FEATURE:
<223> OTHER INFORMATION: DNA CLC-564 P329GLALA IgG1 light chain
```

<400> SEQUENCE: 168

```
gagatcgtgc tgacccagag ccccggcaca ctctccctgt ctcctggga aagggccacc      60
ctttcatgca gagccagcca gtccgtctct agtagctacc tggcatggta tcagcagaag    120
ccaggacaag ccccccgcct cctgatttac ggcgcttcct ctcgggcaac tggtatccct    180
gacaggttct cagggagcgg aagcggaaca gattttacct tgactatttc tagactggag    240
ccagaggact tcgccgtgta ttactgtcag cagtacggta gtagcccct cacctttggc     300
caggggacaa aagtcgaaat caagcgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag acagcacct acagcctcag cagcaccctg     540
acgctgagca agcagactac gagaaacac aaagtctacg cctgcgaagt cacccatcag    600
ggcctgagct cgcccgtcac aaagagcttc aacaggggag agtgt                    645
```

<210> SEQ ID NO 169
<211> LENGTH: 1338
<212> TYPE: DNA
<213> ORGANISM: Artificial
<220> FEATURE:
<223> OTHER INFORMATION: DNA CLC-564 P329GLALA IgG1 heavy chain

<400> SEQUENCE: 169

```
gaggtgcaat tgttggagtc tgggggaggc ttggtacagc ctgggggtc cctgagactc       60
tcctgtgcag cctccggatt cacctttagc agttatgcca tgagctgggt ccgccaggct    120
ccagggaagg ggctggagtg gtctcagct attagtggta gtggtggtag cacatactac     180
gcagactccg tgaagggccg gttcaccatc tccagagaca attccaagaa cacgctgtat    240
ctgcagatga acagcctgag agccgaggac acggccgtat attactgtgc gttcgacgtt    300
ggtccgttcg actactgggg ccaaggaacc ctggtcaccg tctcgagtgc tagcaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaagctg caggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cggcgccccc atcgagaaaa ccatctccaa agccaaaggg   1020
cagccccgag aaccacaggt gtacaccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
```

```
gtcttctcat gctccgtgat gcatgaggct ctgcacaacc actacacgca gaagagcctc    1320
tccctgtctc cgggtaaa                                                  1338
```

<210> SEQ ID NO 170
<211> LENGTH: 215
<212> TYPE: PRT
<213> ORGANISM: Artificial
<220> FEATURE:
<223> OTHER INFORMATION: CLC-564 P329GLALA IgG1 light chain

<400> SEQUENCE: 170

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 171
<211> LENGTH: 446
<212> TYPE: PRT
<213> ORGANISM: Artificial
<220> FEATURE:
<223> OTHER INFORMATION: CLC-564 P329GLALA IgG1 heavy chain

<400> SEQUENCE: 171

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

```
                -continued

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Phe Asp Val Gly Pro Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 172
<211> LENGTH: 639
<212> TYPE: DNA
<213> ORGANISM: Artificial
<220> FEATURE:
<223> OTHER INFORMATION: DNA 17A9 P329GLALA IgG1 light chain
```

<400> SEQUENCE: 172

```
tcgtctgagc tgactcagga ccctgctgtg tctgtggcct tgggacagac agtcaggatc    60
acatgccaag agacagcct cagaagttat tatgcaagct ggtaccagca gaagccagga    120
caggcccctg tacttgtcat ctatggtaaa acaaccggc cctcaggat cccagaccga    180
ttctctggct ccagctcagg aaacacagct tccttgacca tcactggggc tcaggcggaa    240
gatgaggctg actattactg taactcccgt gttatgcctc ataatcgcgt attcggcgga    300
gggaccaagc tgaccgtcct aggtcaaccc aaggctgccc ccagcgtgac cctgttcccc    360
cccagcagcg aggaactgca ggccaacaag gccaccctgg tctgcctgat cagcgacttc    420
tacccaggcg ccgtgaccgt ggcctggaag gccgacagca gccccgtgaa ggccggcgtg    480
gagaccacca cccccagcaa gcagagcaac aacaagtacg ccgccagcag ctacctgagc    540
ctgaccccg agcagtggaa gagccacagg tcctacagct gccaggtgac ccacgagggc    600
agcaccgtgg agaaaaccgt ggcccccacc gagtgcagc                           639
```

<210> SEQ ID NO 173
<211> LENGTH: 1350
<212> TYPE: DNA
<213> ORGANISM: Artificial
<220> FEATURE:
<223> OTHER INFORMATION: DNA 17A9 P329GLALA IgG1 heavy chain

<400> SEQUENCE: 173

```
gaggtgcaat tgttggagtc tggggaggc ttggtacagc ctgggggtc cctgagactc      60
tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gcgtgttttc    300
taccgtggtg gtgtttctat ggactactgg ggccaaggaa ccctggtcac cgtctcgagt    360
gctagcacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaagc tgcaggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcggcgccc catcgagaa aaccatctcc    1020
aaagccaaag ggcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
```

```
cagcagggga acgtcttctc atgctccgtg atgcatgagg ctctgcacaa ccactacacg    1320
cagaagagcc tctccctgtc tccgggtaaa                                    1350
```

<210> SEQ ID NO 174
<211> LENGTH: 213
<212> TYPE: PRT
<213> ORGANISM: Artificial
<220> FEATURE:
<223> OTHER INFORMATION: 17A9 P329GLALA IgG1 light chain

<400> SEQUENCE: 174

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Val Met Pro His Asn Arg
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 175
<211> LENGTH: 450
<212> TYPE: PRT
<213> ORGANISM: Artificial
<220> FEATURE:
<223> OTHER INFORMATION: 17A9 P329GLALA IgG1 heavy chain

<400> SEQUENCE: 175

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Val Phe Tyr Arg Gly Val Ser Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 176
<211> LENGTH: 642
<212> TYPE: DNA
```

<213> ORGANISM: Artificial Sequence
<220> FEATURE:
<223> OTHER INFORMATION: Nucleotide sequence LC (pETR16299) OX40 (49B4) VL/CL

<400> SEQUENCE: 176

```
gacatccaga tgacccagtc tccttccacc ctgtctgcat ctgtaggaga ccgtgtcacc    60
atcacttgcc gtgccagtca gagtattagt agctggttgg cctggtatca gcagaaacca   120
gggaaagccc ctaagctcct gatctatgat gcctccagtt tggaaagtgg ggtcccatca   180
cgtttcagcg gcagtggatc cgggacagaa ttcactctca ccatcagcag cttgcagcct   240
gatgattttg caacttatta ctgccaacag tatagttcgc agcctatac gtttggccag   300
ggcaccaaag tcgagatcaa gcgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacccctgacg   540
ctgagcaaag cagactacga gaaacacaaa gtctacgcct gcgaagtcac ccatcagggc   600
ctgagctcgc ccgtcacaaa gagcttcaac aggggagagt gt                     642
```

<210> SEQ ID NO 177
<211> LENGTH: 2424
<212> TYPE: DNA
<213> ORGANISM: Artificial Sequence
<220> FEATURE:
<223> OTHER INFORMATION: Nucleotide sequence Heavy chain 1 (HC1) pETR17237 OX40 (49B4) VHCH1_VHCH1_Fc_knob_PG/LALA_EpCAM (3-17I) VL

<400> SEQUENCE: 177

```
caggtgcaat ggtgcagtc tggggctgag gtgaagaagc ctgggtcctc ggtgaaggtc     60
tcctgcaagg cctccggagg cacattcagc agctacgcta taagctgggt gcgacaggcc   120
cctggacaag gctcgagtg gatgggaggg atcatcccta tctttggtac agcaaactac   180
gcacagaagt tccagggcag ggtcaccatt actgcagaca aatccacgag cacagcctac   240
atggagctga gcagcctgag atctgaggac accgccgtgt attactgtgc gagagaatac   300
taccgtggtc cgtacgacta ctggggccaa gggaccaccg tgaccgtctc ctcagctagc   360
acaaagggac ctagcgtgtt ccccctggcc ccagcagca agtctacatc tggcggaaca   420
gccgccctgg gctgcctcgt gaaggactac tttcccgagc ccgtgaccgt gtcctggaac   480
tctggcgctc tgacaagcgg cgtgcacacc tttccagccg tgctgcagag cagcggcctg   540
tactctctga gcagcgtcgt gacagtgccc agcagctctc tgggcaccca gacctacatc   600
tgcaacgtga accacaagcc cagcaacacc aaggtggaca gaaggtggaa acccaagagc   660
tgcgacggcg aggggggatc tggcggcgga ggatcccagg tgcaattggt gcagtctggg   720
gctgaggtga agaagcctgg gtcctcggtg aaggtctcct gcaaggcctc cggaggcaca   780
ttcagcagct acgctataag ctgggtgcga caggcccctg acaagggct cgagtggatg   840
ggagggatca tccctatctt tggtacagca aactacgcac agaagttcca gggcagggtc   900
accattactg cagacaaatc cacgagcaca gcctacatgg agctgagcag cctgagatct   960
gaggacaccg ccgtgtatta ctgtgcgaga gaatactacc gtggtccgta cgactactgg  1020
ggccaaggga ccaccgtgac cgtctcctca gctagcacca agggcccatc ggtcttcccc  1080
ctggcaccct cctccaagag cacctctggg ggcacagcgg ccctgggctg cctggtcaag  1140
gactacttcc ccgaaccggt gacggtgtcg tggaactcag gcgccctgac cagcggcgtg  1200
```

-continued

```
cacaccttcc cggctgtcct acagtcctca ggactctact ccctcagcag cgtggtgacc    1260
gtgccctcca gcagcttggg cacccagacc tacatctgca acgtgaatca caagcccagc    1320
aacaccaagg tggacaagaa agttgagccc aaatcttgtg acaaaactca cacatgccca    1380
ccgtgcccag cacctgaagc tgcaggggga ccgtcagtct tcctcttccc cccaaaaccc    1440
aaggacaccc tcatgatctc ccggacccct gaggtcacat gcgtggtggt ggacgtgagc    1500
cacgaagacc ctgaggtcaa gttcaactgg tacgtggacg gcgtggaggt gcataatgcc    1560
aagacaaagc cgcgggagga gcagtacaac agcacgtacc gtgtggtcag cgtcctcacc    1620
gtcctgcacc aggactggct gaatggcaag gagtacaagt gcaaggtctc caacaaagcc    1680
ctcggcgccc ccatcgagaa aaccatctcc aaagccaaag gcagccccg agaaccacag    1740 gtgtacaccc tgcccccctg cagagatgag ctgaccaaga accaggtgtc cctgtggtgt    1800
ctggtcaagg gcttctaccc cagcgatatc gccgtggagt gggagagcaa cggccagcct    1860
gagaacaact acaagaccac ccccctgtg ctggacagcg acggcagctt cttcctgtac    1920
tccaaactga ccgtggacaa gagccggtgg cagcagggca acgtgttcag ctgcagcgtg    1980
atgcacgagg ccctgcacaa ccactacacc cagaagtccc tgagcctgag ccccggcgga    2040
ggcggcggaa gcggaggagg aggatccggc ggaggcggat ctggcggggg aggttcggag    2100
atcgtgatga cccagagccc cgccaccctg agtgtgtctc aggcgaaag agccaccctg    2160 tcctgcagag ccagccagag cgtgtccagc aacctggcct ggtatcagca gaagcccggc    2220
caggccccca gactgattat ctacggcgcc agcacaaccg ccagcggcat ccctgccaga    2280
ttttccgcct ctggcagcgg caccgacttc accctgacaa tcagcagcct gcagtccgag    2340
gacttcgccg tgtactactg ccagcagtac aacaactggc cccctgccta caccttcggc    2400
cagggcacca agctggaaat caag    2424
```

<210> SEQ ID NO 178
<211> LENGTH: 2442
<212> TYPE: DNA
<213> ORGANISM: Artificial Sequence
<220> FEATURE:
<223> OTHER INFORMATION: Nucleotide sequence Heavy chain 2 (HC2)
    pETR17238 OX40 (49B4) VHCH1_VHCH1_Fc_hole_PG/LALA_ EpCAM (3-17I)
    VH

<400> SEQUENCE: 178

```
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag gctcgagtg gatgggaggg atcatccta tctttggtac agcaaactac     180
gcacagaagt tccagggcag ggtcaccatt actgcagaca aatccacgag cacagcctac     240
atggagctga gcagcctgag atctgaggac accgccgtgt attactgtgc gagagaatac     300
taccgtggtc cgtacgacta ctggggccaa gggaccaccg tgaccgtctc ctcagctagc     360
acaaagggac ctagcgtgtt ccccctggcc cccagcagca gtctacatc tggcggaaca     420 gccgccctgg gctgcctcgt gaaggactac tttcccgagc ccgtgaccgt gtcctggaac     480
tctggcgctc tgacaagcgg cgtgcacacc tttccagccg tgctgcagag cagcggcctg     540
tactctctga gcagcgtcgt gacagtgccc agcagctctc tgggcaccca gacctacatc     600
tgcaacgtga accacaagcc cagcaacacc aaggtggaca gaaggtgga acccaagagc     660 tgcgacggcg gagggggatc tggcggcgga ggatcccagg tgcaattggt gcagtctggg     720
```

| gctgaggtga agaagcctgg gtcctcggtg aaggtctcct gcaaggcctc cggaggcaca | 780 |
| ttcagcagct acgctataag ctgggtgcga caggcccctg acaagggct cgagtggatg | 840 |
| ggagggatca tccctatctt tggtacagca aactacgcac agaagttcca gggcagggtc | 900 |
| accattactg cagacaaatc cacgagcaca gcctacatgg agctgagcag cctgagatct | 960 |
| gaggacaccg ccgtgtatta ctgtgcgaga gaatactacc gtggtccgta cgactactgg | 1020 |
| ggccaaggga ccaccgtgac cgtctcctca gctagcacca agggcccatc ggtcttcccc | 1080 |
| ctggcaccct cctccaagag cacctctggg ggcacagcgg ccctgggctg cctggtcaag | 1140 |
| gactacttcc ccgaaccggt gacggtgtcg tggaactcag cgccctgac cagcggcgtg | 1200 |
| cacaccttcc cggctgtcct acagtcctca ggactctact ccctcagcag cgtggtgacc | 1260 |
| gtgccctcca gcagcttggg cacccagacc tacatctgca acgtgaatca caagcccagc | 1320 |
| aacaccaagg tggacaagaa agttgagccc aaatcttgtg acaaaactca cacatgccca | 1380 |
| ccgtgcccag cacctgaagc tgcagggga ccgtcagtct tcctcttccc cccaaaaccc | 1440 |
| aaggacaccc tcatgatctc ccggacccct gaggtcacat gcgtggtggt ggacgtgagc | 1500 |
| cacgaagacc ctgaggtcaa gttcaactgg tacgtggacg gcgtggaggt gcataatgcc | 1560 |
| aagacaaagc cgcgggagga gcagtacaac agcacgtacc gtgtggtcag cgtcctcacc | 1620 |
| gtcctgcacc aggactggct gaatggcaag gagtacaagt gcaaggtctc caacaaagcc | 1680 |
| ctcggcgccc ccatcgagaa aaccatctcc aaagccaaag gcagccccg agaaccacag | 1740 |
| gtgtgcaccc tgcccccatc ccgggatgag ctgaccaaga accaggtcag cctctcgtgc | 1800 |
| gcagtcaaag gcttctatcc cagcgacatc gccgtggagt gggagagcaa tgggcagccg | 1860 |
| gagaacaact acaagaccac gcctcccgtg ctggactccg acggctcctt cttcctcgtg | 1920 |
| agcaagctca ccgtggacaa gagcaggtgg cagcagggga acgtcttctc atgctccgtg | 1980 |
| atgcatgagg ctctgcacaa ccactacacg cagaagagcc tctccctgtc tccgggtgga | 2040 |
| ggcggcggaa gcgaggagg aggatccggc ggaggcggaa gtggcggcgg aggttcgcag | 2100 |
| gtgcagctgg tgcagtctgg cgccgaagtg aagaaacccg gcagcagcgt gaaggtgtcc | 2160 |
| tgcaaggctt ccgcgcggcac cttcagcagc tacgccatt cttgggtgcg ccaggcccct | 2220 |
| ggacagggcc tggaatggat gggcggcatc atccccatct tcggcaccgc caactacgcc | 2280 |
| cagaaattcc agggcagagt gaccatcacc gccgacgaga gcaccagcac cgcctacatg | 2340 |
| gaactgagca gcctgcggag cgaggacacc gccgtgtact attgtgccag aggcctgctg | 2400 |
| tggaactact ggggccaggg cacactcgtg accgtgtcct ct | 2442 |

<210> SEQ ID NO 179
<211> LENGTH: 642
<212> TYPE: DNA
<213> ORGANISM: Artificial Sequence
<220> FEATURE:
<223> OTHER INFORMATION: Nucleotide sequence Light chain 1 (LC1)
    pETR16779 OX40 (49B4) VL CL + charges

<400> SEQUENCE: 179

| gacatccaga tgacccagtc tccttccacc ctgtctgcat ctgtaggaga ccgtgtcacc | 60 |
| atcacttgcc gtgccagtca gagtattagt agctggttgg cctggtatca gcagaaacca | 120 |
| gggaaagccc ctaagctcct gatctatgat gcctccagtt tggaaagtgg ggtcccatca | 180 |
| cgtttcagcg gcagtggatc cgggacagaa ttcactctca ccatcagcag cttgcagcct | 240 |
| gatgattttg caacttatta ctgccaacag tatagttcgc agccgtatac gtttggccag | 300 |

| | |
|---|---|
| ggcaccaaag tcgagatcaa gcgtacggtg gctgcaccat ctgtcttcat cttcccgcca | 360 |
| tctgatcgga agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga aaacacaaa gtctacgcct gcgaagtcac ccatcagggc | 600 |
| ctgagctcgc ccgtcacaaa gagcttcaac aggggagagt gt | 642 |

<210> SEQ ID NO 180
<211> LENGTH: 2739
<212> TYPE: DNA
<213> ORGANISM: Artificial Sequence
<220> FEATURE:
<223> OTHER INFORMATION: Nucleotide sequence Heavy chain pETR17241 OX40
    (49B4) VHCH1_49B4VHCH1_Fc _PG/LALA_ EpCAM (3-17I) 3-17I VLCH1 49B4
    Fab + charges

<400> SEQUENCE: 180

| | |
|---|---|
| caggtgcagc tggtgcagtc tggcgccgaa gtgaagaaac ccggcagcag cgtgaaggtg | 60 |
| tcctgcaagg cttccggcgg caccttcagc agctacgcca tttcttgggt gcgccaggcc | 120 |
| cctggacagg gcctggaatg gatgggcggc atcatcccca tcttcggcac cgccaactac | 180 |
| gcccagaaat tccagggcag agtgaccatc accgccgaca agagccacag caccgcctac | 240 |
| atggaactga gcagcctgcg gagcgaggac accgccgtgt actactgcgc cagagagtac | 300 |
| tacagaggcc cctacgacta ctggggccag ggcacaaccg tgaccgtgtc tagcgccagc | 360 |
| acaaagggcc ccagcgtgtt ccctctggcc cctagcagca gagcacatc tggcggaaca | 420 |
| gccgccctgg gctgcctggt gaagattac ttccccgagc ccgtgacagt gtcctggaac | 480 |
| tctggcgccc tgacaagcgg cgtgcacacc tttccagccg tgctgcagag cagcggcctg | 540 |
| tactcactgt ccagcgtcgt gactgtgccc agcagcagcc tgggaaccca gacctacatc | 600 |
| tgcaacgtga accacaagcc cagcaacacc aaggtggacg agaaggtgga acccaagagc | 660 |
| tgcgacggcg gaggcggatc tggcggcgga ggatcccagg tgcagctggt gcagagcgga | 720 |
| gctgaagtga aaaagcctgg ctcctccgtg aaagtgtctt gtaaagccag cggcggcaca | 780 |
| ttctcatcct acgccatcag ctgggtgcgg caggctccag gcagggact ggaatggatg | 840 |
| ggaggaatta tccctatttt tgggacagcc aattatgctc agaaatttca ggggcgcgtg | 900 |
| acaattacag ccgacaagtc cacctctaca gcttatatgg aactgtcctc cctgcgctcc | 960 |
| gaggatacag ctgtgtatta ttgtgcccgc gagtactacc ggggaccta cgattattgg | 1020 |
| ggacagggaa ccacagtgac tgtgtcctcc gctagcacca agggaccttc cgtgtttccc | 1080 |
| ctggctccca gctccaagtc tacctctggg ggcacagctg ctctgggatg tctggtggaa | 1140 |
| gattattttc ctgaacctgt gaccgtgtca tggaacagcg gagccctgac ctccggggtg | 1200 |
| cacacattcc ctgctgtgct gcagtcctcc ggcctgtata gcctgagcag cgtcgtgacc | 1260 |
| gtgccttcca gctctctggg cacacagaca tatatctgta atgtgaatca caaaccctct | 1320 |
| aataccaaag tggatgagaa agtggaacct aagtcctgcg acaagaccca cacctgtccc | 1380 |
| ccttgtcctg cccctgaagc tgctggcggc ccatctgtgt ttctgttccc cccaaagccc | 1440 |
| aaggacaccc tgatgatcag ccggaccccc gaagtgacct gcgtggtggt ggatgtgtcc | 1500 |
| cacgaggacc cagaagtgaa gttcaattgg tacgtggacg gcgtggaagt gcacaacgcc | 1560 |
| aagaccaagc cgcgggaaga acagtacaac agcacctacc gggtggtgtc cgtgctgaca | 1620 |
| gtgctgcacc aggactggct gaacggcaaa gagtacaagt gcaaggtgtc caacaaggcc | 1680 |

```
ctgggagccc ccatcgagaa aaccatcagc aaggccaagg gccagccccg cgaacctcag    1740
gtgtacaccc tgcccccaag cagggacgag ctgaccaaga accaggtgtc cctgacctgt    1800
ctcgtgaagg gcttctaccc ctccgatatc gccgtggaat gggagagcaa cggccagccc    1860
gagaacaact acaagaccac ccccctgtg  ctggacagcg acggctcatt cttcctgtac    1920
tccaagctga ccgtggacaa gagccggtgg cagcagggca acgtgttcag ctgcagcgtg    1980
atgcacgagg ccctgcacaa ccactacaca cagaagtctc tgagcctgag ccctggcgga    2040
gggggaggat ctgggggagg cggaagtggg ggagggggtt ccggaggcgg tggttcggag    2100
atcgtgatga cccagagccc cgccaccctg agtgtgtctc caggcgaaag agccaccctg    2160
tcctgcagag ccagccagag cgtgtccagc aacctggcct ggtatcagca gaagcccggc    2220
caggccccca gactgattat ctacggcgcc agcacaaccg ccagcggcat ccctgccaga    2280
ttttccgcct ctggcagcgg caccgacttc accctgacaa tcagcagcct gcagtccgag    2340
gacttcgccg tgtactactg ccagcagtac aacaactggc cccctgccta caccttcggc    2400
cagggcacca agctggaaat caagagcagc gcttccacca agggcccctc agtgttccca    2460
ctggcaccat ccagcaagtc cacaagcgga ggaaccgccg ctctgggctg tctcgtgaaa    2520
gactactttc cagagccagt gaccgtgtcc tggaatagtg gcgctctgac ttctggcgtg    2580
cacactttcc ccgcagtgct gcagagttct ggcctgtact ccctgagtag cgtcgtgaca    2640
gtgccctcct ctagcctggg cactcagact acatctgca  atgtgaatca taagccttcc    2700
aacacaaaag tggacaaaaa agtggaaccc aaatcttgc                            2739
```

```
<210> SEQ ID NO 181
<211> LENGTH: 666
<212> TYPE: DNA
<213> ORGANISM: Artificial Sequence
<220> FEATURE:
<223> OTHER INFORMATION: Nucleotide sequence Light chain 2 (LC2)
      pETR17239 EpCAM (3-17I) VHCL

<400> SEQUENCE: 181
```

```
caggtgcagc tggtgcagtc tggcgccgaa gtgaagaaac ccggcagcag cgtgaaggtg     60
tcctgcaagg cttccggcgg caccttcagc agctacgcca tttcttgggt gcgccaggcc    120
cctggacagg gcctggaatg gatgggcggc atcatcccca tcttcggcac cgccaactac    180
gcccagaaat tccagggcag agtgaccatc accgccgacg agagcaccag caccgcctac    240
atggaactga gcagcctgcg gagcgaggac accgccgtgt actattgtgc cagaggcctg    300
ctgtggaact actggggcca gggcacactc gtgaccgtgt cctctgctag cgtggccgct    360
ccctccgtgt tcatcttccc accttccgac gagcagctga gtccggcac  cgcttctgtc    420 gtgtgcctgc tgaacaactt ctacccccgc gaggccaagg tgcagtggaa ggtggacaac    480
gccctgcagt ccggcaacag ccaggaatcc gtgaccgagc aggactccaa ggacagcacc    540
tactccctgt cctccaccct gaccctgtcc aaggccgact acgagaagca caaggtgtac    600
gcctgcgaag tgacccacca gggcctgtct agcccgtga  ccaagtcttt caaccggggc    660
gagtgc                                                                666
```

```
<210> SEQ ID NO 182
<211> LENGTH: 214
<212> TYPE: PRT
<213> ORGANISM: Artificial Sequence
<220> FEATURE:
<223> OTHER INFORMATION: LC (pETR16299) OX40 (49B4) VL/CL
```

<400> SEQUENCE: 182

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```

<210> SEQ ID NO 183
<211> LENGTH: 808
<212> TYPE: PRT
<213> ORGANISM: Artificial Sequence
<220> FEATURE:
<223> OTHER INFORMATION: Heavy chain 1 (HC1) pETR17237 OX40 (49B4)
      VHCH1_VHCH1_Fc_knob_PG/LALA_EpCAM (3-17I) VL

<400> SEQUENCE: 183

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Gly Gly
    210                 215                 220

Gly Gly Ser Gly Gly Gly Gly Ser Gln Val Gln Leu Val Gln Ser Gly
225                 230                 235                 240

Ala Glu Val Lys Lys Pro Gly Ser Ser Val Lys Val Ser Cys Lys Ala
                245                 250                 255

Ser Gly Gly Thr Phe Ser Ser Tyr Ala Ile Ser Trp Val Arg Gln Ala
                260                 265                 270

Pro Gly Gln Gly Leu Glu Trp Met Gly Gly Ile Ile Pro Ile Phe Gly
            275                 280                 285

Thr Ala Asn Tyr Ala Gln Lys Phe Gln Gly Arg Val Thr Ile Thr Ala
    290                 295                 300

Asp Lys Ser Thr Ser Thr Ala Tyr Met Glu Leu Ser Ser Leu Arg Ser
305                 310                 315                 320

Glu Asp Thr Ala Val Tyr Tyr Cys Ala Arg Glu Tyr Tyr Arg Gly Pro
                325                 330                 335

Tyr Asp Tyr Trp Gly Gln Gly Thr Thr Val Thr Val Ser Ser Ala Ser
                340                 345                 350

Thr Lys Gly Pro Ser Val Phe Pro Leu Ala Pro Ser Ser Lys Ser Thr
            355                 360                 365

Ser Gly Gly Thr Ala Ala Leu Gly Cys Leu Val Lys Asp Tyr Phe Pro
    370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Ser Ser Leu Gly Thr Gln Thr Tyr Ile
                420                 425                 430

Cys Asn Val Asn His Lys Pro Ser Asn Thr Lys Val Asp Lys Lys Val
            435                 440                 445

Glu Pro Lys Ser Cys Asp Lys Thr His Thr Cys Pro Pro Cys Pro Ala
    450                 455                 460

Pro Glu Ala Ala Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
                500                 505                 510

Asp Gly Val Glu Val His Asn Ala Lys Thr Lys Pro Arg Glu Glu Gln
            515                 520                 525

Tyr Asn Ser Thr Tyr Arg Val Val Ser Val Leu Thr Val Leu His Gln
    530                 535                 540
```

-continued

Asp Trp Leu Asn Gly Lys Glu Tyr Lys Cys Lys Val Ser Asn Lys Ala
545                 550                 555                 560

Leu Gly Ala Pro Ile Glu Lys Thr Ile Ser Lys Ala Lys Gly Gln Pro
            565                 570                 575

Arg Glu Pro Gln Val Tyr Thr Leu Pro Pro Cys Arg Asp Glu Leu Thr
            580                 585                 590

Lys Asn Gln Val Ser Leu Trp Cys Leu Val Lys Gly Phe Tyr Pro Ser
            595                 600                 605

Asp Ile Ala Val Glu Trp Glu Ser Asn Gly Gln Pro Glu Asn Asn Tyr
        610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
            645                 650                 655

Ser Cys Ser Val Met His Glu Ala Leu His Asn His Tyr Thr Gln Lys
            660                 665                 670

Ser Leu Ser Leu Ser Pro Gly Gly Gly Gly Ser Gly Gly Gly Gly
            675                 680                 685

Ser Gly Gly Gly Gly Ser Gly Gly Gly Gly Ser Glu Ile Val Met Thr
690                 695                 700

Gln Ser Pro Ala Thr Leu Ser Val Ser Pro Gly Glu Arg Ala Thr Leu
705                 710                 715                 720

Ser Cys Arg Ala Ser Gln Ser Val Ser Ser Asn Leu Ala Trp Tyr Gln
            725                 730                 735

Gln Lys Pro Gly Gln Ala Pro Arg Leu Ile Ile Tyr Gly Ala Ser Thr
            740                 745                 750

Thr Ala Ser Gly Ile Pro Ala Arg Phe Ser Ala Ser Gly Ser Gly Thr
            755                 760                 765

Asp Phe Thr Leu Thr Ile Ser Ser Leu Gln Ser Glu Asp Phe Ala Val
            770                 775                 780

Tyr Tyr Cys Gln Gln Tyr Asn Asn Trp Pro Pro Ala Tyr Thr Phe Gly
785                 790                 795                 800

Gln Gly Thr Lys Leu Glu Ile Lys
            805

<210> SEQ ID NO 184
<211> LENGTH: 814
<212> TYPE: PRT
<213> ORGANISM: Artificial Sequence
<220> FEATURE:
<223> OTHER INFORMATION: Heavy chain 2 (HC2) pETR17238 OX40 (49B4)
      VHCH1_VHCH1_Fc_hole_PG/LALA_ EpCAM (3-17I) VH

<400> SEQUENCE: 184

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Glu Tyr Tyr Arg Gly Pro Tyr Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Gly Gly
    210                 215                 220

Gly Gly Ser Gly Gly Gly Gly Ser Gln Val Gln Leu Val Gln Ser Gly
225                 230                 235                 240

Ala Glu Val Lys Lys Pro Gly Ser Ser Val Lys Val Ser Cys Lys Ala
                245                 250                 255

Ser Gly Gly Thr Phe Ser Ser Tyr Ala Ile Ser Trp Val Arg Gln Ala
            260                 265                 270

Pro Gly Gln Gly Leu Glu Trp Met Gly Gly Ile Ile Pro Ile Phe Gly
        275                 280                 285

Thr Ala Asn Tyr Ala Gln Lys Phe Gln Gly Arg Val Thr Ile Thr Ala
    290                 295                 300

Asp Lys Ser Thr Ser Thr Ala Tyr Met Glu Leu Ser Ser Leu Arg Ser
305                 310                 315                 320

Glu Asp Thr Ala Val Tyr Tyr Cys Ala Arg Glu Tyr Tyr Arg Gly Pro
                325                 330                 335

Tyr Asp Tyr Trp Gly Gln Gly Thr Thr Val Thr Val Ser Ser Ala Ser
            340                 345                 350

Thr Lys Gly Pro Ser Val Phe Pro Leu Ala Pro Ser Ser Lys Ser Thr
        355                 360                 365

Ser Gly Gly Thr Ala Ala Leu Gly Cys Leu Val Lys Asp Tyr Phe Pro
    370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Ser Ser Leu Gly Thr Gln Thr Tyr Ile
            420                 425                 430

Cys Asn Val Asn His Lys Pro Ser Asn Thr Lys Val Asp Lys Lys Val
        435                 440                 445

Glu Pro Lys Ser Cys Asp Lys Thr His Thr Cys Pro Pro Cys Pro Ala
    450                 455                 460

Pro Glu Ala Ala Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
            500                 505                 510
```

```
Asp Gly Val Glu Val His Asn Ala Lys Thr Lys Pro Arg Glu Glu Gln
            515                 520                 525

Tyr Asn Ser Thr Tyr Arg Val Val Ser Val Leu Thr Val Leu His Gln
    530                 535                 540

Asp Trp Leu Asn Gly Lys Glu Tyr Lys Cys Lys Val Ser Asn Lys Ala
545                 550                 555                 560

Leu Gly Ala Pro Ile Glu Lys Thr Ile Ser Lys Ala Lys Gly Gln Pro
                565                 570                 575

Arg Glu Pro Gln Val Cys Thr Leu Pro Pro Ser Arg Asp Glu Leu Thr
            580                 585                 590

Lys Asn Gln Val Ser Leu Ser Cys Ala Val Lys Gly Phe Tyr Pro Ser
    595                 600                 605

Asp Ile Ala Val Glu Trp Glu Ser Asn Gly Gln Pro Glu Asn Asn Tyr
610                 615                 620

Lys Thr Thr Pro Pro Val Leu Asp Ser Asp Gly Ser Phe Phe Leu Val
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
            660                 665                 670

Ser Leu Ser Leu Ser Pro Gly Gly Gly Gly Ser Gly Gly Gly Gly
    675                 680                 685

Ser Gly Gly Gly Gly Ser Gly Gly Gly Ser Gln Val Gln Leu Val
690                 695                 700

Gln Ser Gly Ala Glu Val Lys Lys Pro Gly Ser Ser Val Lys Val Ser
705                 710                 715                 720

Cys Lys Ala Ser Gly Gly Thr Phe Ser Ser Tyr Ala Ile Ser Trp Val
                725                 730                 735

Arg Gln Ala Pro Gly Gln Gly Leu Glu Trp Met Gly Gly Ile Ile Pro
            740                 745                 750

Ile Phe Gly Thr Ala Asn Tyr Ala Gln Lys Phe Gln Gly Arg Val Thr
    755                 760                 765

Ile Thr Ala Asp Glu Ser Thr Ser Thr Ala Tyr Met Glu Leu Ser Ser
770                 775                 780

Leu Arg Ser Glu Asp Thr Ala Val Tyr Tyr Cys Ala Arg Gly Leu Leu
785                 790                 795                 800

Trp Asn Tyr Trp Gly Gln Gly Thr Leu Val Thr Val Ser Ser
                805                 810

<210> SEQ ID NO 185
<211> LENGTH: 214
<212> TYPE: PRT
<213> ORGANISM: Artificial Sequence
<220> FEATURE:
<223> OTHER INFORMATION: Light chain 1 (LC1) pETR16779 OX40 (49B4) VL
      CL + charges

<400> SEQUENCE: 185

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60
```

```
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Ser Ser Gln Pro Tyr
             85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 186
<211> LENGTH: 913
<212> TYPE: PRT
<213> ORGANISM: Artificial Sequence
<220> FEATURE:
<223> OTHER INFORMATION: Heavy chain pETR17241 OX40 (49B4)
      VHCH1_49B4VHCH1_Fc _PG/LALA_ EpCAM (3-17I) 3-17I VLCH1
      49B4 Fab + charges

<400> SEQUENCE: 186

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Gln Thr Tyr Ile Cys Asn Val Asn His Lys Pro Ser
            195                 200                 205
Asn Thr Lys Val Asp Glu Lys Val Glu Pro Lys Ser Cys Asp Gly Gly
        210                 215                 220
Gly Gly Ser Gly Gly Gly Ser Gln Val Gln Leu Val Gln Ser Gly
225                 230                 235                 240
Ala Glu Val Lys Lys Pro Gly Ser Ser Val Lys Val Ser Cys Lys Ala
                245                 250                 255
Ser Gly Gly Thr Phe Ser Ser Tyr Ala Ile Ser Trp Val Arg Gln Ala
            260                 265                 270
Pro Gly Gln Gly Leu Glu Trp Met Gly Gly Ile Ile Pro Ile Phe Gly
        275                 280                 285
Thr Ala Asn Tyr Ala Gln Lys Phe Gln Gly Arg Val Thr Ile Thr Ala
    290                 295                 300
Asp Lys Ser Thr Ser Thr Ala Tyr Met Glu Leu Ser Ser Leu Arg Ser
305                 310                 315                 320
Glu Asp Thr Ala Val Tyr Tyr Cys Ala Arg Glu Tyr Tyr Arg Gly Pro
                325                 330                 335
Tyr Asp Tyr Trp Gly Gln Gly Thr Thr Val Thr Val Ser Ser Ala Ser
            340                 345                 350
Thr Lys Gly Pro Ser Val Phe Pro Leu Ala Pro Ser Ser Lys Ser Thr
        355                 360                 365
Ser Gly Gly Thr Ala Ala Leu Gly Cys Leu Val Glu Asp Tyr Phe Pro
    370                 375                 380
Glu Pro Val Thr Val Ser Trp Asn Ser Gly Ala Leu Thr Ser Gly Val
385                 390                 395                 400
His Thr Phe Pro Ala Val Leu Gln Ser Ser Gly Leu Tyr Ser Leu Ser
                405                 410                 415
Ser Val Val Thr Val Pro Ser Ser Ser Leu Gly Thr Gln Thr Tyr Ile
            420                 425                 430
Cys Asn Val Asn His Lys Pro Ser Asn Thr Lys Val Asp Glu Lys Val
        435                 440                 445
Glu Pro Lys Ser Cys Asp Lys Thr His Thr Cys Pro Pro Cys Pro Ala
    450                 455                 460
Pro Glu Ala Ala Gly Gly Pro Ser Val Phe Leu Phe Pro Pro Lys Pro
465                 470                 475                 480
Lys Asp Thr Leu Met Ile Ser Arg Thr Pro Glu Val Thr Cys Val Val
                485                 490                 495
Val Asp Val Ser His Glu Asp Pro Glu Val Lys Phe Asn Trp Tyr Val
            500                 505                 510
Asp Gly Val Glu Val His Asn Ala Lys Thr Lys Pro Arg Glu Glu Gln
        515                 520                 525
Tyr Asn Ser Thr Tyr Arg Val Val Ser Val Leu Thr Val Leu His Gln
    530                 535                 540
Asp Trp Leu Asn Gly Lys Glu Tyr Lys Cys Lys Val Ser Asn Lys Ala
545                 550                 555                 560
Leu Gly Ala Pro Ile Glu Lys Thr Ile Ser Lys Ala Lys Gly Gln Pro
                565                 570                 575
Arg Glu Pro Gln Val Tyr Thr Leu Pro Pro Ser Arg Asp Glu Leu Thr
            580                 585                 590
Lys Asn Gln Val Ser Leu Thr Cys Leu Val Lys Gly Phe Tyr Pro Ser
        595                 600                 605
```

-continued

```
Asp Ile Ala Val Glu Trp Glu Ser Asn Gly Gln Pro Glu Asn Asn Tyr
            610                 615                 620
Lys Thr Thr Pro Pro Val Leu Asp Ser Asp Gly Ser Phe Phe Leu Tyr
625                 630                 635                 640
Ser Lys Leu Thr Val Asp Lys Ser Arg Trp Gln Gln Gly Asn Val Phe
                645                 650                 655
Ser Cys Ser Val Met His Glu Ala Leu His Asn His Tyr Thr Gln Lys
            660                 665                 670
Ser Leu Ser Leu Ser Pro Gly Gly Gly Gly Ser Gly Gly Gly Gly
        675                 680                 685
Ser Gly Gly Gly Gly Ser Gly Gly Gly Ser Glu Ile Val Met Thr
    690                 695                 700
Gln Ser Pro Ala Thr Leu Ser Val Ser Pro Gly Glu Arg Ala Thr Leu
705                 710                 715                 720
Ser Cys Arg Ala Ser Gln Ser Val Ser Ser Asn Leu Ala Trp Tyr Gln
                725                 730                 735
Gln Lys Pro Gly Gln Ala Pro Arg Leu Ile Ile Tyr Gly Ala Ser Thr
            740                 745                 750
Thr Ala Ser Gly Ile Pro Ala Arg Phe Ser Ala Ser Gly Ser Gly Thr
        755                 760                 765
Asp Phe Thr Leu Thr Ile Ser Ser Leu Gln Ser Glu Asp Phe Ala Val
    770                 775                 780
Tyr Tyr Cys Gln Gln Tyr Asn Asn Trp Pro Pro Ala Tyr Thr Phe Gly
785                 790                 795                 800
Gln Gly Thr Lys Leu Glu Ile Lys Ser Ser Ala Ser Thr Lys Gly Pro
                805                 810                 815
Ser Val Phe Pro Leu Ala Pro Ser Ser Lys Ser Thr Ser Gly Gly Thr
            820                 825                 830
Ala Ala Leu Gly Cys Leu Val Lys Asp Tyr Phe Pro Glu Pro Val Thr
        835                 840                 845
Val Ser Trp Asn Ser Gly Ala Leu Thr Ser Gly Val His Thr Phe Pro
    850                 855                 860
Ala Val Leu Gln Ser Ser Gly Leu Tyr Ser Leu Ser Ser Val Val Thr
865                 870                 875                 880
Val Pro Ser Ser Ser Leu Gly Thr Gln Thr Tyr Ile Cys Asn Val Asn
                885                 890                 895
His Lys Pro Ser Asn Thr Lys Val Asp Lys Lys Val Glu Pro Lys Ser
            900                 905                 910
Cys

<210> SEQ ID NO 187
<211> LENGTH: 222
<212> TYPE: PRT
<213> ORGANISM: Artificial Sequence
<220> FEATURE:
<223> OTHER INFORMATION: Light chain 2 (LC2) pETR17239 EpCAM (3-17I)
      VHCL

<400> SEQUENCE: 187

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
```

Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Leu Leu Trp Asn Tyr Trp Gly Gln Gly Thr Leu Val Thr
                100                 105                 110

Val Ser Ser Ala Ser Val Ala Ala Pro Ser Val Phe Ile Phe Pro Pro
            115                 120                 125

Ser Asp Glu Gln Leu Lys Ser Gly Thr Ala Ser Val Val Cys Leu Leu
130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
                180                 185                 190

Asp Tyr Glu Lys His Lys Val Tyr Ala Cys Glu Val Thr His Gln Gly
                195                 200                 205

Leu Ser Ser Pro Val Thr Lys Ser Phe Asn Arg Gly Glu Cys
            210                 215                 220

<210> SEQ ID NO 188
<211> LENGTH: 657
<212> TYPE: DNA
<213> ORGANISM: Artificial Sequence
<220> FEATURE:
<223> OTHER INFORMATION: Nucleotide sequence Light chain (LC) muOX40
      (OX86)VL/CL (pETR14908)

<400> SEQUENCE: 188
gatattgtga tgacccaggg tgcactcccc aatcctgtcc cttctggaga gtcagcttcc    60
atcacctgca ggtctagtca gagtctggta tacaaagacg ccagacata cttgaattgg   120 tttctgcaga ggccaggaca gtctcctcag cttctgacct attggatgtc tacccgtgca   180
tcaggagtct cagacaggtt cagtggcagt gggtcaggaa catatttcac actgaaaatc   240
agtagagtga gggctgagga tgcgggtgtg tattactgtc agcaagttcg agagtatcct   300
ttcactttcg gctcagggac gaagttggaa ataaaacgtg ccgatgctgc accaactgta   360
tcgattttcc caccatccag tgagcagtta acatctggag gtgcctcagt cgtgtgcttc   420
ttgaacaact tctaccccaa agacatcaat gtcaagtgga agattgatgg cagtgaacga   480
caaaatggcg tcctgaacag ttggactgat caggacagca agacagcac ctacagcatg   540 agcagcaccc tcacgttgac caaggacgag tatgaacgac ataacagcta tacctgtgag   600
gccactcaca agacatcaac ttcacccatt gtcaagagct tcaacaggaa tgagtgt     657

<210> SEQ ID NO 189
<211> LENGTH: 2388
<212> TYPE: DNA
<213> ORGANISM: Artificial Sequence
<220> FEATURE:
<223> OTHER INFORMATION: Nucleotide sequence Heavy chain 1 (HC1)
      pETR16412 muOX40 (OX86) VHCH1_VHCH1_Fc_hole_DAPG_DD muEpCAM (G8.8)
      VL

<400> SEQUENCE: 189

```
caggtgcagc tgaaggagtc tggacctggt ctggtgcagc cctcacagac cctgtccctc      60
acctgcactg tctctgggtt ctcactaacc ggttacaatt tacactgggt tcgccagcct     120
ccaggaaagg gtctggagtg gatgggaaga atgaggtatg atggagacac atattataat     180
tcagttctca aatcccgact gagcatcagc aggacacct ccaagaacca agtttcttg       240
aaaatgaaca gtctgcaaac ggatgacaca gccatttact attgtaccag agacgggcgt     300
ggtgactcct ttgattactg gggccaagga gtcatggtca cagtctccag cgctaagacc     360
acccccccct ccgtgtatcc tctggctcct ggatctgccg cccagaccaa cagcatggtc     420
accctgggct gcctcgtgaa gggctacttc cctgagcctg tgaccgtgac ctggaactcc     480
ggctctctgt cctctggcgt gcacaccttc cctgccgtgc tgcagtccga cctgtacacc     540
ctgtcctcca gcgtgaccgt gccttcctcc acctggcctt cccagaccgt gacatgcaac     600
gtggcccacc ctgccagctc caccaaggtg gacaagaaaa tcgtgccccg ggactgcgga     660
gggggcggtt ccggcggagg aggatcccag gtgcagctga aggagtctgg acctggtctg     720
gtgcagccct cacagaccct gtccctcacc tgcactgtct ctgggttctc actaaccggt     780
tacaatttac actgggttcg ccagcctcca ggaaagggtc tggagtggat gggaagaatg     840
aggtatgatg gagacacata ttataattca gttctcaaat cccgactgag catcagcagg     900
gacacctcca agaaccaagt tttcttgaaa atgaacagtc tgcaaacgga tgacacagcc     960
atttactatt gtaccagaga cgggcgtggt gactcctttg attactgggg ccaaggagtc    1020
atggtcacag tctccagcgc taagaccacc cccctagcg tgtaccctct ggcccctgga    1080
tctgccgccc agaccaacag catggtgacc ctgggctgcc tggtgaaggg ctacttcccc    1140
gagcctgtga ccgtgacctg gaacagcggc agcctgagca gcggcgtgca cacctttcca    1200
gccgtgctgc agagcgacct gtacaccctg agcagtccg tgaccgtgcc tagcagcacc    1260
tggcccagcc agacagtgac ctgcaacgtg gcccacctg ccagcagcac caaggtggac    1320
aagaaaatcg tgccccggga ctgcggctgc aagccctgca tctgcaccgt gcccgaggtg    1380
tccagcgtgt tcatcttccc acccaagccc aaggacgtgc tgaccatcac cctgaccccc    1440
aaagtgacct gcgtggtggt ggccatcagc aaggacgacc ccgaggtgca gttctcttgg    1500
tttgtggacg acgtggaggt gcacacagcc cagacaaagc cccgggagga acagatcaac    1560
agcaccttca aagcgtgtc cgagctgccc atcatgcacc aggactggct gaacggcaaa    1620
gaattcaagt gcagagtgaa cagcgccgcc ttcggcgccc catcgagaa accatcagc     1680
aagaccaagg gcagacccaa ggccccccag gtgtacacca tccccccacc caaagaacag    1740
atggccaagg acaaggtgtc cctgacctgc atgatcacca cttttttccc cgaggacatc    1800
accgtggagt ggcagtggaa tggccagccc gccgagaact acgacaacac ccagcccatc    1860
atggacaccg acggcagcta cttcgtgtac agcgacctga cgtgcagaa gtccaactgg    1920
gaggccggca cacccttcac ctgtagcgtg ctgcacgagg cctgcacaa ccaccacacc    1980
gagaagtccc tgagccacag cccaggcggc ggaggcggat ctggcggagg aggttccggt    2040
ggcggaggtt ccggaggcgg tggatccgac atccagatga cacagagccc cgccagcctg    2100
agcgcctctc tgggcgagac agtgtccatc gagtgcctgg ccagcgaggg catcagcaac    2160
gacctggcct ggtatcagca gaagtccggc aagagccccc agctgctgat ctacgccacc    2220
agcagactgc aggacggcgt gcccagcaga ttcagcggca gcggctccgg cacccggtac    2280
```
agcctgaaga tcagcggcat gcagcccgag gacgaggccg actacttctg ccagcagagc    2340
tacaagtacc cctggacctt cggcggcggc accaagctgg aactgaag                 2388

<210> SEQ ID NO 190
<211> LENGTH: 2430
<212> TYPE: DNA
<213> ORGANISM: Artificial Sequence
<220> FEATURE:
<223> OTHER INFORMATION: Nucleotide sequence Heavy chain 2 (HC2)
      pETR16443 muOX40 (OX86) VHCH1_VHCH1_Fc_knob_DAPG_KK_muEpCAM (G8.8)
      VH

<400> SEQUENCE: 190
caggtgcagc tgaaggagtc tggacctggt ctggtgcagc cctcacagac cctgtccctc     60
acctgcactg tctctgggtt ctcactaacc ggttacaatt tacactgggt tcgccagcct    120
ccaggaaagg gtctggagtg gatgggaaga atgaggtatg atggagacac atattataat    180
tcagttctca atcccgact gagcatcagc agggacacct ccaagaacca gttttcttg     240 aaaatgaaca gtctgcaaac ggatgacaca gccattacta ttgtaccag agacgggcgt    300 ggtgactcct ttgattactg gggccaagga gtcatggtca cagtctccag cgctaagacc    360
acccccccct ccgtgtatcc tctggctcct ggatctgccg cccagaccaa cagcatggtc    420
accctgggct gcctcgtgaa gggctacttc cctgagcctg tgaccgtgac ctggaactcc    480
ggctctctgt cctctggcgt gcacaccttc cctgccgtgc tgcagtccga cctgtacacc    540
ctgtcctcca gcgtgaccgt gccttcctcc acctggcctt cccagaccgt gacatgcaac    600
gtggcccacc ctgccagctc caccaaggtg gacaagaaaa tcgtgccccg ggactgcgga    660
gggggcggtt ccggcggagg aggatcccag gtgcagctga aggagtctgg acctggtctg    720
gtgcagccct cacagaccct gtccctcacc tgcactgtct ctgggttctc actaaccggt    780
tacaatttac actgggttcg ccagcctcca ggaaagggtc tggagtggat gggaagaatg    840
aggtatgatg gagacacata ttataattca gttctcaaat cccgactgag catcagcagg    900
gacacctcca gaaccaagt tttcttgaaa atgaacagtc tgcaaacgga tgacacagcc    960
atttactatt gtaccagaga cgggcgtggt gactcctttg attactgggg ccaaggagtc   1020
atggtcacag tctccagcgc taagaccacc cccctagcg tgtaccctct ggcccctgga   1080
tctgccgccc agaccaacag catggtgacc ctggctgcc tggtgaaggg ctacttcccc   1140
gagcctgtga ccgtgacctg aacagcggc agcctgagca gcggcgtgca cacctttcca   1200
gccgtgctgc agagcgacct gtacaccctg agcagtccg tgaccgtgcc tagcagcacc   1260
tggcccagcc agacagtgac ctgcaacgtg gcccaccctg ccagcagcac caaggtggac   1320
aagaaaatcg tgccccggga ctgcggctgc aagccctgca tctgcaccgt gcccgaggtg   1380
tccagcgtgt tcatcttccc acccaagccc aaggacgtgc tgaccatcac cctgaccccc   1440
aaagtgacct gcgtggtggt ggccatcagc aaggacgacc ccgaggtgca gttctcttgg   1500
tttgtggacg acgtggaggt gcacacagcc cagacaaagc cccgggagga acagatcaac   1560
agcaccttca gaagcgtgtc cgagctgccc atcatgcacc aggactggct gaacggcaaa   1620
gaattcaagt gcagagtgaa ctccgccgcc tttggcgccc ctatcgaaaa gaccatctcc   1680
aagaccaagg gcagacccaa ggcccccag gtgtacacaa tcccccacc caagaaacag   1740 atggccaagg acaaggtgtc cctgacctgc atgatcacca cttttttccc agaggacatc   1800
accgtggaat ggcagtggaa cggccagccc gccgagaact acaagaacac ccagcccatc   1860
atgaagaccg acggctccta cttcgtgtac tccaagctga acgtgcagaa gtccaactgg   1920

```
gaggccggca acaccttcac ctgttccgtg ctgcacgagg gcctgcacaa ccaccacacc    1980
gagaagtccc tgtcccactc tcctggcgga ggcggaggat ctggtggcgg tggttctggc    2040
ggtggcggtt ccggaggcgg tggttccgaa gtgcagctgg ccgagagcgg cggaggcctg    2100
gtgcagcctg gcagatccat gaagctgagc tgcgccgcca gcggcttcac cttcagcaac    2160
ttccccatgg cctgggtccg acaggccccc accaagggcc tggaatgggt ggccaccatc    2220
agcaccagcg gcggcagcac ctactaccgg gacagcgtga aggccggttt caccatcagc    2280
cgggacaacg ccaagagcac cctgtacctg cagatgaaca gcctgcggag cgaggacacc    2340
gccacctact actgcacccg gaccctgtat atcctgcggg tgttctactt cgactactgg    2400
ggccagggcg tgatggtcac cgtgtctagc                                     2430
```

<210> SEQ ID NO 191
<211> LENGTH: 219
<212> TYPE: PRT
<213> ORGANISM: Artificial Sequence
<220> FEATURE:
<223> OTHER INFORMATION: Light chain (LC) muOX40 (OX86)VL/CL (pETR14908)

<400> SEQUENCE: 191

```
Asp Ile Val Met Thr Gln Gly Ala Leu Pro Asn Pro Val Pro Ser Gly
1               5                   10                  15
Glu Ser Ala Ser Ile Thr Cys Arg Ser Ser Gln Ser Leu Val Tyr Lys
            20                  25                  30
Asp Gly Gln Thr Tyr Leu Asn Trp Phe Leu Gln Arg Pro Gly Gln Ser
        35                  40                  45
Pro Gln Leu Leu Thr Tyr Trp Met Ser Thr Arg Ala Ser Gly Val Ser
    50                  55                  60
Asp Arg Phe Ser Gly Ser Gly Ser Gly Thr Tyr Phe Thr Leu Lys Ile
65                  70                  75                  80
Ser Arg Val Arg Ala Glu Asp Ala Gly Val Tyr Tyr Cys Gln Gln Val
                85                  90                  95
Arg Glu Tyr Pro Phe Thr Phe Gly Ser Gly Thr Lys Leu Glu Ile Lys
            100                 105                 110
Arg Ala Asp Ala Ala Pro Thr Val Ser Ile Phe Pro Pro Ser Ser Glu
        115                 120                 125
Gln Leu Thr Ser Gly Gly Ala Ser Val Val Cys Phe Leu Asn Asn Phe
    130                 135                 140
Tyr Pro Lys Asp Ile Asn Val Lys Trp Lys Ile Asp Gly Ser Glu Arg
145                 150                 155                 160
Gln Asn Gly Val Leu Asn Ser Trp Thr Asp Gln Asp Ser Lys Asp Ser
                165                 170                 175
Thr Tyr Ser Met Ser Ser Thr Leu Thr Leu Thr Lys Asp Glu Tyr Glu
            180                 185                 190
Arg His Asn Ser Tyr Thr Cys Glu Ala Thr His Lys Thr Ser Thr Ser
        195                 200                 205
Pro Ile Val Lys Ser Phe Asn Arg Asn Glu Cys
    210                 215
```

<210> SEQ ID NO 192
<211> LENGTH: 796
<212> TYPE: PRT
<213> ORGANISM: Artificial Sequence
<220> FEATURE:
<223> OTHER INFORMATION: Heavy chain 1 (HC1) pETR16412 muOX40 (OX86)
      VHCH1_VHCH1_Fc_hole_DAPG_DD muEpCAM (G8.8) VL

<400> SEQUENCE: 192

```
Gln Val Gln Leu Lys Glu Ser Gly Pro Gly Leu Val Gln Pro Ser Gln
  1               5                  10                  15

Thr Leu Ser Leu Thr Cys Thr Val Ser Gly Phe Ser Leu Thr Gly Tyr
             20                  25                  30

Asn Leu His Trp Val Arg Gln Pro Pro Gly Lys Gly Leu Glu Trp Met
         35                  40                  45

Gly Arg Met Arg Tyr Asp Gly Asp Thr Tyr Tyr Asn Ser Val Leu Lys
 50                  55                  60

Ser Arg Leu Ser Ile Ser Arg Asp Thr Ser Lys Asn Gln Val Phe Leu
 65                  70                  75                  80

Lys Met Asn Ser Leu Gln Thr Asp Asp Thr Ala Ile Tyr Tyr Cys Thr
                 85                  90                  95

Arg Asp Gly Arg Gly Asp Ser Phe Asp Tyr Trp Gly Gln Gly Val Met
            100                 105                 110

Val Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Gln Thr Val Thr Cys Asn Val Ala His Pro Ala Ser Ser Thr
        195                 200                 205

Lys Val Asp Lys Lys Ile Val Pro Arg Asp Cys Gly Gly Gly Gly Ser
210                 215                 220

Gly Gly Gly Gly Ser Gln Val Gln Leu Lys Glu Ser Gly Pro Gly Leu
225                 230                 235                 240

Val Gln Pro Ser Gln Thr Leu Ser Leu Thr Cys Thr Val Ser Gly Phe
                245                 250                 255

Ser Leu Thr Gly Tyr Asn Leu His Trp Val Arg Gln Pro Pro Gly Lys
            260                 265                 270

Gly Leu Glu Trp Met Gly Arg Met Arg Tyr Asp Gly Asp Thr Tyr Tyr
        275                 280                 285

Asn Ser Val Leu Lys Ser Arg Leu Ser Ile Ser Arg Asp Thr Ser Lys
290                 295                 300

Asn Gln Val Phe Leu Lys Met Asn Ser Leu Gln Thr Asp Asp Thr Ala
305                 310                 315                 320

Ile Tyr Tyr Cys Thr Arg Asp Gly Arg Gly Asp Ser Phe Asp Tyr Trp
                325                 330                 335

Gly Gln Gly Val Met Val Thr Val Ser Ser Ala Lys Thr Thr Pro Pro
            340                 345                 350

Ser Val Tyr Pro Leu Ala Pro Gly Ser Ala Ala Gln Thr Asn Ser Met
        355                 360                 365

Val Thr Leu Gly Cys Leu Val Lys Gly Tyr Phe Pro Glu Pro Val Thr
370                 375                 380

Val Thr Trp Asn Ser Gly Ser Leu Ser Ser Gly Val His Thr Phe Pro
385                 390                 395                 400
```

Ala Val Leu Gln Ser Asp Leu Tyr Thr Leu Ser Ser Val Thr Val
                405                 410                 415

Pro Ser Ser Thr Trp Pro Ser Gln Thr Val Thr Cys Asn Val Ala His
            420                 425                 430

Pro Ala Ser Ser Thr Lys Val Asp Lys Lys Ile Val Pro Arg Asp Cys
        435                 440                 445

Gly Cys Lys Pro Cys Ile Cys Thr Val Pro Glu Val Ser Ser Val Phe
    450                 455                 460

Ile Phe Pro Pro Lys Pro Lys Asp Val Leu Thr Ile Thr Leu Thr Pro
465                 470                 475                 480

Lys Val Thr Cys Val Val Val Ala Ile Ser Lys Asp Asp Pro Glu Val
                485                 490                 495

Gln Phe Ser Trp Phe Val Asp Asp Val Glu Val His Thr Ala Gln Thr
            500                 505                 510

Lys Pro Arg Glu Glu Gln Ile Asn Ser Thr Phe Arg Ser Val Ser Glu
        515                 520                 525

Leu Pro Ile Met His Gln Asp Trp Leu Asn Gly Lys Glu Phe Lys Cys
    530                 535                 540

Arg Val Asn Ser Ala Ala Phe Gly Ala Pro Ile Glu Lys Thr Ile Ser
545                 550                 555                 560

Lys Thr Lys Gly Arg Pro Lys Ala Pro Gln Val Tyr Thr Ile Pro Pro
                565                 570                 575

Pro Lys Glu Gln Met Ala Lys Asp Lys Val Ser Leu Thr Cys Met Ile
            580                 585                 590

Thr Asn Phe Phe Pro Glu Asp Ile Thr Val Glu Trp Gln Trp Asn Gly
        595                 600                 605

Gln Pro Ala Glu Asn Tyr Asp Asn Thr Gln Pro Ile Met Asp Thr Asp
    610                 615                 620

Gly Ser Tyr Phe Val Tyr Ser Asp Leu Asn Val Gln Lys Ser Asn Trp
625                 630                 635                 640

Glu Ala Gly Asn Thr Phe Thr Cys Ser Val Leu His Glu Gly Leu His
                645                 650                 655

Asn His His Thr Glu Lys Ser Leu Ser His Ser Pro Gly Gly Gly Gly
            660                 665                 670

Gly Ser Gly Gly Gly Gly Ser Gly Gly Gly Gly Ser Gly Gly Gly Gly
        675                 680                 685

Ser Asp Ile Gln Met Thr Gln Ser Pro Ala Ser Leu Ser Ala Ser Leu
    690                 695                 700

Gly Glu Thr Val Ser Ile Glu Cys Leu Ala Ser Glu Gly Ile Ser Asn
705                 710                 715                 720

Asp Leu Ala Trp Tyr Gln Gln Lys Ser Gly Lys Ser Pro Gln Leu Leu
                725                 730                 735

Ile Tyr Ala Thr Ser Arg Leu Gln Asp Gly Val Pro Ser Arg Phe Ser
            740                 745                 750

Gly Ser Gly Ser Gly Thr Arg Tyr Ser Leu Lys Ile Ser Gly Met Gln
        755                 760                 765

Pro Glu Asp Glu Ala Asp Tyr Phe Cys Gln Gln Ser Tyr Lys Tyr Pro
    770                 775                 780

Trp Thr Phe Gly Gly Gly Thr Lys Leu Glu Leu Lys
785                 790                 795

<210> SEQ ID NO 193
<211> LENGTH: 810

<212> TYPE: PRT
<213> ORGANISM: Artificial Sequence
<220> FEATURE:
<223> OTHER INFORMATION: Heavy chain 2 (HC2) pETR16443 muOX40 (OX86)
    VHCH1_VHCH1_Fc_knob_DAPG_KK_muEpCAM (G8.8) VH

<400> SEQUENCE: 193

```
Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Gly Tyr
            20                  25                  30

Asn Leu His Trp Val Arg Gln Pro Pro Gly Lys Gly Leu Glu Trp Met
        35                  40                  45

Gly Arg Met Arg Tyr Asp Gly Asp Thr Tyr Tyr Asn Ser Val Leu Lys
50                  55                  60

Ser Arg Leu Ser Ile Ser Arg Asp Thr Ser Lys Asn Gln Val Phe Leu
65                  70                  75                  80

Lys Met Asn Ser Leu Gln Thr Asp Asp Thr Ala Ile Tyr Tyr Cys Thr
            85                  90                  95

Arg Asp Gly Arg Gly Asp Ser Phe Asp Tyr Trp Gly Gln Gly Val Met
            100                 105                 110

Val Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
            165                 170                 175

Asp Leu Tyr Thr Leu Ser Ser Val Thr Val Pro Ser Ser Thr Trp
            180                 185                 190

Pro Ser Gln Thr Val Thr Cys Asn Val Ala His Pro Ala Ser Ser Thr
            195                 200                 205

Lys Val Asp Lys Lys Ile Val Pro Arg Asp Cys Gly Gly Gly Gly Ser
210                 215                 220

Gly Gly Gly Gly Ser Gln Val Gln Leu Lys Glu Ser Gly Pro Gly Leu
225                 230                 235                 240

Val Gln Pro Ser Gln Thr Leu Ser Leu Thr Cys Thr Val Ser Gly Phe
            245                 250                 255

Ser Leu Thr Gly Tyr Asn Leu His Trp Val Arg Gln Pro Pro Gly Lys
        260                 265                 270

Gly Leu Glu Trp Met Gly Arg Met Arg Tyr Asp Gly Asp Thr Tyr Tyr
        275                 280                 285

Asn Ser Val Leu Lys Ser Arg Leu Ser Ile Ser Arg Asp Thr Ser Lys
        290                 295                 300

Asn Gln Val Phe Leu Lys Met Asn Ser Leu Gln Thr Asp Asp Thr Ala
305                 310                 315                 320

Ile Tyr Tyr Cys Thr Arg Asp Gly Arg Gly Asp Ser Phe Asp Tyr Trp
            325                 330                 335

Gly Gln Gly Val Met Val Thr Val Ser Ser Ala Lys Thr Thr Pro Pro
            340                 345                 350

Ser Val Tyr Pro Leu Ala Pro Gly Ser Ala Ala Gln Thr Asn Ser Met
        355                 360                 365

Val Thr Leu Gly Cys Leu Val Lys Gly Tyr Phe Pro Glu Pro Val Thr
370                 375                 380
```

```
Val Thr Trp Asn Ser Gly Ser Leu Ser Ser Gly Val His Thr Phe Pro
385                 390                 395                 400

Ala Val Leu Gln Ser Asp Leu Tyr Thr Leu Ser Ser Val Thr Val
            405                 410                 415

Pro Ser Ser Thr Trp Pro Ser Gln Thr Val Thr Cys Asn Val Ala His
            420                 425                 430

Pro Ala Ser Ser Thr Lys Val Asp Lys Lys Ile Val Pro Arg Asp Cys
            435                 440                 445

Gly Cys Lys Pro Cys Ile Cys Thr Val Pro Glu Val Ser Ser Val Phe
            450                 455                 460

Ile Phe Pro Pro Lys Pro Lys Asp Val Leu Thr Ile Thr Leu Thr Pro
465                 470                 475                 480

Lys Val Thr Cys Val Val Val Ala Ile Ser Lys Asp Asp Pro Glu Val
                485                 490                 495

Gln Phe Ser Trp Phe Val Asp Asp Val Glu Val His Thr Ala Gln Thr
            500                 505                 510

Lys Pro Arg Glu Glu Gln Ile Asn Ser Thr Phe Arg Ser Val Ser Glu
            515                 520                 525

Leu Pro Ile Met His Gln Asp Trp Leu Asn Gly Lys Glu Phe Lys Cys
530                 535                 540

Arg Val Asn Ser Ala Ala Phe Gly Ala Pro Ile Glu Lys Thr Ile Ser
545                 550                 555                 560

Lys Thr Lys Gly Arg Pro Lys Ala Pro Gln Val Tyr Thr Ile Pro Pro
                565                 570                 575

Pro Lys Lys Gln Met Ala Lys Asp Lys Val Ser Leu Thr Cys Met Ile
            580                 585                 590

Thr Asn Phe Phe Pro Glu Asp Ile Thr Val Glu Trp Gln Trp Asn Gly
            595                 600                 605

Gln Pro Ala Glu Asn Tyr Lys Asn Thr Gln Pro Ile Met Lys Thr Asp
610                 615                 620

Gly Ser Tyr Phe Val Tyr Ser Lys Leu Asn Val Gln Lys Ser Asn Trp
625                 630                 635                 640

Glu Ala Gly Asn Thr Phe Thr Cys Ser Val Leu His Glu Gly Leu His
                645                 650                 655

Asn His His Thr Glu Lys Ser Leu Ser His Ser Pro Gly Gly Gly Gly
            660                 665                 670

Gly Ser Gly Gly Gly Ser Gly Gly Gly Ser Gly Gly Gly Gly
            675                 680                 685

Ser Glu Val Gln Leu Ala Glu Ser Gly Gly Gly Leu Val Gln Pro Gly
            690                 695                 700

Arg Ser Met Lys Leu Ser Cys Ala Ala Ser Gly Phe Thr Phe Ser Asn
705                 710                 715                 720

Phe Pro Met Ala Trp Val Arg Gln Ala Pro Thr Lys Gly Leu Glu Trp
                725                 730                 735

Val Ala Thr Ile Ser Thr Ser Gly Gly Ser Thr Tyr Tyr Arg Asp Ser
            740                 745                 750

Val Lys Gly Arg Phe Thr Ile Ser Arg Asp Asn Ala Lys Ser Thr Leu
            755                 760                 765

Tyr Leu Gln Met Asn Ser Leu Arg Ser Glu Asp Thr Ala Thr Tyr Tyr
            770                 775                 780

Cys Thr Arg Thr Leu Tyr Ile Leu Arg Val Phe Tyr Phe Asp Tyr Trp
785                 790                 795                 800
```

-continued

```
Gly Gln Gly Val Met Val Thr Val Ser Ser
            805                 810
```

BISPECIFIC ANTIGEN BINDING MOLECULE FOR A COSTIMULATORY TNF RECEPTOR

CROSS REFERENCE TO RELATED APPLICATIONS

This application is a bypass Continuation Application of PCT Application No. PCT/EP2018/057734, filed Mar. 27, 2018, which claims priority to European Application No. 17163639.2, filed Mar. 29, 2017, each of which are incorporated herein by reference in its entirety.

SEQUENCE LISTING

This application contains a Sequence Listing which has been submitted electronically in ASCH format and is hereby incorporated by reference in its entirety. Said ASCH copy, created on Feb. 7, 2020, is named P34211-US_Sequence_Listing.txt and is 250,799 bytes in size.

FIELD OF THE INVENTION

The invention relates to novel bispecific antigen binding molecules, comprising (a) at least one moiety capable of specific binding to OX40, and (b) at least one moiety capable of specific binding to epithelial cell adhesion molecule (EpCAM). The invention further relates to methods of producing these molecules and to methods of using the same.

BACKGROUND

Several members of the tumor necrosis factor receptor (TNFR) family function after initial T cell activation to sustain T cell responses and thus have pivotal roles in the organization and function of the immune system. CD27, 4-1BB (CD137), OX40 (CD134), HVEM, CD30, and GITR can have costimulatory effects on T cells, meaning that they sustain T-cell responses after initial T cell activation (Watts T. H. (2005) Annu. Rev. Immunol. 23, 23-68). The effects of these costimulatory TNFR family members can often be functionally, temporally, or spatially segregated from those of CD28 and from each other. The sequential and transient regulation of T cell activation/survival signals by different costimulators may function to allow longevity of the response while maintaining tight control of T cell survival. Depending on the disease condition, stimulation via costimulatory TNF family members can exacerbate or ameliorate disease. Despite these complexities, stimulation or blockade of TNFR family costimulators shows promise for several therapeutic applications, including cancer, infectious disease, transplantation, and autoimmunity.

Among several costimulatory molecules, the tumor necrosis factor (TNF) receptor family member OX40 (CD134) plays a key role in the survival and homeostasis of effector and memory T cells (Croft M. et al. (2009), Immunological Reviews 229, 173-191). OX40 (CD134) is expressed in several types of cells and regulates immune responses against infections, tumors and self-antigens and its expression has been demonstrated on the surface of T-cells, NKT-cells and NK-cells as well as neutrophils (Baumann R. et al. (2004), Eur. J. Immunol. 34, 2268-2275) and shown to be strictly inducible or strongly upregulated in response to various stimulatory signals. Functional activity of the molecule has been demonstrated in every OX40-expressing cell type suggesting complex regulation of OX40-mediated activity in vivo. Combined with T-cell receptor triggering, OX40 engagement on T-cells by its natural ligand or agonistic antibodies leads to synergistic activation of the PI3K and NFκB signalling pathways (Song J. et al. (2008) J. Immunology 180(11), 7240-7248). In turn, this results in enhanced proliferation, increased cytokine receptor and cytokine production and better survival of activated T-cells. In addition to its co-stimulatory activity in effector CD4$^+$ or CD8$^-$ T-cells, OX40 triggering has been recently shown to inhibit the development and immunosuppressive function of T regulatory cells. This effect is likely to be responsible, at least in part, for the enhancing activity of OX40 on anti-tumor or anti-microbial immune responses. Given that OX40 engagement can expand T-cell populations, promote cytokine secretion, and support T-cell memory, agonists including antibodies and soluble forms of the ligand OX40L have been used successfully in a variety of preclinical tumor models (Weinberg et al. (2000), J. Immunol. 164, 2160-2169).

The available pre-clinical and clinical data clearly demonstrate that there is a high clinical need for effective agonists of costimulatory TNFR family members such as OX40 and 4-1BB that are able to induce and enhance effective endogenous immune responses to cancer. However, almost never are the effects limited to a single cell type or acting via a single mechanism and studies designed to elucidate inter- and intracellular signaling mechanisms have revealed increasing levels of complexity. Thus, there is a need of "targeted" agonists that preferably act on a single cell type. The antigen binding molecules of the invention combine a moiety capable of preferred binding to tumor-specific or tumor-associated targets with a moiety capable of agonistic binding to costimulatory TNF receptors. The antigen binding molecules of this invention may be able to trigger TNF receptors not only effectively, but also very selectively at the desired site thereby reducing undesirable side effects.

Epithelial cell adhesion molecule (EpCAM)—also known as tumor-associated calcium signal transducer 1 (TACSTD1), 17-1A and CD326—is a type I ~40 kDa transmembrane glycoprotein that is highly expressed in epithelial cancers, and at lower levels in normal simple epithelia. The structure and function of EpCAM is reviewed, for example, in Schnell et al., Biochimica et Biophysica Acta—Biomembranes (2013), 1828(8): 1989-2001; Trzpis et al. Am J Pathol. (2007) 171(2): 386-395 and Baeuerle and Gires, Br. J. Cancer, (2007) 96:417-423.

EpCAM is expressed at the basolateral membrane, and plays a role in calcium-independent homophilic cell adhesion. The mature EpCAM molecule (after processing to remove the 23 amino acid signal peptide) comprises an N-terminal, 242 amino acid extracellular domain comprising an epidermal growth factor-like repeat region, a human thyroglobulin (TY) repeat region and a cysteine-poor region, a single-pass 23 amino acid transmembrane domain and a C-terminal, 26 amino acid cytoplasmic domain comprising two binding sites for α-actinin and a NPXY internalization motif.

EpCAM is frequently overexpressed in cancers of epithelial origin and is expressed by cancer stem cells, and is therefore a molecule of significant interest for therapy and diagnosis. The extracellular domain EpCAM can be cleaved to yield the soluble extracellular domain molecule EpEX, and the intracellular molecule EpICD. EpICD has been shown to associate with other proteins to form a nuclear complex which upregulates the expression of genes promoting cell proliferation (Maetzel et al., Nat Cell Biol (2009) 11(2):162-171). EpCAM may also be involved in the epithelial to mesenchymal cell transition (EMT), and may contribute to the formation of large metastases (Imrich et al., Cell Adh Migr. (2012) 6(1): 30-38).

Several clinical trials have been conducted for the use of anti-EpCAM antibodies to treat various carcinomas (reviewed e.g. in Münz et al., Cancer Cell Int. (2010) 10:44, and Baeuerle and Gires, supra).

SUMMARY OF THE INVENTION

The present invention provides a bispecific antigen binding molecule, comprising
(a) at least one moiety capable of specific binding to OX40 comprising an antibody light chain variable region (VL) and an antibody heavy chain variable region (VH), and
(b) at least one moiety capable of specific binding to epithelial cell adhesion molecule (EpCAM) comprising an antibody light chain variable region (VL) and an antibody heavy chain variable region (VH).

The novel bispecific antigen binding molecules of the present invention are able to trigger OX40 very selectively at the site where EpCAM is expressed, due to their binding capability towards EpCAM. Side effects may therefore be drastically reduced.

In some embodiments, the bispecific antigen binding molecule additionally comprises (c) a Fc region composed of a first and a second subunit capable of stable association.

In some embodiments, the moiety capable of specific binding to OX40 binds to a polypeptide comprising, or consisting of, the amino acid sequence of SEQ ID NO:1.

In some embodiments, the moiety capable of specific binding to EpCAM binds to a polypeptide comprising, or consisting of, the amino acid sequence of SEQ ID NO:49.

In some embodiments, the moiety capable of specific binding to OX40 comprises a heavy chain variable domain (VH) comprising
(i) a CDR-H1 comprising an amino acid sequence selected from the group consisting of SEQ ID NO:4 and SEQ ID NO:5,
(ii) a CDR-H2 comprising an amino acid sequence selected from the group consisting of SEQ ID NO:6 and SEQ ID NO:7, and
(iii) a CDR-H3 comprising an amino acid sequence selected from the group consisting of SEQ ID NO:8, SEQ ID NO:9, SEQ ID NO:10, SEQ ID NO: 11, SEQ ID NO:12, SEQ ID NO:13 and SEQ ID NO:14,
and a light chain variable domain (VL) comprising
(iv) a CDR-L1 comprising an amino acid sequence selected from the group consisting of SEQ ID NO:15, SEQ ID NO:16 and SEQ ID NO:17,
(v) a CDR-L2 comprising an amino acid sequence selected from the group consisting of SEQ ID NO:18, SEQ ID NO:19 and SEQ ID NO:20, and
(vi) a CDR-L3 comprising an amino acid sequence selected from the group consisting of SEQ ID NO:21, SEQ ID NO:22, SEQ ID NO:23, SEQ ID NO:24, SEQ ID NO:25 and SEQ ID NO:26.

In some embodiments, the moiety capable of specific binding to OX40 comprises a heavy chain variable region (VH) comprising an amino acid sequence that is at least about 95%, 96%, 97%, 98%, 99% or 100% identical to an amino acid sequence selected from the group consisting of SEQ ID NO:33, SEQ ID NO: 35, SEQ ID NO:37, SEQ ID NO:39, SEQ ID NO:41, SEQ ID NO:43 and SEQ ID NO:45 and a light chain variable region (VL) comprising an amino acid sequence that is at least about 95%, 96%, 97%, 98%, 99% or 100% identical to an amino acid sequence selected from the group consisting of SEQ ID NO:34, SEQ ID NO: 36, SEQ ID NO:38, SEQ ID NO:40, SEQ ID NO:42, SEQ ID NO:44 and SEQ ID NO:46.

In some embodiments, the moiety capable of specific binding to OX40 comprises
(i) a VH comprising the amino acid sequence of SEQ ID NO:33 and a VL comprising the amino acid sequence of SEQ ID NO:34,
(ii) a VH comprising the amino acid sequence of SEQ ID NO:35 and a VL comprising the amino acid sequence of SEQ ID NO:36,
(iii) a VH comprising the amino acid sequence of SEQ ID NO:37 and a VL comprising the amino acid sequence of SEQ ID NO:38,
(iv) a VH comprising the amino acid sequence of SEQ ID NO:39 and a VL comprising the amino acid sequence of SEQ ID NO:40,
(v) a VH comprising the amino acid sequence of SEQ ID NO:41 and a VL comprising the amino acid sequence of SEQ ID NO:42,
(vi) a VH comprising the amino acid sequence of SEQ ID NO:43 and a VL comprising the amino acid sequence of SEQ ID NO:44, or
(vii) a VH comprising the amino acid sequence of SEQ ID NO:45 and a VL comprising the amino acid sequence of SEQ ID NO:46.

In some embodiments, the moiety capable of specific binding to EpCAM comprises a VH comprising
(i) a CDR-H1 comprising the amino acid sequence SEQ ID NO:51,
(ii) a CDR-H2 comprising the amino acid sequence SEQ ID NO:52, and
(iii) a CDR-H3 comprising the amino acid sequence SEQ ID NO:53, and a VL comprising
(iv) a CDR-L1 comprising the amino acid sequence SEQ ID NO:54,
(v) a CDR-L2 comprising the amino acid sequence SEQ ID NO:55, and
(vi) a CDR-L3 comprising the amino acid sequence SEQ ID NO:56.

In some embodiments, the moiety capable of specific binding to EpCAM comprises a VH comprising an amino acid sequence that is at least about 95%, 96%, 97%, 98%, 99% or 100% identical to the amino acid sequence of SEQ ID NO:63, and a VL comprising an amino acid sequence that is at least about 95%, 96%, 97%, 98%, 99% or 100% identical to the amino acid sequence of SEQ ID NO:64.

In some embodiments, the moiety capable of specific binding to EpCAM comprises a VH comprising the amino acid sequence of SEQ ID NO:63 and a VL comprising the amino acid sequence of SEQ ID NO:64.

In some embodiments, the bispecific antigen binding molecule comprises
(i) at least one moiety capable of specific binding to OX40, comprising a VH comprising an amino acid sequence that is at least about 95%, 96%, 97%, 98%, 99% or 100% identical to an amino acid sequence selected from the group consisting of SEQ ID NO:33, SEQ ID NO: 35, SEQ ID NO:37, SEQ ID NO:39, SEQ ID NO:41, SEQ ID NO:43 and SEQ ID NO:45 and a VL comprising an amino acid sequence that is at least about 95%, 96%, 97%, 98%, 99% or 100% identical to an amino acid sequence selected from the group consisting of SEQ ID NO:34, SEQ ID NO: 36, SEQ ID NO:38, SEQ ID NO:40, SEQ ID NO:42, SEQ ID NO:44 and SEQ ID NO:46, and (ii) at least one moiety capable of specific binding to EpCAM, comprising a VH comprising an amino acid sequence that is at least about 95%, 96%, 97%, 98%, 99% or 100% identical to the amino acid sequence of SEQ ID NO:63 and a VL comprising an amino acid sequence that is at least about 95%, 96%, 97%, 98%, 99% or 100% identical to the amino acid sequence of SEQ ID NO:64.

In some embodiments, the bispecific antigen binding molecule comprises (i) at least one moiety capable of specific binding to OX40, comprising a VH comprising the amino acid sequence of SEQ ID NO: 35 and a VL comprising the amino acid sequence of SEQ ID NO: 36, and (ii) at least one moiety capable of specific binding to EpCAM, comprising a VH comprising the amino acid sequence of SEQ ID NO:63 and a VL comprising the amino acid sequence of SEQ ID NO: 64.

In some embodiments, the moiety capable of specific binding to OX40 binds to a polypeptide comprising, or consisting of, the amino acid sequence of SEQ ID NO:2.

In some embodiments, the moiety capable of specific binding to EpCAM binds to a polypeptide comprising, or consisting of, the amino acid sequence of SEQ ID NO:50.

In some embodiments, the moiety capable of specific binding to OX40 comprises a VH comprising (i) a CDR-H1 comprising the amino acid sequence SEQ ID NO:27, (ii) a CDR-H2 comprising the amino acid sequence SEQ ID NO:28, and (iii) a CDR-H3 comprising the amino acid sequence SEQ ID NO:29, and a VL comprising (iv) a CDR-L1 comprising the amino acid sequence SEQ ID NO:30, (v) a CDR-L2 comprising the amino acid sequence SEQ ID NO:31, and (vi) a CDR-L3 comprising the amino acid sequence SEQ ID NO:32.

In some embodiments, the moiety capable of specific binding to OX40 comprises a VH comprising an amino acid sequence that is at least about 95%, 96%, 97%, 98%, 99% or 100% identical to the amino acid sequence of SEQ ID NO:47, and a VL comprising an amino acid sequence that is at least about 95%, 96%, 97%, 98%, 99% or 100% identical to the amino acid sequence of SEQ ID NO:48.

In some embodiments, the moiety capable of specific binding to OX40 comprises a VH comprising the amino acid sequence of SEQ ID NO:47 and a VL comprising the amino acid sequence of SEQ ID NO:48.

In some embodiments, the moiety capable of specific binding to EpCAM comprises a VH comprising (i) a CDR-H1 comprising the amino acid sequence SEQ ID NO:57, (ii) a CDR-H2 comprising the amino acid sequence SEQ ID NO:58, and (iii) a CDR-H3 comprising the amino acid sequence SEQ ID NO:59, and a VL comprising (iv) a CDR-L1 comprising the amino acid sequence SEQ ID NO:60, (v) a CDR-L2 comprising the amino acid sequence SEQ ID NO:61, and (vi) a CDR-L3 comprising the amino acid sequence SEQ ID NO:62.

In some embodiments, the moiety capable of specific binding to EpCAM comprises a VH comprising an amino acid sequence that is at least about 95%, 96%, 97%, 98%, 99% or 100% identical to the amino acid sequence of SEQ ID NO:65, and a VL comprising an amino acid sequence that is at least about 95%, 96%, 97%, 98%, 99% or 100% identical to the amino acid sequence of SEQ ID NO:66.

In some embodiments, the moiety capable of specific binding to EpCAM comprises a VH comprising the amino acid sequence of SEQ ID NO:65 and a VL comprising the amino acid sequence of SEQ ID NO:66.

In some embodiments, the bispecific antigen binding molecule comprises (i) at least one moiety capable of specific binding to OX40, comprising a VH comprising the amino acid sequence of SEQ ID NO:47 and a VL comprising the amino acid sequence of SEQ ID NO:48, and (ii) at least one moiety capable of specific binding to EpCAM, comprising a VH comprising the amino acid sequence of SEQ ID NO:65 and a VL comprising the amino acid sequence of SEQ ID NO:66.

In some embodiments, the Fc region is an IgG, particularly an IgG1 Fc region or an IgG4 Fc region.

In some embodiments, the Fc region comprises one or more amino acid substitution that reduces the binding affinity of the antibody to an Fc receptor and/or effector function.

In some embodiments, the Fc region is (i) of human IgG1 subclass with the amino acid mutations L234A, L235A and P329G (numbering according to Kabat EU index), or (ii) of mouse IgG1 subclass with the amino acid mutations D265A and P329G (numbering according to Kabat EU index).

In some embodiments, the Fc region comprises a modification promoting the association of the first and second subunit of the Fc region.

In some embodiments, the first subunit of the Fc region comprises knobs and the second subunit of the Fc region comprises holes according to the knobs into holes method.

In some embodiments, (i) the first subunit of the Fc region comprises the amino acid substitutions S354C and T366W (numbering according to Kabat EU index) and the second subunit of the Fc region comprises the amino acid substitutions Y349C, T366S and Y407V (numbering according to Kabat EU index), or (ii) the first subunit of the Fc region comprises the amino acid substitutions K392D and K409D (numbering according to Kabat EU index) and the second subunit of the Fc region comprises the amino acid substitutions E356K and D399K (numbering according to Kabat EU index).

In some embodiments, the bispecific antigen binding molecule comprises (a) at least two Fab fragments capable of specific binding to OX40 connected to a Fc region, and (b) at least one moiety capable of specific binding to EpCAM connected to the C-terminus of the Fc region.

In some embodiments, the bispecific antigen binding molecule comprises (a) two light chains and two heavy chains of an antibody comprising two Fab fragments capable of specific binding to OX40, and a Fc region, and (b) a VH and a VL of a moiety capable specific binding to EpCAM, wherein the VH is connected to the C-terminus of one of the two heavy chains of (a), and wherein the VL is connected to the C-terminus of the other of the two heavy chains of (a).

In some embodiments, the bispecific antigen binding molecule comprises (a) two light chains and two heavy chains of an antibody comprising two Fab fragments capable of specific binding to OX40, and a Fc region, and (b) two Fab fragments capable of specific binding to EpCAM, wherein one of the Fab fragments is connected to the C-terminus of one of the two heavy chains of (a), and the other of the Fab fragments is connected to the C-terminus of the other of the two heavy chains of (a).

In some embodiments, the bispecific antigen binding molecule comprises (a) two heavy chains, each heavy chain comprising a VH and CH1 domain of a Fab fragment capable of specific binding to OX40 and a Fc region subunit, (b) two light chains, each light chain comprising a VL and CL domain of a Fab fragment capable of specific binding to OX40, and (c) a VH and a VL of a moiety capable specific binding to EpCAM, wherein the VH is connected to the C-terminus of one of the two heavy chains of (a), and wherein the VL is connected to the C-terminus of the other of the two heavy chains of (a).

In some embodiments, the bispecific antigen binding molecule comprises (a) two heavy chains, each heavy chain comprising a VH and CH1 domain of a Fab fragment capable of specific binding to OX40, and a Fc region subunit, (b) two light chains, each light chain comprising a VL and CL domain of a Fab fragment capable of specific binding to OX40, (c) two Fab fragments capable of specific binding to EpCAM, wherein one of the Fab fragments is connected to the C-terminus of one of the two heavy chains of (a), and the other of the Fab fragments is connected to the C-terminus of the other of the two heavy chains of (a).

In some embodiments, the two Fab fragments capable of specific binding to EpCAM are crossover Fab fragments each comprising a VL-CH1 chain and a VH-CL chain, and wherein one of the VL-CH1 chains is connected to the C-terminus of one of the two heavy chains of (a), and the other of the VL-CH1 chains is connected to the C-terminus of the other of the two heavy chains of (a).

In some embodiments, the bispecific antigen binding molecule comprises four Fab fragments capable of specific binding to OX40.

In some embodiments, each of the two heavy chains of (a) comprises two VH domains and two CH1 domains of a Fab fragment capable of specific binding to OX40.

In some embodiments, one or more of the Fab fragments capable of specific binding to OX40 comprises a CL domain comprising an arginine (R) at amino acid at position 123 (EU numbering) and a lysine (K) at amino acid at position 124 (EU numbering), and a CH1 domain comprising a glutamic acid (E) at amino acid at position 147 (EU numbering) and a glutamic acid (E) at amino acid at position 213 (EU numbering).

The present invention also provides a bispecific antigen binding molecule, comprising a first heavy chain comprising the amino acid sequence of SEQ ID NO:183, a second heavy chain comprising the amino acid sequence of SEQ ID NO:184, and four light chains, each comprising the amino acid sequence of SEQ ID NO:182.

The present invention also provides a bispecific antigen binding molecule, comprising two heavy chains, each comprising the amino acid sequence of SEQ ID NO:186, two light chains, each comprising the amino acid sequence of SEQ ID NO:187, and four light chains, each comprising the amino acid sequence of SEQ ID NO:185.

The present invention also provides a bispecific antigen binding molecule, comprising a first heavy chain comprising the amino acid sequence of SEQ ID NO:192, a second heavy chain comprising the amino acid sequence of SEQ ID NO:193, and four light chains, each comprising the amino acid sequence of SEQ ID NO:191.

The present invention also provides a polynucleotide encoding the bispecific antigen binding molecule of the present invention.

The present invention also provides a expression vector comprising the polynucleotide of the invention.

The present invention also provides a host cell comprising the polynucleotide of the invention, or the expression vector of the invention.

The present invention also provides a method of producing a bispecific antigen binding molecule, comprising culturing the host cell of the invention under conditions suitable for the expression of the bispecific antigen binding molecule, and isolating the bispecific antigen binding molecule.

The present invention also provides a pharmaceutical composition comprising the bispecific antigen binding molecule of the invention and at least one pharmaceutically acceptable excipient.

The present invention also provides the bispecific antigen binding molecule of the invention, or the pharmaceutical composition of the invention, for use as a medicament.

The present invention also provides the bispecific antigen binding molecule of the invention, or the pharmaceutical composition of the invention, for use (i) in stimulating T cell response,
(ii) in supporting survival of activated T cells,
(iii) in the treatment of infections,
(iv) in the treatment of cancer,
(v) in delaying progression of cancer, or
(vi) in prolonging the survival of a patient suffering from cancer.

The present invention also provides the bispecific antigen binding molecule of the invention, or the pharmaceutical composition of the invention, for use in the treatment of cancer.

The present invention also provides the use of the bispecific antigen binding molecule of the invention, or the pharmaceutical composition of the invention, in the manufacture of a medicament for the treatment of cancer.

The present invention also provides a method of treating an individual having cancer comprising administering to the individual an effective amount of the bispecific antigen binding molecule of the invention, or the pharmaceutical composition of the invention.

The present invention also provides the bispecific antigen binding molecule of the invention, or the pharmaceutical composition of the invention, for use in up-regulating or prolonging cytotoxic T cell activity.

The present invention also provides the use of the bispecific antigen binding molecule of the invention, or the pharmaceutical composition of the invention, in the manufacture of a medicament for up-regulating or prolonging cytotoxic T cell activity.

The present invention also provides method of up-regulating or prolonging cytotoxic T cell activity in an individual having cancer, comprising administering to the individual an effective amount of the bispecific antigen binding molecule of the invention, or the pharmaceutical composition of the invention.

In some embodiments in accordance with various aspects of the present invention the individual is a mammal, particularly a human.

BRIEF DESCRIPTION OF THE DRAWINGS

FIG. 3A shows binding to activated CD4+ T cells, FIG. 3B shows binding to activated CD8+ T cells, FIG. 3C shows binding to resting CD4+ T cells, and FIG. 3D shows binding to resting CD8+ T cells. Binding is shown as the median of fluorescence intensity (MFI) of PE-conjugated AffiniPure anti-mouse IgG Fcγ-fragment-specific goat IgG F(ab')2 fragment, which is used as secondary detection antibody. MFI was measured by flow cytometry and baseline corrected by subtracting the MFI of the blank control. The x-axis shows the concentration of the antigen binding molecules. All of the antigen binding molecules comprising an OX40-binding domain bind to activated, OX40-expressing mouse CD4+ and CD8+ T cells. OX40 is not expressed on resting mouse CD4+ and CD8+ T cells (FIGS. 3C and 3D). After activation, OX40 is up-regulated on CD4+ and CD8+ T cells (FIGS. 3A and 3B).

FIG. 4A shows binding to CT26muEpCAM cells, which stably express murine EpCAM. FIG. 4B shows binding to CT26muFAP cells, which stably express murine FAP, and which do not express murine EpCAM. Binding is shown as the median of fluorescence intensity (MFI) of FITC-labeled anti-mouse IgG Fcγ-specific goat IgG F(ab')2 fragment, which is used as secondary detection antibody. MFI was measured by flow cytometry and baseline corrected by subtracting the MFI of the blank control. The x-axis shows the concentration of the antigen binding molecules. The antigen binding molecules comprising a murine EpCAM-binding domain bind to CT26muEpCAM cells, but not to the CT26muFAP cells.

FIG. 5A shows CD4+ T cell size as determined by forward scatter (FSC), FIG. 5B shows CD8+ T cell size as determined by FSC, FIG. 5C shows CD4+ T cell event count, and FIG. 5D shows CD8+ T cell event count. Values were baseline-corrected to values for samples containing only the anti-murine CD3 (and not the OX40/EpCAM-targeted constructs).

FIG. 6A shows the percentage of CD25+ cells within the CD4+ T cell population, FIG. 6B shows the percentage of CD25+ cells within the CD8+ T cell population, FIG. 6C shows the mean fluorescence intensity (MFI) for CD25 expressed on CD4+ T cells, and FIG. 6D shows the MFI for CD25 expressed on CD8+ T cells. Values were baseline-corrected to values for samples containing only the anti-murine CD3 (and not the OX40/EpCAM-targeted constructs).

FIG. 7A shows binding to activated CD4+ T cells, FIG. 7B shows binding to activated CD8+ T cells FIG. 7C shows binding to resting CD4+ T cells, and FIG. 7D shows binding to resting CD8+ T cells. Binding is shown as the median of fluorescence intensity (MFI) of FITC conjugated anti-human IgG F(ab')$_2$-fragment-specific goat IgG F(ab')2 fragment, which is used as secondary detection antibody. MFI was measured by flow cytometry and baseline corrected by subtracting the MFI of the blank control. The x-axis shows the concentration of the antigen binding molecules. All of the antigen binding molecules comprising an OX40-binding domain bind to activated, OX40 expressing human CD4+ T cells, and to a lower extent to activated human CD8+ T cells. OX40 is not expressed on resting human PBMCs (FIGS. 7C and 7D). After activation, OX40 is up-regulated on CD4+ and CD8+ T cells (FIGS. 7A and 7B). OX40 expression on human CD8+ T cells is lower than on CD4+ T cells.

FIG. 9 shows analysis of expression of human EpCAM on KATO-III, NIH/3T3huEpCAM clone 44 cells and HeLa_huOX40_NFkB_Luc1 reporter cells as determined by flow cytometry. Binding to huEpCAM was analysed by flow cytometry using by PE conjugated anti-huEpCAM antibody clone EBA-1 on the three cell lines tested. HeLa_huOX40_NFkB_Luc1 reporter cells are negative for human EpCAM, NIH/3T3huEpCAM clone 44 cells express human EpCAM, and KATO-III cells express high levels of human EpCAM.

FIG. 9A shows binding to KATO-II cells, which express human EpCAM. FIG. 9B shows binding to A549 NLR cells, which do not express human EpCAM. Binding is shown as the median of fluorescence intensity (MFI) of FITC conjugated anti-human IgG F(ab')$_2$-fragment-specific goat IgG F(ab')2 fragment, which is used as secondary detection antibody. MFI was measured by flow cytometry and baseline corrected by subtracting the MFI of the blank control. The x-axis shows the concentration of the antigen binding molecules.

FIG. 10A shows NFκB activation in OX40$^+$ HeLa reporter cells by antigen binding molecules in the absence of crosslinking. FIG. 10B shows NFκB activation in OX40$^+$ HeLa reporter cells by antigen binding molecules in the presence of crosslinking by anti-human Fc specific secondary antibody. FIG. 10C shows NFκB activation in OX40$^+$ HeLa reporter cells by antigen binding molecules in the presence of crosslinking by 3T3huEpCAM cells. NF-κB-mediated luciferase activity was characterized by plotting the emitted relative light units (RLUs), measured during 500 ms, versus the concentration of the antigen binding molecule (in nM). RLUs are emitted due to luciferase-mediated oxidation of luciferin to oxyluciferin. The values were baseline-corrected by subtracting the RLUs for a 'blank control' condition. FIG. 10D shows the data of FIGS. 10A to 10C represented as area under the curve (AUC).

FIG. 11A shows CD4+ T cell size as determined by forward scatter (FSC), FIG. 11B shows CD8+ T cell size as determined by FSC, FIG. 11C shows CD4+ T cell event count, and FIG. 11D shows CD8+ T cell event count. Values were baseline-corrected to values for samples containing only the anti-human CD3 (and not the OX40/EpCAM-targeted constructs).

FIGS. 12A to 12D show rescue of suboptimal TCR restihulation of preactivated human CD4+ and CD8+ T cells with the bispecific, tetravalent anti-human OX40, monovalent anti-human EpCAM (4+1 huEpCAM); monospecific, tetravalent anti-human OX40, non-targeted (4+1 control); or monospecific, bivalent anti-human EpCAM IgG (huEpCAM IgG), in the presence of crosslinking by human EpCAM-expressing KATO-III cells, as determined by analysis of CD25 expression. FIG. 12A shows the percentage of CD25+ cells within the CD4+ T cell population, FIG. 12B shows the percentage of CD25+ cells within the CD8+ T cell population, FIG. 12C shows the mean fluorescence intensity (MFI) for CD25 expressed on CD4+ T cells, and FIG. 12D shows the MFI for CD25 expressed on CD8+ T cells. Values were baseline-corrected to values for samples containing only the anti-human CD3 (and not the OX40/EpCAM-targeted constructs).

FIG. 13A shows CD4+ T cell size as determined by forward scatter (FSC), FIG. 13B shows CD8+ T cell size as determined by FSC, FIG. 13C shows CD4+ T cell event count, and FIG. 13D shows CD8+ T cell event count. Values were baseline-corrected to values for samples containing only the anti-human CD3 (and not the OX40/EpCAM-targeted constructs).

FIG. 14A shows the percentage of CD25+ cells within the CD4+ T cell population, FIG. 14B shows the percentage of CD25+ cells within the CD8+ T cell population, FIG. 14C shows the mean fluorescence intensity (MFI) for CD25 expressed on CD4+ T cells, and FIG. 14D shows the MFI for CD25 expressed on CD8+ T cells. Values were baseline-corrected to values for samples containing only the anti-human CD3 (and not the OX40/EpCAM-targeted constructs).

DETAILED DESCRIPTION OF THE INVENTION

Definitions

Figure 1:
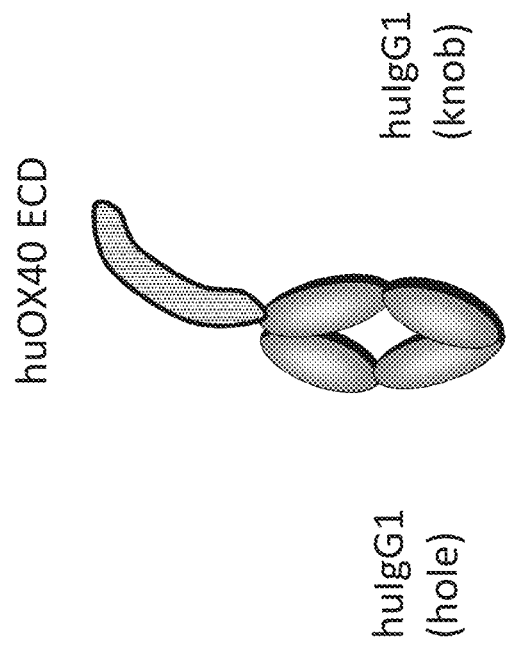
FIG. 1 shows the monomeric form of Fc-linked human OX40 antigen ECD that was used for the preparation of anti-human OX40 antibodies.

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, antibody fragments and scaffold antigen binding proteins.

As used herein, the term "moiety capable of specific binding to epithelial cell adhesion molecule (EpCAM)" refers to a polypeptide molecule that specifically binds to EpCAM. In a particular aspect, the antigen binding moiety is able to direct the entity to which it is attached to a target site, for example to a specific type of tumor cell or tumor stroma bearing EpCAM. Moieties capable of specific binding to EpCAM include antibodies and fragments thereof as further defined herein. In addition, moieties capable of specific binding to EpCAM include scaffold antigen binding proteins as further defined herein, e.g. binding domains which are based on designed repeat proteins or designed repeat domains (see e.g. WO 2002/020565).

In relation to an antibody or fragment thereof, the term "moiety capable of specific binding to epithelial cell adhesion molecule (EpCAM)" refers to the part of the molecule that comprises the area which specifically binds to and is complementary to part or all of EpCAM. A moiety capable of specific binding to EpCAM may be provided, for example, by one or more antibody variable domains (also called antibody variable regions). Particularly, a moiety capable of specific binding to EpCAM comprises an antibody light chain variable region (VL) and an antibody heavy chain variable region (VH). In some embodiments, the "moiety capable of specific binding to epithelial cell adhesion molecule (EpCAM)" may be an scFv, a Fab fragment or a cross-Fab fragment.

The term "moiety capable of specific binding to OX40" refers to a polypeptide molecule that specifically binds to OX40. In one aspect, the antigen binding moiety is able to activate signaling through OX40. Moieties capable of specific binding to OX40 include antibodies and fragments thereof as further defined herein. In addition, moieties capable of specific binding to OX40 include scaffold antigen binding proteins as further defined herein, e.g. binding domains which are based on designed repeat proteins or designed repeat domains (see e.g. WO 2002/020565). Particularly, a moiety capable of specific binding to OX40 comprises an antibody light chain variable region (VL) and an antibody heavy chain variable region (VH). In a particular aspect, the "moiety capable of specific binding to OX40" may be a Fab fragment, a cross-Fab fragment or an scFv.

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants. A bispecific antigen binding molecule comprises at least two antigen binding sites, each of which is specific for a different antigenic determinant. In certain embodiments the bispecific antigen binding molecule is capable of simultaneously binding two antigenic determinants, particularly two antigenic determinants expressed on two distinct cells. For example, the antigen binding molecules of the present invention are bispecific, comprising a moiety capable of specific binding to OX40, and a moiety capable of specific binding to EpCAM.

The term "valent" as used within the current application denotes the presence of a specified number of binding sites in an antigen binding molecule. As such, the terms "bivalent", "tetravalent", and "hexavalent" denote the presence of two binding sites, four binding sites, and six binding sites, respectively, in an antigen binding molecule. Valency of an antigen binding molecule may also be expressed in relation to the number of binding sites for a given antigenic determinant. For example, in some embodiments the antigen binding molecules of the present invention are tetravalent with respect to OX40, and bivalent with respect to EpCAM (i.e. 4+2).

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called $\alpha$ (IgA), $\delta$ (IgD), $\epsilon$ (IgE), $\gamma$ (IgG), or $\mu$ (IgM), some of which may be further divided into subtypes, e.g. $\gamma$1 (IgG1), $\gamma$2 (IgG2), $\gamma$3 (IgG3), $\gamma$4 (IgG4), $\alpha$1 (IgA1) and $\alpha$2 (IgA2). The light chain of an antibody may be assigned to one of two types, called kappa ($\kappa$) and lambda ($\lambda$), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, triabodies, tetrabodies, cross-Fab fragments; linear antibodies; single-chain antibody molecules (e.g. scFv); and single domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL and a constant domain of a light chain (CL), and a VH and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments wherein the cysteine residue(s) of the constant domains bear a free thiol group. Pepsin treatment yields an F(ab')$_2$ fragment that has two antigen-combining sites (two Fab fragments) and a part of the Fc region. According to the present invention, the term "Fab fragment" also includes "cross-Fab fragments" or "crossover Fab fragments" as defined below.

The term "cross-Fab fragment" or "xFab fragment" or "crossover Fab fragment" refers to a Fab fragment, wherein either the variable regions or the constant regions of the heavy and light chain are exchanged. Two different chain compositions of a cross-Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab$_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy ($V_H$) and light chains ($V_L$) of an antibody, connected with a short linker peptide of ten to about 25 amino acids. The linker is usually rich in glycine for flexibility, as well as serine or threonine for solubility, and can either connect the N-terminus of the VH with the C-terminus of the $V_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH, namely being able to assemble together with a VL, or of a VL, namely being able to assemble together with a VH to a functional antigen binding site and thereby providing the antigen binding property of full length antibodies.

"Scaffold antigen binding proteins" are known in the art, for example, fibronectin and designed ankyrin repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13: 695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/Maxibody), a serum transferrin (trans-body); a designed ankyrin repeat protein (DARPin), a variable domain of antibody light chain or heavy chain (single-domain antibody, sdAb), a variable domain of antibody heavy chain (nanobody, aVH), $V_{NAR}$ fragments, a fibronectin (AdNectin), a C-type lectin domain (Tetranectin); a variable domain of a new antigen receptor beta-lactamase ($V_{NAR}$ fragments), a human gamma-crystallin or ubiquitin (Affilin molecules); a kunitz type domain of human protease inhibitors, microbodies such as the proteins from the knottin family, peptide aptamers and fibronectin (adnectin). CTLA-4 (Cytotoxic T Lymphocyte-associated Antigen 4) is a CD28-family receptor expressed on mainly CD4$^+$ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies (e.g. U.S. Pat. No. 7,166,697B1). Evibodies are around the same size as the isolated variable region of an antibody (e.g. a domain antibody). For further details see Journal of Immunological Methods 248 (1-2), 31-45 (2001). Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633. An affibody is a scaffold derived from Protein A of *Staphylococcus aureus* which can be engineered to bind to antigen. The domain consists of a three-helical bundle of approximately 58 amino acids. Libraries have been generated by randomization of surface residues. For further details see Protein Eng. Des. Sel. 2004, 17, 455-462 and EP 1641818A1. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007). A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999). Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1. A single-domain antibody is an antibody fragment consisting of a single monomeric variable antibody domain. The first single domains were derived from the variable domain of the antibody heavy chain from camelids (nanobodies or $V_HH$ fragments). Furthermore, the term single-domain antibody includes an autonomous human heavy chain variable domain (aVH) or $V_{NAR}$ fragments derived from sharks. Fibronectin is a scaffold which can be engineered to bind to antigen. Adnectins consists of a backbone of the natural amino acid sequence of the 10th domain of the 15 repeating units of human fibronectin type III (FN3). Three loops at one end of the .beta.-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1. Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005). Microbodies are derived from naturally occurring microproteins of 25-50 amino acids in length which contain 3-4 cysteine bridges—examples of microproteins include KalataBI and conotoxin and knottins. The microproteins have a loop which can beengineered to include upto 25 amino acids without affecting the overall fold of the microprotein. For further details of engineered knottin domains, see WO2008098796.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

The term "antigen binding domain" or "antigen-binding site" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable region (VL) and an antibody heavy chain variable region (VH).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIACORE® instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, an molecule that binds to the antigen has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "epithelial cell adhesion molecule (EpCAM)" refers to any native EpCAM from any vertebrate source, including mammals such as primates (e.g. humans) non-human primates (e.g. cynomolgus monkeys) and rodents (e.g. mice and rats), unless otherwise indicated. The term encompasses "full-length," unprocessed EpCAM as well as any form of EpCAM that results from processing in the cell. The term also encompasses naturally occurring variants of EpCAM, e.g., splice variants or allelic variants. In one embodiment, the antigen binding molecule of the invention is capable of specific binding to human, mouse and/or cynomolgus EpCAM. The amino acid sequence of human EpCAM is shown in UniProt (www.uniprot.org) accession no. P16422 (version 167, SEQ ID NO:68), or NCBI (www.ncbi.nlm.nih.gov/) RefSeq NP_002345.2. The amino acid sequence of mouse EpCAM is shown in UniProt (www.uniprot.org) accession no. Q99JW5 (version 111, SEQ ID NO:75), or NCBI (www.ncbi.nlm.nih.gov/) RefSeq NP_032558.2.

In certain embodiments, the antigen binding molecule of the present invention comprises a moiety capable of specific binding to the extracellular domain (ECD) of EpCAM. In some embodiments, a moiety capable of specific binding to EpCAM binds to SEQ ID NO:49. In some embodiments, a moiety capable of specific binding to EpCAM binds to SEQ ID NO:50.

The term "variable region" or "variable domain" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL may be sufficient to confer antigen-binding specificity.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

| CDR Definitions[1] | | | |
|---|---|---|---|
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ respectively.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "Fc domain" or "Fc region" herein is used to define a C-terminal region of an antibody heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)).

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J. P., Annu. Rev. Immunol. 9 (1991)

457-492; Capel, P. J., et al., Immunomethods 4 (1994) 25-34; de Haas, M., et al., J. Lab. Clin. Med. 126 (1995) 330-341; and Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. Fc γ RIIIB is highly expressed on neutrophils. Reduced binding to FcγRIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

The term "ADCC" or "antibody-dependent cellular cytotoxicity" is a function mediated by Fc receptor binding and refers to lysis of target cells by an antibody as reported herein in the presence of effector cells. The capacity of the antibody to induce the initial steps mediating ADCC is investigated by measuring their binding to Fcγ receptors expressing cells, such as cells, recombinantly expressing FcγRI and/or FcγRIIA or NK cells (expressing essentially FcγRIIIA). In particular, binding to FcγR on NK cells is measured.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

The "Tumor Necrosis factor receptor superfamily" or "TNF receptor superfamily" currently consists of 27 receptors. It is a group of cytokine receptors characterized by the ability to bind tumor necrosis factors (TNFs) via an extracellular cysteine-rich domain (CRD). These pseudorepeats are defined by intrachain disulphides generated by highly conserved cysteine residues within the receptor chains. With the exception of nerve growth factor (NGF), all TNFs are homologous to the archetypal TNF-alpha. In their active form, the majority of TNF receptors form trimeric complexes in the plasma membrane. Accordingly, most TNF receptors contain transmembrane domains (TMDs). Several of these receptors also contain intracellular death domains (DDs) that recruit caspase-interacting proteins following ligand binding to initiate the extrinsic pathway of caspase activation. Other TNF superfamily receptors that lack death domains bind TNF receptor-associated factors and activate intracellular signaling pathways that can lead to proliferation or differentiation. These receptors can also initiate apoptosis, but they do so via indirect mechanisms. In addition to regulating apoptosis, several TNF superfamily receptors are involved in regulating immune cell functions such as B cell homeostasis and activation, natural killer cell activation, and T cell co-stimulation. Several others regulate cell type-specific responses such as hair follicle development and osteoclast development. Members of the TNF receptor superfamily include the following: Tumor necrosis factor receptor 1 (1A) (TNFRSF1A, CD120a), Tumor necrosis factor receptor 2 (1B) (TNFRSF1B, CD120b), Lymphotoxin beta receptor (LTBR, CD18), OX40 (TNFRSF4, CD134), CD40 (Bp50), Fas receptor (Apo-1, CD95, FAS), Decoy receptor 3 (TR6, M68, TNFRSF6B), CD27 (S152, Tp55), CD30 (Ki-1, TNFRSF8), 4-1BB (CD137, TNFRSF9), DR4 (TRAILR1, Apo-2, CD261, TNFRSF10A), DR5 (TRAILR2, CD262, TNFRSF10B), Decoy Receptor 1 (TRAILR3, CD263, TNFRSF10C), Decoy Receptor 2 (TRAILR4, CD264, TNFRSF10D), RANK (CD265, TNFRSF11A), Osteoprotegerin (OCIF, TR1, TNFRSF11B), TWEAK receptor (Fn14, CD266, TNFRSF12A), TACI (CD267, TNFRSF13B), BAFF receptor (CD268, TNFRSF13C), Herpesvirus entry mediator (HVEM, TR2, CD270, TNFRSF14), Nerve growth factor receptor (p75NTR, CD271, NGFR), B-cell maturation antigen (CD269, TNFRSF17), Glucocorticoid-induced TNFR-related (GITR, AITR, CD357, TNFRSF18), TROY (TNFRSF19), DR6 (CD358, TNFRSF21), DR3 (Apo-3, TRAMP, WS-1, TNFRSF25) and Ectodysplasin A2 receptor (XEDAR, EDA2R).

Several members of the tumor necrosis factor receptor (TNFR) family function after initial T cell activation to sustain T cell responses. The term "costimulatory TNF receptor family member" or "costimulatory TNF family receptor" refers to a subgroup of TNF receptor family members, which are able to costimulate proliferation and cytokine production of T-cells. The term refers to any native TNF family receptor from any vertebrate source, including mammals such as primates (e.g. humans), non-human primates (e.g. cynomolgus monkeys) and rodents (e.g. mice and rats), unless otherwise indicated. In specific embodiments of the invention, costimulatory TNF receptor family members are selected from the group consisting of OX40 (CD134), 4-1BB (CD137), CD27, HVEM (CD270), CD30, and GITR, all of which can have costimulatory effects on T cells. More particularly, the antigen binding molecule of the present invention comprises at least moiety capable of specific binding to the costimulatory TNF receptor family member OX40.

Further information, in particular sequences, of the TNF receptor family members may be obtained from publically accessible databases such as Uniprot (www.uniprot.org). For instance, the human costimulatory TNF receptors have the following amino acid sequences: human OX40 (UniProt accession no. P43489, SEQ ID NO:67), human 4-1BB (UniProt accession no. Q07011, SEQ ID NO:69), human CD27 (UniProt accession no. P26842, SEQ ID NO:70), human HVEM (UniProt accession no. Q92956, SEQ ID NO:71), human CD30 (UniProt accession no. P28908, SEQ ID NO:72), and human GITR (UniProt accession no. Q9Y5U5, SEQ ID NO:73).

The term "OX40", as used herein, refers to any native OX40 from any vertebrate source, including mammals such as primates (e.g. humans) and rodents (e.g., mice and rats), unless otherwise indicated. The term encompasses "full-length," unprocessed OX40 as well as any form of OX40 that results from processing in the cell. The term also encompasses naturally occurring variants of OX40, e.g., splice variants or allelic variants. The amino acid sequence of an exemplary human OX40 is shown in SEQ ID NO:67 (Uniprot P43489, version 112) and the amino acid sequence of an exemplary murine OX40 is shown in SEQ ID NO:74 (Uniprot P47741, version 101).

The terms "anti-OX40 antibody", "anti-OX40", "OX40 antibody and "an antibody that specifically binds to OX40" refer to an antibody that is capable of binding OX40 with sufficient affinity such that the antibody is useful as a diagnostic and/or therapeutic agent in targeting OX40. In one embodiment, the extent of binding of an anti-OX40 antibody to an unrelated, non-OX40 protein is less than about 10% of the binding of the antibody to OX40 as measured, e.g., by a radioimmunoassay (RIA) or flow cytometry (FACS). In certain embodiments, an antibody that binds to OX40 has a dissociation constant ($K_D$) of ≤1 µM, ≤100 nM, ≤10 nM, ≤1 nM, ≤0.1 nM, ≤0.01 nM, or ≤0.001 nM (e.g. $10^{-6}$ M or less, e.g. from $10^{-68}$ M to $10^{-13}$ M, e.g., from $10^{-8}$ M to $10^{-10}$ M).

The terms terms "anti-EpCAM antibody" and "an antibody that binds to EpCAM" refer to an antibody that is capable of binding to epithelial cell adhesion molecule (EpCAM) with sufficient affinity such that the antibody is useful as a diagnostic and/or therapeutic agent in targeting EpCAM. In one embodiment, the extent of binding of an anti-EpCAM antibody to an unrelated, non-EpCAM protein is less than about 10% of the binding of the antibody to EpCAM as measured, e.g., by a radioimmunoassay (RIA). In certain embodiments, an antibody that binds to EpCAM has a dissociation constant (KD) of ≤1 µM, ≤100 nM, ≤10 nM, ≤5 nM, ≤2 nM, ≤1 nM, ≤0.1 nM, ≤0.01 nM, or ≤0.001 nM (e.g., 10-8 M or less, e.g., from 10-8 M to 10-13 M, e.g., from 10-9 M to 10-13 M, e.g., from 10 nM to 0.1 nM, e.g., from 5 nM to 0.1 nM, e.g., from 2 nM to 0.1 nM). In certain embodiments, an anti-EpCAM antibody binds to an epitope of EpCAM that is conserved among EpCAM from different species. In certain embodiments, an antibody that binds to an epitope of EpCAM is specific for the extracellular domain (ECD) of EpCAM. In certain embodiments an antibody specific for SEQ ID NO:49 is provided. In certain embodiments an antibody specific for SEQ ID NO:50 is provided.

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$, $(SG_4)_n$ or $G_4(SG_4)_n$ peptide linkers, wherein "n" is generally a number between 1 and 10, typically between 2 and 4, in particular 2, i.e. the peptides selected from the group consisting of GGGGS (SEQ ID NO:76) GGGGSGGGGS (SEQ ID NO:77), SGGGGSGGGG (SEQ ID NO:78) and GGGGSGGGGSGGGG (SEQ ID NO:80), but also include the sequences GSPGSSSSGS (SEQ ID NO:82), $(G4S)_3$ (SEQ ID NO:79), $(G4S)_4$ (SEQ ID NO:81), GSGSGSGS (SEQ ID NO:83), GSGSGNGS (SEQ ID NO:84), GGSGSGSG (SEQ ID NO:85), GGSGSG (SEQ ID NO:86), GGSG (SEQ ID NO:87), GGSGNGSG (SEQ ID NO:88), GGNGSGSG (SEQ ID NO:89) and GGNGSG (SEQ ID NO:90). Peptide linkers of particular interest are (G4S) (SEQ ID NO:76), $(G_4S)_2$ or GGGGSGGGGS (SEQ ID NO:77) and GSPGSSSSGS (SEQ ID NO:82).

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

By "fused" or "connected" is meant that the components (e.g. a heavy chain of an antibody and a Fab fragment) are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, amino acid sequence variants of the antigen binding molecules provided herein are contemplated. For example, it may be desirable to improve the binding affinity and/or other biological properties of the antigen binding molecules. Amino acid sequence variants of the antigen binding molecules may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table B under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

TABLE B

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more HVR residues are mutated and the variant antigen binding molecules displayed on phage and screened for a particular biological activity (e.g. binding affinity). In certain embodiments, substitutions, insertions, or deletions may occur within one or more HVRs so long as such alterations do not substantially reduce the ability of the antigen binding molecule to bind antigen. For example, conservative alterations (e.g., conservative substitutions as provided herein) that do not substantially reduce binding affinity may be made in HVRs. A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include bispecific antigen binding molecules of the invention with an N-terminal methionyl residue. Other insertional variants of the molecule include the fusion to the N- or C-terminus to a polypeptide which increases the serum half-life of the bispecific antigen binding molecules.

In certain embodiments, the bispecific antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the bispecific antigen binding molecule comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the antigen binding molecule may be made in order to create variants with certain improved properties. In one aspect, variants of bispecific antigen binding molecules or antibodies of the invention are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). In another aspect, variants of the bispecific antigen binding molecules or antibodies of the invention are provided with bisected oligosaccharides, e.g., in which a biantennary oligosaccharide attached to the Fc region is bisected by GlcNAc. Such variants may have reduced fucosylation and/or improved ADCC function., see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain aspects, it may be desirable to create cysteine engineered variants of the bispecific antigen binding molecules of the invention, e.g., "thioMAbs," in which one or more residues of the molecule are substituted with cysteine residues. In particular aspects, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain aspects, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "cancer" as used herein refers to proliferative diseases, such as lymphomas, lymphocytic leukemias, lung cancer, non-small cell lung (NSCL) cancer, bronchioloalveolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenoma and Ewings sarcoma, including refractory versions of any of the above cancers, or a combination of one or more of the above cancers.

Bispecific Antigen Binding Molecules of the Invention

The invention provides novel bispecific antigen binding molecules with particularly advantageous properties such as producibility, stability, binding affinity, biological activity, targeting efficiency and reduced toxicity.

The present invention provides a bispecific antigen binding molecule, comprising (a) at least one moiety capable of specific binding to OX40 comprising an antibody light chain variable region (VL) and an antibody heavy chain variable region (VH), and (b) at least one moiety capable of specific binding to epithelial cell adhesion molecule (EpCAM) comprising an antibody light chain variable region (VL) and an antibody heavy chain variable region (VH).

In some embodiments, the bispecific antigen binding molecule additionally comprises (c) a Fc region composed of a first and a second subunit capable of stable association.

In particular aspects, the bispecific antigen binding molecules of the present invention are characterized by agonistic binding to OX40.

Bispecific Antigen Binding Molecules Binding to OX40

In one aspect, the invention provides bispecific antigen binding molecules, wherein the moiety capable of specific binding to OX40 binds to a polypeptide comprising, or consisting of, the amino acid sequence of SEQ ID NO:1.

In one aspect, provided is a bispecific antigen binding molecule, comprising at least one moiety capable of specific binding to OX40, wherein said moiety comprises a VH comprising
  (i) a CDR-H1 comprising an amino acid sequence selected from the group consisting of SEQ ID NO:4 and SEQ ID NO:5,
  (ii) a CDR-H2 comprising an amino acid sequence selected from the group consisting of SEQ ID NO:6 and SEQ ID NO:7, and
  (iii) a CDR-H3 comprising an amino acid sequence selected from the group consisting of SEQ ID NO:8, SEQ ID NO:9, SEQ ID NO:10, SEQ ID NO: 11, SEQ ID NO:12, SEQ ID NO:13 and SEQ ID NO:14, and a VL comprising
- (iv) a CDR-L1 comprising an amino acid sequence selected from the group consisting of SEQ ID NO:15, SEQ ID NO:16 and SEQ ID NO:17,
- (v) a CDR-L2 comprising an amino acid sequence selected from the group consisting of SEQ ID NO:18, SEQ ID NO:19 and SEQ ID NO:20, and
- (vi) a CDR-L3 comprising an amino acid sequence selected from the group consisting of SEQ ID NO:21, SEQ ID NO:22, SEQ ID NO:23, SEQ ID NO:24, SEQ ID NO:25 and SEQ ID NO:26.

In particular, provided is a bispecific antigen binding molecule, comprising at least one moiety capable of specific binding to OX40, wherein said moiety comprises
- (a) a VH comprising CDR-H1 comprising the amino acid sequence of SEQ ID NO:4, CDR-H2 comprising the amino acid sequence of SEQ ID NO:6, CDR-H3 comprising the amino acid sequence of SEQ ID NO:8 and a VL comprising CDR-L1 comprising the amino acid sequence of SEQ ID NO:15, CDR-L2 comprising the amino acid sequence of SEQ ID NO:18 and CDR-L3 comprising the amino acid sequence of SEQ ID NO:21,
- (b) a VH comprising CDR-H1 comprising the amino acid sequence of SEQ ID NO:4, CDR-H2 comprising the amino acid sequence of SEQ ID NO:6, CDR-H3 comprising the amino acid sequence of SEQ ID NO:9 and a VL comprising CDR-L1 comprising the amino acid sequence of SEQ ID NO:15, CDR-L2 comprising the amino acid sequence of SEQ ID NO:18 and CDR-L3 comprising the amino acid sequence of SEQ ID NO:22,
- (c) a VH comprising CDR-H1 comprising the amino acid sequence of SEQ ID NO:4, CDR-H2 comprising the amino acid sequence of SEQ ID NO:6, CDR-H3 comprising the amino acid sequence of SEQ ID NO:10 and a VL comprising CDR-L1 comprising the amino acid sequence of SEQ ID NO:15, CDR-L2 comprising the amino acid sequence of SEQ ID NO:18 and CDR-L3 comprising the amino acid sequence of SEQ ID NO:23,
- (d) a VH comprising CDR-H1 comprising the amino acid sequence of SEQ ID NO:4, CDR-H2 comprising the amino acid sequence of SEQ ID NO:6, CDR-H3 comprising the amino acid sequence of SEQ ID NO:11 and a VL comprising CDR-L1 comprising the amino acid sequence of SEQ ID NO:15, CDR-L2 comprising the amino acid sequence of SEQ ID NO:18 and CDR-L3 comprising the amino acid sequence of SEQ ID NO:24,
- (e) a VH comprising CDR-H1 comprising the amino acid sequence of SEQ ID NO:5, CDR-H2 comprising the amino acid sequence of SEQ ID NO:7, CDR-H3 comprising the amino acid sequence of SEQ ID NO:12 and a VL comprising CDR-L1 comprising the amino acid sequence of SEQ ID NO:16, CDR-L2 comprising the amino acid sequence of SEQ ID NO:19 and CDR-L3 comprising the amino acid sequence of SEQ ID NO:25,
- (f) a VH comprising CDR-H1 comprising the amino acid sequence of SEQ ID NO:5, CDR-H2 comprising the amino acid sequence of SEQ ID NO:7, CDR-H3 comprising the amino acid sequence of SEQ ID NO:13 and a VL comprising CDR-L1 comprising the amino acid sequence of SEQ ID NO:16, CDR-L2 comprising the amino acid sequence of SEQ ID NO:19 and CDR-L3 comprising the amino acid sequence of SEQ ID NO:25, or
- (g) a VH comprising CDR-H1 comprising the amino acid sequence of SEQ ID NO:5, CDR-H2 comprising the amino acid sequence of SEQ ID NO:7, CDR-H3 comprising the amino acid sequence of SEQ ID NO:14 and a VL comprising CDR-L1 comprising the amino acid sequence of SEQ ID NO:17, CDR-L2 comprising the amino acid sequence of SEQ ID NO:20 and CDR-L3 comprising the amino acid sequence of SEQ ID NO:26.

In one aspect, the invention provides a bispecific antigen binding molecule, comprising at least one moiety capable of specific binding to OX40, wherein said moiety comprises a VH comprising CDR-H1 comprising the amino acid sequence of SEQ ID NO:4, CDR-H2 comprising the amino acid sequence of SEQ ID NO:6, CDR-H3 comprising the amino acid sequence of SEQ ID NO:9 and a VL comprising CDR-L1 comprising the amino acid sequence of SEQ ID NO:15, CDR-L2 comprising the amino acid sequence of SEQ ID NO:18 and CDR-L3 comprising the amino acid sequence of SEQ ID NO:22.

In another aspect, the invention provides a bispecific antigen binding molecule, wherein the moiety capable of specific binding to OX40 comprises a VH comprising an amino acid sequence that is at least about about 95%, 96%, 97%, 98%, 99% or 100% identical to an amino acid sequence selected from the group consisting of SEQ ID NO:33, SEQ ID NO: 35, SEQ ID NO:37, SEQ ID NO:39, SEQ ID NO:41, SEQ ID NO:43 and SEQ ID NO:45 and a VL comprising an amino acid sequence that is at least about 95%, 96%, 97%, 98%, 99% or 100% identical to an amino acid sequence selected from the group consisting of SEQ ID NO:34, SEQ ID NO: 36, SEQ ID NO:38, SEQ ID NO:40, SEQ ID NO:42, SEQ ID NO:44 and SEQ ID NO:46.

Particularly, provided is a bispecific antigen binding molecule, wherein the moiety capable of specific binding to OX40 comprises
- (i) a VH comprising the amino acid sequence of SEQ ID NO:33 and a VL comprising the amino acid sequence of SEQ ID NO:34,
- (ii) a VH comprising the amino acid sequence of SEQ ID NO:35 and a VL comprising the amino acid sequence of SEQ ID NO:36,
- (iii) a VH comprising the amino acid sequence of SEQ ID NO:37 and a VL comprising the amino acid sequence of SEQ ID NO:38,
- (iv) a VH comprising the amino acid sequence of SEQ ID NO:39 and a VL comprising the amino acid sequence of SEQ ID NO:40,
- (v) a VH comprising the amino acid sequence of SEQ ID NO:41 and a VL comprising the amino acid sequence of SEQ ID NO:42,
- (vi) a VH comprising the amino acid sequence of SEQ ID NO:43 and a VL comprising the amino acid sequence of SEQ ID NO:44, or
- (vii) a VH comprising the amino acid sequence of SEQ ID NO:45 and a VL comprising the amino acid sequence of SEQ ID NO:46.

In a particular aspect, provided is a bispecific antigen binding molecule, wherein the moiety capable of specific binding to OX40 comprises a VH comprising the amino acid sequence of SEQ ID NO:35 and a VL comprising the amino acid sequence of SEQ ID NO:36.

In one aspect, the invention provides bispecific antigen binding molecules, wherein the moiety capable of specific binding to OX40 binds to a polypeptide comprising, or consisting of, the amino acid sequence of SEQ ID NO:2.

In one aspect, provided is a bispecific antigen binding molecule, comprising at least one moiety capable of specific binding to OX40, wherein said moiety comprises a VH comprising (i) a CDR-H1 comprising the amino acid sequence SEQ ID NO:27,
(ii) a CDR-H2 comprising the amino acid sequence SEQ ID NO:28, and
(iii) a CDR-H3 comprising the amino acid sequence SEQ ID NO:29, and a VL comprising
(iv) a CDR-L1 comprising the amino acid sequence SEQ ID NO:30,
(v) a CDR-L2 comprising the amino acid sequence SEQ ID NO:31, and
(vi) a CDR-L3 comprising the amino acid sequence SEQ ID NO:32.

In another aspect, the invention provides a bispecific antigen binding molecule, wherein the moiety capable of specific binding to OX40 comprises a VH comprising an amino acid sequence that is at least about about 95%, 96%, 97%, 98%, 99% or 100% identical to the amino acid sequence of SEQ ID NO:47, and a VL comprising an amino acid sequence that is at least about 95%, 96%, 97%, 98%, 99% or 100% identical to the amino acid sequence of SEQ ID NO:48.

Particularly, provided is a bispecific antigen binding molecule, wherein the moiety capable of specific binding to OX40 comprises a VH comprising the amino acid sequence of SEQ ID NO:47 and a VL comprising the amino acid sequence of SEQ ID NO:48.

Bispecific Antigen Binding Molecules Binding to EpCAM

In one aspect, the invention provides bispecific antigen binding molecules, wherein the moiety capable of specific binding to epithelial cell adhesion molecule (EpCAM) binds to a polypeptide comprising, or consisting of, the amino acid sequence of SEQ ID NO:49.

In one aspect, provided is a bispecific antigen binding molecule, comprising at least one moiety capable of specific binding to EpCAM, wherein said moiety comprises a VH comprising
(i) a CDR-H1 comprising the amino acid sequence SEQ ID NO:51,
(ii) a CDR-H2 comprising the amino acid sequence SEQ ID NO:52, and
(iii) a CDR-H3 comprising the amino acid sequence SEQ ID NO:53, and a VL comprising
(iv) a CDR-L1 comprising the amino acid sequence SEQ ID NO:54,
(v) a CDR-L2 comprising the amino acid sequence SEQ ID NO:55, and
(vi) a CDR-L3 comprising the amino acid sequence SEQ ID NO:56.

In another aspect, provided is a bispecific antigen binding molecule, wherein the moiety capable of specific binding to EpCAM comprises a VH comprising an amino acid sequence that is at least about 95%, 96%, 97%, 98%, 99% or 100% identical to the amino acid sequence of SEQ ID NO:63, and a VL comprising an amino acid sequence that is at least about 95%, 96%, 97%, 98%, 99% or 100% identical to the amino acid sequence of SEQ ID NO:64.

Particularly provided is a bispecific antigen binding molecule, wherein the moiety capable of specific binding to EpCAM comprises a VH comprising the amino acid sequence of SEQ ID NO:63 and a VL comprising the amino acid sequence of SEQ ID NO:64.

In one aspect, the invention provides bispecific antigen binding molecules, wherein the moiety capable of specific binding to epithelial cell adhesion molecule (EpCAM) binds to a polypeptide comprising, or consisting of, the amino acid sequence of SEQ ID NO:50.

In one aspect, provided is a bispecific antigen binding molecule, comprising at least one moiety capable of specific binding to EpCAM, wherein said moiety comprises a VH comprising
(i) a CDR-H1 comprising the amino acid sequence SEQ ID NO:57,
(ii) a CDR-H2 comprising the amino acid sequence SEQ ID NO:58, and
(iii) a CDR-H3 comprising the amino acid sequence SEQ ID NO:59,
and a VL comprising
(iv) a CDR-L1 comprising the amino acid sequence SEQ ID NO:60,
(v) a CDR-L2 comprising the amino acid sequence SEQ ID NO:61, and
(vi) a CDR-L3 comprising the amino acid sequence SEQ ID NO:62.

In another aspect, the invention provides a bispecific antigen binding molecule, wherein the moiety capable of specific binding to EpCAM comprises a VH comprising an amino acid sequence that is at least about about 95%, 96%, 97%, 98%, 99% or 100% identical to the amino acid sequence of SEQ ID NO:65, and a VL comprising an amino acid sequence that is at least about 95%, 96%, 97%, 98%, 99% or 100% identical to the amino acid sequence of SEQ ID NO:66.

Particularly, provided is a bispecific antigen binding molecule, wherein the moiety capable of specific binding to EpCAM comprises a VH comprising the amino acid sequence of SEQ ID NO:65 and a VL comprising the amino acid sequence of SEQ ID NO:66.

Bispecific Antigen Binding Molecules Binding to OX40 and EpCAM

In a further aspect, provided is a bispecific antigen binding molecule, wherein
(i) the moiety capable of specific binding to OX40 comprises a VH comprising an amino acid sequence that is at least about 95%, 96%, 97%, 98%, 99% or 100% identical to the amino acid sequence of SEQ ID NO:33, SEQ ID NO: 35, SEQ ID NO:37, SEQ ID NO:39, SEQ ID NO:41, SEQ ID NO:43 and SEQ ID NO:45 and a VL comprising an amino acid sequence that is at least about 95%, 96%, 97%, 98%, 99% or 100% identical to an amino acid sequence selected from the group consisting of SEQ ID NO:34, SEQ ID NO: 36, SEQ ID NO:38, SEQ ID NO:40, SEQ ID NO:42, SEQ ID NO:44 and SEQ ID NO:46, and
(ii) the moiety capable of specific binding to EpCAM comprises a VH comprising an amino acid sequence that is at least about 95%, 96%, 97%, 98%, 99% or 100% identical to the amino acid sequence of SEQ ID NO:63, and a VL comprising an amino acid sequence that is at least about 95%, 96%, 97%, 98%, 99% or 100% identical to the amino acid sequence of SEQ ID NO:64.

In a particular aspect, provided is a bispecific antigen binding molecule, wherein
(a) the moiety capable of specific binding to OX40 comprises a VH comprising the amino acid sequence of SEQ ID NO:33 and a VL comprising the amino acid sequence of SEQ ID NO:34 and the moiety capable of specific binding to EpCAM comprises a VH comprising the amino acid sequence of SEQ ID NO:63 and a VL comprising the amino acid sequence of SEQ ID NO:64,
(b) the moiety capable of specific binding to OX40 comprises a VH comprising the amino acid sequence of SEQ ID NO:35 and a VL comprising the amino acid sequence of SEQ ID NO:36 and the moiety capable of specific binding to EpCAM comprises a VH comprising the amino acid sequence of SEQ ID NO:63 and a VL comprising the amino acid sequence of SEQ ID NO:64,
(c) the moiety capable of specific binding to OX40 comprises a VH comprising the amino acid sequence of SEQ ID NO:37 and a VL comprising the amino acid sequence of SEQ TD NO:38 and the moiety capable of specific binding to EpCAM comprises a VH comprising the amino acid sequence of SEQ ID NO:63 and a VL comprising the amino acid sequence of SEQ ID NO:64,
(d) the moiety capable of specific binding to OX40 comprises a VH comprising the amino acid sequence of SEQ ID NO:39 and a VL comprising the amino acid sequence of SEQ ID NO:40 and the moiety capable of specific binding to EpCAM comprises a VH comprising the amino acid sequence of SEQ ID NO:63 and a VL comprising the amino acid sequence of SEQ ID NO:64,
(e) the moiety capable of specific binding to OX40 comprises a VH comprising the amino acid sequence of SEQ ID NO:41 and a VL comprising the amino acid sequence of SEQ ID NO:42 and the moiety capable of specific binding to EpCAM comprises a VH comprising the amino acid sequence of SEQ ID NO:63 and a VL comprising the amino acid sequence of SEQ ID NO:64,
(f) the moiety capable of specific binding to OX40 comprises a VH comprising the amino acid sequence of SEQ ID NO:43 and a VL comprising the amino acid sequence of SEQ ID NO:44 and the moiety capable of specific binding to EpCAM comprises a VH comprising the amino acid sequence of SEQ ID NO:63 and a VL comprising the amino acid sequence of SEQ ID NO:64,
(g) the moiety capable of specific binding to OX40 comprises a VH comprising the amino acid sequence of SEQ ID NO:45 and a VL comprising the amino acid sequence of SEQ ID NO:46 and the moiety capable of specific binding to EpCAM comprises a VH comprising the amino acid sequence of SEQ ID NO:63 and a VL comprising the amino acid sequence of SEQ ID NO:64.

In a particular aspect, the invention provides a bispecific antigen binding molecule,
wherein
the moiety capable of specific binding to OX40 comprises a VH comprising the amino acid sequence of SEQ ID NO:35 and a VL comprising the amino acid sequence of SEQ ID NO:36, and
the moiety capable of specific binding to EpCAM comprises a VH comprising the amino acid sequence of SEQ ID NO:63 and a VL comprising the amino acid sequence of SEQ ID NO:64.

In a further aspect, provided is a bispecific antigen binding molecule, wherein
(i) the moiety capable of specific binding to OX40 comprises a VH comprising an amino acid sequence that is at least about 95%, 96%, 97%, 98%, 99% or 100% identical to the amino acid sequence of SEQ ID NO:47, and a VL comprising an amino acid sequence that is at least about 95%, 96%, 97%, 98%, 99% or 100% identical to the amino acid sequence of SEQ ID NO:48 and
(ii) the moiety capable of specific binding to EpCAM comprises a VH comprising an amino acid sequence that is at least about 95%, 96%, 97%, 98%, 99% or 100% identical to the amino acid sequence of SEQ ID NO:65, and a VL comprising an amino acid sequence that is at least about 95%, 96%, 97%, 98%, 99% or 100% identical to the amino acid sequence of SEQ ID NO:66.

In a particular aspect, provided is a bispecific antigen binding molecule, wherein
the moiety capable of specific binding to OX40 comprises a VH comprising the amino acid sequence of SEQ ID NO:47 and a VL comprising the amino acid sequence of SEQ ID NO:48, and
the moiety capable of specific binding to EpCAM comprises a VH comprising the amino acid sequence of SEQ ID NO:65 and a VL comprising the amino acid sequence of SEQ ID NO:66.

Bispecific Antigen Binding Molecules Having Tetravalent Binding to OX40, and Monovalent Binding to EpCAM (4+1 Format)

In one aspect, the bispecific antigen binding molecule is tetravalent for OX40 and monovalent for EpCAM.

In one aspect, the bispecific antigen binding molecule of the invention comprises
(a) four Fab fragments capable of specific binding to OX40 connected to a Fc region, and
(b) a moiety capable of specific binding to EpCAM comprising an antibody light chain variable region (VL) and an antibody heavy chain variable region (VH) connected to the C-terminus of the Fc region.

In one aspect, the bispecific antigen binding molecule of the invention comprises
(a) two light chains and two heavy chains of an antibody comprising four Fab fragments capable of specific binding to OX40, and a Fc region, and
(b) a VH and a VL of a moiety capable specific binding to EpCAM, wherein the VH is connected to the C-terminus of one of the two heavy chains of (a), and wherein the VL is connected to the C-terminus of the other of the two heavy chains of (a).

In one aspect, the bispecific antigen binding molecule of the invention comprises
(a) two heavy chains, each heavy chain comprising two VH domains and two CH1 domains of a Fab fragment capable of specific binding to OX40 and a Fc region subunit,
(b) four light chains, each light chain comprising a VL and CL domain of a Fab fragment capable of specific binding to OX40, and
(c) a VH and a VL of a moiety capable specific binding to EpCAM, wherein the VH is connected to the C-terminus of one of the two heavy chains of (a), and wherein the VL is connected to the C-terminus of the other of the two heavy chains of (a).

In some embodiments in accordance with various aspects of the present invention, the VH of a moiety capable specific binding to EpCAM is connected to the C-terminus of one of the two heavy chains of (a) via a peptide linker. In some embodiments in accordance with various aspects of the present invention, the VL of a moiety capable specific binding to EpCAM is connected to the C-terminus of one of the two heavy chains of (a) via a peptide linker. In particular embodiments, the peptide linker is (G4S)$_4$ (SEQ ID NO:81).

In a particular aspect, the invention provides a bispecific antigen binding molecule comprising a first heavy chain comprising the amino acid sequence of SEQ ID NO:183, a second heavy chain comprising the amino acid sequence of SEQ ID NO:184, and a light chain comprising the amino acid sequence of SEQ ID NO:182.

In a particular aspect, the invention provides a bispecific antigen binding molecule comprising
a first heavy chain comprising the amino acid sequence of SEQ ID NO:183,
a second heavy chain comprising the amino acid sequence of SEQ ID NO:184, and four light chains, each comprising the amino acid sequence of SEQ ID NO:182.

In a particular aspect, the invention provides a bispecific antigen binding molecule comprising a first heavy chain comprising the amino acid sequence of SEQ ID NO:192, a second heavy chain comprising the amino acid sequence of SEQ ID NO:193, and a light chain comprising the amino acid sequence of SEQ ID NO:191.

In a particular aspect, the invention provides a bispecific antigen binding molecule comprising a first heavy chain comprising the amino acid sequence of SEQ ID NO:192, a second heavy chain comprising the amino acid sequence of SEQ ID NO:193, and four light chains, each comprising the amino acid sequence of SEQ ID NO:191.

In one aspect, the bispecific antigen binding molecule of the invention comprises a first and a second heavy chain and four light chains that form a first, a second, a third, a forth, and a fifth antigen binding moiety, wherein the first, the second, the third, and the fourth antigen binding moiety each are capable of specific binding to OX40 and the fifth antigen binding moiety is capable of specific binding to EpCAM, wherein (i) the first polypeptide chain comprises in amino (N)-terminal to carboxyl (C)-terminal direction, VH(OX40), CH1, VH(OX40), CH1, CH2, CH3 (Fc knob) and VH(EpCAM), (ii) the second polypeptide chain comprises in N-terminal to C-terminal direction, VH(OX40), CH1, VH(OX40), CH1, CH2, CH3(Fc hole) and VL(EpCAM), and (iii) four light chains comprise in N-terminal to C-terminal direction VL(OX40) and CL.

In another aspect, the bispecific antigen binding molecule of the invention comprises a first and a second heavy chain and four light chains that form a first, a second, a third, a forth, and a fifth antigen binding moiety, wherein the first, the second, the third, and the fourth antigen binding moiety each are capable of specific binding to OX40 and the fifth antigen binding moiety is capable of specific binding to EpCAM, wherein (i) the first polypeptide chain comprises in amino (N)-terminal to carboxyl (C)-terminal direction, VH(OX40), CH1, VH(OX40), CH1, CH2, CH3 (Fc knob) and VL(EpCAM), (ii) the second polypeptide chain comprises in N-terminal to C-terminal direction, VH(OX40), CH1, VH(OX40), CH1, CH2, CH3(Fc hole) and VH(EpCAM), and (iii) the four light chains comprise in N-terminal to C-terminal direction VL(Ox40) and CL.

Bispecific Antigen Binding Molecules Having Tetravalent Binding to OX40, and Bivalent Binding to EpCAM (4+2 Format)

In one aspect, the bispecific antigen binding molecule is tetravalent for OX40 and bivalent for EpCAM.

In one aspect, the bispecific antigen binding molecule of the invention comprises (a) four Fab fragments capable of specific binding to OX40 connected to a Fc region, and (b) a moiety capable of specific binding to EpCAM comprising an antibody light chain variable region (VL) and an antibody heavy chain variable region (VH) connected to the C-terminus of the Fc region.

In one aspect, the bispecific antigen binding molecule of the invention comprises (a) four light chains and two heavy chains of an antibody comprising four Fab fragments capable of specific binding to OX40, and a Fc region, and (b) two Fab fragments capable of specific binding to EpCAM, wherein one of the Fab fragments is connected to the C-terminus of one of the two heavy chains of (a), and the other of the Fab fragments is connected to the C-terminus of the other of the two heavy chains of (a).

In one aspect, the bispecific antigen binding molecule of the invention comprises (a) two heavy chains, each heavy chain comprising two VH domains and two CH1 domains of a Fab fragment capable of specific binding to OX40 and a Fc region subunit, (b) four light chains, each light chain comprising a VL and CL domain of a Fab fragment capable of specific binding to OX40, and (c) two Fab fragments capable of specific binding to EpCAM, wherein one of the Fab fragments is connected to the C-terminus of one of the two heavy chains of (a), and the other of the Fab fragments is connected to the C-terminus of the other of the two heavy chains of (a).

In some embodiments, the two Fab fragments capable of specific binding to EpCAM are crossover Fab fragments each comprising a VL-CH1 chain and a VH-CL chain, and wherein one of the VL-CH1 chains is connected to the C-terminus of one of the two heavy chains of (a), and the other of the VL-CH1 chains is connected to the C-terminus of the other of the two heavy chains of (a).

In some embodiments in accordance with various aspects of the present invention, Fab fragments capable of specific binding to EpCAM are connected to the C-terminus of the heavy chains of (a) via a peptide linker. In some embodiments in accordance with various aspects of the present invention, the VL-CH1 chain of a crossover Fab fragment capable of specific binding to EpCAM is connected to the C-terminus of one of the two heavy chains of (a) via a peptide linker.

In particular embodiments, the peptide linker is $(G4S)_4$ (SEQ ID NO:81).

In a particular aspect, the invention provides a bispecific antigen binding molecule comprising two heavy chains, each comprising the amino acid sequence of SEQ ID NO:186, a first light chain comprising the amino acid sequence of SEQ ID NO:185, and a second light chain comprising the amino acid sequence of SEQ ID NO:187.

In a particular aspect, the invention provides a bispecific antigen binding molecule comprising two heavy chains, each comprising the amino acid sequence of SEQ ID NO:186, two light chains, each comprising the amino acid sequence of SEQ ID NO:187, and four light chains, each comprising the amino acid sequence of SEQ ID NO:185.

In one aspect, the bispecific antigen binding molecule of the invention comprises a first and a second heavy chain and six light chains that form a first, a second, a third, a forth, a fifth, and a sixth antigen binding moiety, wherein the first, the second, the third, and the fourth antigen binding moiety each are capable of specific binding to OX40, and wherein the fifth and the sixth antigen binding moiety each are capable of specific binding to EpCAM, wherein (i) the first and the second polypeptide chains comprise in amino (N)-terminal to carboxyl (C)-terminal direction, VH(OX40), CH1*, VH(OX40), CH1*, CH2, CH3, VL(EpCAM) and CH1,
(ii) four light chains comprise in N-terminal to C-terminal direction VL(OX40) and CL*, and
(iii) two light chains comprise in N-terminal to C-terminal direction VH(EpCAM) and CL and wherein CH1* and CL* comprise amino acid mutations to allow better pairing.

Fc Region Modifications Reducing Fc Receptor Binding and/or Effector Function

In embodiments in accordance with various aspects of the present invention, the bispecific antigen binding molecules further comprise a Fc region composed of a first and a second subunit capable of stable association.

In certain aspects, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

The Fc region confers favorable pharmacokinetic properties to the bispecific antibodies of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells. Accordingly, in particular embodiments the Fc region of the bispecific antibodies of the invention exhibits reduced binding affinity to an Fc receptor and/or reduced effector function, as compared to a native IgG Fc region, in particular an IgG1 Fc region or an IgG4 Fc region. More particularly, the Fc region is an IgG1 Fc region.

In one such aspect the Fc region (or the bispecific antigen binding molecule of the invention comprising said Fc region) exhibits less than 50%, preferably less than 20%, more preferably less than 10% and most preferably less than 5% of the binding affinity to an Fc receptor, as compared to a native IgG1 Fc region (or the bispecific antigen binding molecule of the invention comprising a native IgG1 Fc region), and/or less than 50%, preferably less than 20%, more preferably less than 10% and most preferably less than 5% of the effector function, as compared to a native IgG1 Fc region (or the bispecific antigen binding molecule of the invention comprising a native IgG1 Fc region). In one aspect, the Fc region (or the bispecific antigen binding molecule of the invention comprising said Fc region) does not substantially bind to an Fc receptor and/or induce effector function. In a particular aspect the Fc receptor is an Fcγ receptor. In one aspect, the Fc receptor is a human Fc receptor. In one aspect, the Fc receptor is an activating Fc receptor. In a specific aspect, the Fc receptor is an activating human Fcγ receptor, more specifically human FcγRIIIa, FcγRI or FcγRIIa, most specifically human FcγRIIIa. In one aspect, the Fc receptor is an inhibitory Fc receptor. In a specific aspect, the Fc receptor is an inhibitory human Fcγ receptor, more specifically human FcγRIIB. In one aspect the effector function is one or more of CDC, ADCC, ADCP, and cytokine secretion. In a particular aspect, the effector function is ADCC. In one aspect, the Fc region domain exhibits substantially similar binding affinity to neonatal Fc receptor (FcRn), as compared to a native IgG1 Fc region. Substantially similar binding to FcRn is achieved when the Fc region (or the bispecific antigen binding molecule of the invention comprising said Fc region) exhibits greater than about 70%, particularly greater than about 80%, more particularly greater than about 90% of the binding affinity of a native IgG1 Fc region (or the bispecific antigen binding molecule of the invention comprising a native IgG1 Fc region) to FcRn.

In a particular aspect, the Fc region is engineered to have reduced binding affinity to an Fc receptor and/or reduced effector function, as compared to a non-engineered Fc region. In a particular aspect, the Fc region of the bispecific antigen binding molecule of the invention comprises one or more amino acid mutation that reduces the binding affinity of the Fc region to an Fc receptor and/or effector function. Typically, the same one or more amino acid mutation is present in each of the two subunits of the Fc region. In one aspect, the amino acid mutation reduces the binding affinity of the Fc region to an Fc receptor. In another aspect, the amino acid mutation reduces the binding affinity of the Fc region to an Fc receptor by at least 2-fold, at least 5-fold, or at least 10-fold. In one aspect, the bispecific antigen binding molecule of the invention comprising an engineered Fc region exhibits less than 20%, particularly less than 10%, more particularly less than 5% of the binding affinity to an Fc receptor as compared to bispecific antibodies of the invention comprising a non-engineered Fc region. In a particular aspect, the Fc receptor is an Fcγ receptor. In other aspects, the Fc receptor is a human Fc receptor. In one aspect, the Fc receptor is an inhibitory Fc receptor. In a specific aspect, the Fc receptor is an inhibitory human Fcγ receptor, more specifically human FcγRIIB. In some aspects the Fc receptor is an activating Fc receptor. In a specific aspect, the Fc receptor is an activating human Fcγ receptor, more specifically human FcγRIIIa, FcγRI or FcγRIIa, most specifically human FcγRIIIa. Preferably, binding to each of these receptors is reduced. In some aspects, binding affinity to a complement component, specifically binding affinity to C1q, is also reduced. In one aspect, binding affinity to neonatal Fc receptor (FcRn) is not reduced. Substantially similar binding to FcRn, i.e. preservation of the binding affinity of the Fc region to said receptor, is achieved when the Fc region (or the bispecific antigen binding molecule of the invention comprising said Fc region) exhibits greater than about 70% of the binding affinity of a non-engineered form of the Fc region (or the bispecific antigen binding molecule of the invention comprising said non-engineered form of the Fc region) to FcRn. The Fc region, or the bispecific antigen binding molecule of the invention comprising said Fc region, may exhibit greater than about 80% and even greater than about 90% of such affinity. In certain embodiments the Fc region of the bispecific antigen binding molecule of the invention is engineered to have reduced effector function, as compared to a non-engineered Fc region. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581). Certain antibody variants with improved or diminished binding to FcRs are described. (e.g. U.S. Pat. No. 6,737,056; WO 2004/056312, and Shields, R. L. et al., J. Biol. Chem. 276 (2001) 6591-6604).

In one aspect of the invention, the Fc region comprises an amino acid substitution at a position of E233, L234, L235, N297, P331 and P329. In some aspects, the Fc region comprises the amino acid substitutions L234A and L235A ("LALA"). In one such embodiment, the Fc region is an IgG1 Fc region, particularly a human IgG1 Fc region. In one aspect, the Fc region comprises an amino acid substitution at position P329. In a more specific aspect, the amino acid substitution is P329A or P329G, particularly P329G. In one embodiment the Fc region comprises an amino acid substitution at position P329 and a further amino acid substitution selected from the group consisting of E233P, L234A, L235A, L235E, N297A, N297D or P331S. In more particular embodiments the Fc region comprises the amino acid mutations L234A, L235A and P329G ("P329G LALA"). The "P329G LALA" combination of amino acid substitutions almost completely abolishes Fcγ receptor binding of a human IgG1 Fc region, as described in PCT Patent Application No. WO 2012/130831 A1. Said document also describes methods of preparing such mutant Fc regions and methods for determining its properties such as Fc receptor binding or effector functions such antibody is an IgG1 with mutations L234A and L235A or with mutations L234A, L235A and P329G (numbering according to EU index of Kabat et al, Kabat et al., Sequences of Proteins of Immunological Interest, 5th Ed. Public Health Service, National Institutes of Health, Bethesda, Md., 1991).

In one aspect of the invention, the Fc region comprises an amino acid substitution at positions D265, and P329. In some aspects, the Fc region comprises the amino acid substitutions D265A and P329G ("DAPG") in the CH2 domain. In one such embodiment, the Fc region is an IgG1 Fc region, particularly a mouse IgG1 Fc region. DAPG mutations are described e.g. in WO 2016/030350 A1, and can be introduced in CH2 regions of heavy chains to abrogate binding of antigen binding molecules to murine Fc gamma receptors.

In one aspect, the Fc region is an IgG4 Fc region. In a more specific embodiment, the Fc region is an IgG4 Fc region comprising an amino acid substitution at position S228 (Kabat numbering), particularly the amino acid substitution S228P. In a more specific embodiment, the Fc region is an IgG4 Fc region comprising amino acid substitutions L235E and S228P and P329G. This amino acid substitution reduces in vivo Fab arm exchange of IgG4 antibodies (see Stubenrauch et al., Drug Metabolism and Disposition 38, 84-91 (2010)).

Antibodies with increased half lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan, A. R. and Winter, G., Nature 322 (1988) 738-740; U.S. Pat. Nos. 5,648,260; 5,624,821; and WO 94/29351 concerning other examples of Fc region variants.

Binding to Fc receptors can be easily determined e.g. by ELISA, or by Surface Plasmon Resonance (SPR) using standard instrumentation such as a BIACORE® instrument (GE Healthcare), and Fc receptors such as may be obtained by recombinant expression. A suitable such binding assay is described herein. Alternatively, binding affinity of Fc regions or cell activating bispecific antigen binding molecules comprising an Fc region for Fc receptors may be evaluated using cell lines known to express particular Fc receptors, such as human NK cells expressing FcγIIIa receptor. Effector function of an Fc region, or bispecific antibodies of the invention comprising an Fc region, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

The following section describes preferred aspects of the bispecific antigen binding molecules of the invention comprising Fc region modifications reducing Fc receptor binding and/or effector function. In one aspect, the invention relates to the bispecific antigen binding molecule (a) at least one moiety capable of specific binding to OX40, (b) at least one moiety capable of specific binding to EpCAM, and (c) a Fc region composed of a first and a second subunit capable of stable association, wherein the Fc region comprises one or more amino acid substitution that reduces the binding affinity of the antibody to an Fc receptor, in particular towards Fcγ receptor. In another aspect, the invention relates to the bispecific antigen binding molecule comprising (a) at least one moiety capable of specific binding to OX40, (b) at least one moiety capable of specific binding to EpCAM, and (c) a Fc region composed of a first and a second subunit capable of stable association, wherein the Fc region comprises one or more amino acid substitution that reduces effector function. In particular aspect, the Fc region is of human IgG1 subclass with the amino acid mutations L234A, L235A and P329G (numbering according to Kabat EU index). In particular aspect, the Fc region is of mouse IgG1 subclass with the amino acid mutations D265A and P329G.

Fc Region Modifications Promoting Heterodimerization

The bispecific antigen binding molecules of the invention comprise different antigen-binding sites, fused to one or the other of the two subunits of the Fc region, thus the two subunits of the Fc region may be comprised in two non-identical polypeptide chains. Recombinant co-expression of these polypeptides and subsequent dimerization leads to several possible combinations of the two polypeptides. To improve the yield and purity of the bispecific antibodies of the invention in recombinant production, it will thus be advantageous to introduce in the Fc region of the bispecific antigen binding molecules of the invention a modification promoting the association of the desired polypeptides.

Accordingly, in particular aspects the invention relates to the bispecific antigen binding molecule comprising (a) at least one moiety capable of specific binding to OX40, (b) at least one moiety capable of specific binding to EpCAM, and (c) a Fc region composed of a first and a second subunit capable of stable association, wherein the Fc region comprises a modification promoting the association of the first and second subunit of the Fc region. The site of most extensive protein-protein interaction between the two subunits of a human IgG Fc region is in the CH3 domain of the Fc region. Thus, in one aspect said modification is in the CH3 domain of the Fc region.

In a specific aspect said modification is a so-called "knob-into-hole" modification, comprising a "knob" modification in one of the two subunits of the Fc region and a "hole" modification in the other one of the two subunits of the Fc region. Thus, the invention relates to the bispecific antigen binding molecule comprising (a) at least one moiety capable of specific binding to OX40, (b) at least one moiety capable of specific binding to EpCAM, and (c) a Fc region composed of a first and a second subunit capable of stable association, wherein the first subunit of the Fc region comprises knobs and the second subunit of the Fc region comprises holes according to the knobs into holes method. In a particular aspect, the first subunit of the Fc region comprises the amino acid substitutions S354C and T366W (EU numbering) and the second subunit of the Fc region comprises the amino acid substitutions Y349C, T366S and Y407V (numbering according to Kabat EU index).

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in one aspect, in the CH3 domain of the first subunit of the Fc region of the bispecific antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc region an amino acid residue is replaced with an amino acid residue having a smaller side chain volume, thereby generating a cavity within the CH3 domain of the second subunit within which the protuberance within the CH3 domain of the first subunit is positionable. The protuberance and cavity can be made by altering the nucleic acid encoding the polypeptides, e.g. by site-specific mutagenesis, or by peptide synthesis. In a specific aspect, in the CH3 domain of the first subunit of the Fc region the threonine residue at position 366 is replaced with a tryptophan residue (T366W), and in the CH3 domain of the second subunit of the Fc region the tyrosine residue at position 407 is replaced with a valine residue (Y407V). In one aspect, in the second subunit of the Fc region additionally the threonine residue at position 366 is replaced with a serine residue (T366S) and the leucine residue at position 368 is replaced with an alanine residue (L368A).

In yet a further aspect, in the first subunit of the Fc region additionally the serine residue at position 354 is replaced with a cysteine residue (S354C), and in the second subunit of the Fc region additionally the tyrosine residue at position 349 is replaced by a cysteine residue (Y349C). Introduction of these two cysteine residues results in formation of a disulfide bridge between the two subunits of the Fc region, further stabilizing the dimer (Carter (2001), J Immunol Methods 248, 7-15). In a particular aspect, the first subunit of the Fc region comprises the amino acid substitutions S354C and T366W (EU numbering) and the second subunit of the Fc region comprises the amino acid substitutions Y349C, T366S and Y407V (numbering according to Kabat EU index).

In a further aspect, the first subunit of the Fc region comprises aspartic acid residues (D) at positions 392 and 409, and the second subunit of the Fc region comprises lysine residues (K) at positions 356 and 399. In some embodiments, in the first subunit of the Fc region the lysine residues at positions 392 and 409 are replaced with aspartic acid residues (K392D, K409D), and in the second subunit of the Fc region the glutamate residue at position 356 and the aspartic acid residue at position 399 are replaced with lysine residues (E356K, D399K). "DDKK" knob-into-hole technology is described e.g. in WO 2014/131694 A1, and favours the assembly of the heavy chains bearing subunits providing the complementary amino acid residues.

In an alternative aspect, a modification promoting association of the first and the second subunit of the Fc region comprises a modification mediating electrostatic steering effects, e.g. as described in PCT publication WO 2009/089004. Generally, this method involves replacement of one or more amino acid residues at the interface of the two Fc region subunits by charged amino acid residues so that homodimer formation becomes electrostatically unfavorable but heterodimerization electrostatically favorable.

The C-terminus of the heavy chain of the bispecific antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG. In one aspect of all aspects as reported herein, a bispecific antibody comprising a heavy chain including a C-terminal CH3 domain as specified herein, comprises the C-terminal glycine-lysine dipeptide (G446 and K447, numbering according to Kabat EU index).

In one embodiment of all aspects as reported herein, a bispecific antibody comprising a heavy chain including a C-terminal CH3 domain, as specified herein, comprises a C-terminal glycine residue (G446, numbering according to Kabat EU index).

Modifications in the Fab Domains

In one aspect, the invention relates to a bispecific antigen binding molecule comprising (a) a first Fab fragment capable of specific binding to OX40, (b) a second Fab fragment capable of specific binding to EpCAM, and (c) a Fc region composed of a first and a second subunit capable of stable association, wherein in one of the Fab fragments either the variable domains VH and VL or the constant domains CH1 and CL are exchanged. The bispecific antibodies are prepared according to the Crossmab technology.

Multispecific antibodies with a domain replacement/exchange in one binding arm (CrossMabVH-VL or CrossMabCH-CL) are described in detail in WO2009/080252 and Schaefer, W. et al, PNAS, 108 (2011) 11187-1191. They clearly reduce the byproducts caused by the mismatch of a light chain against a first antigen with the wrong heavy chain against the second antigen (compared to approaches without such domain exchange).

In one aspect, the invention relates to a bispecific antigen binding molecule comprising (a) a first Fab fragment capable of specific binding to OX40, (b) a second Fab fragment capable of specific binding to EpCAM, and (c) a Fc region composed of a first and a second subunit capable of stable association, wherein in one of the Fab fragments the constant domains CL and CH1 are replaced by each other so that the CH1 domain is part of the light chain and the CL domain is part of the heavy chain. More particularly, in the second Fab fragment capable of specific binding to EpCAM the constant domains CL and CH1 are replaced by each other so that the CH1 domain is part of the light chain and the CL domain is part of the heavy chain.

In a particular aspect, the invention relates a bispecific antigen binding molecule comprising (a) a first Fab fragment capable of specific binding to OX40, (b) a second Fab fragment capable of specific binding to EpCAM, wherein the constant domains CL and CH1 are replaced by each other so that the CH1 domain is part of the light chain and the CL domain is part of the heavy chain. Such a molecule is called a monovalent bispecific antigen binding molecule.

In another aspect, the invention relates to a bispecific antigen binding molecule, comprising (a) two light chains and two heavy chains of an antibody comprising two Fab fragments capable of specific binding to OX40 and the Fc region, and (b) two additional Fab fragments capable of specific binding to EpCAM, wherein said additional Fab fragments are each connected via a peptide linker to the C-terminus of the heavy chains of (a). In a particular aspect, the additional Fab fragments are Fab fragments, wherein the variable domains VL and VH are replaced by each other so that the VH is part of the light chain and the VL is part of the heavy chain.

Thus, in a particular aspect, the invention comprises a bispecific, antigen binding molecule, comprising (a) two light chains and two heavy chains of an antibody comprising two Fab fragments capable of specific binding to OX40 and the Fc region, and (b) two additional Fab fragments capable of specific binding to EpCAM, wherein said two additional Fab fragments capable of specific binding to a EpCAM are crossover Fab fragments wherein the variable domains VL and VH are replaced by each other and the VL-CH chains are each connected via a peptide linker to the C-terminus of the heavy chains of (a).

In another aspect, and to further improve correct pairing, the bispecific antigen binding molecule comprising (a) a first Fab fragment capable of specific binding to OX40, (b) a second Fab fragment capable of specific binding to EpCAM, and (c) a Fc region composed of a first and a second subunit capable of stable association, can contain different charged amino acid substitutions (so-called "charged residues"). These modifications are introduced in the crossed or non-crossed CH1 and CL domains. In a particular aspect, the invention relates to a bispecific antigen binding molecule, wherein in one of CL domains the amino acid at position 123 (EU numbering) has been replaced by arginine (R) and the amino acid at position 124 (EU numbering) has been substituted by lysine (K) and wherein in one of the CH1 domains the amino acids at position 147 (EU numbering) and at position 213 (EU numbering) have been substituted by glutamic acid (E).

More particularly, the invention relates to a bispecific antigen binding molecule comprising a Fab, wherein in the CL domain the amino acid at position 123 (EU numbering) has been replaced by arginine (R) and the amino acid at position 124 (EU numbering) has been substituted by lysine (K), and wherein in the CH1 domain the amino acids at position 147 (EU numbering) and at position 213 (EU numbering) have been substituted by glutamic acid (E).

Accordingly, in some embodiments one or more of the Fab fragments (e.g. Fab fragments capable of specific binding to OX40) of the bispecific antigen binding molecule of the present invention comprise a CL domain comprising an arginine (R) at amino acid at position 123 (EU numbering) and a lysine (K) at amino acid at position 124 (EU numbering), and a CH1 domain comprising a glutamic acid (E) at amino acid at position 147 (EU numbering) and a glutamic acid (E) at amino acid at position 213 (EU numbering).

Polynucleotides

The invention further provides isolated polynucleotides encoding a bispecific antigen binding molecule of the invention as described herein, or a fragment thereof.

The isolated polynucleotides encoding bispecific antigen binding molecules of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of a moiety capable of specific binding to EpCAM may be encoded by a separate polynucleotide from the heavy chain portion of the capable of specific binding to EpCAM. When co-expressed, the heavy chain polypeptides will associate with the light chain polypeptides to form the moiety capable of specific binding to EpCAM. Similarly, the light chain portion of a moiety capable of specific binding to OX40 may be encoded by a separate polynucleotide from the heavy chain portion of the capable of specific binding to OX40. When co-expressed, the heavy chain polypeptides will associate with the light chain polypeptides to form the moiety capable of specific binding to OX40.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

According to another aspect of the invention, there is provided an isolated polynucleotide encoding a bispecific antigen binding molecule as defined herein before or a fusion polypeptide as described herein before. The invention further provides a vector, particularly an expression vector, comprising the isolated polynucleotide of the invention and a host cell comprising the isolated polynucleotide or the vector of the invention. In some embodiments the host cell is a eukaryotic cell, particularly a mammalian cell.

In another aspect, provided is a method for producing the bispecific antigen binding molecule of the invention, comprising the steps of (i) culturing the host cell of the invention under conditions suitable for expression of said antigen binding molecule, and (ii) isolating said bispecific antigen binding molecule. The invention also encompasses a bispecific antigen binding molecule produced by the method of the invention.

Recombinant Methods

Bispecific antigen binding molecules of the invention may be obtained, for example, by solid-state peptide synthesis (e.g. Merrifield solid phase synthesis) or recombinant production. For recombinant production one or more polynucleotide encoding the antigen binding molecule or polypeptide fragments thereof, e.g., as described above, is isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the bispecific antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the bispecific antigen binding molecule or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the bispecific antigen binding molecule of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit α-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the bispecific antigen binding molecule or polypeptide fragments thereof is desired, DNA encoding a signal sequence may be placed upstream of the nucleic acid encoding a bispecific antigen binding molecule of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the fusion protein may be included within or at the ends of the polynucleotide encoding a bispecific antigen binding molecule of the invention or polypeptide fragments thereof.

In a further aspect of the invention, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one aspect, a host cell comprises (e.g. has been transformed or transfected with) a vector comprising a polynucleotide that encodes (part of) a bispecific antigen binding molecule of the invention. As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as E. coli, or various eukaryotic cells, such as Chinese hamster ovary cells (CHO), human embryonic kidney (HEK) cells, insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr− CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., YO, NS0, Sp20 cell). Standard technologies are known in the art to express foreign genes in these systems. Cells expressing a polypeptide comprising either the heavy or the light chain of an antigen binding domain, may be engineered so as to also express the other of the immunoglobulin chains such that the expressed product is an antigen binding domain that has both a heavy and a light chain.

In another aspect, provided is a method for producing the bispecific antigen binding molecule of the invention, comprising the steps of (i) culturing the host cell of the invention under conditions suitable for expression of said antigen binding molecule, and (ii) isolating said bispecific antigen binding molecule form the host cell or host cell culture medium.

The components of the bispecific antigen binding molecule are genetically fused to each other. Bispecific antigen binding molecules can be designed such that its components are fused directly to each other or indirectly through a linker sequence. The composition and length of the linker may be determined in accordance with methods well known in the art and may be tested for efficacy. Examples of linker sequences between different components of bispecific antigen binding molecules are found in the sequences provided herein. Additional sequences may also be included to incorporate a cleavage site to separate the individual components of the fusion if desired, for example an endopeptidase recognition sequence.

In certain embodiments the moieties capable of specific binding to EpCAM (e.g. Fab fragments or scFv) forming part of the antigen binding molecule comprise at least an immunoglobulin variable region capable of binding to EpCAM. Similarly, in certain embodiments, the moieties capable of specific binding to OX40 (e.g. Fab fragments or scFv) forming part of the antigen binding molecule comprise at least an immunoglobulin variable region capable of binding to OX40. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of immunoglobulin can be used in the invention. Non-limiting immunoglobulins useful in the present invention can be of murine, primate, or human origin. If the fusion protein is intended for human use, a chimeric form of immunoglobulin may be used wherein the constant regions of the immunoglobulin are from a human. A humanized or fully human form of the immunoglobulin can also be prepared in accordance with methods well known in the art (see e.g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Particular immunoglobulins according to the invention are human immunoglobulins. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain aspects, the moieties capable of specific binding to the relevant target (e.g. Fab fragments or scFv) comprised in the antigen binding molecules of the present invention are engineered to have enhanced binding affinity according to, for example, the methods disclosed in PCT publication WO 2012/020006 (see Examples relating to affinity maturation) or U.S. Pat. Appl. Publ. No. 2004/0132066. The ability of the antigen binding molecules of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antigen binding molecule that competes with a reference antibody for binding to a particular antigen. In certain embodiments, such a competing antigen binding molecule binds to the same epitope (e.g. a linear or a conformational epitope) that is bound by the reference antigen binding molecule. Detailed exemplary methods for mapping an epitope to which an antigen binding molecule binds are provided in Morris (1996) "Epitope Mapping Protocols", in Methods in Molecular Biology vol. 66 (Humana Press, Totowa, N.J.). In an exemplary competition assay, immobilized antigen is incubated in a solution comprising a first labeled antigen binding molecule that binds to the antigen and a second unlabeled antigen binding molecule that is being tested for its ability to compete with the first antigen binding molecule for binding to the antigen. The second antigen binding molecule may be present in a hybridoma supernatant. As a control, immobilized antigen is incubated in a solution comprising the first labeled antigen binding molecule but not the second unlabeled antigen binding molecule. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antigen binding molecule is competing with the first antigen binding molecule for binding to the antigen. See Harlow and Lane (1988) Antibodies: A Laboratory Manual ch. 14 (Cold Spring Harbor Laboratory, Cold Spring Harbor, N.Y.).

Bispecific antigen binding molecules of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the bispecific antigen binding molecule binds. For example, for affinity chromatography purification of fusion proteins of the invention, a matrix with protein A or protein G may be used. Sequential Protein A or G affinity chromatography and size exclusion chromatography can be used to isolate an antigen binding molecule essentially as described in the Examples. The purity of the bispecific antigen binding molecule or fragments thereof can be determined by any of a variety of well-known analytical methods including gel electrophoresis, high pressure liquid chromatography, and the like. For example, the bispecific antigen binding molecule expressed as described in the Examples were shown to be intact and properly assembled as demonstrated by reducing and non-reducing SDS-PAGE.

The invention also encompasses a bispecific antigen binding molecule produced by the methods of the invention.

Assays

The bispecific antigen binding molecules provided herein may be identified, screened for, or characterized for their physical/chemical properties and/or biological activities by various assays known in the art.

1. Affinity Assays

The affinity of the bispecific antigen binding molecule provided herein for OX40 or EpCAM can be determined in accordance with the methods set forth in the Examples by surface plasmon resonance (SPR), using standard instrumentation such as a BIACORE® instrument (GE Healthcare), and receptors or target proteins such as may be obtained by recombinant expression. According to one aspect, $K_D$ is measured by surface plasmon resonance using a BIACORE® T200 machine (GE Healthcare) at 25° C.

2. Binding Assays and Other Assays

Binding of the bispecific antigen binding molecule provided herein to the corresponding OX40 and/or EpCAM expressing cells may be evaluated using cell lines expressing the particular receptor or target antigen, for example by flow cytometry (FACS). In one aspect, fresh peripheral blood mononuclear cells (PBMCs) expressing OX40 are used in the binding assay. These cells are used directly after isolation (naïve PMBCs) or after stimulation (activated PMBCs). In another aspect, activated mouse splenocytes (expressing OX40) can be used to demonstrate binding of the bispecific antigen binding molecule of the invention to the corresponding OX40 expressing cells.

In a further aspect, cancer cell lines expressing EpCAM were used to demonstrate the binding of the antigen binding molecules to EpCAM.

In another aspect, competition assays may be used to identify an antigen binding molecule that competes with a specific antibody or antigen binding molecule for binding to EpCAM or OX40, respectively. In certain embodiments, such a competing antigen binding molecule binds to the same epitope (e.g., a linear or a conformational epitope) that is bound by a specific anti-EpCAM antibody or a specific anti-OX40 antibody. Detailed exemplary methods for mapping an epitope to which an antibody binds are provided in Moms (1996) "Epitope Mapping Protocols," in *Methods in Molecular Biology* vol. 66 (Humana Press, Totowa, N.J.).

3. Activity Assays

In one aspect, assays are provided for identifying bispecific antigen binding molecules that bind to EpCAM and to OX40 having biological activity. Biological activity may include, e.g., agonistic signalling through OX40 on cells expressing OX40. Bispecific antigen binding molecules identified by the assays as having such biological activity in vitro are also provided. In particular, a reporter cell assay detecting NF-κB activation in Hela cells expressing human OX40 and co-cultured with human EpCAM-expressing tumor cells is provided (see e.g. Example 6.1).

In certain aspects, bispecific antigen binding molecules of the invention are tested for such biological activity. Assays for detecting the biological activity of the molecules of the invention are those described in Example 4 or Example 6. Furthermore, assays for detecting cell lysis (e.g. by measurement of LDH release), induced apoptosis kinetics (e.g. by measurement of Caspase 3/7 activity) or apoptosis (e.g. using the TUNEL assay) are well known in the art. In addition the biological activity of such complexes can be assessed by evaluating their effects on survival, proliferation and lymphokine secretion of various lymphocyte subsets such as NK cells, NKT-cells or γδ T-cells or assessing their capacity to modulate phenotype and function of antigen presenting cells such as dendritic cells, monocytes/macrophages or B-cells.

Pharmaceutical Compositions, Formulations and Routes of Administration

In a further aspect, the invention provides pharmaceutical compositions comprising any of the bispecific antigen binding molecules provided herein, e.g., for use in any of the below therapeutic methods. In one embodiment, a pharmaceutical composition comprises a bispecific antigen binding molecule and at least one pharmaceutically acceptable excipient. In another embodiment, a pharmaceutical composition comprises any of the bispecific antigen binding molecules provided herein and at least one additional therapeutic agent, e.g., as described below.

Pharmaceutical compositions of the present invention comprise a therapeutically effective amount of one or more bispecific antigen binding molecule dissolved or dispersed in a pharmaceutically acceptable excipient. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one bispecific antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, antifungal agents), isotonic agents, salts, stabilizers and combinations thereof, as would be known to one of ordinary skill in the art.

Parenteral compositions include those designed for administration by injection, e.g. subcutaneous, intradermal, intralesional, intravenous, intraarterial intramuscular, intrathecal or intraperitoneal injection. For injection, the bispecific antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins or bispecific antigen binding molecules of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

In addition to the compositions described previously, the bispecific antigen binding molecules may also be formulated as a depot preparation. Such long acting formulations may be administered by implantation (for example subcutaneously or intramuscularly) or by intramuscular injection. Thus, for example, the bispecific antigen binding molecules may be formulated with suitable polymeric or hydrophobic materials (for example as emulsion in a pharmaceutically acceptable oil) or ion exchange resins, or as sparingly soluble derivatives, for example, as a sparingly soluble salt.

Pharmaceutical compositions comprising the bispecific antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The bispecific antigen binding molecules may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The pharmaceutical compositions may also contain more than one active ingredients as necessary for the particular indication being treated, preferably those with complementary activities that do not adversely affect each other. Such active ingredients are suitably present in combination in amounts that are effective for the purpose intended. In one aspect, the pharmaceutical composition comprises a bispecific antigen binding molecule and another active anti-cancer agent.

The formulations to be used for in vivo administration are generally sterile. Sterility may be readily accomplished, e.g., by filtration through sterile filtration membranes.

Therapeutic Methods and Compositions

Any of the bispecific antigen binding molecules provided herein may be used in therapeutic methods. For use in therapeutic methods, the antigen binding molecules of the invention can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, the bispecific antigen binding molecules of the invention are provided for use as a medicament. In further aspects, the bispecific antigen binding molecules of the invention are provided for use in treating a disease, in particular for use in the treatment of cancer. In certain embodiments, the bispecific antigen binding molecules of the invention are provided for use in a method of treatment. In one embodiment, the invention provides a bispecific antigen binding molecule as described herein for use in the treatment of a disease in an individual in need thereof. In certain embodiments, the invention provides a bispecific antigen binding molecule for use in a method of treating an individual having a disease comprising administering to the individual a therapeutically effective amount of the bispecific antigen binding molecule. In certain embodiments the disease to be treated is cancer. In certain embodiments the disease to be treated is a proliferative disorder, particularly cancer. Examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a bispecific antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. The subject, patient, or "individual" in need of treatment is typically a mammal, more specifically a human.

Also encompassed by the invention is the bispecific antigen binding molecule of the invention, or the pharmaceutical composition of the invention, for use in up-regulating or prolonging cytotoxic T cell activity.

In a further aspect, the invention provides for the use of a bispecific antigen binding molecule of the invention in the manufacture or preparation of a medicament for the treatment of a disease in an individual in need thereof. In one aspect, the medicament is for use in a method of treating a disease comprising administering to an individual having the disease a therapeutically effective amount of the medicament. In certain embodiments the disease to be treated is a proliferative disorder, particularly cancer. Examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a bispecific antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. A skilled artisan readily recognizes that in many cases the bispecific antigen binding molecule may not provide a cure but may only provide partial benefit. In some embodiments, a physiological change having some benefit is also considered therapeutically beneficial. Thus, in some embodiments, an amount of bispecific antigen binding molecule that provides a physiological change is considered an "effective amount" or a "therapeutically effective amount". In any of the above embodiments the individual is preferably a mammal, particularly a human.

In a further aspect, the invention provides a method for treating a disease in an individual, comprising administering to said individual a therapeutically effective amount of a bispecific antigen binding molecule of the invention. In one embodiment a composition is administered to said individual, comprising a fusion protein of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g. an anti-cancer agent if the disease to be treated is cancer. An "individual" according to any of the above embodiments may be a mammal, preferably a human.

For the prevention or treatment of disease, the appropriate dosage of a bispecific antigen binding molecule of the invention (when used alone or in combination with one or more other additional therapeutic agents) will depend on the type of disease to be treated, the route of administration, the body weight of the patient, the type of fusion protein, the severity and course of the disease, whether the fusion protein is administered for preventive or therapeutic purposes, previous or concurrent therapeutic interventions, the patient's clinical history and response to the fusion protein, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The bispecific antigen binding molecule is suitably administered to the patient at one time or over a series of treatments. Depending on the type and severity of the disease, about 1 µg/kg to 15 mg/kg (e.g. 0.1 mg/kg-10 mg/kg) of the antigen binding molecule can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the fusion protein would be in the range from about 0.005 mg/kg to about 10 mg/kg. In other examples, a dose may also comprise from about 1 µg/kg body weight, about 5 µg/kg body weight, about 10 µg/kg body weight, about 50 gg/kg body weight, about 100 µg/kg body weight, about 200 µg/kg body weight, about 350 µg/kg body weight, about 500 µg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In examples of a derivable range from the numbers listed herein, a range of about 5 mg/kg body weight to about 100 mg/kg body weight, about 5 µg/kg body weight to about 500 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the bispecific antigen binding molecule). An initial higher loading dose, followed by one or more lower doses may be administered. However, other dosage regimens may be useful. The progress of this therapy is easily monitored by conventional techniques and assays.

The bispecific antigen binding molecule of the invention will generally be used in an amount effective to achieve the intended purpose. For use to treat or prevent a disease condition, the bispecific antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the bispecific antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the bispecific antigen binding molecules may not be related to plasma concentration. One skilled in the art will be able to optimize therapeutically effective local dosages without undue experimentation.

A therapeutically effective dose of the bispecific antigen binding molecules described herein will generally provide therapeutic benefit without causing substantial toxicity. Toxicity and therapeutic efficacy of a fusion protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Bispecific antigen binding molecules that exhibit large therapeutic indices are preferred. In one embodiment, the bispecific antigen binding molecule according to the present invention exhibits a high therapeutic index. The data obtained from cell culture assays and animal studies can be used in formulating a range of dosages suitable for use in humans. The dosage lies preferably within a range of circulating concentrations that include the ED50 with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with the bispecific antigen binding molecules of the invention will know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The bispecific antigen binding molecules of the invention may be administered in combination with one or more other agents in therapy. For instance, a fusion protein of the invention may be co-administered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is another anti-cancer agent.

Such other agents are suitably present in combination in amounts that are effective for the purpose intended. The effective amount of such other agents depends on the amount of fusion protein used, the type of disorder or treatment, and other factors discussed above. The bispecific antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the bispecific antigen binding molecule of the invention can occur prior to, simultaneously, and/or following, administration of the additional therapeutic agent and/or adjuvant.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a bispecific antigen binding molecule of the invention.

The label or package insert indicates that the composition is used for treating the condition of choice. Moreover, the article of manufacture may comprise (a) a first container with a composition contained therein, wherein the composition comprises a bispecific antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE C

Sequences

| SEQ ID NO: | Name | Sequence |
|---|---|---|
| 1 | human OX40 ECD | Uniprot No. P43489, aa 29-214 |
| 2 | murine OX40 ECD | Uniprot No. P47741, aa 10-211 |
| 3 | cynomolgus OX40 ECD | aa 29-214 |
| 4 | OX40 (8H9, 49B4, 1G4, 20B7) CDR-H1 | SYAIS |
| 5 | OX40 (CLC-563, CLC-564, 17A9) CDR-H1 | SYAMS |
| 6 | OX40 (8H9, 49B4, 1G4, 20B7) CDR-H2 | GIIPIFGTANYAQKFQG |
| 7 | OX40 (CLC-563, CLC-564, 17A9) CDR-H2 | AISGSGGSTYYADSVKG |
| 8 | OX40 (8H9) CDR-H3 | EYGWMDY |
| 9 | OX40 (49B4) CDR-H3 | EYYRGPYDY |
| 10 | OX40 (1G4) CDR-H3 | EYGSMDY |
| 11 | OX40 (20B7) CDR-H3 | VNYPYSYWGDFDY |
| 12 | OX40 (CLC-563) CDR-H3 | DVGAFDY |
| 13 | OX40 (CLC-564) CDR-H3 | DVGPFDY |
| 14 | OX40 (17A9)-CDR-H3 | VFYRGGVSMDY |
| 15 | OX40 (8H9, 49B4, 1G4, 20B7) CDR-L1 | RASQSISSWLA |
| 16 | OX40 (CLC-563, CLC564) CDR-L1 | RASQSVSSSYLA |
| 17 | OX40 (17A9) CDR-L1 | QGDSLRSYYAS |
| 18 | OX40 (8H9, 49B4, 1G4, 20B7) CDR-L2 | DASSLES |
| 19 | OX40 (CLC-563, CLC564) CDR-L2 | GASSRAT |
| 20 | OX40 (17A9) CDR-L2 | GKNNRPS |
| 21 | OX40 (8H9) CDR-L3 | QQYLTYSRFT |
| 22 | OX40 (49B4) CDR-L3 | QQYSSQPYT |
| 23 | OX40 (1G4) CDR-L3 | QQYISYSMLT |
| 24 | OX40 (20B7) CDR-L3 | QQYQAFSLT |
| 25 | OX40 (CLC-563, CLC-164) CDR-L3 | QQYGSSPLT |
| 26 | OX40 (17A9) CDR-L3 | NSRVMPHNRV |
| 27 | muOX40 (OX86) CDR-H1 | GYNLH |
| 28 | muOX40 (OX86) CDR-H2 | RMRYDGDTYYNSVLKS |
| 29 | muOX40 (OX86) CDR-H3 | DGRGDSFDY |
| 30 | muOX40 (OX86) CDR-L1 | RSSQSLVYKDGQTYLN |
| 31 | muOX40 (OX86) CDR-L2 | WMSTRAS |
| 32 | muOX40 (OX86) CDR-L3 | QQVREYPFT |
| 33 | OX40 (8H9) VH | QVQLVQSGAEVKKPGSSVKVSCKASGGTFS<u>SY AIS</u>WVRQAPGQGLEWMG<u>GIIPIFGTANYAQKF</u> |

TABLE C-continued

Sequences

| SEQ ID NO: | Name | Sequence |
|---|---|---|
| | | QGRVTITADKSTSTAYMELSSLRSEDTAVYYC AREYGWMDYWGQGTTVTVSS |
| 34 | OX40 (8H9) VL | DIQMTQSPSTLSASVGDRVTITCRASQSISSWLA WYQQKPGKAPKLLIYDASSLESGVPSRFSGSGS GTEFTLTISSLQPDDFATYYCQQYLTYSRFTFG QGTKVEIK |
| 35 | OX40 (49B4) VH | QVQLVQSGAEVKKPGSSVKVSCKASGGTFSSY AISWVRQAPGQGLEWMGGIIPIFGTANYAQKF QGRVTITADKSTSTAYMELSSLRSEDTAVYYC AREYYRGPYDYWGQGTTVTVSS |
| 36 | OX40 (49B4) VL | DIQMTQSPSTLSASVGDRVTITCRASQSISSWLA WYQQKPGKAPKLLIYDASSLESGVPSRFSGSGS GTEFTLTISSLQPDDFATYYCQQYSSQPYTFGQ GTKVEIK |
| 37 | OX40 (1G4) VH | QVQLVQSGAEVKKPGSSVKVSCKASGGTFSSY AISWVRQAPGQGLEWMGGIIPIFGTANYAQKF QGRVTITADKSTSTAYMELSSLRSEDTAVYYC AREYGSMDYWGQGTTVTVSS |
| 38 | OX40 (1G4) VL | DIQMTQSPSTLSASVGDRVTITCRASQSISSWLA WYQQKPGKAPKLLIYDASSLESGVPSRFSGSGS GTEFTLTISSLQPDDFATYYCQQYISYSMLTFG QGTKVEIK |
| 39 | OX40 (20B7) VH | QVQLVQSGAEVKKPGSSVKVSCKASGGTFSSY AISWVRQAPGQGLEWMGGIIPIFGTANYAQKF QGRVTITADKSTSTAYMELSSLRSEDTAVYYC ARVNYPYSYWGDFDYWGQGTTVTVSS |
| 40 | OX40 (20B7) VL | DIQMTQSPSTLSASVGDRVTITCRASQSISSWLA WYQQKPGKAPKLLIYDASSLESGVPSRFSGSGS GTEFTLTISSLQPDDFATYYCQQYQAFSLTFGQ GTKVEIK |
| 41 | OX40 (CLC-563) VH | EVQLLESGGGLVQPGGSLRLSCAASGFTFSSYA MSWVRQAPGKGLEWVSAISGSGGSTYYADSV KGRFTISRDNSKNTLYLQMNSLRAEDTAVYYC ALDVGAFDYWGQGALVTVSS |
| 42 | OX40 (CLC-563) VL | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPLTFG QGTKVEIK |
| 43 | OX40 (CLC-564) VH | EVQLLESGGGLVQPGGSLRLSCAASGFTFSSYA MSWVRQAPGKGLEWVSAISGSGGSTYYADSV KGRFTISRDNSKNTLYLQMNSLRAEDTAVYYC AFDVGPFDYWGQGTLVTVSS |
| 44 | OX40 (CLC-564) VL | EIVLTQSPGTLSLSPGERATLSCRASQSVSSSYL AWYQQKPGQAPRLLIYGASSRATGIPDRFSGSG SGTDFTLTISRLEPEDFAVYYCQQYGSSPLTFG QGTKVEIK |
| 45 | OX40 (17A9) VH | EVQLLESGGGLVQPGGSLRLSCAASGFTFSSYA MSWVRQAPGKGLEWVSAISGSGGSTYYADSV KGRFTISRDNSKNTLYLQMNSLRAEDTAVYYC ARVFYRGGVSMDYWGQGTLVTVSS |
| 46 | OX40 (17A9) VL | SSELTQDPAVSVALGQTVRITCQGDSLRSYYAS WYQQKPGQAPVLVIYGKNNRPSGIPDRFSGSSS GNTASLTITGAQAEDEADYYCNSRVMPHNRVF GGGTKLTV |
| 47 | muOX40 (OX86) VH | QVQLKESGPGLVQPSQTLSLTCTVSGFSLTGYN LHWVRQPPGKGLEWMGRMRYDGDTYYNSVL KSRLSISRDTSKNQVFLKMNSLQTDDTAIYYCT RDGRGDSFDYWGQGVMVTVSS |
| 48 | muOX40 (OX86) VL | DIVMTQGALPNPVPSGESASITCRSSQSLVYKD GQTYLNWFLQRPGQSPQLLTYWMSTRASGVS |

TABLE C-continued

Sequences

| SEQ ID NO: | Name | Sequence |
|---|---|---|
| | | DRFSGSGSGTYFTLKISRVRAEDAGVYYCQQV REYPFTFGSGTKLEIK |
| 49 | human EpCAM ECD | Uniprot No. P16422, aa 24 to 265 |
| 50 | murine EpCAM ECD | Uniprot No. Q99JW5, aa 24 to 266 |
| 51 | EpCAM (3-17I) CDR-H1 | SYAIS |
| 52 | EpCAM (3-17I) CDR-H2 | GIIPIFGTANYAQKFQG |
| 53 | EpCAM (3-17I) CDR-H3 | GLLW |
| 54 | EpCAM (3-17I) CDR-L1 | RASQSVSSNLA |
| 55 | EpCAM (3-17I) CDR-L2 | GASTTAS |
| 56 | EpCAM (3-17I) CDR-L3 | QQYNNWPPAYT |
| 57 | muEpCAM (G8.8) CDR-H1 | NFPMA |
| 58 | muEpCAM (G8.8) CDR-H2 | TISTSGGSTYYRDSVKG |
| 59 | muEpCAM (G8.8) CDR-H3 | TLYILRVFYF |
| 60 | muEpCAM (G8.8) CDR-L1 | LASEGISNDLA |
| 61 | muEpCAM (G8.8) CDR-L2 | ATSRLQD |
| 62 | muEpCAM (G8.8) CDR-L3 | QQSYKYPWT |
| 63 | [EpCAM (3-17I) VH | QVQLVQSGAEVKKPGSSVKVSCKASGGTFSSY AISWVRQAPGQGLEWMGGIIPIFGTANYAQKF QGRVTITADESTSTAYMELSSLRSEDTAVYYCA RGLLWNYWGQGTLVTVSS |
| 64 | EpCAM (3-17I) VL | EIVMTQSPATLSVSPGERATLSCRASQSVSSNL AWYQQKPGQAPRLIIYGASTTASGIPARFSASG SGTDFTLTISSLQSEDFAVYYCQQYNNWPPAYT FGQGTKLEIK |
| 65 | muEpCAM (G8.8) VH | EVQLAESGGGLVQPGRSMKLSCAASGFTFSNF PMAWVRQAPTKGLEWVATISTSGGSTYYRDS VKGRFTISRDNAKSTLYLQMNSLRSEDTATYY CTRTLYILRVFYFDYWGQGVMVTVSS |
| 66 | muEpCAM (G8.8) VL | DIQMTQSPASLSASLGETVSIECLASEGISNDLA WYQQKSGKSPQLLIYATSRLQDGVPSRFSGSGS GTRYSLKISGMQPEDEADYFCQQSYKYPWTFG GGTKLELK |
| 67 | human OX40 | UniProt no. P43489 |
| 68 | human EpCAM | UniProt no. P16422 |
| 69 | human 4-1BB | UniProt no. Q07011 |
| 70 | human CD27 | UniProt no. P26842 |
| 71 | human HVEM | UniProt no. Q92956 |
| 72 | human CD30 | UniProt no. P28908 |
| 73 | human GITR | UniProt no. Q9Y5U5 |
| 74 | murine OX40 | UniProt no. P47741 |
| 75 | murine EpCAM | UniProt no. Q99JW5 |
| 76 | Petpide linker G4S | GGGGS |
| 77 | Peptide linker (G4S)2 | GGGGSGGGGS |
| 78 | Peptide linker (SG4)2 | SGGGGSGGGG |

TABLE C-continued

Sequences

| SEQ ID NO: | Name | Sequence |
|---|---|---|
| 79 | Peptide linker (G4S)3 | GGGGSGGGGSGGGGS |
| 80 | Peptide linker G4(SG4)2 | GGGGSGGGGSGGGG |
| 81 | Peptide linker (G4S)4 | GGGGSGGGGSGGGGSGGGGS |
| 82 | Peptide linker | GSPGSSSSGS |
| 83 | Peptide linker | GSGSGSGS |
| 84 | Peptide linker | GSGSGNGS |
| 85 | Peptide linker | GGSGSGSG |
| 86 | Peptide linker | GGSGSG |
| 87 | Peptide linker | GGSG |
| 88 | Peptide linker | GGSGNGSG |
| 89 | Peptide linker | GGNGSGSG |
| 90 | Peptide linker | GGNGSG |
| 91 | nucleotide sequence Fc hole chain | see Table 2 |
| 92 | nucleotide sequence human OX40 antigen Fc knob chain | see Table 2 |
| 93 | nucleotide sequence cynomolgus OX40 antigen Fc knob chain | see Table 2 |
| 94 | nucleotide sequence murine OX40 antigen Fc knob chain | see Table 2 |
| 95 | Fc hole chain | see Table 2 |
| 96 | human OX40 antigen Fc knob chain | see Table 2 |
| 97 | cynomolgus OX40 antigen Fc knob chain | see Table 2 |
| 98 | murine OX40 antigen Fc knob chain | see Table 2 |
| 99 | nucleotide sequence of library DP88-4 | see Table 3 |
| 100 | nucleotide sequence of Fab light chain Vk1_5 | see Table 4 |
| 101 | Fab light chain Vk1_5 | see Table 4 |
| 102 | nucleotide sequence of Fab heavy chain VH1_69 | see Table 4 |
| 103 | Fab heavy chain VH1_69 | see Table 4 |
| 104 | LMB3 | see Table 5 |
| 105 | Vk1_5_L3r_S | see Table 5 |
| 106 | Vk1_5_L3r_SY | see Table 5 |
| 107 | Vk1_5_L3r_SPY | see Table 5 |
| 108 | RJH31 | see Table 5 |
| 109 | RJH32 | see Table 5 |
| 110 | DP88-v4-4 | see Table 5 |
| 111 | DP88-v4-6 | see Table 5 |
| 112 | DP88-v4-8 | see Table 5 |

TABLE C-continued

Sequences

| SEQ ID NO: | Name | Sequence |
|---|---|---|
| 113 | fdseqlong | see Table 5 |
| 114 | (Vk3_20/VH3_23) template | see Table 6 |
| 115 | nucleotide sequence of Fab light chain Vk3_20 | see Table 7 |
| 116 | Fab light chain Vk3_20 | see Table 7 |
| 117 | nucleotide sequence of Fab heavy chain VH3_23 | see Table 7 |
| 118 | Fab heavy chain VH3_23 (DP47) | see Table 7 |
| 119 | MS64 | see Table 8 |
| 120 | DP47CDR3_ba (mod.) | see Table 8 |
| 121 | DP47-v4-4 | see Table 8 |
| 122 | DP47-v4-6 | see Table 8 |
| 123 | DP47-v4-8 | see Table 8 |
| 124 | fdseqlong | see Table 8 |
| 125 | Vl3_19/VH3_23 library template | see Table 9 |
| 126 | nucleotide sequence of Fab light chain Vl3_19 | see Table 10 |
| 127 | Fab light chain Vl3_19 | see Table 10 |
| 128 | LMB3 | see Table 11 |
| 129 | Vl_3_19_L3r_V | see Table 11 |
| 130 | Vl_3_19_L3r_HV | see Table 11 |
| 131 | Vl_3_19_L3r_HLV | see Table 11 |
| 132 | RJH80 | see Table 11 |
| 133 | MS63 | see Table 11 |
| 134 | Nucleotide sequence OX40 (8H9) VL | see Table 12 |
| 135 | Nucleotide sequence OX40 (8H9) VH | see Table 12 |
| 136 | Nucleotide sequence OX40 (49B4) VL | see Table 12 |
| 137 | Nucleotide sequence OX40 (49B4) VH | see Table 12 |
| 138 | Nucleotide sequence OX40 (1G4) VL | see Table 12 |
| 139 | Nucleotide sequence OX40 (1G4) VH | see Table 12 |
| 140 | Nucleotide sequence OX40 (20B7) VL | see Table 12 |
| 141 | Nucleotide sequence OX40 (20B7) VH | see Table 12 |
| 142 | Nucleotide sequence OX40 (CLC-563) VL | see Table 12 |
| 143 | Nucleotide sequence OX40 (CLC-563) VH | see Table 12 |
| 144 | Nucleotide sequence OX40 (CLC-564) VL | see Table 12 |
| 145 | Nucleotide sequence OX40 (CLC-564) VH | see Table 12 |
| 146 | Nucleotide sequence OX40 (17A9) VL | see Table 12 |

TABLE C-continued

Sequences

| SEQ ID NO: | Name | Sequence |
|---|---|---|
| 147 | Nucleotide sequence OX40 (17A9) VH | see Table 12 |
| 148 | Nucleotide sequence OX40 (8B9) light chain in P329GLALA human IgG1 format | see Table 13 |
| 149 | Nucleotide sequence OX40 (8B9) heavy chain in P329GLALA human IgG1 format | see Table 13 |
| 150 | OX40 (8B9) light chain in P329GLALA human IgG1 format | see Table 13 |
| 151 | OX40 (8B9) heavy chain in P329GLALA human IgG1 format | see Table 13 |
| 152 | Nucleotide sequence OX40 (49B4) light chain in P329GLALA human IgG1 format | see Table 13 |
| 153 | Nucleotide sequence OX40 (49B4) heavy chain in P329GLALA human IgG1 format | see Table 13 |
| 154 | OX40 (49B4) light chain in P329GLALA human IgG1 format | see Table 13 |
| 155 | OX40 (49B4) heavy chain in P329GLALA human IgG1 format | see Table 13 |
| 156 | Nucleotide sequence OX40 (1G4) light chain in P329GLALA human IgG1 format | see Table 13 |
| 157 | Nucleotide sequence OX40 (1G4) heavy chain in P329GLALA human IgG1 format | see Table 13 |
| 158 | OX40 (1G4) light chain in P329GLALA human IgG1 format | see Table 13 |
| 159 | OX40 (1G4) heavy chain in P329GLALA human IgG1 format | see Table 13 |
| 160 | Nucleotide sequence OX40 (20B7) light chain in P329GLALA human IgG1 format | see Table 13 |
| 161 | Nucleotide sequence OX40 (20B7) heavy chain in P329GLALA human IgG1 format | see Table 13 |
| 162 | OX40 (20B7) light chain in P329GLALA human IgG1 format | see Table 13 |
| 163 | OX40 (20B7) heavy chain in P329GLALA human IgG1 format | see Table 13 |
| 164 | Nucleotide sequence OX40 (CLC-563) light chain in P329GLALA human IgG1 format | see Table 13 |
| 165 | Nucleotide sequence OX40 (CLC-563) heavy chain in P329GLALA human IgG1 format | see Table 13 |
| 166 | OX40 (CLC-563) light chain in P329GLALA human IgG1 format | see Table 13 |
| 167 | OX40 (CLC-563) heavy chain in P329GLALA human IgG1 format | see Table 13 |

TABLE C-continued

Sequences

| SEQ ID NO: | Name | Sequence |
|---|---|---|
| 168 | Nucleotide sequence OX40 (CLC-564) light chain in P329GLALA human IgG1 format | see Table 13 |
| 169 | Nucleotide sequence OX40 (CLC-564) heavy chain in P329GLALA human IgG1 format | see Table 13 |
| 170 | OX40 (CLC-564) light chain in P329GLALA human IgG1 format | see Table 13 |
| 171 | OX40 (CLC-564) heavy chain in P329GLALA human IgG1 format | see Table 13 |
| 172 | Nucleotide sequence OX40 (17A9) light chain in P329GLALA human IgG1 format | see Table 13 |
| 173 | Nucleotide sequence OX40 (17A9) heavy chain in P329GLALA human IgG1 format | see Table 13 |
| 174 | OX40 (17A9) light chain in P329GLALA human IgG1 format | see Table 13 |
| 175 | OX40 (17A9) heavy chain in P329GLALA human IgG1 format | see Table 13 |
| 176 | Nucleotide sequence LC (pETR16299) OX40 (49B4) VL/CL | see Table 15 |
| 177 | Nucleotide sequence Heavy chain 1 (HC1) pETR17237 OX40 (49B4) VHCH1_VHCH1_Fc_knob_PG/LALA_EpCAM (3-17I) VL | see Table 15 |
| 178 | Nucleotide sequence Heavy chain 2 (HC2) pETR17238 OX40 (49B4) VHCH1_VHCH1_Fc_hole_PG/LALA_EpCAM (3-17I) VH | see Table 15 |
| 179 | Nucleotide sequence Light chain 1 (LC1) pETR16779 OX40 (49B4) VL CL + charges | see Table 15 |
| 180 | Nucleotide sequence Heavy chain pETR17241 OX40 (49B4) VHCH1_49B4VHCH1_Fc_PG/LALA_EpCAM (3-17I) 3-17I VLCH1 49B4 Fab + charges | see Table 15 |
| 181 | Nucleotide sequence Light chain 2 (LC2) pETR17239 EpCAM (3-17I) VHCL | see Table 15 |
| 182 | LC (pETR16299) OX40 (49B4) VL/CL | see Table 16 |
| 183 | Heavy chain 1 (HC1) pETR17237 OX40 (49B4) VHCH1_VHCH1_Fc_knob_PG/LALA_EpCAM (3-17I) VL | see Table 16 |
| 184 | Heavy chain 2 (HC2) pETR17238 OX40 (49B4) VHCH1_VHCH1_Fc_hole_PG/LALA_EpCAM (3-17I) VH | see Table 16 |

TABLE C-continued

Sequences

| SEQ ID NO: | Name | Sequence |
|---|---|---|
| 185 | Light chain 1 (LC1) pETR16779 OX40 (49B4) VL CL + charges | see Table 16 |
| 186 | Heavy chain pETR17241 OX40 (49B4) VHCH1_49B4VHCH1_Fc_PG/LALA_ EpCAM (3-17I) 3-17I VLCH1 49B4 Fab + charges | see Table 16 |
| 187 | Light chain 2 (LC2) pETR17239 EpCAM (3-17I) VHCL | see Table 16 |
| 188 | Nucleotide sequence Light chain (LC) muOX40 (OX86)VL/CL (pETR14908) | see Table 17 |
| 189 | Nucleotide sequence Heavy chain 1 (HC1) pETR16412 muOX40 (OX86) VHCH1_VHCH1_Fc_hole_D APG_DD muEpCAM (G8.8) VL | see Table 17 |
| 190 | Nucleotide sequence Heavy chain 2 (HC2) pETR16443 muOX40 (OX86) VHCH1_VHCH1_Fc_knob_DAPG_KK_muEpCAM (G8.8) VH | see Table 17 |
| 191 | Light chain (LC) muOX40 (OX86) VL/CL (pETR14908) | see Table 18 |
| 192 | Heavy chain 1 (HC1) pETR16412 muOX40 (OX86) VHCH1_VHCH1_Fc_hole_DAPG_DD muEpCAM (G8.8) VL | see Table 18 |
| 193 | Heavy chain 2 (HC2) pETR16443 muOX40 (OX86) VHCH1_VHCH1_Fc_knob_DAPG_KK_muEpCAM (G8.8) VH | see Table 18 |

The following numbered paragraphs (paras) describe aspects of the present invention:
1. A bispecific antigen binding molecule, comprising
(a) at least one moiety capable of specific binding to OX40, and
(b) at least one moiety capable of specific binding to epithelial cell adhesion molecule (EpCAM).
2. The bispecific antigen binding molecule of para 1, additionally comprising
(c) a Fc region composed of a first and a second subunit capable of stable association.
3. The bispecific antigen binding molecule of para 1 or para 2, wherein the moiety capable of specific binding to OX40 binds to a polypeptide comprising, or consisting of, the amino acid sequence of SEQ ID NO:1.
4. The bispecific antigen binding molecule of any one of paras 1 to 3, wherein the moiety capable of specific binding to EpCAM binds to a polypeptide comprising, or consisting of, the amino acid sequence of SEQ ID NO:49.
5. The bispecific antigen binding molecule of any one of paras 1 to 4, wherein the moiety capable of specific binding to OX40 comprises a VH comprising
(i) a CDR-H1 comprising an amino acid sequence selected from the group consisting of SEQ ID NO:4 and SEQ ID NO:5,
(ii) a CDR-H2 comprising an amino acid sequence selected from the group consisting of SEQ ID NO:6 and SEQ ID NO:7, and
(iii) a CDR-H3 comprising an amino acid sequence selected from the group consisting of SEQ ID NO:8, SEQ ID NO:9, SEQ ID NO:10, SEQ ID NO:11, SEQ ID NO:12, SEQ ID NO:13 and SEQ ID NO:14,
and a VL comprising
(iv) a CDR-L1 comprising an amino acid sequence selected from the group consisting of SEQ ID NO:15, SEQ ID NO:16 and SEQ ID NO:17,
(v) a CDR-L2 comprising an amino acid sequence selected from the group consisting of SEQ ID NO:18, SEQ ID NO:19 and SEQ ID NO:20, and
(vi) a CDR-L3 comprising an amino acid sequence selected from the group consisting of SEQ ID NO:21, SEQ ID NO:22, SEQ ID NO:23, SEQ ID NO:24, SEQ ID NO:25 and SEQ ID NO:26.
6. The bispecific antigen binding molecule of any one of paras 1 to 5, wherein the moiety capable of specific binding to OX40 comprises a VH comprising an amino acid sequence that is at least about 95%, 96%, 97%, 98%, 99% or 100% identical to an amino acid sequence selected from the group consisting of SEQ ID NO:33, SEQ ID NO: 35, SEQ ID NO:37, SEQ ID NO:39, SEQ ID NO:41, SEQ ID NO:43 and SEQ ID NO:45 and a VL comprising an amino acid sequence that is at least about 95%, 96%, 97%, 98%, 99% or 100% identical to an amino acid sequence selected from the group consisting of SEQ ID NO:34, SEQ ID NO: 36, SEQ ID NO:38, SEQ ID NO:40, SEQ ID NO:42, SEQ ID NO:44 and SEQ ID NO:46.

7. The bispecific antigen binding molecule of any one of paras 1 to 6, wherein the moiety capable of specific binding to OX40 comprises
(i) a VH comprising the amino acid sequence of SEQ ID NO:33 and a VL comprising the amino acid sequence of SEQ ID NO:34,
(ii) a VH comprising the amino acid sequence of SEQ ID NO:35 and a VL comprising the amino acid sequence of SEQ ID NO:36,
(iii) a VH comprising the amino acid sequence of SEQ ID NO:37 and a VL comprising the amino acid sequence of SEQ ID NO:38,
(iv) a VH comprising the amino acid sequence of SEQ ID NO:39 and a VL comprising the amino acid sequence of SEQ ID NO:40,
(v) a VH comprising the amino acid sequence of SEQ ID NO:41 and a VL comprising the amino acid sequence of SEQ ID NO:42,
(vi) a VH comprising the amino acid sequence of SEQ ID NO:43 and a VL comprising the amino acid sequence of SEQ ID NO:44, or
(vii) a VH comprising the amino acid sequence of SEQ ID NO:45 and a VL comprising the amino acid sequence of SEQ ID NO:46.

8. The bispecific antigen binding molecule of any one of paras 1 to 7, wherein the moiety capable of specific binding to EpCAM comprises a VH comprising
(i) a CDR-H1 comprising the amino acid sequence SEQ ID NO:51,
(ii) a CDR-H2 comprising the amino acid sequence SEQ ID NO:52, and
(iii) a CDR-H3 comprising the amino acid sequence SEQ ID NO:53, and a VL comprising
(iv) a CDR-L1 comprising the amino acid sequence SEQ ID NO:54,
(v) a CDR-L2 comprising the amino acid sequence SEQ ID NO:55, and
(vi) a CDR-L3 comprising the amino acid sequence SEQ ID NO:56.

9. The bispecific antigen binding molecule of any one of paras 1 to 8, wherein the moiety capable of specific binding to EpCAM comprises a VH comprising an amino acid sequence that is at least about 95%, 96%, 97%, 98%, 99% or 100% identical to the amino acid sequence of SEQ ID NO:63, and a VL comprising an amino acid sequence that is at least about 95%, 96%, 97%, 98%, 99% or 100% identical to the amino acid sequence of SEQ ID NO:64.

10. The bispecific antigen binding molecule of any one of paras 1 to 9, wherein the moiety capable of specific binding to EpCAM comprises a VH comprising the amino acid sequence of SEQ ID NO:63 and a VL comprising the amino acid sequence of SEQ ID NO:64.

11. The bispecific antigen binding molecule of any one of paras 1 to 10, comprising
(i) at least one moiety capable of specific binding to OX40, comprising a VH comprising an amino acid sequence that is at least about 95%, 96%, 97%, 98%, 99% or 100% identical to an amino acid sequence selected from the group consisting of SEQ ID NO:33, SEQ ID NO: 35, SEQ ID NO:37, SEQ ID NO:39, SEQ ID NO:41, SEQ ID NO:43 and SEQ ID NO:45 and a VL comprising an amino acid sequence that is at least about 95%, 96%, 97%, 98%, 99% or 100% identical to an amino acid sequence selected from the group consisting of SEQ ID NO:34, SEQ ID NO: 36, SEQ ID NO:38, SEQ ID NO:40, SEQ ID NO:42, SEQ ID NO:44 and SEQ ID NO:46, and
(ii) at least one moiety capable of specific binding to EpCAM, comprising a VH comprising an amino acid sequence that is at least about 95%, 96%, 97%, 98%, 99% or 100% identical to the amino acid sequence of SEQ ID NO:63 and a VL comprising an amino acid sequence that is at least about 95%, 96%, 97%, 98%, 99% or 100% identical to the amino acid sequence of SEQ ID NO:64.

12. The bispecific antigen binding molecule of any one of paras 1 to 11, comprising
(i) at least one moiety capable of specific binding to OX40, comprising a VH comprising the amino acid sequence of SEQ ID NO: 35 and a VL comprising the amino acid sequence of SEQ ID NO: 36, and
(ii) at least one moiety capable of specific binding to EpCAM, comprising a VH comprising the amino acid sequence of SEQ ID NO:63 and a VL comprising the amino acid sequence of SEQ ID NO: 64.

13. The bispecific antigen binding molecule of para 1 or para 2, wherein the moiety capable of specific binding to OX40 binds to a polypeptide comprising, or consisting of, the amino acid sequence of SEQ ID NO:2.

14. The bispecific antigen binding molecule of any one of paras 1, 2 or 13, wherein the moiety capable of specific binding to EpCAM binds to a polypeptide comprising, or consisting of, the amino acid sequence of SEQ ID NO:50.

15. The bispecific antigen binding molecule of any one of paras 1, 2, 13 or 14, wherein the moiety capable of specific binding to OX40 comprises a VH comprising
(i) a CDR-H1 comprising the amino acid sequence SEQ ID NO:27,
(ii) a CDR-H2 comprising the amino acid sequence SEQ ID NO:28, and
(iii) a CDR-H3 comprising the amino acid sequence SEQ ID NO:29, and a VL comprising
(iv) a CDR-L1 comprising the amino acid sequence SEQ ID NO:30,
(v) a CDR-L2 comprising the amino acid sequence SEQ ID NO:31, and
(vi) a CDR-L3 comprising the amino acid sequence SEQ ID NO:32.

16. The bispecific antigen binding molecule of any one of paras 1, 2, or 13 to 15, wherein the moiety capable of specific binding to OX40 comprises a VH comprising an amino acid sequence that is at least about 95%, 96%, 97%, 98%, 99% or 100% identical to the amino acid sequence of SEQ ID NO:47, and a VL comprising an amino acid sequence that is at least about 95%, 96%, 97%, 98%, 99% or 100% identical to the amino acid sequence of SEQ ID NO:48.

17. The bispecific antigen binding molecule of any one of paras 1, 2, or 13 to 16, wherein the moiety capable of specific binding to OX40 comprises a VH comprising the amino acid sequence of SEQ ID NO:47 and a VL comprising the amino acid sequence of SEQ ID NO:48.

18. The bispecific antigen binding molecule of any one of paras 1, 2, or 13 to 17, wherein the moiety capable of specific binding to EpCAM comprises a VH comprising
(i) a CDR-H1 comprising the amino acid sequence SEQ ID NO:57,
(ii) a CDR-H2 comprising the amino acid sequence SEQ ID NO:58, and (iii) a CDR-H3 comprising the amino acid sequence SEQ ID NO:59, and a VL comprising
(iv) a CDR-L1 comprising the amino acid sequence SEQ ID NO:60,
(v) a CDR-L2 comprising the amino acid sequence SEQ ID NO:61, and
(vi) a CDR-L3 comprising the amino acid sequence SEQ ID NO:62.

19. The bispecific antigen binding molecule of any one of paras 1, 2, or 13 to 18, wherein the moiety capable of specific binding to EpCAM comprises a VH comprising an amino acid sequence that is at least about 95%, 96%, 97%, 98%, 99% or 100% identical to the amino acid sequence of SEQ ID NO:65, and a VL comprising an amino acid sequence that is at least about 95%, 96%, 97%, 98%, 99% or 100% identical to the amino acid sequence of SEQ ID NO:66.

20. The bispecific antigen binding molecule of any one of paras 1, 2, or 13 to 19, wherein the moiety capable of specific binding to EpCAM comprises a VH comprising the amino acid sequence of SEQ ID NO:65 and a VL comprising the amino acid sequence of SEQ ID NO:66.

21. The bispecific antigen binding molecule of any one of paras 1, 2, or 13 to 20, comprising
(i) at least one moiety capable of specific binding to OX40, comprising a VH comprising the amino acid sequence of SEQ ID NO:47 and a VL comprising the amino acid sequence of SEQ ID NO:48, and
(ii) at least one moiety capable of specific binding to EpCAM, comprising a VH comprising the amino acid sequence of SEQ ID NO:65 and a VL comprising the amino acid sequence of SEQ ID NO:66.

22. The bispecific antigen binding molecule of any one of paras 2 to 21, wherein the Fc region is an IgG, particularly an IgG1 Fc region or an IgG4 Fc region.

23. The bispecific antigen binding molecule of any one of paras 2 to 22, wherein the Fc region comprises one or more amino acid substitution that reduces the binding affinity of the antibody to an Fc receptor and/or effector function.

24. The bispecific antigen binding molecule of any one of paras 2 to 23, wherein the Fc region is (i) of human IgG1 subclass with the amino acid mutations L234A, L235A and P329G (numbering according to Kabat EU index), or (ii) of mouse IgG1 subclass with the amino acid mutations D265A and P329G (numbering according to Kabat EU index).

25. The bispecific antigen binding molecule of any one of paras 2 to 24, wherein the Fc region comprises a modification promoting the association of the first and second subunit of the Fc region.

26. The bispecific antigen binding molecule of any one of paras 2 to 25, wherein the first subunit of the Fc region comprises knobs and the second subunit of the Fc region comprises holes according to the knobs into holes method.

27. The bispecific antibody of any one of paras 2 to 26, wherein
(i) the first subunit of the Fc region comprises the amino acid substitutions S354C and T366W (numbering according to Kabat EU index) and the second subunit of the Fc region comprises the amino acid substitutions Y349C, T366S and Y407V (numbering according to Kabat EU index), or
(ii) the first subunit of the Fc region comprises the amino acid substitutions K392D and K409D (numbering according to Kabat EU index) and the second subunit of the Fc region comprises the amino acid substitutions E356K and D399K (numbering according to Kabat EU index).

28. The bispecific antigen binding molecule of any one of paras 1 to 27, wherein the bispecific antigen binding molecule comprises
(a) at least two Fab fragments capable of specific binding to OX40 connected to a Fc region, and
(b) at least one moiety capable of specific binding to EpCAM connected to the C-terminus of the Fc region.

29. The bispecific antigen binding molecule of any one of paras 1 to 28, wherein the bispecific antigen binding molecule comprises
(a) two light chains and two heavy chains of an antibody comprising two Fab fragments capable of specific binding to OX40, and a Fc region, and
(b) a VH and a VL of a moiety capable specific binding to EpCAM, wherein the VH is connected to the C-terminus of one of the two heavy chains of (a), and wherein the VL is connected to the C-terminus of the other of the two heavy chains of (a).

30. The bispecific antigen binding molecule of any one of paras 1 to 29, wherein the bispecific antigen binding molecule comprises
(a) two light chains and two heavy chains of an antibody comprising two Fab fragments capable of specific binding to OX40, and a Fc region, and
(b) two Fab fragments capable of specific binding to EpCAM, wherein one of the Fab fragments is connected to the C-terminus of one of the two heavy chains of (a), and the other of the Fab fragments is connected to the C-terminus of the other of the two heavy chains of (a).

31. The bispecific antigen binding molecule of any one of paras 1 to 30, wherein the bispecific antigen binding molecule comprises
(a) two heavy chains, each heavy chain comprising a VH and CH1 domain of a Fab fragment capable of specific binding to OX40 and a Fc region subunit,
(b) two light chains, each light chain comprising a VL and CL domain of a Fab fragment capable of specific binding to OX40, and
(c) a VH and a VL of a moiety capable specific binding to EpCAM, wherein the VH is connected to the C-terminus of one of the two heavy chains of (a), and wherein the VL is connected to the C-terminus of the other of the two heavy chains of (a).

32. The bispecific antigen binding molecule of any one of paras 1 to 28 or para 30, wherein the bispecific antigen binding molecule comprises
(a) two heavy chains, each heavy chain comprising a VH and CH1 domain of a Fab fragment capable of specific binding to OX40, and a Fc region subunit,
(b) two light chains, each light chain comprising a VL and CL domain of a Fab fragment capable of specific binding to OX40,
(c) two Fab fragments capable of specific binding to EpCAM, wherein one of the Fab fragments is connected to the C-terminus of one of the two heavy chains of (a), and the other of the Fab fragments is connected to the C-terminus of the other of the two heavy chains of (a).

33. The bispecific antigen binding molecule of para 30 or para 32, wherein the two Fab fragments capable of specific binding to EpCAM are crossover Fab fragments each comprising a VL-CH1 chain and a VH-CL chain, and wherein one of the VL-CH1 chains is connected to the C-terminus of one of the two heavy chains of (a), and the other of the VL-CH1 chains is connected to the C-terminus of the other of the two heavy chains of (a).

34. The bispecific antigen binding molecule of any one of paras 1 to 33, wherein the bispecific antigen binding molecule comprises four Fab fragments capable of specific binding to OX40.
35. The bispecific antigen binding molecule of any one of paras 29 to 34, wherein each of the two heavy chains of (a) comprises two VH domains and two CH1 domains of a Fab fragment capable of specific binding to OX40.
36. The bispecific antigen binding molecule of any one of paras 28 to 35, one or more of the Fab fragments capable of specific binding to OX40 comprises
a CL domain comprising an arginine (R) at amino acid at position 123 (EU numbering) and a lysine (K) at amino acid at position 124 (EU numbering), and
a CH1 domain comprising a glutamic acid (E) at amino acid at position 147 (EU numbering) and
a glutamic acid (E) at amino acid at position 213 (EU numbering).
37. A bispecific antigen binding molecule, comprising
a first heavy chain comprising the amino acid sequence of SEQ ID NO:183,
a second heavy chain comprising the amino acid sequence of SEQ ID NO:184, and
four light chains, each comprising the amino acid sequence of SEQ ID NO:182.
38. A bispecific antigen binding molecule, comprising
two heavy chains, each comprising the amino acid sequence of SEQ ID NO:186,
two light chains, each comprising the amino acid sequence of SEQ ID NO:187, and
four light chains, each comprising the amino acid sequence of SEQ ID NO:185.
39. A bispecific antigen binding molecule, comprising
a first heavy chain comprising the amino acid sequence of SEQ ID NO:192,
a second heavy chain comprising the amino acid sequence of SEQ ID NO:193, and
four light chains, each comprising the amino acid sequence of SEQ ID NO:191.
40. A polynucleotide encoding the bispecific antigen binding molecule of any one of paras 1 to 39.
41. An expression vector comprising the polynucleotide of para 40.
42. A host cell comprising the polynucleotide of para 40 or the expression vector of para 41.
43. A method of producing a bispecific antigen binding molecule, comprising culturing the host cell of para 42 under conditions suitable for the expression of the bispecific antigen binding molecule, and isolating the bispecific antigen binding molecule.
44. A pharmaceutical composition comprising the bispecific antigen binding molecule of any one of paras 1 to 39 and at least one pharmaceutically acceptable excipient.
45. The bispecific antigen binding molecule of any one of paras 1 to 39, or the pharmaceutical composition of para 44, for use as a medicament.
46. The bispecific antigen binding molecule of any one of paras 1 to 39, or the pharmaceutical composition of para 44, for use
(i) in stimulating T cell response,
(ii) in supporting survival of activated T cells,
(iii) in the treatment of infections,
(iv) in the treatment of cancer,
(v) in delaying progression of cancer, or
(vi) in prolonging the survival of a patient suffering from cancer.
47. The bispecific antigen binding molecule of any one of paras 1 to 39, or the pharmaceutical composition of para 44, for use in the treatment of cancer.
48. Use of the bispecific antigen binding molecule of any one of paras 1 to 39, or the pharmaceutical composition of para 44, in the manufacture of a medicament for the treatment of cancer.
49. A method of treating an individual having cancer comprising administering to the individual an effective amount of the bispecific antigen binding molecule of any one of paras 1 to 39, or the pharmaceutical composition of para 44.
50. The bispecific antigen binding molecule of any one of paras 1 to 39, or the pharmaceutical composition of para 44, for use in up-regulating or prolonging cytotoxic T cell activity.
51. Use of the bispecific antigen binding molecule of any one of paras 1 to 39, or the pharmaceutical composition of para 44, in the manufacture of a medicament for up-regulating or prolonging cytotoxic T cell activity.
52. A method of up-regulating or prolonging cytotoxic T cell activity in an individual having cancer, comprising administering to the individual an effective amount of the bispecific antigen binding molecule of any one of paras 1 to 39, or the pharmaceutical composition of para 44.

EXAMPLES

The following are examples of methods and compositions of the invention. It is understood that various other embodiments may be practiced, given the general description provided above.
Recombinant DNA Techniques
Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.
DNA Sequencing
DNA sequences were determined by double strand sequencing.
Gene Synthesis
Desired gene segments were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Protein Purification

Proteins were purified from filtered cell culture supernatants referring to standard protocols. In brief, antibodies were applied to a Protein A SEPHAROSE® column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS™ (tris (hydroxymethyl)aminomethane) Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Example 1

Generation of OX40 Antibodies 1.1 Preparation, Purification and Characterization of Antigens and Screening Tools for the Generation of Novel OX40 Binders by Phage Display DNA sequences encoding the ectodomains of human, mouse or cynomolgus OX40 (Table 1) were subcloned in frame with the human IgG1 heavy chain CH2 and CH3 domains on the knob (Merchant et al., Nat Biotechnol (1998) 16, 677-681). An AcTEV protease cleavage site was introduced between an antigen ectodomain and the Fc of human IgG1. An Avi tag for directed biotinylation was introduced at the C-terminus of the antigen-Fc knob. Combination of the antigen-Fc knob chain containing the S354C/T366W mutations, with a Fc hole chain containing the Y349C/T366S/L368A/Y407V mutations allows generation of a heterodimer which includes a single copy of the OX40 ectodomain containing chain, thus creating a monomeric form of Fc-linked antigen (FIG. 1). Table 1 shows the amino acid sequences of the various OX40 ectodomains. Table 2 the cDNA and amino acid sequences of monomeric antigen Fc(kih) fusion molecules as depicted in FIG. 1.

TABLE 1

Amino acid numbering of antigen ectodomains (ECD) and their origin

| SEQ ID NO: | Construct | Origin | ECD |
| --- | --- | --- | --- |
| 1 | human OX40 ECD | Synthetized according to P43489 | aa 29-214 |
| 3 | cynomolgus OX40 ECD | Isolated from cynomolgus blood | aa 29-214 |
| 2 | murine OX40 ECD | Synthetized according to P47741 | aa 10-211 |

TABLE 2 cDNA and amino acid sequences of monomeric antigen Fc(kih) fusion molecules (produced by combination of one Fc hole chain with one antigen Fc knob chain)

| SEQ ID NO: | Antigen | Sequence |
| --- | --- | --- |
| 91 | Nucleotide sequence Fc hole chain | GACAAAACTCACACATGCCCACCGTGCCCAGCACCTG AACTCCTGGGGGGACCGTCAGTCTTCCTCTTCCCCCCA AAACCCAAGGACACCCTCATGATCTCCCGGACCCCTGA GGTCACATGCGTGGTGGTGGACGTGAGCCACGAAGAC CCTGAGGTCAAGTTCAACTGGTACGTGGACGGCGTGG AGGTGCATAATGCCAAGACAAAGCCGCGGGAGGAGCA GTACAACAGCACGTACCGTGTGGTCAGCGTCCTCACCG TCCTGCACCAGGACTGGCTGAATGGCAAGGAGTACAA GTGCAAGGTCTCCAACAAAGCCCTCCCAGCCCCCATCG AGAAAACCATCTCCAAAGCCAAAGGGCAGCCCCGAGA ACCACAGGTGTGCACCCTGCCCCCATCCCGGGATGAGC TGACCAAGAACCAGGTCAGCCTCTCGTGCGCAGTCAA AGGCTTCTATCCCAGCGACATCGCCGTGGAGTGGGAG AGCAATGGGCAGCCGGAGAACAACTACAAGACCACGC CTCCCGTGCTGGACTCCGACGGCTCCTTCTTCCTCGTGA GCAAGCTCACCGTGGACAAGAGCAGGTGGCAGCAGGG GAACGTCTTCTCATGCTCCGTGATGCATGAGGCTCTGC ACAACCACTACACGCAGAAGAGCCTCTCCCTGTCTCCG GGTAAA |
| 92 | Nucleotide sequence human OX40 antigen Fc knob chain | CTGCACTGCGTGGGCGACACCTACCCCAGCAACGACC GGTGCTGCCACGAGTGCAGACCCGGCAACGGCATGGT GTCCCGGTGCAGCCGGTCCCAGAACACCGTGTGCAGA CCTTGCGGCCCTGGCTTCTACAACGACGTGGTGTCCAG CAAGCCCTGCAAGCCTTGTACCTGGTGCAACCTGCGGA GCGGCAGCGAGCGGAAGCAGCTGTGTACCGCCACCCA GGATACCGTGTGCCGGTGTAGAGCCGGCACCCAGCCC CTGGACAGCTACAAACCCGGCGTGGACTGCGCCCCTTG |

TABLE 2-continued cDNA and amino acid sequences of monomeric antigen Fc(kih) fusion molecules (produced by combination of one Fc hole chain with one antigen Fc knob chain)

| SEQ ID NO: | Antigen | Sequence |
|---|---|---|
| | | CCCTCCTGGCCACTTCAGCCCTGGCGACAACCAGGCCT GCAAGCCTTGGACCAACTGCACCCTGGCCGGCAAGCA CACCCTGCAGCCCGCCAGCAATAGCAGCGACGCCATCT GCGAGGACCGGGATCCTCCTGCCACCCAGCCTCAGGA AACCCAGGGCCCTCCCGCCAGACCCATCACCGTGCAGC CTACAGAGGCCTGGCCCAGAACCAGCCAGGGGCCTAG CACCAGACCCGTGGAAGTGCCTGGCGGCAGAGCCGTC GACGAACAGTTATATTTTCAGGGCGGCTCACCCAAATC TGCAGACAAAACTCACACATGCCCACCGTGCCCAGCA CCTGAACTCCTGGGGGGACCGTCAGTCTTCCTCTTCCC CCCAAAACCCAAGGACACCCTCATGATCTCCCGGACCC CTGAGGTCACATGCGTGGTGGTGGACGTGAGCCACGA AGACCCTGAGGTCAAGTTCAACTGGTACGTGGACGGC GTGGAGGTGCATAATGCCAAGACAAAGCCGCGGGAGG AGCAGTACAACAGCACGTACCGTGTGGTCAGCGTCCTC ACCGTCCTGCACCAGGACTGGCTGAATGGCAAGGAGT ACAAGTGCAAGGTCTCCAACAAAGCCCTCCCAGCCCCC ATCGAGAAAACCATCTCCAAAGCCAAAGGGCAGCCCC GAGAACCACAGGTGTACACCCTGCCCCCATGCCGGGA TGAGCTGACCAAGAACCAGGTCAGCCTGTGGTGCCTG GTCAAAGGCTTCTATCCCAGCGACATCGCCGTGGAGTG GGAGAGCAATGGGCAGCCGGAGAACAACTACAAGACC ACGCCTCCCGTGCTGGACTCCGACGGCTCCTTCTTCCTC TACAGCAAGCTCACCGTGGACAAGAGCAGGTGGCAGC AGGGGAACGTCTTCTCATGCTCCGTGATGCATGAGGCT CTGCACAACCACTACACGCAGAAGAGCCTCTCCCTGTC TCCGGGTAAATCCGGAGGCCTGAACGACATCTTCGAG GCCCAGAAGATTGAATGGCACGAG |
| 93 | Nucleotide sequence cynomolgus OX40 antigen Fc knob chain | CTCCACTGTGTCGGGGACACCTACCCCAGCAACGACCG GTGCTGTCAGGAGTGCAGGCCAGGCAACGGGATGGTG AGCCGCTGCAACCGCTCCCAGAACACGGTGTGCCGTCC GTGCGGGCCCGGCTTCTACAACGACGTGGTCAGCGCCA GCACCTGCAAGGCCTGCACATGGTGCAACCTCAGAAG TGGGAGTGAGCGGAAACAGCCGTGCAGGCCACACAG GACACAGTCTGCCGCTGCCGGGCGGGCACCCAGCCCCT GGACAGCTACAAGCCTGGAGTTGACTGTGCCCCCTGCC CTCCAGGGCACTTCTCCCCGGGCGACAACCAGGCCTGC AAGCCCTGGACCAACTGCACCTTGGCCGGGAAGCACA CCCTGCAGCCAGCCAGCAATAGCTCGGACGCCATCTGT GAGGACAGGGACCCCCCACCCACACAGCCCCAGGAGA CCCAGGGCCCCCCGGCCAGGCCCACCACTGTCCAGCCC ACTGAAGCCTGGCCCAGAACCTCACAGAGACCCTCCA CCCGGCCCGTGGAGGTCCCCAGGGGCCCTGCGGTCGA CGAACAGTTATATTTTCAGGGCGGCTCACCCAAATCTG CAGACAAAACTCACACATGCCCACCGTGCCCAGCACCT GAACTCCTGGGGGGACCGTCAGTCTTCCTCTTCCCCCC AAAACCCAAGGACACCCTCATGATCTCCCGGACCCCTG AGGTCACATGCGTGGTGGTGGACGTGAGCCACGAAGA CCCTGAGGTCAAGTTCAACTGGTACGTGGACGGCGTGG AGGTGCATAATGCCAAGACAAAGCCGCGGGAGGAGCA GTACAACAGCACGTACCGTGTGGTCAGCGTCCTCACCG TCCTGCACCAGGACTGGCTGAATGGCAAGGAGTACAA GTGCAAGGTCTCCAACAAAGCCCTCCCAGCCCCCATCG AGAAAACCATCTCCAAAGCCAAAGGGCAGCCCCGAGA ACCACAGGTGTACACCCTGCCCCCATGCCGGGATGAGC TGACCAAGAACCAGGTCAGCCTGTGGTGCCTGGTCAA AGGCTTCTATCCCAGCGACATCGCCGTGGAGTGGGAG AGCAATGGGCAGCCGGAGAACAACTACAAGACCACGC CTCCCGTGCTGGACTCCGACGGCTCCTTCTTCCTCTACA GCAAGCTCACCGTGGACAAGAGCAGGTGGCAGCAGGG GAACGTCTTCTCATGCTCCGTGATGCATGAGGCTCTGC ACAACCACTACACGCAGAAGAGCCTCTCCCTGTCTCCG GGTAAATCCGGAGGCCTGAACGACATCTTCGAGGCCC AGAAGATTGAATGGCACGAG |
| 94 | Nucleotide sequence murine OX40 antigen Fc knob chain | GTGACCGCCAGACGGCTGAACTGCGTGAAGCACACCT ACCCCAGCGGCCACAAGTGCTGCAGAGAGTGCCAGCC CGGCCACGGCATGGTGTCCAGATGCGACCACACACGG GACACCCTGTGCACCCTTGCGAGACAGGCTTCTACAA CGAGGCCGTGAACTACGATACCTGCAAGCAGTGCACC CAGTGCAACCACAGAAGCGGCAGCGAGCTGAAGCAGA ACTGCACCCCCACCCAGGATACCGTGTGCAGATGCAG |

TABLE 2-continued cDNA and amino acid sequences of monomeric antigen
Fc(kih) fusion molecules (produced by combination
of one Fc hole chain with one antigen Fc knob chain)

| SEQ ID NO: | Antigen | Sequence |
|---|---|---|
| | | ACCCGGCACCCAGCCCAGACAGGACAGCGGCTACAAG
CTGGGCGTGGACTGCGTGCCCTGCCCTCCTGGCCACTT
CAGCCCCGGCAACAACCAGGCCTGCAAGCCCTGGACC
AACTGCACCCTGAGCGGCAAGCAGACCAGACACCCCG
CCAGCGACAGCCTGGATGCCGTGTGCGAGGACAGAAG
CCTGCTGGCCACCCTGCTGTGGGAGACACAGCGGCCCA
CCTTCAGACCCACCACCGTGCAGAGCACCACCGTGTGG
CCCAGAACCAGCGAGCTGCCCAGTCCTCCTACCCTCGT
GACACCTGAGGGCCCCGTCGACGAACAGTTATATTTTC
AGGGCGGCTCACCCAAATCTGCAGACAAAACTCACAC
ATGCCCACCGTGCCCAGCACCTGAACTCCTGGGGGGAC
CGTCAGTCTTCCTCTTCCCCCCAAAACCCAAGGACACC
CTCATGATCTCCCGGACCCCTGAGGTCACATGCGTGGT
GGTGGACGTGAGCCACGAAGACCCTGAGGTCAAGTTC
AACTGGTACGTGGACGGCGTGGAGGTGCATAATGCCA
AGACAAAGCCGCGGGAGGAGCAGTACAACAGCACGTA
CCGTGTGGTCAGCGTCCTCACCGTCCTGCACCAGGACT
GGCTGAATGGCAAGGAGTACAAGTGCAAGGTCTCCAA
CAAAGCCCTCCCAGCCCCCATCGAGAAAACCATCTCCA
AAGCCAAAGGGCAGCCCCGAGAACCACAGGTGTACAC
CCTGCCCCCATGCCGGGATGAGCTGACCAAGAACCAG
GTCAGCCTGTGGTGCCTGGTCAAAGGCTTCTATCCCAG
CGACATCGCCGTGGAGTGGGAGAGCAATGGGCAGCCG
GAGAACAACTACAAGACCACGCCTCCCGTGCTGGACT
CCGACGGCTCCTTCTTCCTCTACAGCAAGCTCACCGTG
GACAAGAGCAGGTGGCAGCAGGGGAACGTCTTCTCAT
GCTCCGTGATGCATGAGGCTCTGCACAACCACTACACG
CAGAAGAGCCTCTCCCTGTCTCCGGGTAAATCCGGAGG
CCTGAACGACATCTTCGAGGCCCAGAAGATTGAATGG
CACGAG |
| 95 | Fc hole chain | DKTHTCPPCPAPELLGGPSVFLFPPKPKDTLMISRTPEVTC
VVVDVSHEDPEVKFNWYVDGVEVHNAKTKPREEQYNST
YRVVSVLTVLHQDWLNGKEYKCKVSNKALPAPIEKTISK
AKGQPREPQVCTLPPSRDELTKNQVSLSCAVKGFYPSDIA
VEWESNGQPENNYKTTPPVLDSDGSFFLVSKLTVDKSRW
QQGNVFSCSVMHEALHNHYTQKSLSLSPGK |
| 96 | human OX40 antigen Fc knob chain | LHCVGDTYPSNDRCCHECRPGNGMVSRCSRSQNTVCRPC
GPGFYNDVVSSKPCKPCTWCNLRSGSERKQLCTATQDTV
CRCRAGTQPLDSYKPGVDCAPCPPGHFSPGDNQACKPWE
pCAMTLAGKHTLQPASNSSDAICEDRDPPATQPQETQGPP
ARPITVQPTEAWPRTSQGPSTRPVEVPGGRAVDEQLYFQ
GGSPKSADKTHTCPPCPAPELLGGPSVFLFPPKPKDTLMIS
RTPEVTCVVVDVSHEDPEVKFNWYVDGVEVHNAKTKPR
EEQYNSTYRVVSVLTVLHQDWLNGKEYKCKVSNKALPA
PIEKTISKAKGQPREPQVYTLPPCRDELTKNQVSLWCLVK
GFYPSDIAVEWESNGQPENNYKTTPPVLDSDGSFFLYSKL
TVDKSRWQQGNVFSCSVMHEALHNHYTQKSLSLSPGKS
GGLNDIFEAQKIEWHE |
| 97 | cynomolgus OX40 antigen Fc knob chain | LHCVGDTYPSNDRCCQECRPGNGMVSRCNRSQNTVCRP
CGPGFYNDVVSAKPCKACTWCNLRSGSERKQPCTATQD
TVCRCRAGTQPLDSYKPGVDCAPCPPGHFSPGDNQACKP
WEpCAMTLAGKHTLQPASNSSDAICEDRDPPPTQPQETQ
GPPARPTTVQPTEAWPRTSQRPSTRPVEVPRGPAVDEQLY
FQGGSPKSADKTHTCPPCPAPELLGGPSVFLFPPKPKDTL
MISRTPEVTCVVVDVSHEDPEVKFNWYVDGVEVHNAKT
KPREEQYNSTYRVVSVLTVLHQDWLNGKEYKCKVSNKA
LPAPIEKTISKAKGQPREPQVYTLPPCRDELTKNQVSLWC
LVKGFYPSDIAVEWESNGQPENNYKTTPPVLDSDGSFFLY
SKLTVDKSRWQQGNVFSCSVMHEALHNHYTQKSLSLSP
GKSGGLNDIFEAQKIEWHE |
| 98 | murine OX40 antigen Fc knob chain | VTARRLNCVKHTYPSGHKCCRECQPGHGMVSRCDHTRD
TLCHPCETGFYNEAVNYDTCKQCTQCNHRSGSELKQNCT
PTQDTVCRCRPGTQPRQDSGYKLGVDCVPCPPGHFSPGN
NQACKPWEpCAMTLSGKQTRHPASDSLDAVCEDRSLLAT
LLWETQRPTFRPTTVQSTTVWPRTSELPSPPTLVTPEGPV
DEQLYFQGGSPKSADKTHTCPPCPAPELLGGPSVFLFPPK
PKDTLMISRTPEVTCVVVDVSHEDPEVKFNWYVDGVEV
HNAKTKPREEQYNSTYRVVSVLTVLHQDWLNGKEYKCK
VSNKALPAPIEKTISKAKGQPREPQVYTLPPCRDELTKNQ |

TABLE 2-continued cDNA and amino acid sequences of monomeric antigen
Fc(kih) fusion molecules (produced by combination
of one Fc hole chain with one antigen Fc knob chain)

| SEQ ID NO: | Antigen | Sequence |
|---|---|---|
| | | VSLWCLVKGFYPSDIAVEWESNGQPENNYKTTPPVLDSD GSFFLYSKLTVDKSRWQQGNVFSCSVMHEALHNHYTQK SLSLSPGKSGGLNDIFEAQKIEWHE |

All OX40-Fc-fusion encoding sequences were cloned into a plasmid vector driving expression of the insert from an MPSV promoter and containing a synthetic polyA signal sequence located at the 3' end of the CDS. In addition, the vector contained an EBV OriP sequence for episomal maintenance of the plasmid.

For preparation of the biotinylated monomeric antigen/Fc fusion molecules, exponentially growing suspension HEK293 EBNA cells were co-transfected with three vectors encoding the two components of fusion protein (knob and hole chains) as well as BirA, an enzyme necessary for the biotinylation reaction. The corresponding vectors were used at a 2:1:0.05 ratio ("antigen ECD-AcTEV-Fc knob": "Fc hole": "BirA").

For protein production in 500 ml shake flasks, 400 million HEK293 EBNA cells were seeded 24 hours before transfection. For transfection cells were centrifuged for 5 minutes at 210 g, and supernatant was replaced by pre-warmed CD CHO medium. Expression vectors were resuspended in 20 mL of CD CHO medium containing 200 µg of vector DNA. After addition of 540 µL of polyethylenimine (PEI), the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere. After the incubation, 160 mL of F17 medium was added and cells were cultured for 24 hours. One day after transfection, 1 mM valproic acid and 7% Feed were added to the culture. After 7 days of culturing, the cell supernatant was collected by spinning down cells for 15 min at 210 g. The solution was sterile filtered (0.22 µm filter), supplemented with sodium azide to a final concentration of 0.01% (w/v), and kept at 4° C.

Secreted proteins were purified from cell culture supernatants by affinity chromatography using Protein A, followed by size exclusion chromatography. For affinity chromatography, the supernatant was loaded on a HiTrap ProteinA HP column (CV=5 mL, GE Healthcare) equilibrated with 40 mL 20 mM sodium phosphate, 20 mM sodium citrate pH 7.5. Unbound protein was removed by washing with at least 10 column volumes of a buffer containing 20 mM sodium phosphate, 20 mM sodium citrate and 0.5 M sodium chloride (pH 7.5). The bound protein was eluted using a linear pH-gradient of sodium chloride (from 0 to 500 mM) created over 20 column volumes of 20 mM sodium citrate, 0.01% (v/v) TWEEN 20™ (polysorbate 20), pH 3.0. The column was then washed with 10 column volumes of a solution containing 20 mM sodium citrate, 500 mM sodium chloride and 0.01% (v/v) TWEEN 20™ (polysorbate 20), pH 3.0.

The pH of the collected fractions was adjusted by adding 1/40 (v/v) of 2M TRIS™ (tris(hydroxymethyl)aminomethane), pH8.0. The protein was concentrated and filtered prior to loading on a HiLoad Superdex 200 column (GE Healthcare) equilibrated with 2 mM MOPS, 150 mM sodium chloride, 0.02% (w/v) sodium azide solution of pH 7.4.

1.2 Selection of OX40-Specific 8H9, 20B7, 49B4, 1G4, CLC-563, CLC-564 and 17A9 Antibodies from Generic Fab and Common Light Chain Libraries Anti-OX40 antibodies were selected from three different generic phage display libraries: DP88-4 (clones 20B7, 8H9 1G4 and 49B4), the common light chain library Vk3_20/VH3_23 (clones CLC-563 and CLC-564) and lambda-DP47 (clone 17A9).

The DP88-4 library was constructed on the basis of human germline genes using the V-domain pairing Vk1_5 (kappa light chain) and VH1_69 (heavy chain) comprising randomized sequence space in CDR3 of the light chain (L3, 3 different lengths) and CDR3 of the heavy chain (H3, 3 different lengths). Library generation was performed by assembly of 3 PCR-amplified fragments applying splicing by overlapping extension (SOE) PCR. Fragment 1 comprises the 5' end of the antibody gene including randomized L3, fragment 2 is a central constant fragment spanning from L3 to H3 whereas fragment 3 comprises randomized H3 and the 3' portion of the antibody gene. The following primer combinations were used to generate these library fragments for DP88-4 library: fragment 1 (forward primer LMB3 combined with reverse primers Vk1_5_L3r_S or Vk1_5_L3r_SY or Vk1_5_L3r_SPY), fragment 2 (forward primer RJH31 combined with reverse primer RJH32) and fragment 3 (forward primers DP88-v4-4 or DP88-v4-6 or DP88-v4-8 combined with reverse primer fdseqlong), respectively. PCR parameters for production of library fragments were 5 min initial denaturation at 94° C., 25 cycles of 1 min 94° C., 1 min 58° C., 1 min 72° C. and terminal elongation for 10 min at 72° C. For assembly PCR, using equimolar ratios of the gel-purified single fragments as template, parameters were 3 min initial denaturation at 94° C. and 5 cycles of 30 s 94° C., 1 min 58° C., 2 min 72° C. At this stage, outer primers (LMB3 and fdseqlong) were added and additional 20 cycles were performed prior to a terminal elongation for 10 min at 72° C. After assembly of sufficient amounts of full length randomized Fab constructs, they were digested NcoI/NheI and ligated into similarly treated acceptor phagemid vector. Purified ligations were used for ~60 transformations into electrocompetent E. coli TG1. Phagemid particles displaying the Fab library were rescued and purified by PEG/NaCl purification to be used for selections. These library construction steps were repeated three times to obtain a final library size of 4.4×109. Percentages of functional clones, as determined by C-terminal tag detection in dot blot, were 92.6% for the light chain and 93.7% for the heavy chain, respectively.

The common light chain library Vk3_20/VH3_23 was constructed on the basis of human germline genes using the V-domain pairing Vk3_20 (kappa light chain) and VH3_23 (heavy chain) comprising a constant non-randomized common light chain Vk3_20 and randomized sequence space in CDR3 of the heavy chain (H3, 3 different lengths). Library generation was performed by assembly of 2 PCR-amplified fragments applying splicing by overlapping extension (SOE) PCR. Fragment 1 is a constant fragment spanning from L3 to H3 whereas fragment 2 comprises randomized H3 and the 3' portion of the antibody gene. The following primer combinations were used to generate these library fragments for the Vk3_20/VH3_23 common light chain library: fragment 1 (forward primer MS64 combined with reverse primer DP47CDR3_ba (mod.)) and fragment 2 (forward primers DP47-v4-4, DP47-v4-6, DP47-v4-8 combined with reverse primer fdseqlong), respectively. PCR parameters for production of library fragments were 5 min initial denaturation at 94° C., 25 cycles of 1 min 94° C., 1 min 58° C., 1 min 72° C. and terminal elongation for 10 min at 72° C. For assembly PCR, using equimolar ratios of the gel-purified single fragments as template, parameters were 3 min initial denaturation at 94° C. and 5 cycles of 30 s 94° C., 1 min 58° C., 2 min 72° C. At this stage, outer primers (MS64 and fdseqlong) were added and additional 18 cycles were performed prior to a terminal elongation for 10 min at 72° C. After assembly of sufficient amounts of full length randomized VH constructs, they were digested MunI/NotI and ligated into similarly treated acceptor phagemid vector. Purified ligations were used for ~60 transformations into electrocompetent E. coli TG1. Phagemid particles displaying the Fab library were rescued and purified by PEG/NaCl purification to be used for selections. A final library size of 3.75×10⁹ was obtained. Percentages of functional clones, as determined by C-terminal tag detection in dot blot, were 98.9% for the light chain and 89.5% for the heavy chain, respectively.

The lambda-DP47 library was constructed on the basis of human germline genes using the following V-domain pairings: V1_3_19 lambda light chain with VH3_23 heavy chain. The library was randomized in CDR3 of the light chain (L3) and CDR3 of the heavy chain (H3) and was assembled from 3 fragments by "splicing by overlapping extension" (SOE) PCR. Fragment 1 comprises the 5' end of the antibody gene including randomized L3, fragment 2 is a central constant fragment spanning from the end of L3 to the beginning of H3 whereas fragment 3 comprises randomized H3 and the 3' portion of the Fab fragment. The following primer combinations were used to generate library fragments for library: fragment 1 (LMB3-V1_3_19_L3r_V/V1_3_19_L3r_HV/V1_3_19_L3r_HLV), fragment 2 (RJH80-DP47CDR3_ba (mod)) and fragment 3 (DP47-v4-4/DP47-v4-6/DP47-v4-8-fdseqlong). PCR parameters for production of library fragments were 5 min initial denaturation at 94° C., 25 cycles of 60 sec at 94° C., 60 sec at 55° C., 60 sec at 72° C. and terminal elongation for 10 min at 72° C. For assembly PCR, using equimolar ratios of the 3 fragments as template, parameters were 3 min initial denaturation at 94° C. and 5 cycles of 60 sec at 94° C., 60 sec at 55° C., 120 sec at 72° C. At this stage, outer primers were added and additional 20 cycles were performed prior to a terminal elongation for 10 min at 72° C. After assembly of sufficient amounts of full length randomized Fab fragments, they were digested with NcoI/NheI alongside with similarly treated acceptor phagemid vector. 15 ug of Fab library insert were ligated with 13.3 ug of phagemid vector. Purified ligations were used for 60 transformations resulting in 1.5×10⁹ transformants. Phagemid particles displaying the Fab library were rescued and purified by PEG/NaCl purification to be used for selections.

Human OX40 (CD134) as antigen for the phage display selections was transiently expressed as N-terminal monomeric Fc-fusion in HEK EBNA cells and in vivo site-specifically biotinylated via co-expression of BirA biotin ligase at the avi-tag recognition sequence located a the C-terminus of the Fc portion carrying the receptor chain (Fc knob chain).

Selection rounds (biopanning) were performed in solution according to the following pattern:

1. Pre-clearing of ~10¹² phagemid particles on maxisorp plates coated with 10 ug/ml of an unrelated human IgG to deplete the libraries of antibodies recognizing the Fc-portion of the antigen, 2. incubation of the non-binding phagemid particles with 100 nM biotinylated human OX40 for 0.5 h in the presence of 100 nM unrelated non-biotinylated Fc knob-into-hole construct for further depletion of Fc-binders in a total volume of 1 ml, 3. capture of biotinylated hu OX40 and attached specifically binding phage by transfer to 4 wells of a neutravidin pre-coated microtiter plate for 10 min (in rounds 1 & 3), 4. washing of respective wells using 5×PBS/TWEEN 20™ (polysorbate 20) and 5×PBS, 5. elution of phage particles by addition of 250 ul 100 mM TEA (triethylamine) per well for 10 min and neutralization by addition of 500 ul 1M TRIS™ (tris(hydroxymethyl) aminomethane)/HCl pH 7.4 to the pooled eluates from 4 wells, 6. post-clearing of neutralized eluates by incubation on neutravidin pre-coated microtiter plate with 100 nM biotin-captured Fc knob-into-hole construct for final removal of Fc-binders, 7. re-infection of log-phase E. coli TG1 cells with the supernatant of eluted phage particles, infection with helperphage VCSM13, incubation on a shaker at 30° C. over night and subsequent PEG/NaCl precipitation of phagemid particles to be used in the next selection round.

Selections were carried out over 3 or 4 rounds using constant antigen concentrations of 100 nM. In order to increase the likelihood for binders that are cross-reactive not only to cynomolgus OX40 but also murine OX40, in some selection rounds the murine target was used instead of the human OX40. In rounds 2 and 4, in order to avoid enrichment of binders to neutravidin, capture of antigen: phage complexes was performed by addition of 5.4×10⁷ streptavidin-coated magnetic beads. Specific binders were identified by ELISA as follows: 100 ul of 25 nM biotinylated human OX40 and 10 ug/ml of human IgG were coated on neutravidin plates and maxisorp plates, respectively. Fab-containing bacterial supernatants were added and binding Fabs were detected via their Flag-tags using an anti-Flag/HRP secondary antibody. Clones exhibiting signals on human OX40 and being negative on human IgG were short-listed for further analyses and were also tested in a similar fashion against cynomolgus and murine OX40. They were bacterially expressed in a 0.5 liter culture volume, affinity purified and further characterized by SPR-analysis using BioRad's ProteOn XPR36 biosensor.

Table 3 shows the sequence of generic phage-displayed antibody library (DP88-4), Table 4 provides cDNA and amino acid sequences of library DP88-4 germline template and Table 5 shows the Primer sequences used for generation of DP88-4 germline template.

TABLE 3

Sequence of generic phage-displayed antibody library (DP88-4)

| SEQ ID NO: | Description | Sequence |
| --- | --- | --- |
| 99 | nucleotide sequence of pRJH33 library template DP88-4 library; complete Fab coding region comprising PelB leader sequence + Vk1_5 kappa V-domain + CL constant domain for light chain and PelB + VH1_69 V-domain + CH1 constant domain for heavy chain including tags | TGAAATACCTATTGCCTACGGCAGCCGCTGGATTGTTATTACTC GCGGCCCAGCCGGCCATGGCCGACATCCAGATGACCCAGTCTC CTTCCACCCTGTCTGCATCTGTAGGAGACCGTGTCACCATCACT TGCCGTGCCAGTCAGAGTATTAGTAGCTGGTTGGCCTGGTATC AGCAGAAACCAGGGAAAGCCCCTAAGCTCCTGATCTATGATGC CTCCAGTTTGGAAAGTGGGGTCCCATCACGTTTCAGCGGCAGT GGATCCGGGACAGAATTCACTCTCACCATCAGCAGCTTGCAGC CTGATGATTTTGCAACTTATTACTGCCAACAGTATAATAGTTAT TCTACGTTTGGCCAGGGCACCAAAGTCGAGATCAAGCGTACGG TGGCTGCACCATCTGTCTTCATCTTCCCGCCATCTGATGAGCAG TTGAAATCTGGAACTGCCTCTGTTGTGTGCCTGCTGAATAACTT CTATCCCAGAGAGGCCAAAGTACAGTGGAAGGTGGATAACGC CCTCCAATCGGGTAACTCCCAGGAGAGTGTCACAGAGCAGGA CAGCAAGGACAGCACCTACAGCCTCAGCAGCACCCTGACGCT GAGCAAAGCAGACTACGAGAAACACAAAGTCTACGCCTGCGA AGTCACCCATCAGGGCCTGAGCTCGCCCGTCACAAAGAGCTTC AACAGGGGAGAGTGTGGAGCCGCAGAACAAAAACTCATCTCA GAAGAGGATCTGAATGGAGCCGCAGACTACAAGGACGACGAC GACAAGGGTGCCGCATAATAAGGCGCGCCAATTCTATTTCAAG GAGACAGTCATATGAAATACCTGCTGCCGACCGCTGCTGCTGG TCTGCTGCTCCTCGCTGCCCAGCCGGCGATGGCCCAGGTGCAA TTGGTGCAGTCTGGGGCTGAGGTGAAGAAGCCTGGGTCCTCGG TGAAGGTCTCCTGCAAGGCCTCCGGAGGCACATTCAGCAGCTA CGCTATAAGCTGGGTGCGACAGGCCCCTGGACAAGGGCTCGA GTGGATGGGAGGGATCATCCCTATCTTTGGTACAGCAAACTAC GCACAGAAGTTCCAGGGCAGGGTCACCATTACTGCAGACAAA CTCACGAGCACAGCCTACATGGAGCTGAGCAGCCTGAGATCTG AGGACACCGCCGTGTATTACTGTGCGAGACTATCCCCAGGCGG TTACTATGTTATGGATGCCTGGGGCCAAGGGACCACCGTGACC GTCTCCTCAGCTAGCACCAAGGCCCATCGGTCTTCCCCCTGG CACCCTCCTCCAAGAGCACCTCTGGGGGCACAGCGGCCCTGGG CTGCCTGGTCAAGGACTACTTCCCCGAACCGGTGACGGTGTCG TGGAACTCAGGCGCCCTGACCAGCGGCGTGCACACCTTCCCGG CTGTCCTACAGTCCTCAGGACTCTACTCCCTCAGCAGCGTGGT GACCGTGCCCTCCAGCAGCTTGGGCACCCAGACCTACATCTGC AACGTGAATCACAAGCCCAGCAACACCAAAGTGGACAAGAAA GTTGAGCCCAAATCTTGTGACGCGGCCGCAAGCACTAGTGCCC ATCACCATCACCATCACGCCGCGGCA |

TABLE 4 cDNA and amino acid sequences of library DP88-4 germline template

| SEQ ID NO: | Description | Sequence |
| --- | --- | --- |
| 100 | nucleotide sequence of Fab light chain Vk1_5 | GACATCCAGATGACCCAGTCTCCTTCCACCCTGTCTG CATCTGTAGGAGACCGTGTCACCATCACTTGCCGTGC CAGTCAGAGTATTAGTAGCTGGTTGGCCTGGTATCAG CAGAAACCAGGGAAAGCCCCTAAGCTCCTGATCTAT GATGCCTCCAGTTTGGAAAGTGGGGTCCCATCACGTT TCAGCGGCAGTGGATCCGGGACAGAATTCACTCTCAC CATCAGCAGCTTGCAGCCTGATGATTTTGCAACTTAT TACTGCCAACAGTATAATAGTTATTCTACGTTTGGCC AGGGCACCAAAGTCGAGATCAAGCGTACGGTGGCTG CACCATCTGTCTTCATCTTCCCGCCATCTGATGAGCA GTTGAAATCTGGAACTGCCTCTGTTGTGTGCCTGCTG AATAACTTCTATCCCAGAGAGGCCAAAGTACAGTGG AAGGTGGATAACGCCCTCCAATCGGGTAACTCCCAG GAGAGTGTCACAGAGCAGGACAGCAAGGACAGCACC TACAGCCTCAGCAGCACCCTGACGCTGAGCAAAGCA GACTACGAGAAACACAAAGTCTACGCCTGCGAAGTC ACCCATCAGGGCCTGAGCTCGCCCGTCACAAAGAGCT TCAACAGGGGAGAGTGTGGAGCCGCAGAACAAAAAC TCATCTCAGAAGAGGATCTGAATGGAGCCGCAGACT ACAAGGACGACGACGACAAGGGTGCCGCA |
| 101 | Fab light chain Vk1_5 | DIQMTQSPSTLSASVGDRVTITCRASQSISSWLAWYQQK PGKAPKLLIYDASSLESGVPSRFSGSGSGTEFTLTISSLQP DDFATYYCQQYNSYSTFGQGTKVEIKRTVAAPSVFIFPP SDEQLKSGTASVVCLLNNFYPREAKVQWKVDNALQSG |

TABLE 4-continued cDNA and amino acid sequences of library DP88-4 germline template

| SEQ ID NO: | Description | Sequence |
| --- | --- | --- |
| | | NSQESVTEQDSKDSTYSLSSTLTLSKADYEKHKVYACE VTHQGLSSPVTKSFNRGECGAAEQKLISEEDLNGAADY KDDDDKGAA |
| 102 | nucleotide sequence of Fab heavy chain VH1_69 | CAGGTGCAATTGGTGCAGTCTGGGGCTGAGGTGAAG AAGCCTGGGTCCTCGGTGAAGGTCTCCTGCAAGGCCT CCGGAGGCACATTCAGCAGCTACGCTATAAGCTGGGT GCGACAGGCCCCTGGACAAGGGCTCGAGTGGATGGG AGGGATCATCCCTATCTTTGGTACAGCAAACTACGCA CAGAAGTTCCAGGGCAGGGTCACCATTACTGCAGAC AAATCCACGAGCACAGCCTACATGGAGCTGAGCAGC CTGAGATCTGAGGACACCGCCGTGTATTACTGTGCGA GACTATCCCCAGGCGGTTACTATGTTATGGATGCCTG GGGCCAAGGGACCACCGTGACCGTCTCCTCAGCTAGC ACCAAAGGCCCATCGGTCTTCCCCCTGGCACCCTCCT CCAAGAGCACCTCTGGGGGCACAGCGGCCCTGGGCT GCCTGGTCAAGGACTACTTCCCCGAACCGGTGACGGT GTCGTGGAACTCAGGCGCCCTGACCAGCGGCGTGCA CACCTTCCCGGCTGTCCTACAGTCCTCAGGACTCTAC TCCCTCAGCAGCGTGGTGACCGTGCCCTCCAGCAGCT TGGGCACCCAGACCTACATCTGCAACGTGAATCACAA GCCCAGCAACACCAAAGTGGACAAGAAAGTTGAGCC CAAATCTTGTGACGCGGCCGCAAGCACTAGTGCCCAT CACCATCACCATCACGCCGCGGCA |
| 103 | Fab heavy chain VH1_69 | QVQLVQSGAEVKKPGSSVKVSCKASGGTFSSYAISWVR QAPGQGLEWMGGIIPIFGTANYAQKFQGRVTITADKSTS TAYMELSSLRSEDTAVYYCARLSPGGYYVMDAWGQGT TVTVSSASTKGPSVFPLAPSSKSTSGGTAALGCLVKDYF PEPVTVSWNSGALTSGVHTFPAVLQSSGLYSLSSVVTVP SSSLGTQTYICNVNHKPSNTKVDKKVEPKSCDAAASTS AHHHHHHAAA |

TABLE 5

Primer sequences used for generation of DP88-4 library

| SEQ ID NO: | Primer name | Primer sequence 5' - 3' |
| --- | --- | --- |
| 104 | LMB3 | CAGGAAACAGCTATGACCATGATTAC |
| 105 | Vk1_5_L3r_S | CTCGACTTTGGTGCCCTGGCCAAACGTSBAATACGAATTATACTGTTGGCAGTAATAAGTTGCAAA ATCAT<br>underlined: 60% original base and 40% randomization as M.<br>bolded and italic: 60% original base and 40% randomization as N |
| 106 | Vk1_5_L3r_SY | CTCGACTTTGGTGCCCTGGCCAAACGTMHRSGR ATACGAATTATACTGTTGGCAGTAATAAGTTGCA AAATCAT<br>underlined: 60% original base and 40% randomization as M.<br>bolded and italic: 60% original base and 40% randomization as N |
| 107 | Vk1_5_L3r_SPY | CTCGACTTTGGTGCCCTGGCCAAACGTMHHMSS SGRATACGAATTATACTGTTGGCAGTAATAAGTT GCAAATCAT<br>underlined: 60% original base and 40% randomization as M.<br>bolded and italic: 60% original base and 40% randomization as N |
| 108 | RJH31 | ACGTTTGGCCAGGGCACCAAAGTCGAG |
| 109 | RJH32 | TCTCGCACAGTAATACACGGCGGTGTCC |
| 110 | DP88-v4-4 | GGACACCGCCGTGTATTACTGTGCGAGA-1-2-2-3-4-GAC-TAC- |

TABLE 5-continued

Primer sequences used for generation of DP88-4 library

| SEQ ID NO: | Primer name | Primer sequence 5' - 3' |
|---|---|---|
| | | TGGGGCCAAGGGACCACCGTGACCGTCTCC<br>1: G/D = 20%, E/V/S = 10%, A/P/R/L/T/Y = 5%; 2: G/Y/S = 15%, A/D/T/R/P/L/V/N/W/F/I/E = 4,6%; 3: G/A/Y = 20%, P/W/S/D/T = 8%; 4: F = 46%, L/M = 15%, G/I/Y = 8%. |
| 111 | DP88-v4-6 | GGACACCGCCGTGTATTACTGTGCGAGA-1-2-2-2-2-3 -4-GAC-TAC-TGGGGCCAAGGGACCACCGTGACCGTCTCC<br>1: G/D = 20%, E/V/S = 10%, A/P/R/L/T/Y = 5%; 2: G/Y/S = 15%, A/D/T/R/P/L/V/N/W/F/I/E = 4,6%; 3: G/A/Y = 20%, P/W/S/D/T = 8%; 4: F = 46%, L/M = 15%, G/I/Y = 8%. |
| 112 | DP88-v4-8 | GGACACCGCCGTGTATTACTGTGCGAGA-1-2-2-2-2-2-2-3-4-GAC-TAC-TGGGGCCAAGGGACCACCGTGACCGTCTCC<br>1: G/D = 20%, E/V/S = 10%, A/P/R/L/T/Y = 5%; 2: G/Y/S = 15%, A/D/T/R/P/L/V/N/W/F/I/E = 4,6%; 3: G/A/Y = 20%, P/W/S/D/T = 8%; 4: F = 46%, L/M = 15%, G/I/Y = 8%. |
| 113 | fdseqlong | GACGTTAGTAAATGAATTTTCTGTATGAGG |

Table 6 shows the sequence of generic phage-displayed antibody common light chain library (Vk3_20/VH3_23). Table 7 provides cDNA and amino acid sequences of common light chain library (Vk3_20/VH3_23) germline template and Table 8 shows the Primer sequences used for generation of common light chain library (Vk3_20/VH3_23).

TABLE 6

Sequence of generic phage- displayed antibody common light chain library (Vk3_20/VH3_23) template used for PCR

| SEQ ID NO: | Description | Sequence |
|---|---|---|
| 114 | pRJH110 library template of common light chain library Vk3_20/VH3_23; complete Fab coding region comprising PelB leader sequence + Vk3_20 kappa V-domain + CL constant domain for light chain and PelB + VH3+23 V-domain + CH1 constant domain for heavy chain including tags | ATGAAATACCTATTGCCTACGGCAGCCGCTGGATTGTTATTACTC<br>GCGGCCCAGCCGGCCATGGCCGAAATCGTGTTAACGCAGTCTCC<br>AGGCACCCTGTCTTTGTCTCCAGGGGAAAGAGCCACCCTCTCTT<br>GCAGGGCCAGTCAGAGTGTTAGCAGCAGCTACTTAGCCTGGTAC<br>CAGCAGAAACCTGGCCAGGCTCCCAGGCTCCTCATCTATGGAGC<br>ATCCAGCAGGGCCACTGGCATCCCAGACAGGTTCAGTGGCAGTG<br>GATCCGGGACAGACTTCACTCTCACCATCAGCAGACTGGAGCCT<br>GAAGATTTTGCAGTGTATTACTGTCAGCAGTATGGTAGCTCACC<br>GCTGACGTTCGGCCAGGGGACCAAAGTGGAAATCAAACGTACG<br>GTGGCTGCACCATCTGTCTTCATCTTCCCGCCATCTGATGAGCAG<br>TTGAAATCTGGAACTGCCTCTGTTGTGTGCCTGCTGAATAACTTC<br>TATCCCAGAGAGGCCAAAGTACAGTGGAAGGTGGATAACGCCC<br>TCCAATCGGGTAACTCCCAGGAGAGTGTCACAGAGCAGGACAG<br>CAAGGACAGCACCTACAGCCTCAGCAGCACCCTGACGCTGAGC<br>AAAGCAGACTACGAGAAACACAAAGTCTACGCCTGCGAAGTCA<br>CCCATCAGGGCCTGAGCTCGCCCGTCACAAAGAGCTTCAACAGG<br>GGAGAGTGTGGAGCCGCACATCACCATCACCATCACGGAGCCG<br>CAGACTACAAGGACGACGACGACAAGGGTGCCGCATAATAAGG<br>CGCGCCAATTCTATTTCAAGGAGACAGTCATATGAAATACCTGC<br>TGCCGACCGCTGCTGCTGGTCTGCTGCTCCTCGCTGCCCAGCCGG<br>CGATGGCCGAGGTGCAATTGCTGGAGTCTGGGGGAGGCTTGGTA<br>CAGCCTGGGGGGTCCCTGAGACTCTCCTGTGCAGCCTCCGGATT<br>CACCTTTAGCAGTTATGCCATGAGCTGGGTCCGCCAGGCTCCAG<br>GGAAGGGGCTGGAGTGGGTCTCAGCTATTAGTGGTAGTGGTGGT<br>AGCACATACTACGCAGACTCCGTGAAGGGCCGGTTCACCATCTC<br>CAGAGACAATTCCAAGAACACGCTGTATCTGCAGATGAACAGCC<br>TGAGAGCCGAGGACACGGCCGTATATTACTGTGCGAAACCGTTT<br>CCGTATTTTGACTACTGGGGCCAAGGAACCCTGGTCACCGTCTC<br>GAGTGCTAGCACCAAAGGCCCATCGGTCTTCCCCCTGGCACCCT<br>CCTCCAAGAGCACCTCTGGGGGCACAGCGGCCCTGGGCTGCCTG<br>GTCAAGGACTACTTCCCCGAACCGGTGACGGTGTCGTGGAACTC<br>AGGCGCCCTGACCAGCGGCGTGCACACCTTCCCGGCTGTCCTAC<br>AGTCCTCAGGACTCTACTCCCTCAGCAGCGTGGTGACCGTGCCC<br>TCCAGCAGCTTGGGCACCCAGACCTACATCTGCAACGTGAATCA |

TABLE 6-continued

Sequence of generic phage-displayed antibody common
light chain library (Vk3_20/VH3_23) template used for PCR

| SEQ ID NO: | Description | Sequence |
|---|---|---|
| | | CAAGCCCAGCAACACCAAAGTGGACAAGAAAGTTGAGCCCAAA<br>TCTTGTGACGCGGCCGCAGAACAAAAACTCATCTCAGAAGAGGA<br>TCTGAATGCCGCGGCA |

TABLE 7 cDNA and amino acid sequences of common
light chain library (Vk3_20/VH3_23) germline template

| SEQ ID NO: | Description | Sequence |
|---|---|---|
| 115 | nucleotide sequence of Fab light chain Vk3_20 | GAAATCGTGTTAACGCAGTCTCCAGGCACCCTGTCTTT<br>GTCTCCAGGGGAAAGAGCCACCCTCTCTTGCAGGGCCA<br>GTCAGAGTGTTAGCAGCAGCTACTTAGCCTGGTACCAG<br>CAGAAACCTGGCCAGGCTCCCAGGCTCCTCATCTATGG<br>AGCATCCAGCAGGGCCACTGGCATCCCAGACAGGTTC<br>AGTGGCAGTGGATCCGGGACAGACTTCACTCTCACCAT<br>CAGCAGACTGGAGCCTGAAGATTTTGCAGTGTATTACT<br>GTCAGCAGTATGGTAGCTCACCGCTGACGTTCGGCCAG<br>GGGACCAAAGTGGAAATCAAACGTACGGTGGCTGCAC<br>CATCTGTCTTCATCTTCCCGCCATCTGATGAGCAGTTGA<br>AATCTGGAACTGCCTCTGTTGTGTGCCTGCTGAATAAC<br>TTCTATCCCAGAGAGGCCAAAGTACAGTGGAAGGTGG<br>ATAACGCCCTCCAATCGGGTAACTCCCAGGAGAGTGTC<br>ACAGAGCAGGACAGCAAGGACAGCACCTACAGCCTCA<br>GCAGCACCCTGACGCTGAGCAAAGCAGACTACGAGAA<br>ACACAAAGTCTACGCCTGCGAAGTCACCCATCAGGGC<br>CTGAGCTCGCCCGTCACAAAGAGCTTCAACAGGGGAG<br>AGTGTGGAGCCGCACATCACCATCACCATCACGGAGC<br>CGCAGACTACAAGGACGACGACGACAAGGGTGCCGCA |
| 116 | Fab light chain Vk3_20 | EIVLTQSPGTLSLSPGERATLSCRASQSVSSSYLAWYQQK<br>PGQAPRLLIYGASSRATGIPDRFSGSGSGTDFTLTISRLEPE<br>DFAVYYCQQYGSSPLTFGQGTKVEIKRTVAAPSVFIFPPS<br>DEQLKSGTASVVCLLNNFYPREAKVQWKVDNALQSGNS<br>QESVTEQDSKDSTYSLSSTLTLSKADYEKHKVYACEVTH<br>QGLSSPVTKSFNRGECGAAHHHHHHGAADYKDDDDKG<br>AA |
| 117 | nucleotide sequence of Fab heavy chain VH3_23 | GAGGTGCAATTGCTGGAGTCTGGGGGAGGCTTGGTAC<br>AGCCTGGGGGGTCCCTGAGACTCTCCTGTGCAGCCTCC<br>GGATTCACCTTTAGCAGTTATGCCATGAGCTGGGTCCG<br>CCAGGCTCCAGGGAAGGGGCTGGAGTGGGTCTCAGCT<br>ATTAGTGGTAGTGGTGGTAGCACATACTACGCAGACTC<br>CGTGAAGGGCCGGTTCACCATCTCCAGAGACAATTCCA<br>AGAACACGCTGTATCTGCAGATGAACAGCCTGAGAGC<br>CGAGGACACGGCCGTATATTACTGTGCGAAACCGTTTC<br>CGTATTTTGACTACTGGGGCCAAGGAACCCTGGTCACC<br>GTCTCGAGTGCTAGCACCAAAGGCCCATCGGTCTTCCC<br>CCTGGCACCCTCCTCCAAGAGCACCTCTGGGGGCACAG<br>CGGCCCTGGGCTGCCTGGTCAAGGACTACTTCCCCGAA<br>CCGGTGACGGTGTCGTGGAACTCAGGCGCCCTGACCA<br>GCGGCGTGCACACCTTCCCGGCTGTCCTACAGTCCTCA<br>GGACTCTACTCCCTCAGCAGCGTGGTGACCGTGCCCTC<br>CAGCAGCTTGGGCACCCAGACCTACATCTGCAACGTGA<br>ATCACAAGCCCAGCAACACCAAAGTGGACAAGAAAGT<br>TGAGCCCAAATCTTGTGACGCGGCCGCAGAACAAAAA<br>CTCATCTCAGAAGAGGATCTGAATGCCGCGGCA |
| 118 | Fab heavy chain VH3_23 (DP47) | EVQLLESGGGLVQPGGSLRLSCAASGFTFSSYAMSWVRQ<br>APGKGLEWVSAISGSGGSTYYADSVKGRFTISRDNSKNTL<br>YLQMNSLRAEDTAVYYCAKPFPYFDYWGQGTLVTVSSA<br>STKGPSVFPLAPSSKSTSGGTAALGCLVKDYFPEPVTVSW<br>NSGALTSGVHTFPAVLQSSGLYSLSSVVTVPSSSLGTQTYI<br>CNVNHKPSNTKVDKKVEPKSCDAAAEQKLISEEDLNAAA |

TABLE 8

Primer sequences used for generation of common light chain library (Vk3_20/VH3_23)

| SEQ ID NO: | Primer name | Primer sequence 5' - 3' |
|---|---|---|
| 119 | MS64 | ACGTTCGGCCAGGGGACCAAAGTGG |
| 120 | DP47CDR3_ba (mod.) | CGCACAGTAATATACGGCCGTGTCC |
| 121 | DP47-v4-4 | CGAGGACACGGCCGTATATTACTGTGCG-5-1-2-2-3-4-GAC-TAC-TGGGGCCAAGGAACCCTGGTCACCGTCTCG |
| 122 | DP47-v4-6 | CGAGGACACGGCCGTATATTACTGTGCG-5-1-2-2-2-2-3-4-GAC-TAC-TGGGGCCAAGGAACCCTGGTCACCGTCTCG |
| 123 | DP47-v4-8 | CGAGGACACGGCCGTATATTACTGTGCG-5-1-2-2-2-2-2-2-3-4-GAC-TAC-TGGGGCCAAGGAACCCTGGTCACCGTCTCG |
| 124 | fdseqlong | GACGTTAGTAAATGAATTTTCTGTATGAGG<br>1: G/D = 20%, E/V/S = 10%, A/P/R/L/T/Y = 5%; 2: G/Y/S = 15%, A/D/T/R/P/L/V/N/W/F/I/E = 4,6%; 3: G/A/Y = 20%, P/W/S/D/T = 8%; 4: F = 46%, L/M = 15%, G/I/Y = 8%; 5: K = 70%, R = 30%. |

Table 9 shows the sequence of generic phage-displayed lambda-DP47 library (V13_19/VH3_23) template used for PCRs. Table 10 provides cDNA and amino acid sequences of lambda-DP47 library (V13_19/VH3_23) germline template and Table 11 shows the Primer sequences used for generation of lambda-DP47 library (V13_19/VH3_23).

TABLE 9

Sequence of generic phage- displayed lambda-DP47 library (V13_19/VH3_23) template used for PCRs

| SEQ ID NO: | Description | Sequence |
|---|---|---|
| 125 | pRJH53 library template of lambda-DP47 library V13_19/VH3_23; complete Fab coding region comprising PelB leader sequence + V13_19 lambda V-domain + CL constant domain for light chain and PelB + VH3_23 V-domain + CH1 constant domain for heavy chain including tags | ATGAAATACCTATTGCCTACGGCAGCCGCTGGATTGTTATTACTC<br>GCGGCCCAGCCGGCCATGGCCTCGTCTGAGCTGACTCAGGACCC<br>TGCTGTGTCTGTGGCCTTGGGACAGACAGTCAGGATCACATGCC<br>AAGGAGACAGCCTCAGAAGTTATTATGCAAGCTGGTACCAGCAG<br>AAGCCAGGACAGGCCCCTGTACTTGTCATCTATGGTAAAAACAA<br>CCGGCCCTCAGGGATCCCAGACCGATTCTCTGGCTCCAGCTCAG<br>GAAACACAGCTTCCTTGACCATCACTGGGGCTCAGGCGGAAGAT<br>GAGGCTGACTATTACTGTAACTCCCGTGATAGTAGCGGTAATCA<br>TGTGGTATTCGGCGGAGGGACCAAGCTGACCGTCCTAGGACAAC<br>CCAAGGCTGCCCCCAGCCGTGACCCTGTTCCCCCCCAGCAGCGAG<br>GAATTGCAGGCCAACAAGGCCACCCTGGTCTGCCTGATCAGCGA<br>CTTCTACCCAGGCGCCGTGACCGTGGCCTGGAAGGCCGACAGCA<br>GCCCCGTGAAGGCCGGCGTGGAGACCACCACCCCCAGCAAGCA<br>GAGCAACAACAAGTACGCCGCCAGCAGCTACCTGAGCCTGACC<br>CCCGAGCAGTGGAAGAGCCACAGGTCCTACAGCTGCCAGGTGA<br>CCCACGAGGGCAGCACCGTGGAGAAAACCGTGGCCCCCACCGA<br>GTGCAGCGGAGCCGCAGAACAAAAACTCATCTCAGAAGAGGAT<br>CTGAATGGAGCCGCAGACTACAAGGACGACGACGACAAGGGTG<br>CCGCATAATAAGGCGCGCCAATTCTATTTCAAGGAGACAGTCAT<br>ATGAAATACCTGCTGCCGACCGCTGCTGCTGGTCTGCTGCTCCTC<br>GCTGCCCAGCCGGCGATGGCCGAGGTGCAATTGCTGGAGTCTGG<br>GGGAGGCTTGGTACAGCCTGGGGGGTCCCTGAGACTCTCCTGTG<br>CAGCCTCCGGATTCACCTTTAGCAGTTATGCCATGAGCTGGGTCC<br>GCCAGGCTCCAGGGAAGGGGCTGGAGTGGGTCTCAGCTATTAGT<br>GGTAGTGGTGGTAGCACATACTACGCAGACTCCGTGAAGGGCCG<br>GTTCACCATCTCCAGAGACAATTCCAAGAACACGCTGTATCTGC<br>AGATGAACAGCCTGAGAGCCGAGGACACGGCCGTATATTACTGT<br>GCGAAACCGTTTCCGTATTTTGACTACTGGGGCCAAGGAACCCT<br>GGTCACCGTCTCGAGTGCTAGCACCAAAGGCCCATCGGTCTTCC<br>CCCTGGCACCCTCCTCCAAGAGCACCTCTGGGGGCACAGCGGCC<br>CTGGGCTGCCTGGTCAAGGACTACTTCCCCGAACCGGTGACGGT<br>GTCGTGGAACTCAGGCGCCCTGACCAGCGGCGTGCACACCTTCC<br>CGGCTGTCCTACAGTCCTCAGGACTCTACTCCCTCAGCAGCGTG<br>GTGACCGTGCCCTCCAGCAGCTTGGGCACCCAGACCTACATCTG<br>CAACGTGAATCACAAGCCCAGCAACACCAAAGTGGACAAGAAA<br>GTTGAGCCCAAATCTTGTGACGCGGCCGCAAGCACTAGTGCCCA<br>TCACCATCACCATCACGCCGCGGCA |

TABLE 9-continued

Sequence of generic phage- displayed lambda-DP47
library (Vl3_19/VH3_23) template used for PCRs

| SEQ ID NO: | Description | Sequence |
|---|---|---|

TABLE 10 cDNA and amino acid sequences of lambda-DP47
library (Vl3_19/VH3_23) germline template

| SEQ ID NO: | Description | Sequence |
|---|---|---|
| 126 | nucleotide sequence of Fab light chain Vl3_19 | TCGTCTGAGCTGACTCAGGACCCTGCTGTGTCTGTGGCCT TGGGACAGACAGTCAGGATCACATGCCAAGGAGACAGCC TCAGAAGTTATTATGCAAGCTGGTACCAGCAGAAGCCAG GACAGGCCCCTGTACTTGTCATCTATGGTAAAAACAACCG GCCCTCAGGGATCCCAGACCGATTCTCTGGCTCCAGCTCA GGAAACACAGCTTCCTTGACCATCACTGGGGCTCAGGCG GAAGATGAGGCTGACTATTACTGTAACTCCCGTGATAGTA GCGGTAATCATGTGGTATTCGGCGGAGGGACCAAGCTGA CCGTCCTAGGACAACCCAAGGCTGCCCCCAGCGTGACCCT GTTCCCCCCCAGCAGCGAGGAATTGCAGGCCAACAAGGC CACCCTGGTCTGCCTGATCAGCGACTTCTACCCAGGCGCC GTGACCGTGGCCTGGAAGGCCGACAGCAGCCCCGTGAAG GCCGGCGTGGAGACCACCACCCCCAGCAAGCAGAGCAAC AACAAGTACGCCGCCAGCAGCTACCTGAGCCTGACCCCC GAGCAGTGGAAGAGCCACAGGTCCTACAGCTGCCAGGTG ACCCACGAGGGCAGCACCGTGGAGAAAACCGTGGCCCCC ACCGAGTGCAGCGGGAGCCGCAGAACAAAAACTCATCTCA GAAGAGGATCTGAATGGAGCCGCAGACTACAAGGACGAC GACGACAAGGGTGCCGCA |
| 127 | Fab light chain Vl3_19 | SSELTQDPAVSVALGQTVRITCQGDSLRSYYASWYQQKPGQ APVLVIYGKNNRPSGIPDRFSGSSSGNTASLTITGAQAEDEAD YYCNSRDSSGNHVVFGGGTKLTVLGQPKAAPSVTLFPPSSEE LQANKATLVCLISDFYPGAVTVAWKADSSPVKAGVETTTPS KQSNNKYAASSYLSLTPEQWKSHRSYSCQVTHEGSTVEKTV APTECSGAAEQKLISEEDLNGAADYKDDDDKGAA |
| 117 | nucleotide sequence of Fab heavy chain VH3_23 | see Table 7 |
| 118 | Fab heavy chain VH3_23 (DP47) | see Table 7 |

TABLE 11

Primer sequences used for generation of lambda-DP47 library (Vl3_19/VH3_23)

| SEQ ID NO: | Primer name | Primer sequence 5' - 3' |
|---|---|---|
| 128 | LMB3 | CAGGAAACAGCTATGACCATGATTAC |
| 129 | Vl_3_9_L3r_V | GGACGGTCAGCTTGGTCCCTCCGCCGAATAC**V*HV*
*ATT*ACC G*CT A*CT A*TC A***CG*
GGAGTTACAGTAATAGTCAGCCTCATCTTCCGC
underlined: 60% original base and 40% randomization as M
bold and italic: 60% original base and 40% randomization as N |
| 130 | Vl_3_19_L3r_HV | GGACGGTCAGCTTGGTCCCTCCGCCGAATAC**C*MM*
*ATG A*TT A*CC G*CT A*CT A*TC A***CG*
GGAGTTACAGTAATAGTCAGCCTCATCTTCCGC
underlined: 60% original base and 40% randomization as M
bolded and italic: 60% original base and 40% randomization as N |

TABLE 11-continued

Primer sequences used for generation of lambda-DP47 library (Vl3_19/VH3_23)

| SEQ ID NO: | Primer name | Primer sequence 5' - 3' |
|---|---|---|
| 131 | Vl_3_19_L3r_HLV | GGACGGTCAGCTTGGTCCCTCCGCCGAATACRHM VWG ATG ATT ACC GCT ACT ATC ACG GGAGTTACAGTAATAGTCAGCCTCATCTTCCGC underlined: 60% original base and 40% randomization as M bolded and italic: 60% original base and 40% randomization as N |
| 132 | RJH80 | TTCGGCGGAGGGACCAAGCTGACCGTCC |
| 133 | MS63 | TTTCGCACAGTAATATACGGCCGTGTCC |

Additional primers used for construction of the lambda-DP47 library, i.e. DP47CDR3_ba (mod.), DP47-v4-4, DP47-v4-6, DP47-v4-8 and fdseqlong, are identical to the primers used for the construction of the common light chain library (Vk3_20/VH3_23) and have already been listed in Table 8.

Clones 8H9, 20B7, 49B4, 1G4, CLC-563, CLC-564 and 17A9 were identified as human OX40-specific binders through the procedure described above. The cDNA sequences of their variable regions are shown in Table 12 below, the corresponding amino acid sequences can be found in Table C.

TABLE 12

Variable region base pair sequences for phage-derived anti-OX40 antibodies.

| Clone | SEQ ID NO: | Sequence |
|---|---|---|
| 8H9 | 134 (VL) | TCGTCTGAGCTGACTCAGGACCCTGCTGTGTCTGTGGCCTTGG GACAGACAGTCAGGATCACATGC<u>CAAGGAGACAGCCTCAGAA GTTATTATGCAAG</u>CTGGTACCAGCAGAAGCCAGGACAGGCCC CTGTACTTGTCATCTAT<u>GGTAAAAACAACCGGCCCT</u>CAGGGAT CCCAGACCGATTCTCTGGCTCCAGCTCAGGAAACACAGCTTCC TTGACCATCACTGGGGCTCAGGCGGAAGATGAGGCTGACTATT ACTGT<u>AACTCCCGTGTTATGCCTCATAATCGCGT</u>ATTCGGCGG AGGGACCAAGCTGACCGTC |
| | 135 (VH) | GAGGTGCAATTGTTGGAGTCTGGGGGAGGCTTGGTACAGCCT GGGGGGTCCCTGAGACTCTCCTGTGCAGCCTCCGGATTCACCT TTAGC<u>AGTTATGCCATGAGC</u>TGGGTCCGCCAGGCTCCAGGGAA GGGGCTGGAGTGGGTCTC<u>AGCTATTAGTGGTAGTGGTGGTAGC ACATACTACGCAGACTCCGTGAAGGGC</u>CGGTTCACCATCTCCA GAGACAATTCCAAGAACACGCTGTATCTGCAGATGAACAGCC TGAGAGCCGAGGACACGGCCGTATATTACTGTGCGCGT<u>GTTTT CTACCGTGTGGTGTTTCTATGGACTAC</u>TGGGGCCAAGGAACC CTGGTCACCGTCTCGAGT |
| 49B4 | 136 (VL) | GACATCCAGATGACCCAGTCTCCTTCCACCCTGTCTGCATCTG TAGGAGACCGTGTCACCATCACTTGC<u>CGTGCCAGTCAGAGTAT TAGTAGCTGGTTGGCC</u>TGGTATCAGCAGAAACCAGGGAAAGC CCCTAAGCTCCTGATCTAT<u>GATGCCTCCAGTTTGGAAAGT</u>GGG GTCCCATCACGTTTCAGCGGCAGTGGATCCGGGACAGAATTCA CTCTCACCATCAGCAGCTTGCAGCCTGATGATTTTGCAACTTA TTACTGC<u>CAACAGTATAGTTCGCAGCCGTATACG</u>TTTGGCCAG GGCACCAAAGTCGAGATCAAG |
| | 137 (VH) | CAGGTGCAATTGGTGCAGTCTGGGGCTGAGGTGAAGAAGCCT GGGTCCTCGGTGAAGGTCTCCTGCAAGGCCTCCGGAGGCACAT TCAGC<u>AGCTACGCTATAAGC</u>TGGGTGCGACAGGCCCCTGGAC AAGGGCTCGAGTGGATGGGA<u>GGGATCATCCCTATCTTTGGTAC AGCAAACTACGCACAGAAGTTCCAGGGC</u>AGGGTCACCATTAC TGCAGACAAATCCACGAGCACAGCCTACATGGAGCTGAGCAG CCTGAGATCTGAGGACACCGCCGTGTATTACTGTGCGAGA<u>GA ATACTACCGTGGTCCGTACGACTAC</u>TGGGGCCAAGGGACCAC CGTGACCGTCTCCTCA |
| 1G4 | 138 (VL) | GACATCCAGATGACCCAGTCTCCTTCCACCCTGTCTGCATCTG TAGGAGACCGTGTCACCATCACTTGC<u>CGTGCCAGTCAGAGTAT TAGTAGCTGGTTGGCC</u>TGGTATCAGCAGAAACCAGGGAAAGC CCTAAGCTCCTGATCTAT<u>GATGCCTCCAGTTTGGAAAGT</u>GGG GTCCCATCACGTTTCAGCGGCAGTGGATCCGGGACAGAATTCA CTCTCACCATCAGCAGCTTGCAGCCTGATGATTTTGCAACTTA |

TABLE 12-continued

Variable region base pair sequences for phage-derived anti-OX40 antibodies.

| Clone | SEQ ID NO: | Sequence |
|---|---|---|
| | | TTACTGC<u>CAACAGTATATTTCGTATTCCATGTTGAC</u>GTTTGGCC<br>AGGGCACCAAAGTCGAGATCAAG |
| | 139 (VH) | CAGGTGCAATTGGTGCAGTCTGGGGCTGAGGTGAAGAAGCCT<br>GGGTCCTCGGTGAAGGTCTCCTGCAAGGCCTCCGGAGGCACAT<br>TCAGC<u>AGCTACGCTATAAGC</u>TGGGTGCGACAGGCCCCTGGAC<br>AAGGGCTCGAGTGGATGGG<u>AGGGATCATCCCTATCTTTGGTAC<br>AGCAAACTACGCACAGAAGTTCCAGGGC</u>AGGGTCACCATTAC<br>TGCAGACAAATCCACGAGCACAGCCTACATGGAGCTGAGCAG<br>CCTGAGATCTGAGGACACCGCCGTGTATTACTGTGCGAGA<u>GA<br>ATACGGTTCTATGGACTAC</u>TGGGGCCAAGGGACCACCGTGAC<br>CGTCTCCTCA |
| 20B7 | 140 (VL) | GACATCCAGATGACCCAGTCTCCTTCCACCCTGTCTGCATCTG<br>TAGGAGACCGTGTCACCATCACTTGC<u>CGTGCCAGTCAGAGTAT<br>TAGTAGCTGGTTGGCC</u>TGGTATCAGCAGAAACCAGGGAAAGC<br>CCCTAAGCTCCTGATCTAT<u>GATGCCTCCAGTTTGGAAAGT</u>GGG<br>GTCCCATCACGTTTCAGCGGCAGTGGATCCGGGACAGAATTCA<br>CTCTCACCATCAGCAGCTTGCAGCCTGATGATTTTGCAACTTA<br>TTACTGC<u>CAACAGTATCAGGCTTTTTCGCTTAC</u>GTTTGGCCAG<br>GGCACCAAAGTCGAGATCAAG |
| | 141 (VH) | CAGGTGCAATTGGTGCAGTCTGGGGCTGAGGTGAAGAAGCCT<br>GGGTCCTCGGTGAAGGTCTCCTGCAAGGCCTCCGGAGGCACAT<br>TCAGC<u>AGCTACGCTATAAGC</u>TGGGTGCGACAGGCCCCTGGAC<br>AAGGGCTCGAGTGGATGGG<u>AGGGATCATCCCTATCTTTGGTAC<br>AGCAAACTACGCACAGAAGTTCCAGGGC</u>AGGGTCACCATTAC<br>TGCAGACAAATCCACGAGCACAGCCTACATGGAGCTGAGCAG<br>CCTGAGATCTGAGGACACCGCCGTGTATTACTGTGCGAGA<u>GTT<br>AACTACCCGTACTCTTACTGGGGTGACTTCGACTAC</u>TGGGGCC<br>AAGGGACCACCGTGACCGTCTCCTCA |
| CLC-<br>563 | 142 (VL) | GAGATCGTGCTGACCCAGAGCCCCGGCACACTCTCCCTGTCTC<br>CTGGGGAAAGGGCCACCCTTTCATGC<u>AGAGCCAGCCAGTCCG<br>TCTCTAGTAGCTACCTGGCA</u>TGGTATCAGCAGAAGCCAGGACA<br>AGCCCCCCGCCTCCTGATTTAC<u>GGCGCTTCCTCTCGGGCAACT</u><br>GGTATCCCTGACAGGTTCTCAGGGAGCGGAAGCGGAACAGAT<br>TTTACCTTGACTATTTCTAGACTGGAGCCAGAGGACTTCGCCG<br>TGTATTACTGT<u>CAGCAGTACGGTAGTAGCCCCCTCACC</u>TTTGG<br>CCAGGGGACAAAAGTCGAAATCAAG |
| | 143 (VH) | GAGGTGCAATTGTTGGAGTCTGGGGGAGGCTTGGTACAGCCT<br>GGGGGGTCCCTGAGACTCTCCTGTGCAGCCTCCGGATTCACCT<br>TTAGC<u>AGTTATGCCATGAGC</u>TGGGTCCGCCAGGCTCCAGGGAA<br>GGGGCTGGAGTGGGTCTCAG<u>CTATTAGTGGTAGTGGTGGTAGC<br>ACATACTACGCAGATCCGTGAAGGGC</u>CGGTTCACCATCTCCA<br>GAGACAATTCCAAGAACACGCTGTATCTGCAGATGAACAGCC<br>TGAGAGCCGAGGACACGGCCGTATATTACTGTGCGCTT<u>GACGT<br>TGGTGCTTTCGACTAC</u>TGGGGCCAAGGAGCCCTGGTCACCGTC<br>TCGAGT |
| CLC-<br>564 | 144 (VL) | GAGATCGTGCTGACCCAGAGCCCCGGCACACTCTCCCTGTCTC<br>CTGGGGAAAGGGCCACCCTTTCATGC<u>AGAGCCAGCCAGTCCG<br>TCTCTAGTAGCTACCTGGCA</u>TGGTATCAGCAGAAGCCAGGACA<br>AGCCCCCCGCCTCCTGATTTAC<u>GGCGCTTCCTCTCGGGCAACT</u><br>GGTATCCCTGACAGGTTCTCAGGGAGCGGAAGCGGAACAGAT<br>TTTACCTTGACTATTTCTAGACTGGAGCCAGAGGACTTCGCCG<br>TGTATTACTGT<u>CAGCAGTACGGTAGTAGCCCCCTCACC</u>TTTGG<br>CCAGGGGACAAAAGTCGAAATCAAG |
| | 145 (VH) | GAGGTGCAATTGTTGGAGTCTGGGGGAGGCTTGGTACAGCCT<br>GGGGGGTCCCTGAGACTCTCCTGTGCAGCCTCCGGATTCACCT<br>TTAGC<u>AGTTATGCCATGAGC</u>TGGGTCCGCCAGGCTCCAGGGAA<br>GGGGCTGGAGTGGGTCTCAG<u>CTATTAGTGGTAGTGGTGGTAGC<br>ACATACTACGCAGATCCGTGAAGGGC</u>CGGTTCACCATCTCCA<br>GAGACAATTCCAAGAACACGCTGTATCTGCAGATGAACAGCC<br>TGAGAGCCGAGGACACGGCCGTATATTACTGTGCGTTC<u>GACGT<br>TGGTCCGTTCGACTAC</u>TGGGGCCAAGGAACCCTGGTCACCGTC<br>TCGAGT |
| 17A9 | 146 (VL) | TCGTCTGAGCTGACTCAGGACCCTGCTGTGTCTGTGGCCTTGG<br>GACAGACAGTCAGGATCACATGC<u>CAAGGAGACAGCCTCAGAA<br>GTTATTATGCAAG</u>CTGGTACCAGCAGAAGCCAGGACAGGCCC<br>CTGTACTTGTCATCTAT<u>GGTAAAAACAACCGGCCCTC</u>AGGGAT<br>CCCAGACCGATTCTCTGGCTCCAGCTCAGGAAACACAGCTTCC |

TABLE 12-continued

Variable region base pair sequences for phage-derived anti-OX40 antibodies.

| Clone | SEQ ID NO: | Sequence |
|---|---|---|
| | | TTGACCATCACTGGGGCTCAGGCGGAAGATGAGGCTGACTATT<br>ACTGTAACTCCCGTGTTATGCCTCATAATCGCGTATTCGGCGG<br>AGGGACCAAGCTGACCGTC |
| | 147 (VH) | GAGGTGCAATTGTTGGAGTCTGGGGGAGGCTTGGTACAGCCT<br>GGGGGGTCCCTGAGACTCTCCTGTGCAGCCTCCGGATTCACCT<br>TTAGCAGTTATGCCATGAGCTGGGTCCGCCAGGCTCCAGGGAA<br>GGGGCTGGAGTGGGTCTCAGCTATTAGTGGTAGTGGTGGTAGC<br>ACATACTACGCAGACTCCGTGAAGGGCCGGTTCACCATCTCCA<br>GAGACAATTCCAAGAACACGCTGTATCTGCAGATGAACAGCC<br>TGAGAGCCGAGGACACGGCCGTATATTACTGTGCGCGTGTTTT<br>CTACCGTGGTGGTGTTTCTATGGACTACTGGGGCCAAGGAACC<br>CTGGTCACCGTCTCGAGT |

Underlined are the complementarity determining regions (CDRs).

1.3 Preparation, Purification and Characterization of Anti-OX40 IgG1P329G LALA Antibodies The variable regions of heavy and light chain DNA sequences of selected anti-OX40 binders were subcloned in frame with either the constant heavy chain or the constant light chain of human IgG1. The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831 A1.

The cDNA and amino acid sequences of the anti-OX40 clones are shown in Table 13. All anti-OX40-Fc-fusion encoding sequences were cloned into a plasmid vector, which drives expression of the insert from an MPSV promoter and contains a synthetic polyA signal sequence located at the 3' end of the CDS. In addition, the vector contains an EBV OriP sequence for episomal maintenance of the plasmid.

TABLE 13

Sequences of anti-OX40 clones in P329GLALA human IgG1 format

| Clone | SEQ ID No. | Sequence |
|---|---|---|
| 8B9 | 148 (nucleotide sequence light chain) | GACATCCAGATGACCCAGTCTCCTTCCACCCTGTCTGCATC<br>TGTAGGAGACCGTGTCACCATCACTTGCCGTGCCAGTCAG<br>AGTATTAGTAGCTGGTTGGCCTGGTATCAGCAGAAACCAG<br>GGAAAGCCCCTAAGCTCCTGATCTATGATGCCTCCAGTTTG<br>GAAAGTGGGGTCCCATCACGTTTCAGCGGCAGTGGATCCG<br>GGACAGAATTCACTCTCACCATCAGCAGCTTGCAGCCTGAT<br>GATTTTGCAACTTATTACTGCCAACAGTATTTGACGTATTC<br>GCGGTTTACGTTTGGCCAGGGCACCAAAGTCGAGATCAAG<br>CGTACGGTGGCTGCACCATCTGTCTTCATCTTCCCGCCATC<br>TGATGAGCAGTTGAAATCTGGAACTGCCTCTGTTGTGTGCC<br>TGCTGAATAACTTCTATCCCAGAGAGGCCAAAGTACAGTG<br>GAAGGTGGATAACGCCCTCCAATCGGGTAACTCCCAGGAG<br>AGTGTCACAGAGCAGGACAGCAAGGACAGCACCTACAGCC<br>TCAGCAGCACCCTGACGCTGAGCAAAGCAGACTACGAGAA<br>ACACAAAGTCTACGCCTGCGAAGTCACCCATCAGGGCCTG<br>AGCTCGCCCGTCACAAAGAGCTTCAACAGGGGAGAGTGT |
| | 149 (nucleotide sequence heavy chain) | CAGGTGCAATTGGTGCAGTCTGGGGCTGAGGTGAAGAAGC<br>CTGGGTCCTCGGTGAAGGTCTCCTGCAAGGCCTCCGGAGG<br>CACATTCAGCAGCTACGCTATAAGCTGGGTGCGACAGGCC<br>CCTGGACAAGGGCTCGAGTGGATGGGAGGGATCATCCCTA<br>TCTTTGGTACAGCAAACTACGCACAGAAGTTCCAGGGCAG<br>GGTCACCATTACTGCAGACAAATCCACGAGCACAGCCTAC<br>ATGGAGCTGAGCAGCCTGAGATCTGAGGACACCGCCGTGT<br>ATTACTGTGCGAGAGAATACGGTTGGATGGACTACTGGGG<br>CCAAGGGACCACCGTGACCGTCTCCTCAGCTAGCACCAAG<br>GGCCCATCGGTCTTCCCCCTGGCACCCTCCTCCAAGAGCAC<br>CTCTGGGGGCACAGCGGCCCTGGGCTGCCTGGTCAAGGAC<br>TACTTCCCCGAACCGGTGACGGTGTCGTGGAACTCAGGCG<br>CCCTGACCAGCGGCGTGCACACCTTCCCGGCTGTCCTACAG<br>TCCTCAGGACTCTACTCCCTCAGCAGCGTGGTGACCGTGCC<br>CTCCAGCAGCTTGGGCACCCAGACCTACATCTGCAACGTG<br>AATCACAAGCCCAGCAACACCAAGGTGGACAAGAAAGTTG<br>AGCCCAAATCTTGTGACAAAACTCACACATGCCCACCGTG<br>CCCAGCACCTGAAGCTGCAGGGGACCGTCAGTCTTCCTCT<br>TCCCCCCAAAACCCAAGGACACCCTCATGATCTCCCGGAC<br>CCCTGAGGTCACATGCGTGGTGGTGGACGTGAGCCACGAA<br>GACCCTGAGGTCAAGTTCAACTGGTACGTGGACGGCGTGG<br>AGGTGCATAATGCCAAGACAAAGCCGCGGGAGGAGCAGT |

TABLE 13-continued

Sequences of anti-OX40 clones in P329GLALA human IgG1 format

| Clone | SEQ ID No. | Sequence |
|---|---|---|
| | | ACAACAGCACGTACCGTGTGGTCAGCGTCCTCACCGTCCTG<br>CACCAGGACTGGCTGAATGGCAAGGAGTACAAGTGCAAGG<br>TCTCCAACAAAGCCCTCGGCGCCCCCATCGAGAAAACCAT<br>CTCCAAAGCCAAAGGGCAGCCCCGAGAACCACAGGTGTAC<br>ACCCTGCCCCCATCCCGGGATGAGCTGACCAAGAACCAGG<br>TCAGCCTGACCTGCCTGGTCAAAGGCTTCTATCCCAGCGAC<br>ATCGCCGTGGAGTGGGAGAGCAATGGGCAGCCGGAGAAC<br>AACTACAAGACCACGCCTCCCGTGCTGGACTCCGACGGCT<br>CCTTCTTCCTCTACAGCAAGCTCACCGTGGACAAGAGCAG<br>GTGGCAGCAGGGGAACGTCTTCTCATGCTCCGTGATGCAT<br>GAGGCTCTGCACAACCACTACACGCAGAAGAGCCTCTCCC<br>TGTCTCCGGGTAAA |
| | 150<br>(Light chain) | DIQMTQSPSTLSASVGDRVTITCRASQSISSWLAWYQQKPGK<br>APKLLIYDASSLESGVPSRFSGSGSGTEFTLTISSLQPDDFATY<br>YCQQYLTYSRFTFGQGTKVEIKRTVAAPSVFIFPPSDEQLKSG<br>TASVVCLLNNFYPREAKVQWKVDNALQSGNSQESVTEQDSK<br>DSTYSLSSTLTLSKADYEKHKVYACEVTHQGLSSPVTKSFNR<br>GEC |
| | 151<br>(Heavy chain) | QVQLVQSGAEVKKPGSSVKVSCKASGGTFSSYAISWVRQAPG<br>QGLEWMGGIIPIFGTANYAQKFQGRVTITADKSTSTAYMELSS<br>LRSEDTAVYYCAREYGWMDYWGQGTTVTVSSASTKGPSVFP<br>LAPSSKSTSGGTAALGCLVKDYFPEPVTVSWNSGALTSGVHT<br>FPAVLQSSGLYSLSSVVTVPSSSLGTQTYICNVNHKPSNTKVD<br>KKVEPKSCDKTHTCPPCPAPEAAGGPSVFLFPPKPKDTLMISR<br>TPEVTCVVVDVSHEDPEVKFNWYVDGVEVHNAKTKPREEQY<br>NSTYRVVSVLTVLHQDWLNGKEYKCKVSNKALGAPIEKTISK<br>AKGQPREPQVYTLPPSRDELTKNQVSLTCLVKGFYPSDIAVE<br>WESNGQPENNYKTTPPVLDSDGSFFLYSKLTVDKSRWQQGN<br>VFSCSVMHEALHNHYTQKSLSLSPGK |
| 49B4 | 152<br>(nucleotide<br>sequence light<br>chain) | GACATCCAGATGACCCAGTCTCCTTCCACCCTGTCTGCATC<br>TGTAGGAGACCGTGTCACCATCACTTGCCGTGCCAGTCAG<br>AGTATTAGTAGCTGGTTGGCCTGGTATCAGCAGAAACCAG<br>GGAAAGCCCCTAAGCTCCTGATCTATGATGCCTCCAGTTTG<br>GAAAGTGGGGTCCCATCACGTTTCAGCGGCAGTGGATCCG<br>GGACAGAATTCACTCTCACCATCAGCAGCTTGCAGCCTGAT<br>GATTTTGCAACTTATTACTGCCAACAGTATAGTTCGCAGCC<br>GTATACGTTTGGCCAGGGCACCAAAGTCGAGATCAAGCGT<br>ACGGTGGCTGCACCATCTGTCTTCATCTTCCCGCCATCTGA<br>TGAGCAGTTGAAATCTGGAACTGCCTCTGTTGTGTGCCTGC<br>TGAATAACTTCTATCCCAGAGAGGCCAAAGTACAGTGGAA<br>GGTGGATAACGCCCTCCAATCGGGTAACTCCCAGGAGAGT<br>GTCACAGAGCAGGACAGCAAGGACAGCACCTACAGCCTCA<br>GCAGCACCCTGACGCTGAGCAAAGCAGACTACGAGAAACA<br>CAAAGTCTACGCCTGCGAAGTCACCCATCAGGGCCTGAGC<br>TCGCCCGTCACAAAGAGCTTCAACAGGGGAGAGTGT |
| | 153<br>(nucleotide<br>sequence heavy<br>chain) | CAGGTGCAATTGGTGCAGTCTGGGGCTGAGGTGAAGAAGC<br>CTGGGTCCTCGGTGAAGGTCTCCTGCAAGGCCTCCGGAGG<br>CACATTCAGCAGCTACGCTATAAGCTGGGTGCGACAGGCC<br>CCTGGACAAGGGCTCGAGTGGATGGGAGGGATCATCCCTA<br>TCTTTGGTACAGCAAACTACGCACAGAAGTTCCAGGGCAG<br>GGTCACCATTACTGCAGACAAATCCACGAGCACAGCCTAC<br>ATGGAGCTGAGCAGCCTGAGATCTGAGGACACCGCCGTGT<br>ATTACTGTGCGAGAGAATACTACCGTGGTCCGTACGACTA<br>CTGGGGCCAAGGGACCACCGTGACCGTCTCCTCAGCTAGC<br>ACCAAGGGCCCATCGGTCTTCCCCCTGGCACCCTCCTCCAA<br>GAGCACCTCTGGGGGCACAGCGGCCCTGGGCTGCCTGGTC<br>AAGGACTACTTCCCCGAACCGGTGACGGTGTCGTGGAACT<br>CAGGCGCCCTGACCAGCGGCGTGCACACCTTCCCGGCTGT<br>CCTACAGTCCTCAGGACTCTACTCCCTCAGCAGCGTGGTGA<br>CCGTGCCCTCCAGCAGCTTGGGCACCCAGACCTACATCTGC<br>AACGTGAATCACAAGCCCAGCAACACCAAGGTGGACAAG<br>AAAGTTGAGCCCAAATCTTGTGACAAAACTCACACATGCC<br>CACCGTGCCCAGCACCTGAAGCTGCAGGGGGACCGTCAGT<br>CTTCCTCTTCCCCCCAAAACCCAAGGACACCCTCATGATCT<br>CCCGGACCCCTGAGGTCACATGCGTGGTGGTGGACGTGAG<br>CCACGAAGACCCTGAGGTCAAGTTCAACTGGTACGTGGAC<br>GGCGTGGAGGTGCATAATGCCAAGACAAAGCCGCGGGAG<br>GAGCAGTACAACAGCACGTACCGTGTGGTCAGCGTCCTCA<br>CCGTCCTGCACCAGGACTGGCTGAATGGCAAGGAGTACAA<br>GTGCAAGGTCTCCAACAAAGCCCTCGGCGCCCCCATCGAG<br>AAAACCATCTCCAAAGCCAAAGGGCAGCCCCGAGAACCAC<br>AGGTGTACACCCTGCCCCCATCCCGGGATGAGCTGACCAA |

TABLE 13-continued

Sequences of anti-OX40 clones in P329GLALA human IgG1 format

| Clone | SEQ ID No. | Sequence |
|---|---|---|
| | | GAACCAGGTCAGCCTGACCTGCCTGGTCAAAGGCTTCTATC<br>CCAGCGACATCGCCGTGGAGTGGGAGAGCAATGGGCAGCC<br>GGAGAACAACTACAAGACCACGCCTCCCGTGCTGGACTCC<br>GACGGCTCCTTCTTCCTCTACAGCAAGCTCACCGTGGACAA<br>GAGCAGGTGGCAGCAGGGGAACGTCTTCTCATGCTCCGTG<br>ATGCATGAGGCTCTGCACAACCACTACACGCAGAAGAGCC<br>TCTCCCTGTCTCCGGGTAAA |
| | 154<br>(Light chain) | DIQMTQSPSTLSASVGDRVTITCRASQSISSWLAWYQQKPGK<br>APKLLIYDASSLESGVPSRFSGSGSGTEFTLTISSLQPDDFATY<br>YCQQYSSQPYTFGQGTKVEIKRTVAAPSVFIFPPSDEQLKSGT<br>ASVVCLLNNFYPREAKVQWKVDNALQSGNSQESVTEQDSKD<br>STYSLSSTLTLSKADYEKHKVYACEVTHQGLSSPVTKSFNRG<br>EC |
| | 155<br>(Heavy chain) | QVQLVQSGAEVKKPGSSVKVSCKASGGTFSSYAISWVRQAPG<br>QGLEWMGGIIPIFGTANYAQKFQGRVTITADKSTSTAYMELSS<br>LRSEDTAVYYCAREYYRGPYDYWGQGTTVTVSSASTKGPSV<br>FPLAPSSKSTSGGTAALGCLVKDYFPEPVTVSWNSGALTSGV<br>HTFPAVLQSSGLYSLSSVVTVPSSSLGTQTYICNVNHKPSNTK<br>VDKKVEPKSCDKTHTCPPCPAPEAAGGPSVFLFPPKPKDTLMI<br>SRTPEVTCVVVDVSHEDPEVKFNWYVDGVEVHNAKTKPREE<br>QYNSTYRVVSVLTVLHQDWLNGKEYKCKVSNKALGAPIEKT<br>ISKAKGQPREPQVYTLPPSRDELTKNQVSLTCLVKGFYPSDIA<br>VEWESNGQPENNYKTTPPVLDSDGSFFLYSKLTVDKSRWQQ<br>GNVFSCSVMHEALHNHYTQKSLSLSPGK |
| 1G4 | 156<br>(nucleotide<br>sequence light<br>chain) | GACATCCAGATGACCCAGTCTCCTTCCACCCTGTCTGCATC<br>TGTAGGAGACCGTGTCACCATCACTTGCCGTGCCAGTCAG<br>AGTATTAGTAGCTGGTTGGCCTGGTATCAGCAGAAACCAG<br>GGAAAGCCCCTAAGCTCCTGATCTATGATGCCTCCAGTTTG<br>GAAAGTGGGGTCCCATCACGTTTCAGCGGCAGTGGATCCG<br>GGACAGAATTCACTCTCACCATCAGCAGCTTGCAGCCTGAT<br>GATTTTGCAACTTATTACTGCCAACAGTATATTTCGTATTC<br>CATGTTGACGTTTGGCCAGGGCACCAAAGTCGAGATCAAG<br>CGTACGGTGGCTGCACCATCTGTCTTCATCTTCCCGCCATC<br>TGATGAGCAGTTGAAATCTGGAACTGCCTCTGTTGTGTGCC<br>TGCTGAATAACTTCTATCCCAGAGAGGCCAAAGTACAGTG<br>GAAGGTGGATAACGCCCTCCAATCGGGTAACTCCCAGGAG<br>AGTGTCACAGAGCAGGACAGCAAGGACAGCACCTACAGCC<br>TCAGCAGCACCCTGACGCTGAGCAAAGCAGACTACGAGAA<br>ACACAAAGTCTACGCCTGCGAAGTCACCCATCAGGGCCTG<br>AGCTCGCCCGTCACAAAGAGCTTCAACAGGGGAGAGTGT |
| | 157<br>(nucleotide<br>sequence heavy<br>chain) | CAGGTGCAATTGGTGCAGTCTGGGGCTGAGGTGAAGAAGC<br>CTGGGTCCTCGGTGAAGGTCTCCTGCAAGGCCTCCGGAGG<br>CACATTCAGCAGCTACGCTATAAGCTGGGTGCGACAGGCC<br>CCTGGACAAGGGCTCGAGTGGATGGGAGGGATCATCCCTA<br>TCTTTGGTACAGCAAACTACGCACAGAAGTTCCAGGGCAG<br>GGTCACCATTACTGCAGACAAATCCACGAGCACAGCCTAC<br>ATGGAGCTGAGCAGCCTGAGATCTGAGGACACCGCCGTGT<br>ATTACTGTGCGAGAGAATACGGTTCTATGGACTACTGGGG<br>CCAAGGGACCACCGTGACCGTCTCCTCAGCTAGCACCAAG<br>GGCCCATCGGTCTTCCCCCTGGCACCCTCCTCCAAGAGCAC<br>CTCTGGGGGCACAGCGGCCCTGGGCTGCCTGGTCAAGGAC<br>TACTTCCCCGAACCGGTGACGGTGTCGTGGAACTCAGGCG<br>CCCTGACCAGCGGCGTGCACACCTTCCCGGCTGTCCTACAG<br>TCCTCAGGACTCTACTCCCTCAGCAGCGTGGTGACCGTGCC<br>CTCCAGCAGCTTGGGCACCCAGACCTACATCTGCAACGTG<br>AATCACAAGCCCAGCAACACCAAGGTGGACAAGAAAGTTG<br>AGCCCAAATCTTGTGACAAAACTCACACATGCCCACCGTG<br>CCCAGCACCTGAAGCTGCAGGGGACCGTCAGTCTTCCTCT<br>TCCCCCCAAAACCCAAGGACACCCTCATGATCTCCCGGAC<br>CCCTGAGGTCACATGCGTGGTGGTGGACGTGAGCCACGAA<br>GACCCTGAGGTCAAGTTCAACTGGTACGTGGACGGCGTGG<br>AGGTGCATAATGCCAAGACAAAGCCGCGGGAGGAGCAGT<br>ACAACAGCACGTACCGTGTGGTCAGCGTCCTCACCGTCCTG<br>CACCAGGACTGGCTGAATGGCAAGGAGTACAAGTGCAAGG<br>TCTCCAACAAAGCCCTCGGCGCCCCCATCGAGAAAACCAT<br>CTCCAAAGCCAAAGGGCAGCCCCGAGAACCACAGGTGTAC<br>ACCCTGCCCCCATCCCGGGATGAGCTGACCAAGAACCAGG<br>TCAGCCTGACCTGCCTGGTCAAAGGCTTCTATCCCAGCGAC<br>ATCGCCGTGGAGTGGGAGAGCAATGGGCAGCCGGAGAAC<br>AACTACAAGACCACGCCTCCCGTGCTGGACTCCGACGGCT<br>CCTTCTTCCTCTACAGCAAGCTCACCGTGGACAAGAGCAG<br>GTGGCAGCAGGGGAACGTCTTCTCATGCTCCGTGATGCAT |

TABLE 13-continued

Sequences of anti-OX40 clones in P329GLALA human IgG1 format

| Clone | SEQ ID No. | Sequence |
|---|---|---|
| | | GAGGCTCTGCACAACCACTACACGCAGAAGAGCCTCTCC<br>TGTCTCCGGGTAAA |
| | 158<br>(Light chain) | DIQMTQSPSTLSASVGDRVTITCRASQSISSWLAWYQQKPGK<br>APKLLIYDASSLESGVPSRFSGSGSGTEFTLTISSLQPDDFATY<br>YCQQYISYSMLTFGQGTKVEIKRTVAAPSVFIFPPSDEQLKSG<br>TASVVCLLNNFYPREAKVQWKVDNALQSGNSQESVTEQDSK<br>DSTYSLSSTLTLSKADYEKHKVYACEVTHQGLSSPVTKSFNR<br>GEC |
| | 159<br>(Heavy chain) | QVQLVQSGAEVKKPGSSVKVSCKASGGTFSSYAISWVRQAPG<br>QGLEWMGGIIPIFGTANYAQKFQGRVTITADKSTSTAYMELSS<br>LRSEDTAVYYCAREYGSMDYWGQGTTVTVSSASTKGPSVFP<br>LAPSSKSTSGGTAALGCLVKDYFPEPVTVSWNSGALTSGVHT<br>FPAVLQSSGLYSLSSVVTVPSSSLGTQTYICNVNHKPSNTKVD<br>KKVEPKSCDKTHTCPPCPAPEAAGGPSVFLFPPKPKDTLMISR<br>TPEVTCVVVDVSHEDPEVKFNWYVDGVEVHNAKTKPREEQY<br>NSTYRVVSVLTVLHQDWLNGKEYKCKVSNKALGAPIEKTISK<br>AKGQPREPQVYTLPPSRDELTKNQVSLTCLVKGFYPSDIAVE<br>WESNGQPENNYKTTPPVLDSDGSFFLYSKLTVDKSRWQQGN<br>VFSCSVMHEALHNHYTQKSLSLSPGK |
| 20B7 | 160<br>(nucleotide<br>sequence light<br>chain) | GACATCCAGATGACCCAGTCTCCTTCCACCCTGTCTGCATC<br>TGTAGGAGACCGTGTCACCATCACTTGCCGTGCCAGTCAG<br>AGTATTAGTAGCTGGTTGGCCTGGTATCAGCAGAAACCAG<br>GGAAAGCCCCTAAGCTCCTGATCTATGATGCCTCCAGTTTG<br>GAAAGTGGGGTCCCATCACGTTTCAGCGGCAGTGGATCCG<br>GGACAGAATTCACTCTCACCATCAGCAGCTTGCAGCCTGAT<br>GATTTTGCAACTTATTACTGCCAACAGTATCAGGCTTTTTC<br>GCTTACGTTTGGCCAGGGCACCAAAGTCGAGATCAAGCGT<br>ACGGTGGCTGCACCATCTGTCTTCATCTTCCCGCCATCTGA<br>TGAGCAGTTGAAATCTGGAACTGCCTCTGTTGTGTGCCTGC<br>TGAATAACTTCTATCCCAGAGAGGCCAAAGTACAGTGGAA<br>GGTGGATAACGCCCTCCAATCGGGTAACTCCCAGGAGAGT<br>GTCACAGAGCAGGACAGCAAGGACAGCACCTACAGCCTCA<br>GCAGCACCCTGACGCTGAGCAAAGCAGACTACGAGAAACA<br>CAAAGTCTACGCCTGCGAAGTCACCCATCAGGGCCTGAGC<br>TCGCCCGTCACAAAGAGCTTCAACAGGGGAGAGTGT |
| | 161<br>(nucleotide<br>sequence heavy<br>chain) | CAGGTGCAATTGGTGCAGTCTGGGGCTGAGGTGAAGAAGC<br>CTGGGTCCTCGGTGAAGGTCTCCTGCAAGGCCTCCGGAGG<br>CACATTCAGCAGCTACGCTATAAGCTGGGTGCGACAGGCC<br>CCTGGACAAGGGCTCGAGTGGATGGGAGGGATCATCCCTA<br>TCTTTGGTACAGCAAACTACGCACAGAAGTTCCAGGGCAG<br>GGTCACCATTACTGCAGACAAATCCACGAGCACAGCCTAC<br>ATGGAGCTGAGCAGCCTGAGATCTGAGGACACCGCCGTGT<br>ATTACTGTGCGAGAGTTAACTACCCGTACTCTTACTGGGGT<br>GACTTCGACTACTGGGGCCAAGGGACCACCGTGACCGTCT<br>CCTCAGCTAGCACCAAGGGCCCATCGGTCTTCCCCCTGGCA<br>CCCTCCTCCAAGAGCACCTCTGGGGGCACAGCGGCCCTGG<br>GCTGCCTGGTCAAGGACTACTTCCCCGAACCGGTGACGGT<br>GTCGTGGAACTCAGGCGCCCTGACCAGCGGCGTGCACACC<br>TTCCCGGCTGTCCTACAGTCCTCAGGACTCTACTCCCTCAG<br>CAGCGTGGTGACCGTGCCCTCCAGCAGCTTGGGCACCCAG<br>ACCTACATCTGCAACGTGAATCACAAGCCCAGCAACACCA<br>AGGTGGACAAGAAAGTTGAGCCCAAATCTTGTGACAAAAC<br>TCACACATGCCCACCGTGCCCAGCACCTGAAGCTGCAGGG<br>GGACCGTCAGTCTTCCTCTTCCCCCCAAAACCCAAGGACAC<br>CCTCATGATCTCCCGGACCCCTGAGGTCACATGCGTGGTG<br>TGGACGTGAGCCACGAAGACCCTGAGGTCAAGTTCAACTG<br>GTACGTGGACGGCGTGGAGGTGCATAATGCCAAGACAAAG<br>CCGCGGGAGGAGCAGTACAACAGCACGTACCGTGTGGTCA<br>GCGTCCTCACCGTCCTGCACCAGGACTGGCTGAATGGCAA<br>GGAGTACAAGTGCAAGGTCTCCAACAAAGCCCTCGGCGCC<br>CCCATCGAGAAAACCATCTCCAAAGCCAAAGGGCAGCCCC<br>GAGAACCACAGGTGTACACCCTGCCCCCATCCCGGGATGA<br>GCTGACCAAGAACCAGGTCAGCCTGACCTGCCTGGTCAAA<br>GGCTTCTATCCCAGCGACATCGCCGTGGAGTGGGAGAGCA<br>ATGGGCAGCCGGAGAACAACTACAAGACCACGCCTCCCGT<br>GCTGGACTCCGACGGCTCCTTCTTCCTCTACAGCAAGCTCA<br>CCGTGGACAAGAGCAGGTGGCAGCAGGGGAACGTCTTCTC<br>ATGCTCCGTGATGCATGAGGCTCTGCACAACCACTACACG<br>CAGAAGAGCCTCTCCCTGTCTCCGGGTAAA |
| | 162<br>(Light chain) | DIQMTQSPSTLSASVGDRVTITCRASQSISSWLAWYQQKPGK<br>APKLLIYDASSLESGVPSRFSGSGSGTEFTLTISSLQPDDFATY |

TABLE 13-continued

Sequences of anti-OX40 clones in P329GLALA human IgG1 format

| Clone | SEQ ID No. | Sequence |
|---|---|---|
| | | YCQQYQAFSLTFGQGTKVEIKRTVAAPSVFIFPPSDEQLKSGT ASVVCLLNNFYPREAKVQWKVDNALQSGNSQESVTEQDSKD STYSLSSTLTLSKADYEKHKVYACEVTHQGLSSPVTKSFNRG EC |
| | 163 (Heavy chain) | QVQLVQSGAEVKKPGSSVKVSCKASGGTFSSYAISWVRQAPG QGLEWMGGIIPIFGTANYAQKFQGRVTITADKSTSTAYMELSS LRSEDTAVYYCARVNYPYSYWGDFDYWGQGTTVTVSSAST KGPSVFPLAPSSKSTSGGTAALGCLVKDYFPEPVTVSWNSGA LTSGVHTFPAVLQSSGLYSLSSVVTVPSSSLGTQTYICNVNHK PSNTKVDKKVEPKSCDKTHTCPPCPAPEAAGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALG APIEKTISKAKGQPREPQVYTLPPSRDELTKNQVSLTCLVKGF YPSDIAVEWESNGQPENNYKTTPPVLDSDGSFFLYSKLTVDKS RWQQGNVFSCSVMHEALHNHYTQKSLSLSPGK |
| CLC-563 | 164 (nucleotide sequence light chain) | GAGATCGTGCTGACCCAGAGCCCCGGCACACTCTCCCTGTC TCCTGGGGAAAGGGCCACCCTTTCATGCAGAGCCAGCCAG TCCGTCTCTAGTAGCTACCTGGCATGGTATCAGCAGAAGCC AGGACAAGCCCCCCGCCTCCTGATTTACGGCGCTTCCTCTC GGGCAACTGGTATCCCTGACAGGTTCTCAGGGAGCGGAAG CGGAACAGATTTTACCTTGACTATTTCTAGACTGGAGCCAG AGGACTTCGCCGTGTATTACTGTCAGCAGTACGGTAGTAGC CCCCTCACCTTTGGCCAGGGGACAAAAGTCGAAATCAAGC GTACGGTGGCTGCACCATCTGTCTTCATCTTCCCGCCATCT GATGAGCAGTTGAAATCTGGAACTGCCTCTGTTGTGTGCCT GCTGAATAACTTCTATCCCAGAGAGGCCAAAGTACAGTGG AAGGTGGATAACGCCCTCCAATCGGGTAACTCCCAGGAGA GTGTCACAGAGCAGGACAGCAAGGACAGCACCTACAGCCT CAGCAGCACCCTGACGCTGAGCAAAGCAGACTACGAGAAA CACAAAGTCTACGCCTGCGAAGTCACCCATCAGGGCCTGA GCTCGCCCGTCACAAAGAGCTTCAACAGGGGAGAGTGT |
| | 165 (nucleotide sequence heavy chain) | GAGGTGCAATTGTTGGAGTCTGGGGGAGGCTTGGTACAGC CTGGGGGGTCCCTGAGACTCTCCTGTGCAGCCTCCGGATTC ACCTTTAGCAGTTATGCCATGAGCTGGGTCCGCCAGGCTCC AGGGAAGGGGCTGGAGTGGGTCTCAGCTATTAGTGGTAGT GGTGGTAGCACATACTACGCAGACTCCGTGAAGGGCCGGT TCACCATCTCCAGAGACAATTCCAAGAACACGCTGTATCTG CAGATGAACAGCCTGAGAGCCGAGGACACGGCCGTATATT ACTGTGCGCTTGACGTTGGTGCTTTCGACTACTGGGGCCAA GGAGCCCTGGTCACCGTCTCGAGTGCTAGCACCAAGGGCC CATCGGTCTTCCCCCTGGCACCCTCCTCCAAGAGCACCTCT GGGGGCACAGCGGCCCTGGGCTGCCTGGTCAAGGACTACT TCCCCGAACCGGTGACGGTGTCGTGGAACTCAGGCGCCCT GACCAGCGGCGTGCACACCTTCCCGGCTGTCCTACAGTCCT CAGGACTCTACTCCCTCAGCAGCGTGGTGACCGTGCCCTCC AGCAGCTTGGGCACCCAGACCTACATCTGCAACGTGAATC ACAAGCCCAGCAACACCAAGGTGGACAAGAAAGTTGAGC CCAAATCTTGTGACAAAACTCACACATGCCCACCGTGCCC AGCACCTGAAGCTGCAGGGGGACCGTCAGTCTTCCTCTTCC CCCCAAAACCCAAGGACACCCTCATGATCTCCCGGACCCC TGAGGTCACATGCGTGGTGGTGGACGTGAGCCACGAAGAC CCTGAGGTCAAGTTCAACTGGTACGTGGACGGCGTGGAGG TGCATAATGCCAAGACAAAGCCGCGGGAGGAGCAGTACA ACAGCACGTACCGTGTGGTCAGCGTCCTCACCGTCCTGCAC CAGGACTGGCTGAATGGCAAGGAGTACAAGTGCAAGGTCT CCAACAAAGCCCTCGGCGCCCCCATCGAGAAAACCATCTC CAAAGCCAAAGGGCAGCCCCGAGAACCACAGGTGTACACC CTGCCCCCATCCCGGGATGAGCTGACCAAGAACCAGGTCA GCCTGACCTGCCTGGTCAAAGGCTTCTATCCCAGCGACATC GCCGTGGAGTGGGAGAGCAATGGGCAGCCGGAGAACAAC TACAAGACCACGCCTCCCGTGCTGGACTCCGACGGCTCCTT CTTCCTCTACAGCAAGCTCACCGTGGACAAGAGCAGGTGG CAGCAGGGGAACGTCTTCTCATGCTCCGTGATGCATGAGG CTCTGCACAACCACTACACGCAGAAGAGCCTCTCCCTGTCT CCGGGTAAA |
| | 166 (Light chain) | EIVLTQSPGTLSLSPGERATLSCRASQSVSSSYLAWYQQKPGQ APRLLIYGASSRATGIPDRFSGSGSGTDFTLTISRLEPEDFAVY YCQQYGSSPLTFGQGTKVEIKRTVAAPSVFIFPPSDEQLKSGT ASVVCLLNNFYPREAKVQWKVDNALQSGNSQESVTEQDSKD STYSLSSTLTLSKADYEKHKVYACEVTHQGLSSPVTKSFNRG EC |

TABLE 13-continued

Sequences of anti-OX40 clones in P329GLALA human IgG1 format

| Clone | SEQ ID No. | Sequence |
|---|---|---|
|  | 167 (Heavy chain) | EVQLLESGGGLVQPGGSLRLSCAASGFTFSSYAMSWVRQAPG KGLEWVSAISGSGGSTYYADSVKGRFTISRDNSKNTLYLQMN SLRAEDTAVYYCALDVGAFDYWGQGALVTVSSASTKGPSVF PLAPSSKSTSGGTAALGCLVKDYFPEPVTVSWNSGALTSGVH TFPAVLQSSGLYSLSSVVTVPSSSLGTQTYICNVNHKPSNTKV DKKVEPKSCDKTHTCPPCPAPEAAGGPSVFLFPPKPKDTLMIS RTPEVTCVVVDVSHEDPEVKFNWYVDGVEVHNAKTKPREEQ YNSTYRVVSVLTVLHQDWLNGKEYKCKVSNKALGAPIEKTIS KAKGQPREPQVYTLPPSRDELTKNQVSLTCLVKGFYPSDIAVE WESNGQPENNYKTTPPVLDSDGSFFLYSKLTVDKSRWQQGN VFSCSVMHEALHNHYTQKSLSLSPGK |
| CLC-564 | 168 (nucleotide sequence light chain) | GAGATCGTGCTGACCCAGAGCCCCGGCACACTCTCCCTGTC TCCTGGGGAAAGGGCCACCCTTTCATGCAGAGCCAGCCAG TCCGTCTCTAGTAGCTACCTGGCATGGTATCAGCAGAAGCC AGGACAAGCCCCCCGCCTCCTGATTTACGGCGCTTCCTCTC GGGCAACTGGTATCCCTGACAGGTTCTCAGGGAGCGGAAG CGGAACAGATTTTACCTTGACTATTTCTAGACTGGAGCCAG AGGACTTCGCCGTGTATTACTGTCAGCAGTACGGTAGTAGC CCCCTCACCTTTGGCCAGGGGACAAAAGTCGAAATCAAGC GTACGGTGGCTGCACCATCTGTCTTCATCTTCCCGCCATCT GATGAGCAGTTGAAATCTGGAACTGCCTCTGTTGTGTGCCT GCTGAATAACTTCTATCCCAGAGAGGCCAAAGTACAGTGG AAGGTGGATAACGCCCTCCAATCGGGTAACTCCCAGGAGA GTGTCACAGAGCAGGACAGCAAGGACACCACCTACAGCCT CAGCAGCACCCTGACGCTGAGCAAAGCAGACTACGAGAAA CACAAAGTCTACGCCTGCGAAGTCACCCATCAGGGCCTGA GCTCGCCCGTCACAAAGAGCTTCAACAGGGGAGAGTGT |
|  | 169 (nucleotide sequence heavy chain) | GAGGTGCAATTGTTGGAGTCTGGGGGAGGCTTGGTACAGC CTGGGGGGTCCCTGAGACTCTCCTGTGCAGCCTCCGGATTC ACCTTTAGCAGTTATGCCATGAGCTGGGTCCGCCAGGCTCC AGGGAAGGGGCTGGAGTGGGTCTCAGCTATTAGTGGTAGT GGTGGTAGCACATACTACGCAGACTCCGTGAAGGGCCGGT TCACCATCTCCAGAGACAATTCCAAGAACACGCTGTATCTG CAGATGAACAGCCTGAGAGCCGAGGACACGGCCGTATATT ACTGTGCGTTCGACGTTGGTCCGTTCGACTACTGGGGCCAA GGAACCCTGGTCACCGTCTCGAGTGCTAGCACCAAGGGCC CATCGGTCTTCCCCCTGGCACCCTCCTCCAAGAGCACCTCT GGGGGCACAGCGGCCCTGGGCTGCCTGGTCAAGGACTACT TCCCCGAACCGGTGACGGTGTCGTGGAACTCAGGCGCCCT GACCAGCGGCGTGCACACCTTCCCGGCTGTCCTACAGTCCT CAGGACTCTACTCCCTCAGCAGCGTGGTGACCGTGCCCTCC AGCAGCTTGGGCACCCAGACCTACATCTGCAACGTGAATC ACAAGCCCAGCAACACCAAGGTGGACAAGAAAGTTGAGC CCAAATCTTGTGACAAAACTCACACATGCCCACCGTGCCC AGCACCTGAAGCTGCAGGGGGACCGTCAGTCTTCCTCTTCC CCCCAAAACCCAAGGACACCCTCATGATCTCCCGGACCCC TGAGGTCACATGCGTGGTGGTGGACGTGAGCCACGAAGAC CCTGAGGTCAAGTTCAACTGGTACGTGGACGGCGTGGAGG TGCATAATGCCAAGACAAAGCCGCGGGAGGAGCAGTACA ACAGCACGTACCGTGTGGTCAGCGTCCTCACCGTCCTGCAC CAGGACTGGCTGAATGGCAAGGAGTACAAGTGCAAGGTCT CCAACAAAGCCCTCGGCGCCCCCATCGAGAAAACCATCTC CAAAGCCAAAGGGCAGCCCCGAGAACCACAGGTGTACACC CTGCCCCCATCCCGGGATGAGCTGACCAAGAACCAGGTCA GCCTGACCTGCCTGGTCAAAGGCTTCTATCCCAGCGACATC GCCGTGGAGTGGGAGAGCAATGGGCAGCCGGAGAACAAC TACAAGACCACGCCTCCCGTGCTGGACTCCGACGGCTCCTT CTTCCTCTACAGCAAGCTCACCGTGGACAAGAGCAGGTGG CAGCAGGGGAACGTCTTCTCATGCTCCGTGATGCATGAGG CTCTGCACAACCACTACACGCAGAAGAGCCTCTCCCTGTCT CCGGGTAAA |
|  | 170 (Light chain) | EIVLTQSPGTLSLSPGERATLSCRASQSVSSSYLAWYQQKPGQ APRLLIYGASSRATGIPDRFSGSGSGTDFTLTISRLEPEDFAVY YCQQYGSSPLTFGQGTKVEIKRTVAAPSVFIFPPSDEQLKSGT ASVVCLLNNFYPREAKVQWKVDNALQSGNSQESVTEQDSKD STYSLSSTLTLSKADYEKHKVYACEVTHQGLSSPVTKSFNRG EC |
|  | 171 (Heavy chain) | EVQLLESGGGLVQPGGSLRLSCAASGFTFSSYAMSWVRQAPG KGLEWVSAISGSGGSTYYADSVKGRFTISRDNSKNTLYLQMN SLRAEDTAVYYCAFDVGPFDYWGQGTLVTVSSASTKGPSVFP LAPSSKSTSGGTAALGCLVKDYFPEPVTVSWNSGALTSGVHT FPAVLQSSGLYSLSSVVTVPSSSLGTQTYICNVNHKPSNTKVD |

TABLE 13-continued

Sequences of anti-OX40 clones in P329GLALA human IgG1 format

| Clone | SEQ ID No. | Sequence |
|---|---|---|
| | | KKVEPKSCDKTHTCPPCPAPEAAGGPSVFLFPPKPKDTLMISR
TPEVTCVVVDVSHEDPEVKFNWYVDGVEVHNAKTKPREEQY
NSTYRVVSVLTVLHQDWLNGKEYKCKVSNKALGAPIEKTISK
AKGQPREPQVYTLPPSRDELTKNQVSLTCLVKGFYPSDIAVE
WESNGQPENNYKTTPPVLDSDGSFFLYSKLTVDKSRWQQGN
VFSCSVMHEALHNHYTQKSLSLSPGK |
| 17A9 | 172
(nucleotide
sequence light
chain) | TCGTCTGAGCTGACTCAGGACCCTGCTGTGTCTGTGGCCTT
GGGACAGACAGTCAGGATCACATGCCAAGGAGACAGCCTC
AGAAGTTATTATGCAAGCTGGTACCAGCAGAAGCCAGGAC
AGGCCCCTGTACTTGTCATCTATGGTAAAAACAACCGGCCC
TCAGGGATCCCAGACCGATTCTCTGGCTCCAGCTCAGGAA
ACACAGCTTCCTTGACCATCACTGGGGCTCAGGCGGAAGA
TGAGGCTGACTATTACTGTAACTCCCGTGTTATGCCTCATA
ATCGCGTATTCGGCGGAGGGACCAAGCTGACCGTCCTAGG
TCAACCCAAGGCTGCCCCAGCGTGACCCTGTTCCCCCCCA
GCAGCGAGGAACTGCAGGCCAACAAGGCCACCCTGGTCTG
CCTGATCAGCGACTTCTACCCAGGCGCCGTGACCGTGGCCT
GGAAGGCCGACAGCAGCCCCGTGAAGGCCGGCGTGGAGA
CCACCACCCCCAGCAAGCAGAGCAACAACAAGTACGCCGC
CAGCAGCTACCTGAGCCTGACCCCCGAGCAGTGGAAGAGC
CACAGGTCCTACAGCTGCCAGGTGACCCACGAGGGCAGCA
CCGTGGAGAAAACCGTGGCCCCCACCGAGTGCAGC |
| | 173
(nucleotide
sequence heavy
chain) | GAGGTGCAATTGTTGGAGTCTGGGGGAGGCTTGGTACAGC
CTGGGGGGTCCCTGAGACTCTCCTGTGCAGCCTCCGGATTC
ACCTTTAGCAGTTATGCCATGAGCTGGGTCCGCCAGGCTCC
AGGGAAGGGGCTGGAGTGGGTCTCAGCTATTAGTGGTAGT
GGTGGTAGCACATACTACGCAGACTCCGTGAAGGGCCGGT
TCACCATCTCCAGAGACAATTCCAAGAACACGCTGTATCTG
CAGATGAACAGCCTGAGAGCCGAGGACACGGCCGTATATT
ACTGTGCGCGTGTTTTCTACCGTGGTGGTGTTTCTATGGAC
TACTGGGGCCAAGGAACCCTGGTCACCGTCTCGAGTGCTA
GCACCAAGGGCCCATCGGTCTTCCCCCTGGCACCCTCCTCC
AAGAGCACCTCTGGGGGCACAGCGGCCCTGGGCTGCCTGG
TCAAGGACTACTTCCCCGAACCGGTGACGGTGTCGTGGAA
CTCAGGCGCCCTGACCAGCGGCGTGCACACCTTCCCGGCT
GTCCTACAGTCCTCAGGACTCTACTCCCTCAGCAGCGTGGT
GACCGTGCCCTCCAGCAGCTTGGGCACCCAGACCTACATCT
GCAACGTGAATCACAAGCCCAGCAACACCAAGGTGGACAA
GAAAGTTGAGCCCAAATCTTGTGACAAAACTCACACATGC
CCACCGTGCCCAGCACCTGAAGCTGCAGGGGGACCGTCAG
TCTTCCTCTTCCCCCCAAAACCCAAGGACACCCTCATGATC
TCCCGGACCCCTGAGGTCACATGCGTGGTGGTGGACGTGA
GCCACGAAGACCCTGAGGTCAAGTTCAACTGGTACGTGGA
CGGCGTGGAGGTGCATAATGCCAAGACAAAGCCGCGGGA
GGAGCAGTACAACAGCACGTACCGTGTGGTCAGCGTCCTC
ACCGTCCTGCACCAGGACTGGCTGAATGGCAAGGAGTACA
AGTGCAAGGTCTCCAACAAAGCCCTCGGCGCCCCCATCGA
GAAAACCATCTCCAAAGCCAAAGGGCAGCCCCGAGAACCA
CAGGTGTACACCCTGCCCCCATCCCGGGATGAGCTGACCA
AGAACCAGGTCAGCCTGACCTGCCTGGTCAAAGGCTTCTA
TCCCAGCGACATCGCCGTGGAGTGGGAGAGCAATGGGCAG
CCGGAGAACAACTACAAGACCACGCCTCCCGTGCTGGACT
CCGACGGCTCCTTCTTCCTCTACAGCAAGCTCACCGTGGAC
AAGAGCAGGTGGCAGCAGGGGAACGTCTTCTCATGCTCCG
TGATGCATGAGGCTCTGCACAACCACTACACGCAGAAGAG
CCTCTCCCTGTCTCCGGGTAAA |
| | 174
(Light chain) | SSELTQDPAVSVALGQTVRITCQGDSLRSYYASWYQQKPGQA
PVLVIYGKNNRPSGIPDRFSGSSSGNTASLTITGAQAEDEADY
YCNSRVMPHNRVFGGGTKLTVLGQPKAAPSVTLFPPSSEELQ
ANKATLVCLISDFYPGAVTVAWKADSSPVKAGVETTTPSKQS
NNKYAASSYLSLTPEQWKSHRSYSCQVTHEGSTVEKTVAPTE
CS |
| | 175
(Heavy chain) | EVQLLESGGGLVQPGGSLRLSCAASGFTFSSYAMSWVRQAPG
KGLEWVSAISGSGGSTYYADSVKGRFTISRDNSKNTLYLQMN
SLRAEDTAVYYCARVFYRGGVSMDYWGQGTLVTVSSASTK
GPSVFPLAPSSKSTSGGTAALGCLVKDYFPEPVTVSWNSGALT
SGVHTFPAVLQSSGLYSLSSVVTVPSSSLGTQTYICNVNHKPS
NTKVDKKVEPKSCDKTHTCPPCPAPEAAGGPSVFLFPPKPKD
TLMISRTPEVTCVVVDVSHEDPEVKFNWYVDGVEVHNAKTK
PREEQYNSTYRVVSVLTVLHQDWLNGKEYKCKVSNKALGAP
IEKTISKAKGQPREPQVYTLPPSRDELTKNQVSLTCLVKGFYP |

TABLE 13-continued

Sequences of anti-OX40 clones in P329GLALA human IgG1 format

| Clone | SEQ ID No. | Sequence |
|---|---|---|
| | | SDIAVEWESNGQPENNYKTTPPVLDSDGSFFLYSKLTVDKSR WQQGNVFSCSVMHEALHNHYTQKSLSLSPGK |

The anti-OX40 antibodies were produced by co-transfecting HEK293-EBNA cells with the mammalian expression vectors using polyethylenimine. The cells were transfected with the corresponding expression vectors in a 1:1 ratio ("vector heavy chain": "vector light chain").

For production in 500 mL shake flasks, 400 million HEK293 EBNA cells were seeded 24 hours before transfection. For transfection cells were centrifuged for 5 minutes at 210×g, and the supernatant was replaced by pre-warmed CD CHO medium. Expression vectors (200 µg of total DNA) were mixed in 20 mL CD CHO medium. After addition of 540 µL PEI, the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere. After the incubation, 160 mL of F17 medium was added and cells were cultured for 24 hours. One day after transfection 1 mM valproic acid and 7% Feed with supplements were added. After culturing for 7 days, the supernatant was collected by centrifugation for 15 minutes at 210×g. The solution was sterile filtered (0.22 µm filter), supplemented with sodium azide to a final concentration of 0.01% (w/v), and kept at 4° C.

Purification of antibody molecules from cell culture supernatants was carried out by affinity chromatography using Protein A as described above for purification of antigen Fc fusions.

The protein was concentrated and filtered prior to loading on a HiLoad Superdex 200 column (GE Healthcare) equilibrated with 20 mM Histidine, 140 mM NaCl solution of pH 6.0.

The protein concentration of purified antibodies was determined by measuring the OD at 280 nm, using the molar extinction coefficient calculated on the basis of the amino acid sequence. Purity and molecular weight of the antibodies were analyzed by CE-SDS in the presence and absence of a reducing agent (Invitrogen, USA) using a LabChipGXII (Caliper). The aggregate content of antibody samples was analyzed using a TSKgel G3000 SW XL analytical size-exclusion column (Tosoh) equilibrated in a 25 mM $K_2HPO_4$, 125 mM NaCl, 200 mM L-Arginine Monohydrochloride, 0.02% (w/v) $NaN_3$, pH 6.7 running buffer at 25° C.

Table 14 summarizes the yield and final content of the anti-OX40 P329G LALA IgG1 antibodies.

TABLE 14

Biochemical analysis of anti-OX40 P329G LALA IgG1 clones

| Clone | Yield [mg/l] | Monomer [%] | CE-SDS (non red) | CE-SDS (red) |
|---|---|---|---|---|
| 8H9 P329GLALA IgG1 | 7 | 100 | 1.2% (176 kDa) 96.1% (158 kDa) 1.3% (142 kDa) | 66.9% (54 kDa) 28.9% (25 kDa) |
| 49B4 P329GLALA IgG1 | 7.5 | 100 | 99% (163 kDa) 1% (149 kDa) | 81% (61.7 kDa) 18% (28.9 kDa) |
| 1G4 P329GLALA IgG1 | 1 | 100 | 98.9% (167.4 kDa) 1.1% (151 kDa) | 80% (63.4 kDa) 19% (28.9 kDa) |
| 20B7 P329GLALA IgG1 | 17 | 93 | 97.9% (174 kDa) | 79.8% (65.4 kDa) 19.9% (29.5 kDa) |
| CLC-563 P329GLALA IgG1 | 6.2 | 100 | 97.7% (160 kDa) | 77.7% (60 kDa) 19.8% (26.4 kDa) |
| CLC-564 P329GLALA IgG1 | 13.5 | 100 | 98.4% (155 kDa) | 79.3% (60.1 kDa) 19.8% (26.5 kDa) |
| 17A9 P329GLALA IgG1 | 7.5 | 100 | 98.6% (175 kDa) 1.4% (153 kDa) | 74.1% (61 kDa) 25.5% (38 kDa) |

Example 2

Generation of Bispecific Antibodies Targeting OX40 and Epithelial Cell Adhesion Molecule (EpCAM)

2.1 Generation of Bispecific Antibodies Targeting Human OX40 and Human Epithelial Cell Adhesion Molecule (EpCAM)

Bispecific agonistic OX40 constructs with tetravalent binding for OX40, and monovalent binding for EpCAM (i.e. '4+1' constructs) were prepared.

In this example, the antigen binding molecule comprised a first heavy chain (HC1) comprising VHCH1_VHCH1 of anti-OX40 49B4 Fc knob (P329G/LALA), followed by a (G4S)4 linker and VL of anti-EpCAM antibody clone 3-171; and a second heavy chain (HC2) comprising VHCH1_VHCH1 of anti-OX40 49B4 Fc hole (P329G/LALA), followed by a (G4S)4 linker and VH of anti-EpCam 3-171.

The generation of anti-EpCAM antibody 3-171 is described e.g. in WO 2010142990 A1. Nucleotide and amino acid sequences for 3-171 in scFv and IgG1 format (and VH and VL sequences thereof) are disclosed e.g. at Table 1 and FIG. 1 of WO 2010142990 A1.

The knob into hole technology is described in e.g. in U.S. Pat. Nos. 5,731,168 and 7,695,936 and allows the assembly of the HC1 and HC2. The Pro329Gly, Leu234Ala and Leu235Ala mutations have been introduced in the constant region of the heavy chains to abrogate binding to Fc gamma receptors according to the method described in International Patent Appl. Publ. No. WO 2012/130831 A1.

Figure 2A:
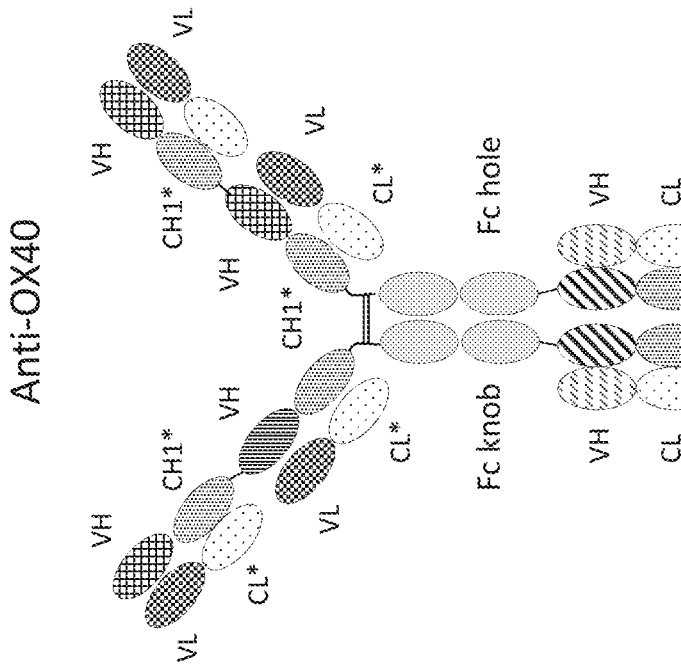
FIG. 2A shows a schematic representation of the bispecific, tetravalent anti-OX40, monovalent anti EpCAM hu/muIgG1 P329GLALA/DAPG kih 4+1 construct.

The heavy chain fusion polypeptides HC1 and HC2 were co-expressed with the light chain of the anti-OX40 clone 49B4 (CLVL), to produce a molecule having tetravalent binding for OX40 and monovalent binding for EpCAM (i.e. '4+1' constructs)—see FIG. 2A. The nucleotide and amino acid sequences are shown in Table 15 and Table 16, respectively.

Bispecific agonistic OX40 constructs with tetravalent binding for OX40, and bivalent binding for EpCAM (i.e. '4+2' constructs) were also prepared.

For the 4+2 construct, the heavy chains comprise VHCH1_VHCH1 of anti-OX40 49B4_Fc (P329G/LALA) followed by a (G4S)4 linker and a crossed Fab unit (VLCH1) of EpCAM-binding antibody 3-171 fused to the C-terminus of the Fc. The heavy chain fusion polypeptides were co-expressed with the light chain (LC1) of the anti-OX40 clone 49B4 (CLVL). The CH and CL of the anti-OX40 Fabs contained charged residues to prevent the generation of Bence Jones proteins and to further stabilize the correct pairing of LC1 to the HCs. Specifically, the substitutions E123R and Q124K (residues according to EU numbering) were made in the CL domain of the OX40(49B4) VLCL light chain, resulting in the light chain sequence SEQ ID NO:185; and the substitutions K147E and K213E (residues according to EU numbering) were made in the CH1 domain of OX40(49B4), resulting in the heavy chain sequence SEQ ID NO:186.

In this case the introduction of a knob into hole was not necessary as both HCs contain the same domains. The heavy chain fusion polypeptides and LC1 polypeptides were co-expressed with polypeptide encoding the VH and CL of the anti-EpCAM binding clone 3-171.

Figure 2B:
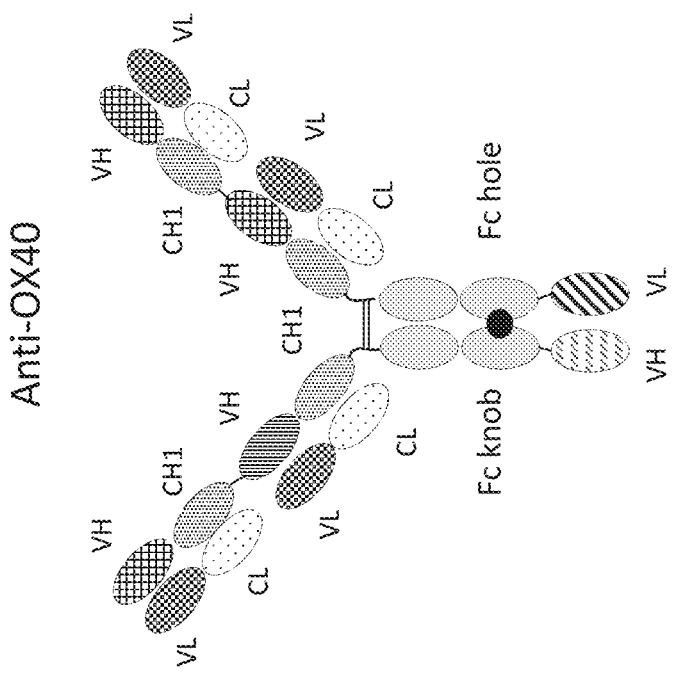
FIG. 2B shows a schematic representation of the bispecific, tetravalent anti-human OX40, bivalent anti-human EpCAM huIgG1 P329GLALA kih 4+2 construct. Charged residues are depicted as stars.
Figures 3A, 3B, 3C, 3D:
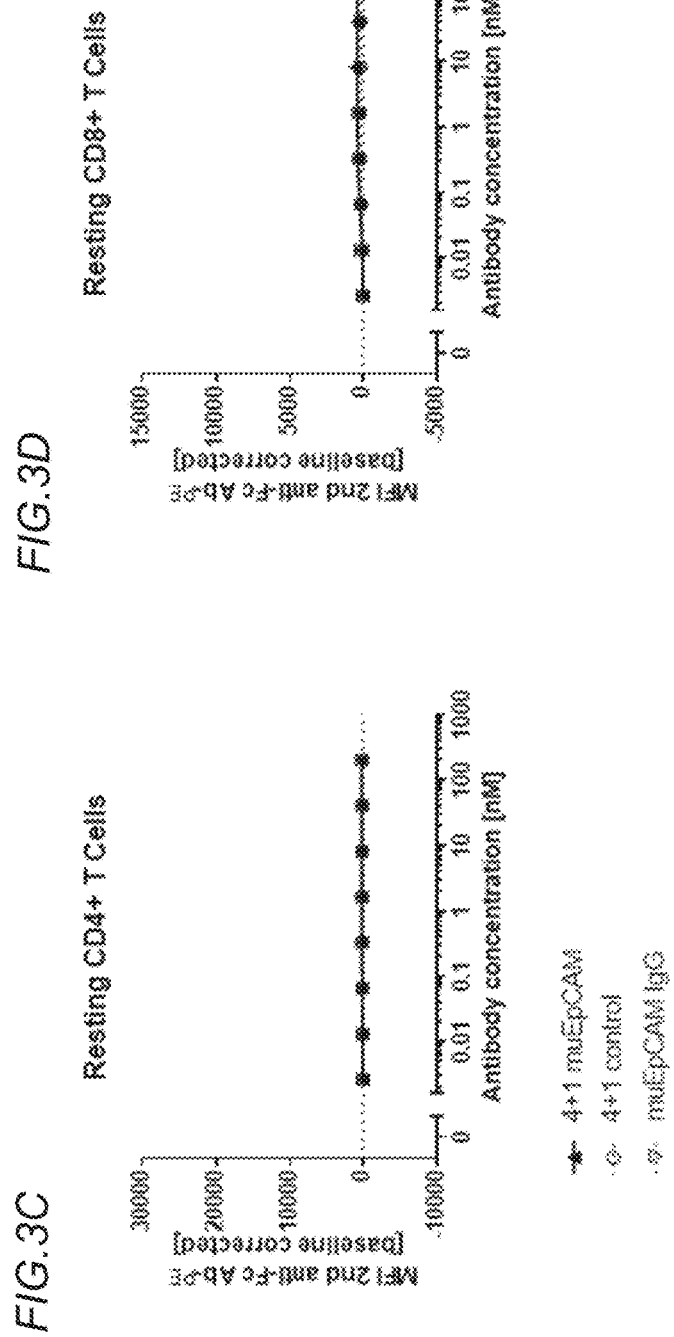
FIGS. 3A to 3D show the binding of the bispecific, tetravalent anti-murine OX40, monovalent anti-murine EpCAM (4+1 muEpCAM); monospecific, tetravalent anti-murine OX40, non-targeted (4+1 control); or monospecific, bivalent anti-murine EpCAM IgG (muEpCAM IgG) to resting and activated murine CD4+ and CD8+ T cells.

The resulting molecule having tetravalent binding for OX40 and bivalent binding for EpCAM (i.e. '4+2' constructs) is shown in FIG. 2B. The nucleotide and amino acid sequences are shown in Table 15 and Table 16, respectively.

TABLE 15

Base pair sequences of mature bispecific, tetravalent anti-OX40, monovalent and bivalent anti-EpCAM huIgG1 P329GLALA molecules

| Clone | | SEQ ID NO: | Base pair sequence |
|---|---|---|---|
| 49B4/EpCAM 3-171 P329GLALA 4 + 1 | LC 49B4 VLCL | 176 | GACATCCAGATGACCCAGTCTCCTTCCACC CTGTCTGCATCTGTAGGAGACCGTGTCACC ATCACTTGCCGTGCCAGTCAGAGTATTAGT AGCTGGTTGGCCTGGTATCAGCAGAAACCA GGGAAAGCCCCTAAGCTCCTGATCTATGAT GCCTCCAGTTTGGAAAGTGGGGTCCCATCA CGTTTCAGCGGCAGTGGATCCGGGACAGAA TTCACTCTCACCATCAGCAGCTTGCAGCCT GATGATTTTGCAACTTATTACTGCCAACAG TATAGTTCGCAGCCGTATACGTTTGGCCAG GGCACCAAAGTCGAGATCAAGCGTACGGTG GCTGCACCATCTGTCTTCATCTTCCCGCCA TCTGATGAGCAGTTGAAATCTGGAACTGCC TCTGTTGTGTGCCTGCTGAATAACTTCTAT CCCAGAGAGGCCAAAGTACAGTGGAAGGTG GATAACGCCCTCCAATCGGGTAACTCCCAG GAGAGTGTCACAGAGCAGGACAGCAAGGAC AGCACCTACAGCCTCAGCAGCACCCTGACG CTGAGCAAAGCAGACTACGAGAAACACAAA GTCTACGCCTGCGAAGTCACCCATCAGGGC CTGAGCTCGCCCGTCACAAAGAGCTTCAAC AGGGGAGAGTGT |
| | HC1 49B4VHCH1_ VHCH1_Fc_ knob_PG/ LALA_3-171 VL | 177 | CAGGTGCAATTGGTGCAGTCTGGGGCTGAG GTGAAGAAGCCTGGGTCCTCGGTGAAGGTC TCCTGCAAGGCCTCCGGAGGCACATTCAGC AGCTACGCTATAAGCTGGGTGCGACAGGCC CCTGGACAAGGGCTCGAGTGGATGGGAGGG ATCATCCCTATCTTTGGTACAGCAAACTAC GCACAGAAGTTCCAGGGCAGGGTCACCATT ACTGCAGACAAATCCACGAGCACAGCCTAC ATGGAGCTGAGCAGCCTGAGATCTGAGGAC ACCGCCGTGTATTACTGTGCGAGAGAATAC TACCGTGGTCCGTACGACTACTGGGGCCAA GGGACCACCGTGACCGTCTCCTCAGCTAGC ACAAAGGGACCTAGCGTGTTCCCCCTGGCC CCCAGCAGCAAGTCTACATCTGGCGGAACA GCCGCCCTGGGCTGCCTCGTGAAGGACTAC TTTCCCGAGCCCGTGACCGTGTCCTGGAAC TCTGGCGCTCTGACAAGCGGCGTGCACACC TTTCCAGCCGTGCTGCAGAGCAGCGGCCTG TACTCTCTGAGCAGCGTCGTGACAGTGCCC AGCAGCTCTCTGGGCACCCAGACCTACATC TGCAACGTGAACCACAAGCCCAGCAACACC AAGGTGGACAAGAAGGTGGAACCCAAGAGC TGCGACGGCGGAGGGGGATCTGGCGGCGGA GGATCCCAGGTGCAATTGGTGCAGTCTGGG GCTGAGGTGAAGAAGCCTGGGTCCTCGGTG AAGGTCTCCTGCAAGGCCTCCGGAGGCACA |

TABLE 15-continued

Base pair sequences of mature bispecific, tetravalent anti-OX40, monovalent and bivalent anti-EpCAM huIgG1 P329GLALA molecules

| Clone | SEQ ID NO: | Base pair sequence |
|---|---|---|
| | | TTCAGCAGCTACGCTATAAGCTGGGTGCGA |
| | | CAGGCCCCTGGACAAGGGCTCGAGTGGATG |
| | | GGAGGGATCATCCCTATCTTTGGTACAGCA |
| | | AACTACGCACAGAAGTTCCAGGGCAGGGTC |
| | | ACCATTACTGCAGACAAATCCACGAGCACA |
| | | GCCTACATGGAGCTGAGCAGCCTGAGATCT |
| | | GAGGACACCGCCGTGTATTACTGTGCGAGA |
| | | GAATACTACCGTGGTCCGTACGACTACTGG |
| | | GGCCAAGGGACCACCGTGACCGTCTCCTCA |
| | | GCTAGCACCAAGGGCCCATCGGTCTTCCCC |
| | | CTGGCACCCTCCTCCAAGAGCACCTCTGGG |
| | | GGCACAGCGGCCCTGGGCTGCCTGGTCAAG |
| | | GACTACTTCCCCGAACCGGTGACGGTGTCG |
| | | TGGAACTCAGGCGCCCTGACCAGCGGCGTG |
| | | CACACCTTCCCGGCTGTCCTACAGTCCTCA |
| | | GGACTCTACTCCCTCAGCAGCGTGGTGACC |
| | | GTGCCCTCCAGCAGCTTGGGCACCCAGACC |
| | | TACATCTGCAACGTGAATCACAAGCCCAGC |
| | | AACACCAAGGTGGACAAGAAAGTTGAGCCC |
| | | AAATCTTGTGACAAAACTCACACATGCCCA |
| | | CCGTGCCCAGCACCTGAAGCTGCAGGGGGA |
| | | CCGTCAGTCTTCCTCTTCCCCCCAAAACCC |
| | | AAGGACACCCTCATGATCTCCCGGACCCCT |
| | | GAGGTCACATGCGTGGTGGTGGACGTGAGC |
| | | CACGAAGACCCTGAGGTCAAGTTCAACTGG |
| | | TACGTGGACGGCGTGGAGGTGCATAATGCC |
| | | AAGACAAAGCCGCGGGAGGAGCAGTACAAC |
| | | AGCACGTACCGTGTGGTCAGCGTCCTCACC |
| | | GTCCTGCACCAGGACTGGCTGAATGGCAAG |
| | | GAGTACAAGTGCAAGGTCTCCAACAAAGCC |
| | | CTCGGCGCCCCCATCGAGAAAACCATCTCC |
| | | AAAGCCAAAGGGCAGCCCCGAGAACCACAG |
| | | GTGTACACCCTGCCCCCCTGCAGAGATGAG |
| | | CTGACCAAGAACCAGGTGTCCCTGTGGTGT |
| | | CTGGTCAAGGGCTTCTACCCCAGCGATATC |
| | | GCCGTGGAGTGGGAGAGCAACGGCCAGCCT |
| | | GAGAACAACTACAAGACCACCCCCCCTGTG |
| | | CTGGACAGCGACGGCAGCTTCTTCCTGTAC |
| | | TCCAAACTGACCGTGGACAAGAGCCGGTGG |
| | | CAGCAGGGCAACGTGTTCAGCTGCAGCGTG |
| | | ATGCACGAGGCCCTGCACAACCACTACACC |
| | | CAGAAGTCCCTGAGCCTGAGCCCCGGCGGA |
| | | GGCGGCGGAAGCGGAGGAGGAGGATCCGGC |
| | | GGAGGCGGATCTGGCGGGGGAGGTTCGGAG |
| | | ATCGTGATGACCCAGAGCCCCGCCACCCTG |
| | | AGTGTGTCTCCAGGCGAAAGAGCCACCCTG |
| | | TCCTGCAGAGCCAGCCAGAGCGTGTCCAGC |
| | | AACCTGGCCTGGTATCAGCAGAAGCCCGGC |
| | | CAGGCCCCCAGACTGATTATCTACGGCGCC |
| | | AGCACAACCGCCAGCGGCATCCCTGCCAGA |
| | | TTTTCCGCCTCTGGCAGCGGCACCGACTTC |
| | | ACCCTGACAATCAGCAGCCTGCAGTCCGAG |
| | | GACTTCGCCGTGTACTACTGCCAGCAGTAC |
| | | AACAACTGGCCCCCTGCCTACACCTTCGGC |
| | | CAGGGCACCAAGCTGGAAATCAAG |
| HC2 49B4VHCH1_ VHCH1_Fc_ hole_PG/ LALA_3-171 VH | 178 | CAGGTGCAATTGGTGCAGTCTGGGGCTGAG |
| | | GTGAAGAAGCCTGGGTCCTCGGTGAAGGTC |
| | | TCCTGCAAGGCCTCCGGAGGCACATTCAGC |
| | | AGCTACGCTATAAGCTGGGTGCGACAGGCC |
| | | CCTGGACAAGGGCTCGAGTGGATGGGAGGG |
| | | ATCATCCCTATCTTTGGTACAGCAAACTAC |
| | | GCACAGAAGTTCCAGGGCAGGGTCACCATT |
| | | ACTGCAGACAAATCCACGAGCACAGCCTAC |
| | | ATGGAGCTGAGCAGCCTGAGATCTGAGGAC |
| | | ACCGCCGTGTATTACTGTGCGAGAGAATAC |
| | | TACCGTGGTCCGTACGACTACTGGGGCCAA |
| | | GGGACCACCGTGACCGTCTCCTCAGCTAGC |
| | | ACAAAGGGACCTAGCGTGTTCCCCCTGGCC |
| | | CCCAGCAGCAAGTCTACATCTGGCGGAACA |
| | | GCCGCCCTGGGCTGCCTCGTGAAGGACTAC |
| | | TTTCCCGAGCCCGTGACCGTGTCCTGGAAC |
| | | TCTGGCGCTCTGACAAGCGGCGTGCACACC |
| | | TTTCCAGCCGTGCTGCAGAGCAGCGGCCTG |
| | | TACTCTCTGAGCAGCGTCGTGACAGTGCCC |
| | | AGCAGCTCTCTGGGCACCCAGACCTACATC |

TABLE 15-continued

Base pair sequences of mature bispecific, tetravalent anti-OX40, monovalent and bivalent anti-EpCAM huIgG1 P329GLALA molecules

| Clone | SEQ ID NO: | Base pair sequence |
|---|---|---|
| | | TGCAACGTGAACCACAAGCCCAGCAACACC |
| | | AAGGTGGACAAGAAGGTGGAACCCAAGAGC |
| | | TGCGACGGCGGAGGGGGATCTGGCGGCGGA |
| | | GGATCCCAGGTGCAATTGGTGCAGTCTGGG |
| | | GCTGAGGTGAAGAAGCCTGGGTCCTCGGTG |
| | | AAGGTCTCCTGCAAGGCCTCCGGAGGCACA |
| | | TTCAGCAGCTACGCTATAAGCTGGGTGCGA |
| | | CAGGCCCCTGGACAAGGGCTCGAGTGGATG |
| | | GGAGGGATCATCCCTATCTTTGGTACAGCA |
| | | AACTACGCACAGAAGTTCCAGGGCAGGGTC |
| | | ACCATTACTGCAGACAAATCCACGAGCACA |
| | | GCCTACATGGAGCTGAGCAGCCTGAGATCT |
| | | GAGGACACCGCCGTGTATTACTGTGCGAGA |
| | | GAATACTACCGTGGTCCGTACGACTACTGG |
| | | GGCCAAGGGACCACCGTGACCGTCTCCTCA |
| | | GCTAGCACCAAGGGCCCATCGGTCTTCCCC |
| | | CTGGCACCCTCCTCCAAGAGCACCTCTGGG |
| | | GGCACAGCGGCCCTGGGCTGCCTGGTCAAG |
| | | GACTACTTCCCCGAACCGGTGACGGTGTCG |
| | | TGGAACTCAGGCGCCCTGACCAGCGGCGTG |
| | | CACACCTTCCCGGCTGTCCTACAGTCCTCA |
| | | GGACTCTACTCCCTCAGCAGCGTGGTGACC |
| | | GTGCCCTCCAGCAGCTTGGGCACCCAGACC |
| | | TACATCTGCAACGTGAATCACAAGCCCAGC |
| | | AACACCAAGGTGGACAAGAAAGTTGAGCCC |
| | | AAATCTTGTGACAAAACTCACACATGCCCA |
| | | CCGTGCCCAGCACCTGAAGCTGCAGGGGGA |
| | | CCGTCAGTCTTCCTCTTCCCCCCAAAACCC |
| | | AAGGACACCCTCATGATCTCCCGGACCCCT |
| | | GAGGTCACATGCGTGGTGGTGGACGTGAGC |
| | | CACGAAGACCCTGAGGTCAAGTTCAACTGG |
| | | TACGTGGACGGCGTGGAGGTGCATAATGCC |
| | | AAGACAAAGCCGCGGGAGGAGCAGTACAAC |
| | | AGCACGTACCGTGTGGTCAGCGTCCTCACC |
| | | GTCCTGCACCAGGACTGGCTGAATGGCAAG |
| | | GAGTACAAGTGCAAGGTCTCCAACAAAGCC |
| | | CTCGGCGCCCCCATCGAGAAAACCATCTCC |
| | | AAAGCCAAAGGGCAGCCCCGAGAACCACAG |
| | | GTGTGCACCCTGCCCCCATCCCGGGATGAG |
| | | CTGACCAAGAACCAGGTCAGCCTCTCGTGC |
| | | GCAGTCAAAGGCTTCTATCCCAGCGACATC |
| | | GCCGTGGAGTGGGAGAGCAATGGGCAGCCG |
| | | GAGAACAACTACAAGACCACGCCTCCCGTG |
| | | CTGGACTCCGACGGCTCCTTCTTCCTCGTG |
| | | AGCAAGCTCACCGTGGACAAGAGCAGGTGG |
| | | CAGCAGGGGAACGTCTTCTCATGCTCCGTG |
| | | ATGCATGAGGCTCTGCACAACCACTACACG |
| | | CAGAAGAGCCTCTCCCTGTCTCCGGGTGGA |
| | | GGCGGCGGAAGCGGAGGAGGAGGATCCGGC |
| | | GGAGGCGGAAGTGGCGGCGGAGGTTCGCAG |
| | | GTGCAGCTGGTGCAGTCTGGCGCCGAAGTG |
| | | AAGAAACCCGGCAGCAGCGTGAAGGTGTCC |
| | | TGCAAGGCTTCCGGCGGCACCTTCAGCAGC |
| | | TACGCCATTTCTTGGGTGCGCCAGGCCCCT |
| | | GGACAGGGCCTGGAATGGATGGGCGGCATC |
| | | ATCCCCATCTTCGGCACCGCCAACTACGCC |
| | | CAGAAATTCCAGGGCAGAGTGACCATCACC |
| | | GCCGACGAGAGCACCAGCACCGCCTACATG |
| | | GAACTGAGCAGCCTGCGGAGCGAGGACACC |
| | | GCCGTGTACTATTGTGCCAGAGGCCTGCTG |
| | | TGGAACTACTGGGGCCAGGGCACACTCGTG |
| | | ACCGTGTCCTCT |
| OX40 49B4/ LC1 EpCAM 3-17I 49B4 VLCL P329GLALA charges 4 + 2 | 179 | GACATCCAGATGACCCAGTCTCCTTCCACC CTGTCTGCATCTGTAGGAGACCGTGTCACC ATCACTTGCCGTGCCAGTCAGAGTATTAGT AGCTGGTTGGCCTGGTATCAGCAGAAACCA GGGAAAGCCCCTAAGCTCCTGATCTATGAT GCCTCCAGTTTGGAAAGTGGGGTCCCATCA CGTTTCAGCGGCAGTGGATCCGGGACAGAA TTCACTCTCACCATCAGCAGCTTGCAGCCT GATGATTTTGCAACTTATTACTGCCAACAG TATAGTTCGCAGCCGTATACGTTTGGCCAG GGCACCAAAGTCGAGATCAAGCGTACGGTG GCTGCACCATCTGTCTTCATCTTCCCGCCA |

TABLE 15-continued

Base pair sequences of mature bispecific, tetravalent anti-OX40, monovalent and bivalent anti-EpCAM huIgG1 P329GLALA molecules

| Clone | SEQ ID NO: | Base pair sequence |
|---|---|---|
| | | TCTGATCGGAAGTTGAAATCTGGAACTGCC<br>TCTGTTGTGTGCCTGCTGAATAACTTCTAT<br>CCCAGAGAGGCCAAAGTACAGTGGAAGGTG<br>GATAACGCCCTCCAATCGGGTAACTCCCAG<br>GAGAGTGTCACAGAGCAGGACAGCAAGGAC<br>AGCACCTACAGCCTCAGCAGCACCCTGACG<br>CTGAGCAAAGCAGACTACGAGAAACACAAA<br>GTCTACGCCTGCGAAGTCACCCATCAGGGC<br>CTGAGCTCGCCCGTCACAAAGAGCTTCAAC<br>AGGGGAGAGTGT |
| HC 49B4VHCH1_49B4VHCH1_Fc_PG/LALA_3-17I VLCH1 49B4 Fab charges | 180 | CAGGTGCAGCTGGTGCAGTCTGGCGCCGAA<br>GTGAAGAAACCCGGCAGCAGCGTGAAGGTG<br>TCCTGCAAGGCTTCCGGCGGCACCTTCAGC<br>AGCTACGCCATTTCTTGGGTGCGCCAGGCC<br>CCTGGACAGGGCCTGGAATGGATGGGCGGC<br>ATCATCCCCATCTTCGGCACCGCCAACTAC<br>GCCCAGAAATTCCAGGGCAGAGTGACCATC<br>ACCGCCGACAAGAGCACCAGCACCGCCTAC<br>ATGGAACTGAGCAGCCTGCGGAGCGAGGAC<br>ACCGCCGTGTACTACTGCGCCAGAGAGTAC<br>TACAGAGGCCCCTACGACTACTGGGGCCAG<br>GGCACAACCGTGACCGTGTCTAGCGCCAGC<br>ACAAAGGGCCCCAGCGTGTTCCCTCTGGCC<br>CCTAGCAGCAAGAGCACATCTGGCGGAACA<br>GCCGCCCTGGGCTGCCTGGTGGAAGATTAC<br>TTCCCCGAGCCCGTGACAGTGTCCTGGAAC<br>TCTGGCGCCCTGACAAGCGGCGTGCACACC<br>TTTCCAGCCGTGCTGCAGAGCAGCGGCCTG<br>TACTCACTGTCCAGCGTCGTGACTGTGCCC<br>AGCAGCAGCCTGGGAACCCAGACCTACATC<br>TGCAACGTGAACCACAAGCCCAGCAACACC<br>AAGGTGGACGAGAAGGTGGAACCCAAGAGC<br>TGCGACGGCGGAGGCGGATCTGGCGGCGGA<br>GGATCCCAGGTGCAGCTGGTGCAGAGCGGA<br>GCTGAAGTGAAAAAGCCTGGCTCCTCCGTG<br>AAAGTGTCTTGTAAAGCCAGCGGCGGCACA<br>TTCTCATCCTACGCCATCAGCTGGGTGCGG<br>CAGGCTCCAGGCCAGGGACTGGAATGGATG<br>GGAGGAATTATCCCTATTTTTGGGACAGCC<br>AATTATGCTCAGAAATTTCAGGGGCGCGTG<br>ACAATTACAGCCGACAAGTCCACCTCTACA<br>GCTTATATGGAACTGTCCTCCCTGCGCTCC<br>GAGGATACAGCTGTGTATTATTGTGCCCGC<br>GAGTACTACCGGGGACCTTACGATTATTGG<br>GGACAGGGAACCACAGTGACTGTGTCCTCC<br>GCTAGCACCAAGGGACCTTCCGTGTTTCCC<br>CTGGCTCCCAGCTCCAAGTCTACCTCTGGG<br>GGCACAGCTGCTCTGGGATGTCTGGTGGAA<br>GATTATTTTCCTGAACCTGTGACCGTGTCA<br>TGGAACAGCGGAGCCCTGACCTCCGGGGTG<br>CACACATTCCCTGCTGTGCTGCAGTCCTCC<br>GGCCTGTATAGCCTGAGCAGCGTCGTGACC<br>GTGCCTTCCAGCTCTCTGGGCACACAGACA<br>TATATCTGTAATGTGAATCACAAACCCTCT<br>AATACCAAAGTGGATGAGAAAGTGGAACCT<br>AAGTCCTGCGACAAGACCCACACCTGTCCC<br>CCTTGTCCTGCCCCTGAAGCTGCTGGCGGC<br>CCATCTGTGTTTCTGTTCCCCCCAAAGCCC<br>AAGGACACCCTGATGATCAGCCGGACCCCC<br>GAAGTGACCTGCGTGGTGGTGGATGTGTCC<br>CACGAGGACCCAGAAGTGAAGTTCAATTGG<br>TACGTGGACGGCGTGGAAGTGCACAACGCC<br>AAGACCAAGCCGCGGGAAGAACAGTACAAC<br>AGCACCTACCGGGTGGTGTCCGTGCTGACA<br>GTGCTGCACCAGGACTGGCTGAACGGCAAA<br>GAGTACAAGTGCAAGGTGTCCAACAAGGCC<br>CTGGGAGCCCCCATCGAGAAAACCATCAGC<br>AAGGCCAAGGGCCAGCCCCGCGAACCTCAG<br>GTGTACACCCTGCCCCCAAGCAGGGACGAG<br>CTGACCAAGAACCAGGTGTCCCTGACCTGT<br>CTCGTGAAGGGCTTCTACCCCTCCGATATC<br>GCCGTGGAATGGGAGAGCAACGGCCAGCCC<br>GAGAACAACTACAAGACCACCCCCCCTGTG<br>CTGGACAGCGACGGCTCATTCTTCCTGTAC |

TABLE 15-continued

Base pair sequences of mature bispecific, tetravalent anti-OX40, monovalent and bivalent anti-EpCAM huIgG1 P329GLALA molecules

| Clone | SEQ ID NO: | Base pair sequence |
|---|---|---|
| | | TCCAAGCTGACCGTGGACAAGAGCCGGTGG CAGCAGGGCAACGTGTTCAGCTGCAGCGTG ATGCACGAGGCCCTGCACAACCACTACACA CAGAAGTCTCTGAGCCTGAGCCCTGGCGGA GGGGGAGGATCTGGGGGAGGCGGAAGTGGG GGAGGGGGTTCCGGAGGCGGTGGTTCGGAG ATCGTGATGACCCAGAGCCCCGCCACCCTG AGTGTGTCTCCAGGCGAAAGAGCCACCCTG TCCTGCAGAGCCAGCCAGAGCGTGTCCAGC AACCTGGCCTGGTATCAGCAGAAGCCCGGC CAGGCCCCCAGACTGATTATCTACGGCGCC AGCACAACCGCCAGCGGCATCCCTGCCAGA TTTTCCGCCTCTGGCAGCGGCACCGACTTC ACCCTGACAATCAGCAGCCTGCAGTCCGAG GACTTCGCCGTGTACTACTGCAGCAGTAC AACAACTGGCCCCCTGCCTACACCTTCGGC CAGGGCACCAAGCTGGAAATCAAGAGCAGC GCTTCCACCAAGGGCCCCTCAGTGTTCCCA CTGGCACCATCCAGCAAGTCCACAAGCGGA GGAACCGCCGCTCTGGGCTGTCTCGTGAAA GACTACTTTCCAGAGCCAGTGACCGTGTCC TGGAATAGTGGCGCTCTGACTTCTGGCGTG CACACTTTCCCCGCAGTGCTGCAGAGTTCT GGCCTGTACTCCCTGAGTAGCGTCGTGACA GTGCCCTCCTCTAGCCTGGGCACTCAGACT TACATCTGCAATGTGAATCATAAGCCTTCC AACACAAAAGTGGACAAAAAAGTGGAACCC AAATCTTGC |
| LC2 EpCAM 3-171 VHCL | 181 | CAGGTGCAGCTGGTGCAGTCTGGCGCCGAA GTGAAGAAACCCGGCAGCAGCGTGAAGGTG TCCTGCAAGGCTTCCGGCGGCACCTTCAGC AGCTACGCCATTTCTTGGGTGCGCCAGGCC CCTGGACAGGGCCTGGAATGGATGGGCGGC ATCATCCCCATCTTCGGCACCGCCAACTAC GCCCAGAAATTCCAGGGCAGAGTGACCATC ACCGCCGACGAGAGCACCAGCACCGCCTAC ATGGAACTGAGCAGCCTGCGGAGCGAGGAC ACCGCCGTGTACTATTGTGCCAGAGGCCTG CTGTGGAACTACTGGGGCCAGGGCACACTC GTGACCGTGTCCTCTGCTAGCGTGGCCGCT CCCTCCGTGTTCATCTTCCCACCTTCCGAC GAGCAGCTGAAGTCCGGCACCGCTTCTGTC GTGTGCCTGCTGAACAACTTCTACCCCCGC GAGGCCAAGGTGCAGTGGAAGGTGGACAAC GCCCTGCAGTCCGGCAACAGCCAGGAATCC GTGACCGAGCAGGACTCCAAGGACAGCACC TACTCCCTGTCCTCCACCCTGACCCTGTCC AAGGCCGACTACGAGAAGCACAAGGTGTAC GCCTGCGAAGTGACCCACCAGGGCCTGTCT AGCCCCGTGACCAAGTCTTTCAACCGGGGC GAGTGC |

TABLE 16

Amino acid sequences of mature bispecific, tetravalent anti-OX40, monovalent and bivalent anti-EpCAM huIgG1 P329GLALA molecules

| Clone | | SEQ ID NO: | Amino acid sequence |
|---|---|---|---|
| OX40 49B4/ EpCam 3-171 P329GLALA 4 + 1 | LC 49B4 VLCL | 182 | DIQMTQSPSTLSASVGDRVTITCRASQSISSW LAWYQQKPGKAPKLLIYDASSLESGVPSRFSG SGSGTEFTLTISSLQPDDFATYYCQQYSSQPY TFGQGTKVEIKRTVAAPSVFIFPPSDEQLKSG TASVVCLLNNFYPREAKVQWKVDNALQSGNSQ ESVTEQDSKDSTYSLSSTLTLSKADYEKHKVY ACEVTHQGLSSPVTKSFNRGEC |
| | HC1 49B4 VHCH1_VHCH1_ Fc_knob_ PG/LALA_ 3-171 VL | 183 | QVQLVQSGAEVKKPGSSVKVSCKASGGTFSSY AISWVRQAPGQGLEWMGGIIPIFGTANYAQKF QGRVTITADKSTSTAYMELSSLRSEDTAVYYC AREYYRGPYDYWGQGTTVTVSSASTKGPSVFP LAPSSKSTSGGTAALGCLVKDYFPEPVTVSWN SGALTSGVHTFPAVLQSSGLYSLSSVVTVPSS |

TABLE 16-continued

Amino acid sequences of mature bispecific, tetravalent anti-OX40, monovalent and bivalent anti-EpCAM huIgG1 P329GLALA molecules

| Clone | | SEQ ID NO: | Amino acid sequence |
|---|---|---|---|
| | | | SLGTQTYICNVNHKPSNTKVDKKVEPKSCDGG GGSGGGGSQVQLVQSGAEVKKPGSSVKVSCKA SGGTFSSYAISWVRQAPGQGLEWMGGIIPIFG TANYAQKFQGRVTITADKSTSTAYMELSSLRS EDTAVYYCAREYYRGPYDYWGQGTTVTVSSAS TKGPSVFPLAPSSKSTSGGTAALGCLVKDYFP EPVTVSWNSGALTSGVHTFPAVLQSSGLYSLS SVVTVPSSSLGTQTYICNVNHKPSNTKVDKKV EPKSCDKTHTCPPCPAPEAAGGPSVFLFPPKP KDTLMISRTPEVTCVVVDVSHEDPEVKFNWYV DGVEVHNAKTKPREEQYNSTYRVVSVLTVLHQ DWLNGKEYKCKVSNKALGAPIEKTISKAKGQP REPQVYTLPPCRDELTKNQVSLWCLVKGFYPS DIAVEWESNGQPENNYKTTPPVLDSDGSFFLY SKLTVDKSRWQQGNVFSCSVMHEALHNHYTQK SLSLSPGGGGSGGGGSGGGGSGGGGSEIVMT QSPATLSVSPGERATLSCRASQSVSSNLAWYQ QKPGQAPRLIIYGASTTASGIPARFSASGSGT DFTLTISSLQSEDFAVYYCQQYNNWPPAYTFG QGTKLEIK |
| | HC2 49B4 VHCH1_VHCH1_ Fc_hole_ PG/LALA_ 3-171 VH | 184 | QVQLVQSGAEVKKPGSSVKVSCKASGGTFSSY AISWVRQAPGQGLEWMGGHPIFGTANYAQKFQ GRVTITADKSTSTAYMELSSLRSEDTAVYYCA REYYRGPYDYWGQGTTVTVSSASTKGPSVFPL APSSKSTSGGTAALGCLVKDYFPEPVTVSWNS GALTSGVHTFPAVLQSSGLYSLSSVVTVPSSS LGTQTYICNVNHKPSNTKVDKKVEPKSCDGGG GSGGGGSQVQLVQSGAEVKKPGSSVKVSCKAS GGTFSSYAISWVRQAPGQGLEWMGGIIPIFGT ANYAQKFQGRVTITADKSTSTAYMELSSLRSE DTAVYYCAREYYRGPYDYWGQGTTVTVSSAST KGPSVFPLAPSSKSTSGGTAALGCLVKDYFPE PVTVSWNSGALTSGVHTFPAVLQSSGLYSLSS VVTVPSSSLGTQTYICNVNHKPSNTKVDKKVE PKSCDKTHTCPPCPAPEAAGGPSVFLFPPKPK DTLMISRTPEVTCVVVDVSHEDPEVKFNWYVD GVEVHNAKTKPREEQYNSTYRVVSVLTVLHQD WLNGKEYKCKVSNKALGAPIEKTISKAKGQPR EPQVCTLPPSRDELTKNQVSLSCAVKGFYPSD IAVEWESNGQPENNYKTTPPVLDSDGSFFLVS KLTVDKSRWQQGNVFSCSVMHEALHNHYTQKS LSLSPGGGGSGGGGSGGGGSGGGGSQVQLVQ SGAEVKKPGSSVKVSCKASGGTFSSYAISWVR QAPGQGLEWMGGHPIFGTANYAQKFQGRVTIT ADESTSTAYMELSSLRSEDTAVYYCARGLLWN YWGQGTLVTVSS |
| OX40 49B4/ EpCAM 3-171 P329GLALA 4 + 2 | LC1 49B4 VLCL charges | 185 | DIQMTQSPSTLSASVGDRVTITCRASQSISSW LAWYQQKPGKAPKLLIYDASSLESGVPSRFSG SGSGTEFTLTISSLQPDDFATYYCQQYSSQPY TFGQGTKVEIKRTVAAPSVFIFPPSDRKLKSG TASVVCLLNNFYPREAKVQWKVDNALQSGNSQ ESVTEQDSKDSTYSLSSTLTLSKADYEKHKVY ACEVTHQGLSSPVTKSFNRGEC |
| | HC 49B4VHCH1_ 49B4VHCH1_ Fc_PG/LALA_ 3-171 VLCH1 49B4 Fab charges | 186 | QVQLVQSGAEVKKPGSSVKVSCKASGGTFSSY AISWVRQAPGQGLEWMGGHPIFGTANYAQKFQ GRVTITADKSTSTAYMELSSLRSEDTAVYYCA REYYRGPYDYWGQGTTVTVSSASTKGPSVFPL APSSKSTSGGTAALGCLVEDYFPEPVTVSWNS GALTSGVHTFPAVLQSSGLYSLSSVVTVPSSS LGTQTYICNVNHKPSNTKVDEKVEPKSCDGGG GSGGGGSQVQLVQSGAEVKKPGSSVKVSCKAS GGTFSSYAISWVRQAPGQGLEWMGGIIPIFGT ANYAQKFQGRVTITADKSTSTAYMELSSLRSE DTAVYYCAREYYRGPYDYWGQGTTVTVSSAST KGPSVFPLAPSSKSTSGGTAALGCLVEDYFPE PVTVSWNSGALTSGVHTFPAVLQSSGLYSLSS VVTVPSSSLGTQTYICNVNHKPSNTKVDEKVE PKSCDKTHTCPPCPAPEAAGGPSVFLFPPKPK DTLMISRTPEVTCVVVDVSHEDPEVKFNWYVD GVEVHNAKTKPREEQYNSTYRVVSVLTVLHQD WLNGKEYKCKVSNKALGAPIEKTISKAKGQPR EPQVYTLPPSRDELTKNQVSLTCLVKGFYPSD IAVEWESNGQPENNYKTTPPVLDSDGSFFLYS KLTVDKSRWQQGNVFSCSVMHEALHNHYTQKS |

TABLE 16-continued

Amino acid sequences of mature bispecific, tetravalent anti-OX40, monovalent and bivalent anti-EpCAM huIgG1 P329GLALA molecules

| Clone | SEQ ID NO: | Amino acid sequence |
|---|---|---|
| LC2<br>EpCAM 3-171<br>VHCL | 187 | LSLSPGGGGSGGGGSGGGGSGGGGSEIVMTQ<br>SPATLSVSPGERATLSCRASQSVSSNLAWYQQ<br>KPGQAPRLITYGASTTASGIPARFSASGSGTD<br>FTLTISSLQSEDFAVYYCQQYNNWPPAYTFGQ<br>GTKLEIKSSASTKGPSVFPLAPSSKSTSGGTA<br>ALGCLVKDYFPEPVTVSWNSGALTSGVHTFPA<br>VLQSSGLYSLSSVVTVPSSSLGTQTYICNVNH<br>KPSNTKVDKKVEPKSC<br>QVQLVQSGAEVKKPGSSVKVSCKASGGTFSSY<br>AISWVRQAPGQGLEWMGGIIPIFGTANYAQKF<br>QGRVTITADESTSTAYMELSSLRSEDTAVYYC<br>ARGLLWNYWGQGTLVTVSSASVAAPSVFIFPP<br>SDEQLKSGTASVVCLLNNFYPREAKVQWKVDN<br>ALQSGNSQESVTEQDSKDSTYSLSSTLTLSKA<br>DYEKHKVYACEVTHQGLSSPVTKSFNRGEC |

2.2 Generation of Bispecific Antibodies Targeting Murine OX40 and Murine Epithelial Cell Adhesion Molecule (EpCAM)

Bispecific constructs with tetravalent binding for murine OX40, and monovalent binding for murine EpCAM (i.e. '4+1' constructs) were also prepared.

In this example, the antigen binding molecule comprised a first heavy chain (HC1) comprising VHCH1_VHCH1 of anti-mouse OX40 antibody clone OX86 Fc knob (DAPG), followed by a (G4S)4 linker and VL of anti-mouse EpCAM antibody clone G8.8; and a second heavy chain (HC2) comprising VHCH1_VHCH1 of anti-mouse OX40 OX86 Fc hole (DAPG), followed by a (G4S)4 linker and VH of anti-mouse EpCAM G8.8.

The generation of rat anti-mouse OX40 antibody clone OX86 is described e.g. in Al-Shamkhani et al. Eur J Chem (1996) 26:1695-1699 or in WO 2016/057667.

The generation of rat anti-mouse EpCAM antibody G8.8 is described e.g. in Farr et al., J Histochem Cytochem. (1991) 39(5):645-53, and is available from the Developmental Studies Hybridoma Bank, University of Iowa, Iowa City, Iowa. The antibody is also described in WO 2013/113615.

The 'DDKK' knob-into-hole technology is described in e.g. in WO 2014/131694 A1, and allows the assembly of the HC1 and HC2. Briefly, aspartic acid residues (D) are provided in the Fc region subunit of one of the heavy chains (HC1) at positions corresponding to positions 392 and 409 (numbering according to Kabat EU index; i.e. K392D and K409D), and lysine (K) residues are provided in the Fc region subunit of the other of the heavy chains (HC2) at positions corresponding to positions 356 and 399 (numbering according to Kabat EU index; i.e. E356K and D399K).

DAPG mutations were introduced in the constant regions of the heavy chains to abrogate binding to murine Fc gamma receptors according to the method described e.g. in Baudino et al. J. Immunol. (2008), 181, 6664-6669, or in WO 2016/030350 A1. Briefly, alanine (A) is provided in the Fc region at the position corresponding to position 265, and glycine (G) is provided in the Fc region at the position corresponding to position 329 (numbering according to Kabat EU index; i.e. D265A, P329G).

The heavy chain fusion polypeptides HC1 and HC2 were co-expressed with the light chain of the anti-OX40 clone OX86 (CLVL), to produce a molecule having tetravalent binding for mouse OX40 and monovalent binding for mouse EpCAM (i.e. '4+1' constructs). The nucleotide and amino acid sequences are shown respectively in Table 17 and Table 18.

TABLE 17

Base pair sequences of mature bispecific, tetravalent anti-muOX40, monovalent anti-muEpCAM huIgG1 DAPG kih 4 + 1 molecules

| Clone | | SEQ ID NO: | Base pair sequence |
|---|---|---|---|
| muOX40<br>OX86/<br>muEpCAM<br>G8.8 DAPG<br>4 + 1 | LC<br>OX40 OX86<br>VLCL | 188 | GATATTGTGATGACCCAGGGTGCACTCCCC<br>AATCCTGTCCCTTCTGGAGAGTCAGCTTCC<br>ATCACCTGCAGGTCTAGTCAGAGTCTGGTA<br>TACAAAGACGGCCAGACATACTTGAATTGG<br>TTTCTGCAGAGGCCAGGACAGTCTCCTCAG<br>CTTCTGACCTATTGGATGTCTACCCGTGCA<br>TCAGGAGTCTCAGACAGGTTCAGTGGCAGT<br>GGGTCAGGAACATATTTCACACTGAAAATC<br>AGTAGAGTGAGGGCTGAGGATGCGGGTGTG<br>TATTACTGTCAGCAAGTTCGAGAGTATCCT<br>TTCACTTTCGGCTCAGGGACGAAGTTGGAA<br>ATAAAACGTGCCGATGCTGCACCAACTGTA<br>TCGATTTTCCCACCATCCAGTGAGCAGTTA<br>ACATCTGGAGGTGCCTCAGTCGTGTGCTTC<br>TTGAACAACTTCTACCCCAAAGACATCAAT<br>GTCAAGTGGAAGATTGATGGCAGTGAACGA<br>CAAAATGGCGTCCTGAACAGTTGGACTGAT<br>CAGGACAGCAAAGACAGCACCTACAGCATG<br>AGCAGCACCCTCACGTTGACCAAGGACGAG |

TABLE 17-continued

Base pair sequences of mature bispecific, tetravalent anti-muOX40,
monovalent anti-muEpCAM huIgG1 DAPG kih 4 + 1 molecules

| Clone | SEQ ID NO: | Base pair sequence |
|---|---|---|
| HC1 OX86 VHCH1_VHCH1_ Fc_hole_ DAPG_DD G8.8_VL | 189 | TATGAACGACATAACAGCTATACCTGTGAG GCCACTCACAAGACATCAACTTCACCCATT GTCAAGAGCTTCAACAGGAATGAGTGT CAGGTGCAGCTGAAGGAGTCTGGACCTGGT CTGGTGCAGCCCTCACAGACCCTGTCCCTC ACCTGCACTGTCTCTGGGTTCTCACTAACC GGTTACAATTTACACTGGGTTCGCCAGCCT CCAGGAAAGGGTCTGGAGTGGATGGGAAGA ATGAGGTATGATGGAGACACATATTATAAT TCAGTTCTCAAATCCCGACTGAGCATCAGC AGGGACACCTCCAAGAACCAAGTTTTCTTG AAAATGAACAGTCTGCAAACGGATGACACA GCCATTTACTATTGTACCAGAGACGGGCGT GGTGACTCCTTTGATTACTGGGGCCAAGGA GTCATGGTCACAGTCTCCAGCGCTAAGACC ACCCCCCCCTCCGTGTATCCTCTGGCTCCT GGATCTGCCGCCCAGACCAACAGCATGGTC ACCCTGGGCTGCCTCGTGAAGGGCTACTTC CCTGAGCCTGTGACCGTGACCTGGAACTCC GGCTCTCTGTCCTCTGGCGTGCACACCTTC CCTGCCGTGCTGCAGTCCGACCTGTACACC CTGTCCTCCAGCGTGACCGTGCCTTCCTCC ACCTGGCCTTCCCAGACCGTGACATGCAAC GTGGCCCACCCTGCCAGCTCCACCAAGGTG GACAAGAAAATCGTGCCCCGGGACTGCGGA GGGGGCGGTTCCGGCGGAGGAGGATCCCAG GTGCAGCTGAAGGAGTCTGGACCTGGTCTG GTGCAGCCCTCACAGACCCTGTCCCTCACC TGCACTGTCTCTGGGTTCTCACTAACCGGT TACAATTTACACTGGGTTCGCCAGCCTCCA GGAAAGGGTCTGGAGTGGATGGGAAGAATG AGGTATGATGGAGACACATATTATAATTCA GTTCTCAAATCCCGACTGAGCATCAGCAGG GACACCTCCAAGAACCAAGTTTTCTTGAAA ATGAACAGTCTGCAAACGGATGACACAGCC ATTTACTATTGTACCAGAGACGGGCGTGGT GACTCCTTTGATTACTGGGGCCAAGGAGTC ATGGTCACAGTCTCCAGCGCTAAGACCACC CCCCCTAGCGTGTACCCTCTGGCCCCTGGA TCTGCCGCCCAGACCAACAGCATGGTGACC CTGGGCTGCCTGGTGAAGGGCTACTTCCCC GAGCCTGTGACCGTGACCTGGAACAGCGGC AGCCTGAGCAGCGGCGTGCACACCTTTCCA GCCGTGCTGCAGAGCGACCTGTACACCCTG AGCAGCTCCGTGACCGTGCCTAGCAGCACC TGGCCCAGCCAGACAGTGACCTGCAACGTG GCCCACCCTGCCAGCAGCACCAAGGTGGAC AAGAAAATCGTGCCCCGGGACTGCGGCTGC AAGCCCTGCATCTGCACCGTGCCCGAGGTG TCCAGCGTGTTCATCTTCCCACCCAAGCCC AAGGACGTGCTGACCATCACCCTGACCCCC AAAGTGACCTGCGTGGTGGTGGCCATCAGC AAGGACGACCCCGAGGTGCAGTTCTCTTGG TTTGTGGACGACGTGGAGGTGCACACAGCC CAGACAAAGCCCCGGGAGGAACAGATCAAC AGCACCTTCAGAAGCGTGTCCGAGCTGCCC ATCATGCACCAGGACTGGCTGAACGGCAAA GAATTCAAGTGCAGAGTGAACAGCGCCGCC TTCGGCGCCCCCATCGAGAAAACCATCAGC AAGACCAAGGGCAGACCCAAGGCCCCCCAG GTGTACACCATCCCCCCACCCAAAGAACAG ATGGCCAAGGACAAGGTGTCCCTGACCTGC ATGATCACCAACTTTTTCCCCGAGGACATC ACCGTGGAGTGGCAGTGGAATGGCAGCCCC GCCGAGAACTACGACAACACCCAGCCCATC ATGGACACCGACGGCAGCTACTTCGTGTAC AGCGACCTGAACGTGCAGAAGTCCAACTGG GAGGCCGGCAACACCTTCACCTGTAGCGTG CTGCACGAGGGCCTGCACAACCACCACACC GAGAAGTCCCTGAGCCACAGCCCAGGCGGC GGAGGCGGATCTGGCGGAGGAGGTTCCGGT GGCGGAGGTTCCGGAGGCGGTGGATCCGAC ATCCAGATGACACAGAGCCCCGCCAGCCTG AGCGCCTCTCTGGGCGAGACAGTGTCCATC GAGTGCCTGGCCAGCGAGGGCATCAGCAAC |

TABLE 17-continued

Base pair sequences of mature bispecific, tetravalent anti-muOX40,
monovalent anti-muEpCAM huIgG1 DAPG kih 4 + 1 molecules

| Clone | SEQ ID NO: | Base pair sequence |
|---|---|---|
| | | GACCTGGCCTGGTATCAGCAGAAGTCCGGC |
| | | AAGAGCCCCCAGCTGCTGATCTACGCCACC |
| | | AGCAGACTGCAGGACGGCGTGCCCAGCAGA |
| | | TTCAGCGGCAGCGGCTCCGGCACCCGGTAC |
| | | AGCCTGAAGATCAGCGGCATGCAGCCCGAG |
| | | GACGAGGCCGACTACTTCTGCCAGCAGAGC |
| | | TACAAGTACCCCTGGACCTTCGGCGGCGGC |
| | | ACCAAGCTGGAACTGAAG |
| HC2 OX86 VHCH1_VHCH1_H1_Fc_knob_DAPG_KK_G8.8 VH | 190 | CAGGTGCAGCTGAAGGAGTCTGGACCTGGT |
| | | CTGGTGCAGCCCTCACAGACCCTGTCCCTC |
| | | ACCTGCACTGTCTCTGGGTTCTCACTAACC |
| | | GGTTACAATTTACACTGGGTTCGCCAGCCT |
| | | CCAGGAAAGGGTCTGGAGTGGATGGGAAGA |
| | | ATGAGGTATGATGGAGACACATATTATAAT |
| | | TCAGTTCTCAAATCCCGACTGAGCATCAGC |
| | | AGGGACACCTCCAAGAACCAAGTTTTCTTG |
| | | AAAATGAACAGTCTGCAAACGGATGACACA |
| | | GCCATTTACTATTGTACCAGAGACGGGCGT |
| | | GGTGACTCCTTTGATTACTGGGGCCAAGGA |
| | | GTCATGGTCACAGTCTCCAGCGCTAAGACC |
| | | ACCCCCCCCTCCGTGTATCCTCTGGCTCCT |
| | | GGATCTGCCGCCCAGACCAACAGCATGGTC |
| | | ACCCTGGGCTGCCTCGTGAAGGGCTACTTC |
| | | CCTGAGCCTGTGACCGTGACCTGGAACTCC |
| | | GGCTCTCTGTCCTCTGGCGTGCACACCTTC |
| | | CCTGCCGTGCTGCAGTCCGACCTGTACACC |
| | | CTGTCCTCCAGCGTGACCGTGCCTTCCTCC |
| | | ACCTGGCCTTCCCAGACCGTGACATGCAAC |
| | | GTGGCCCACCCTGCCAGCTCCACCAAGGTG |
| | | GACAAGAAAATCGTGCCCCGGGACTGCGGA |
| | | GGGGGCGGTTCCGGCGGAGGAGGATCCCAG |
| | | GTGCAGCTGAAGGAGTCTGGACCTGGTCTG |
| | | GTGCAGCCCTCACAGACCCTGTCCCTCACC |
| | | TGCACTGTCTCTGGGTTCTCACTAACCGGT |
| | | TACAATTTACACTGGGTTCGCCAGCCTCCA |
| | | GGAAAGGGTCTGGAGTGGATGGGAAGAATG |
| | | AGGTATGATGGAGACACATATTATAATTCA |
| | | GTTCTCAAATCCCGACTGAGCATCAGCAGG |
| | | GACACCTCCAAGAACCAAGTTTTCTTGAAA |
| | | ATGAACAGTCTGCAAACGGATGACACAGCC |
| | | ATTTACTATTGTACCAGAGACGGGCGTGGT |
| | | GACTCCTTTGATTACTGGGGCCAAGGAGTC |
| | | ATGGTCACAGTCTCCAGCGCTAAGACCACC |
| | | CCCCCTAGCGTGTACCCTCTGGCCCCTGGA |
| | | TCTGCCGCCCAGACCAACAGCATGGTGACC |
| | | CTGGGCTGCCTGGTGAAGGGCTACTTCCCC |
| | | GAGCCTGTGACCGTGACCTGGAACAGCGGC |
| | | AGCCTGAGCAGCGGCGTGCACACCTTTCCA |
| | | GCCGTGCTGCAGAGCGACCTGTACACCCTG |
| | | AGCAGCTCCGTGACCGTGCCTAGCAGCACC |
| | | TGGCCCAGCCAGACAGTGACCTGCAACGTG |
| | | GCCCACCCTGCCAGCAGCACCAAGGTGGAC |
| | | AAGAAAATCGTGCCCCGGGACTGCGGCTGC |
| | | AAGCCCTGCATCTGCACCGTGCCCGAGGTG |
| | | TCCAGCGTGTTCATCTTCCCACCCAAGCCC |
| | | AAGGACGTGCTGACCATCACCCTGACCCCC |
| | | AAAGTGACCTGCGTGGTGGTGGCCATCAGC |
| | | AAGGACGACCCCGAGGTGCAGTTCTCTTGG |
| | | TTTGTGGACGACGTGGAGGTGCACACAGCC |
| | | CAGACAAAGCCCCGGGAGGAACAGATCAAC |
| | | AGCACCTTCAGAAGCGTGTCCGAGCTGCCC |
| | | ATCATGCACCAGGACTGGCTGAACGGCAAA |
| | | GAATTCAAGTGCAGAGTGAACTCCGCCGCC |
| | | TTTGGCGCCCCTATCGAAAAGACCATCTCC |
| | | AAGACCAAGGGCAGACCCAAGGCCCCCCAG |
| | | GTGTACACAATCCCCCCACCCAAGAAACAG |
| | | ATGGCCAAGGACAAGGTGTCCCTGACCTGC |
| | | ATGATCACCAACTTTTTCCCAGAGGACATC |
| | | ACCGTGGAATGGCAGTGGAACGGCCAGCCC |
| | | GCCGAGAACTACAAGAACACCCAGCCCATC |
| | | ATGAAGACCGACGGCTCCTACTTCGTGTAC |
| | | TCCAAGCTGAACGTGCAGAAGTCCAACTGG |
| | | GAGGCCGGCAACACCTTCACCTGTTCCGTG |
| | | CTGCACGAGGGCCTGCACAACCACCACACC |
| | | GAGAAGTCCCTGTCCCACTCTCCTGGCGGA |

TABLE 17-continued

Base pair sequences of mature bispecific, tetravalent anti-muOX40, monovalent anti-muEpCAM huIgG1 DAPG kih 4 + 1 molecules

| Clone | SEQ ID NO: | Base pair sequence |
|---|---|---|
| | | GGCGGAGGATCTGGTGGCGGTGGTTCTGGC GGTGGCGGTTCCGGAGGCGGTGGTTCCGAA GTGCAGCTGGCCGAGAGCGGCGGAGGCCTG GTGCAGCCTGGCAGATCCATGAAGCTGAGC TGCGCCGCCAGCGGCTTCACCTTCAGCAAC TTCCCCATGGCCTGGGTCCGACAGGCCCCC ACCAAGGGCCTGGAATGGGTGGCCACCATC AGCACCAGCGGCGGCAGCACCTACTACCGG GACAGCGTGAAGGGCCGGTTCACCATCAGC CGGGACAACGCCAAGAGCACCCTGTACCTG CAGATGAACAGCCTGCGGAGCGAGGACACC GCCACCTACTACTGCACCCGGACCCTGTAT ATCCTGCGGGTGTTCTACTTCGACTACTGG GGCCAGGGCGTGATGGTCACCGTGTCTAGC |

TABLE 18

Amino acid sequences of mature bispecific, tetravalent anti-muOX40, monovalent anti-muEpCAM muIgG1 DAPG kih 4 + 1 molecules

| Clone | | SEQ ID NO: | Amino acid sequence |
|---|---|---|---|
| muOX40 OX86/muEpC AM G8.8 DAPG 4 + 1 | LC OX40 VLCL | 191 | DIVMTQGALPNPVPSGESASITCRSSQSLVYKDGQTYLN WFLQRPGQSPQLLTYWMSTRASGVSDRFSGSGSGTYFTL KISRVRAEDAGVYYCQQVREYPFTFGSGTKLEIKRADAA PTVSIFPPSSEQLTSGGASVVCFLNNFYPKDINVKWKID GSERQNGVLNSWTDQDSKDSTYSMSSTLTLTKDEYERHN SYTCEATHKTSTSPIVKSFNRNEC |
| | HC1 OX86 VHCH1_VHCH1_ Fc_hole_ DAPG_DD_G8.8 VL | 192 | QVQLKESGPGLVQPSQTLSLTCTVSGFSLTGYNLHWVRQ PPGKGLEWMGRMRYDGDTYYNSVLKSRLSISRDTSKNQV FLKMNSLQTDDTAIYYCTRDGRGDSFDYWGQGVMVTVSS AKTTPPSVYPLAPGSAAQTNSMVTLGCLVKGYFPEPVTV TWNSGSLSSGVHTFPAVLQSDLYTLSSSVTVPSSTWPSQ TVTCNVAHPASSTKVDKKIVPRDCGGGGSGGGGSQVQLK ESGPGLVQPSQTLSLTCTVSGFSLTGYNLHWVRQPPGKG LEWMGRMRYDGDTYYNSVLKSRLSISRDTSKNQVFLKMN SLQTDDTAIYYCTRDGRGDSFDYWGQGVMVTVSSAKTTP PSVYPLAPGSAAQTNSMVTLGCLVKGYFPEPVTVTWNSG SLSSGVHTFPAVLQSDLYTLSSSVTVPSSTWPSQTVTCN VAHPASSTKVDKKIVPRDCGCKPCICTVPEVSSVFIFPP KPKDVLTITLTPKVTCVVVAISKDDPEVQFSWFVDDVEV HTAQTKPREEQINSTFRSVSELPIMHQDWLNGKEFKCRV NSAAFGAPIEKTISKTKGRPKAPQVYTIPPPKEQMAKDK VSLTCMITNFFPEDITVEWQWNGQPAENYDNTQPIMDTD GSYFVYSDLNVQKSNWEAGNTFTCSVLHEGLHNHHTEKS LSHSPGGGGSGGGGSGGGGSGGGGSDIQMTQSPASLSA SLGETVSIECLASEGISNDLAWYQQKSGKSPQLLIYATS RLQDGVPSRFSGSGSGTRYSLKISGMQPEDEADYFCQQS YKYPWTFGGGTKLELK |
| | HC2 OX86 VHCH1_VHCH1_ Fc_knob_ DAPG_KK_G 8.8 VH | 193 | QVQLKESGPGLVQPSQTLSLTCTVSGFSLTGYNLHWVRQ PPGKGLEWMGRMRYDGDTYYNSVLKSRLSISRDTSKNQV FLKMNSLQTDDTAIYYCTRDGRGDSFDYWGQGVMVTVSS AKTTPPSVYPLAPGSAAQTNSMVTLGCLVKGYFPEPVTV TWNSGSLSSGVHTFPAVLQSDLYTLSSSVTVPSSTWPSQ TVTCNVAHPASSTKVDKKIVPRDCGGGGSGGGGSQVQLK ESGPGLVQPSQTLSLTCTVSGFSLTGYNLHWVRQPPGKG LEWMGRMRYDGDTYYNSVLKSRLSISRDTSKNQVFLKMN SLQTDDTAIYYCTRDGRGDSFDYWGQGVMVTVSSAKTTP PSVYPLAPGSAAQTNSMVTLGCLVKGYFPEPVTVTWNSG SLSSGVHTFPAVLQSDLYTLSSSVTVPSSTWPSQTVTCN VAHPASSTKVDKKIVPRDCGCKPCICTVPEVSSVFIFPP KPKDVLTITLTPKVTCVVVAISKDDPEVQFSWFVDDVEV HTAQTKPREEQINSTFRSVSELPIMHQDWLNGKEFKCRV NSAAFGAPIEKTISKTKGRPKAPQVYTIPPPKKQMAKDK VSLTCMITNFFPEDITVEWQWNGQPAENYKNTQPIMKTD GSYFVYSKLNVQKSNWEAGNTFTCSVLHEGLHNHHTEKS LSHSPGGGGSGGGGSGGGGSGGGGSEVQLAESGGGLVQ PGRSMKLSCAASGFTFSNFPMAWVRQAPTKGLEWVATIS TSGGSTYYRDSVKGRFTISRDNAKSTLYLQMNSLRSEDT ATYYCTRTLYILRVFYFDYWGQGVMVTVSS |

For production of the different bispecific anti-OX40, anti-EpCAM antigen binding molecules, all genes were transiently expressed under control of a chimeric MPSV promoter consisting of the MPSV core promoter combined with the CMV promoter enhancer fragment.

The expression vector also contains the oriP region for episomal replication in EBNA (Epstein Barr Virus Nuclear Antigen) containing host cells.

The bispecific anti-OX40, anti-EpCam molecules were produced by co-transfecting HEK293-EBNA cells with the mammalian expression vectors using polyethylenimine. The cells were transfected with the corresponding expression vectors in a 1:1:4 ratio ("vector heavy chain": "vector light chain1": "vector light chain2" for 4+2 molecules) and 1:1:4 ("vector heavy chain1": "vector heavy chain2": "vector light chain" for 4+1 molecules).

For a 200 mL production in 500 mL shake flasks, 250 million HEK293 EBNA cells were seeded 24 hours before transfection in Excell media with supplements. For transfection, the cells were centrifuged for 5 minutes at 210×g, and supernatant was replaced by pre-warmed CD-CHO medium. Expression vectors were mixed in 20 mL CD-CHO medium to a final amount of 200 μg DNA. After addition of 540 μL PEI (1 mg/mL), the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere and shaking at 165 rpm. After the incubation, 160 mL Excell medium with supplements was added and cells were cultured for 24 hours. At this point the valproic acid concentration is 1 mM (in the media there's as well 5 g/L PepSoy and 6 mM L-Glutamine). 24 h after transfection the cells are supplement with Feed 7 at 12% final volume (24 mL) and 3 g/L glucose (1.2 mL from 500 g/L stock). After culturing for 7 days, the cell supernatant was collected by centrifugation for 45 minutes at 2000-3000×g. The solution was sterile filtered (0.22 μm filter), supplemented with sodium azide to a final concentration of 0.01% (w/v), and kept at 4° C.

For affinity chromatography of the anti-human OX40, anti-human EpCAM molecules, the supernatant was loaded on a ProtA MabSelect Sure column (CV=5 mL, GE Healthcare) equilibrated with 30 mL 20 mM Sodium Citrate, 20 mM Sodium Phosphate, pH 7.5. Unbound protein was removed by washing with 6-10 column volumes of a buffer containing 20 mM sodium phosphate, 20 mM sodium citrate, pH 7.5. The bound protein was eluted using a step elution with 8 CV of 20 mM Sodium Citrate, 100 mM Sodium Chloride, 100 mM Glycine, pH 3.0.

For affinity chromatography of the anti-mouse OX40, anti-mouse EpCAM molecules, the supernatant was loaded on a ProtA MabSelect Sure column (CV=5 mL, GE Healthcare) equilibrated with 30 mL 1 M Glycine, 0.3 M Sodium Chloride, pH 8.6. Unbound protein was removed by washing with 6-10 column volumes of equilibration buffer. The bound protein was eluted with 15 CV using a gradient elution from 20-100% of 20 mM Sodium Citrate, 0.3 M NaCl, 0.01% TWEEN™ (polysorbate) pH 2.5.

For both of the anti-human OX40, anti-human EpCAM and anti-mouse OX40, anti-mouse EpCAM molecules, the pH of the collected fractions was adjusted by adding 1/10 (v/v) of 0.5 M $Na_2HPO_4$, pH8.0. The protein was concentrated and filtered prior to loading on a HiLoad Superdex 200 column (GE Healthcare) equilibrated with 20 mM Histidine, 140 mM NaCl, 0.01% TWEEN 20™ (polysorbate 20), pH 6.0.

The protein concentration of purified bispecific tetravalent 4+1 and 4+2 constructs was determined by measuring the OD at 280 nm, using the molar extinction coefficient calculated on the basis of the amino acid sequence. Purity and molecular weight of the bispecific constructs were analyzed by CE-SDS in the presence and absence of a reducing agent (Invitrogen, USA) using a LabChipGXII (Caliper). The aggregate content of bispecific constructs was analyzed using a TSKgel G3000 SW XL analytical size-exclusion column (Tosoh) equilibrated in a 25 mM K2HPO4, 125 mM NaCl, 200 mM L-Arginine Monohydrochloride, 0.02% (w/v) NaN3, pH 6.7 running buffer at 25° C.

TABLE 19

Biochemical analysis of bispecific, tetravalent anti-OX40, anti-EpCAM IgG1 4 + 1 and 4 + 2 constructs.

| Clone | Yield [mg/l] | Monomer [%] | CE-SDS (non red) | CE-SDS (red) |
|---|---|---|---|---|
| OX40 49B4/EpCam 3-171 P329GLALA 4 + 1 | 6.21 | 97.62<br>2.38<br>HMW | 96.42 (268.29 kDa)<br>3.58 (261.83 kDa) | 42.19 (29.77 kDa)<br>0.98 (32.55 kDa)<br>56.83 (107.63 kDa) |
| OX40 49B4/EpCam 3-171 P329GLALA 4 + 2 | 5 | 99.02<br>0.98<br>HMW | 97.06 (335.74 kDa)<br>2.94 (113.94 kDa) | 17.26 (28.33 kDa)<br>39.2 (30.25 kDa)<br>1.37 (32.9 kDa)<br>37.59 (125.18 kDa)<br>0.82 (133.46 kDa)<br>3.76 (150.25 kDa) |
| OX40 OX86/EpCam G8.8 DAPG 4 + 1 | 5.73 | 98.56<br>0.22<br>HMW<br>1.23<br>LMW | 95.27<br>4.56<br>LMW<br>0.18<br>HMW | 59.07 (30.87 kDa)<br>20.78 (101.98 kDa)<br>17.69 (108.11 kDa)<br>2.46 (310.44 kDa) |

2.3 Determination of the Aggregation Temperature of Anti-OX40, Anti-EpCAM 4+1 and 4+2 Constructs For direct comparison of all formats the thermal stability was monitored by Static Light Scattering (SLS) and by measuring the intrinsic protein fluorescence in response to applied temperature stress. 30 μg of filtered protein sample with a protein concentration of 1 mg/ml was applied in duplicate to an Optim 2 instrument (Avacta Analytical Ltd). The temperature was ramped from 25 to 85° C. at 0.1° C./min, with the radius and total scattering intensity being collected. For determination of intrinsic protein fluorescence the sample was excited at 266 nm and emission was collected between 275 nm and 460 nm.

TABLE 20

Aggregation temperatures for the bispecific, anti-OX40, anti-EpCAM 4 + 1 and 4 + 2 constructs

| construct | OX40 49B4/ EpCam 3-171 P329GLALA 4 + 1 | OX40 49B4/ EpCam 3-171 P329G/LALA 4 + 2 | OX40 OX86/ EpCam G8.8 DAPG 4 + 1 |
|---|---|---|---|
| $T_{agg}$ (° C.) | 50 | 53 | nd |

Example 3

Binding of Bispecific Antibodies Targeting Murine OX40 and Murine Epithelial Cell Adhesion Molecule (EpCAM)

3.1 Analysis of Binding to Murine OX40 Expressing Cells: Naïve and Activated Splenocytes Murine spleens were obtained from C57Bl/6 female mice and collected in 3 mL DPBS. Single cell suspension was generated by mashing the spleens onto a 70 µm cell strainer using the back of a syringe. The filter was washed with 10 ml of T cell medium consisting of RPMI 1640 medium (Gibco by Life Technology, Cat. No. 42401-042) supplemented with 10% heat-inactivated Fetal Bovine Serum (Gibco Cat No. 16140-071, Lot No. 1797306A), 1% (v/v) GLUTAMAX® I (GIBCO by Life Technologies, Cat. No. 35050 038), 1 mM Sodium-Pyruvate (SIGMA, Cat. No. S8636), 1% (v/v) non-essential amino acids (SIGMA, Cat. No. M7145) and 50 µM P-Mercaptoethanol (SIGMA, M3148) and cells were centrifuged for 7 min at 350×g at 4° C. After centrifugation, the cell pellet was re-suspended in 6 ml 1× lysis buffer (BD Pharm Lyse™: concentrated (10×) ammonium chloride-based lysing reagent, BD Biosciences, Cat No. 555899) and incubated for 3 min at room temperature. Erythrolysis was stopped by addition of 10 ml T cell medium. Cells were washed once with X-Vivo 15 medium (Lonza, Cat No. 04-744Q), re-suspended in 10 ml X-Vivo 15 medium and filtered through a 70 µm cell strainer to remove debris.

Splenocytes were activated to upregulate murine OX40 in X-Vivo 15 medium containing anti-CD3 [Clone 145-2C11, BD Bioscience, Cat. No. 553057 at 1 µg/mL] and anti-CD28 [Clone 37.51, BIOLEGEND®, Cat. No. 102102 at 1 µg/mL] antibodies at a density of 1*10⁶ cells/mL in 6 well plates and incubated at 37° C., 5% CO₂ for two days. For detection of OX40, naïve splenocytes and activated splenocytes were mixed. To enable distinction of naïve from activated splenocytes, naïve cells were labeled prior to the binding assay using the EFLUOR® 670 cell proliferation dye (eBioscience, Cat.-No. 65-0840-85).

For labeling cells were harvested, washed with prewarmed (37° C.) DPBS and adjusted to a cell density of 1×10⁷ cells/mL in DPBS. EFLUOR® 670 cell proliferation dye (eBioscience, Cat.-No. 65-0840-85) was added to the suspension of naïve splenocytes at a final concentration of 2.5 µM and a final cell density of 0.5×10⁷ cells/mL in DPBS. Cells were then incubated for 10 min at room temperature in the dark. To stop labeling reaction, 4 mL heat inactivated FBS were added and cells were washed three times with T cell medium. A mixture of 1×10⁵ resting EFLUOR® 670 labeled splenocytes and 1×10⁵ unlabeled activated splenocytes were then added to wells of round-bottomed suspension 96-well plates (Greiner bio-one, cellstar, Cat. No. 650185).

For discrimination between live and dead cells, samples were stained with ZOMBIE AQUA™ Viability Dye (BIOLEGEND®, Cat. No. 423102) in DPBS for 10 minutes at room temperature. Cells were then washed once with FACS buffer and subsequently stained for 90 minutes at 4° C. in the dark in 50 µL/well 4° C. FACS buffer containing titrated anti-OX40 antigen binding molecules. After washing three times with excess FACS buffer, cells were stained for 30 minutes at 4° C. in the dark in 25 µL/well 4° C. FACS buffer containing a mixture of fluorescently labeled anti-mouse CD4 (clone GK1.5, Rat IgG2b, c, BIOLEGEND®, Cat. No. 100438), anti-mouse CD8 (clone 53-6.7, Rat IgG2a, κ, BIOLEGEND®, Cat.-No. 100748) and PE-conjugated AffiniPure anti-mouse IgG Fcγ-fragment-specific goat IgG F(ab')₂ fragment (Jackson ImmunoResearch, Cat. No. 115-116-71).

Plates were finally resuspended in 85 µL/well FACS buffer and acquired the same day using 4-laser LSR-II cytometer (BD Bioscience with DIVA software).

As shown in FIG. 3A to 3D, none of the OX40-specific antigen binding molecules displayed binding to resting murine CD4+ T-cells or CD8+ T-cells, which are negative for OX40. By contrast, all of the OX40-specific antigen binding molecules displayed binding to activated CD8+ or CD4+ T-cells, which express OX40. The different bispecific anti-murine OX40 molecules having tetravalent binding for murine OX40 showed comparable binding strength for OX40 (EC50 values Table 21). The presence of a muEpCAM binding moiety had minimal impact on OX40 binding for the 4+1 OX40 molecules (compare triangle vs open circle).

3.2 Binding to Murine EpCAM-Expressing and EpCAM-Negative Tumor Cells

The binding to cell surface murine EpCAM was analysed using mouse EpCAM-positive CT26muEpCAM cl25 cells, which stably expresses murine EpCAM. The specificity of binding was analysed by determination of binding to muEpCAM-negative cell line CT26muFAP, which stably expresses murine FAP.

For analysis of binding of the antigen binding molecules, 0.5×10⁵ CT26muEpCAM or 0.5×10⁵ CT26muFAP cells were added to wells of round-bottomed suspension cell 96-well plates (greiner bio-one, cellstar, Cat. No. 650185). For discrimination of live and dead cells, samples were stained with ZOMBIE AQUA™ Viability Dye (BIOLEGEND®, Cat. No 423102) in PBS for 10 minutes at room temperature. Cells were then washed once with FACS buffer and subsequently stained for 90 minutes at 4° C. in the dark in 50 µL/well 4° C. FACS buffer (DPBS (Gibco by Life Technologies, Cat. No. 14190 326) w/BSA (0.1% v/w, Sigma-Aldrich, Cat. No. A9418) containing titrated antiOX40 antigen binding molecules. After washing three times with excess FACS buffer, cells were stained for 30 minutes at 4° C. in the dark in 25 µL/well 4° C. FACS buffer containing Fluorescein isothiocyanate (FITC)-conjugated AffiniPure anti-mouse IgG Fcγ-fragment-specific goat IgG F(ab')2 fragment (Jackson ImmunoResearch, Cat. No. 115-096-071).

Plates were finally resuspended in 85 µL/well FACS-buffer and acquired the same day using 4-laser LSR-II cytometer (BD Bioscience with DIVA software).

Figure 4A:
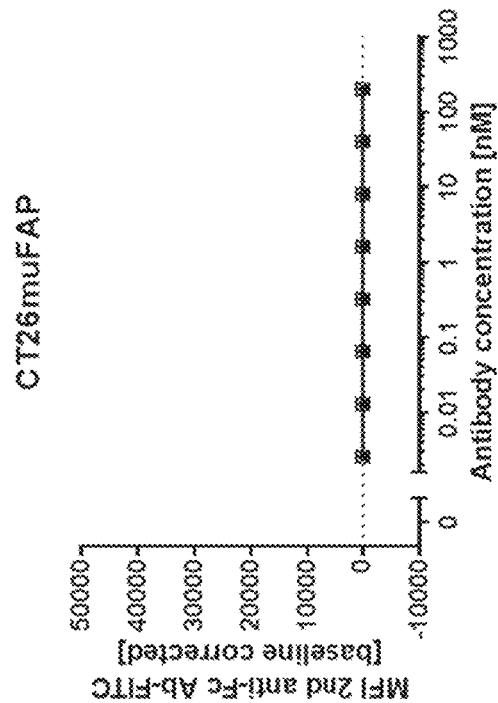
FIGS. 4A and 4B show the binding of the bispecific, tetravalent anti-murine OX40, monovalent anti-murine EpCAM (4+1 muEpCAM); bispecific, tetravalent anti-murine OX40, non-targeted (4+1 control); or monospecific, bivalent anti-murine EpCAM IgG (muEpCAM IgG) molecules to CT26muEpCAM and CT26muFAP cells.
Figure 4B:
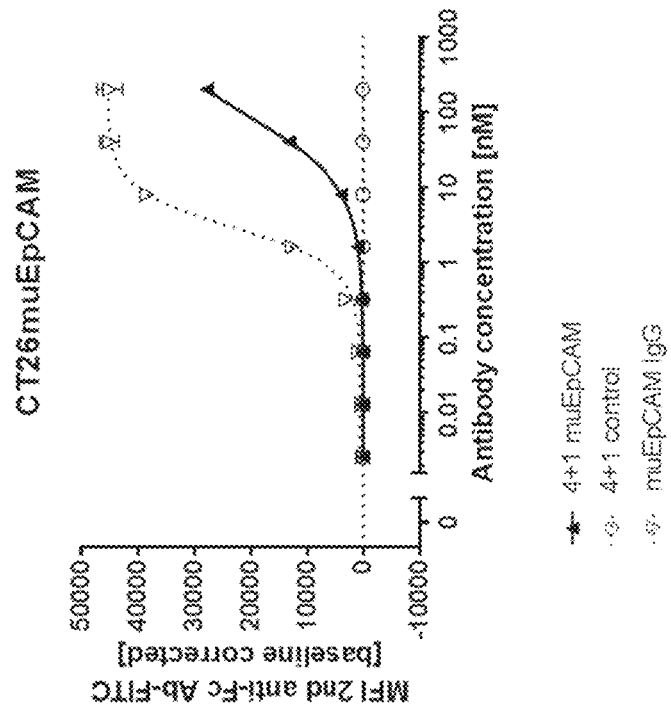
Figure 5A:
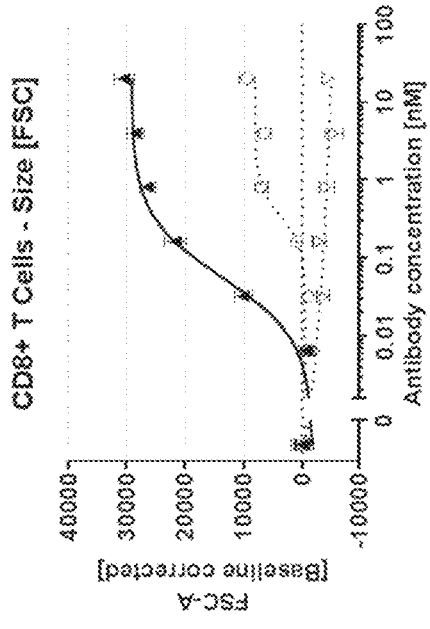
FIGS. 5A to 5D show rescue of suboptimal TCR restimulation of preactivated murine CD4+ and CD8+ T cells with the bispecific, tetravalent anti-murine OX40, monovalent anti-murine EpCAM (4+1 muEpCAM); monospecific, tetravalent anti-murine OX40, non-targeted (4+1 control); or monospecific, bivalent anti-murine EpCAM IgG (muEpCAM IgG) molecules, in the presence of crosslinking by CT26muEpCAM cells, as determined by analysis of cell size and cell number.
Figure 5B:
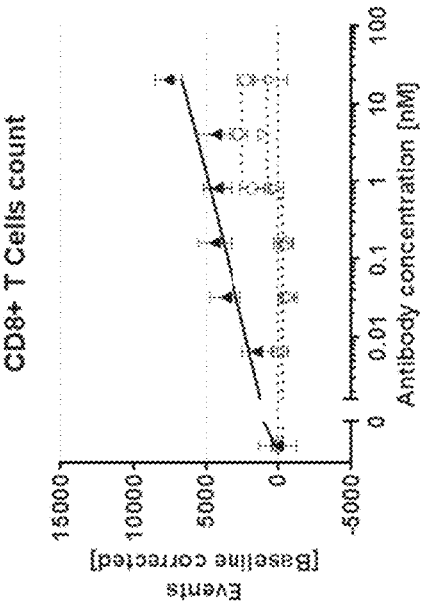
Figure 5C:
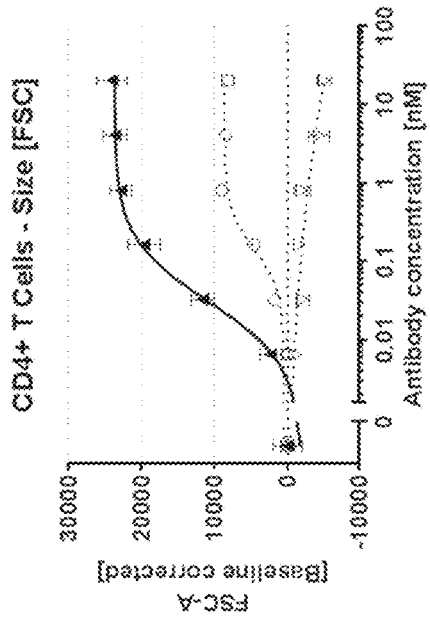
Figure 5D:
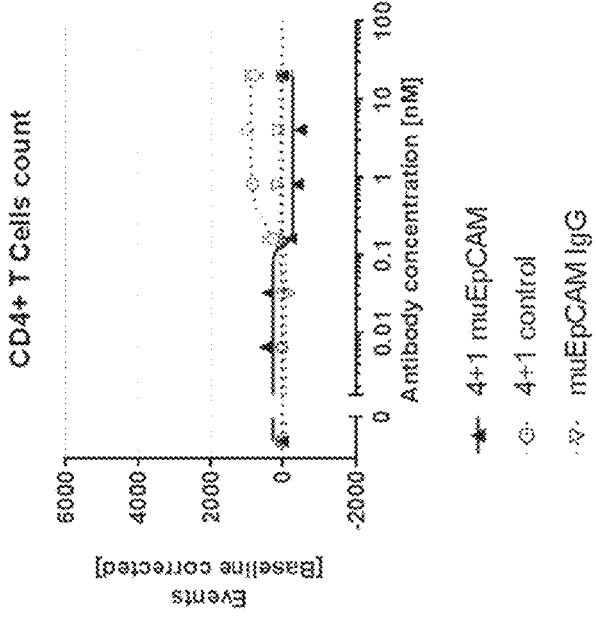
Figure 6A:
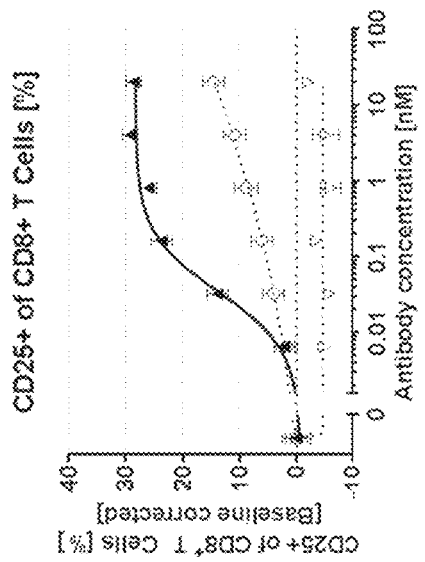
FIGS. 6A to 6D show rescue of suboptimal TCR restimulation of preactivated murine CD4+ and CD8+ T cells with the bispecific, tetravalent anti-murine OX40, monovalent anti-murine EpCAM (4+1 muEpCAM); monospecific, tetravalent anti-murine OX40, non-targeted (4+1 control); or monospecific, bivalent anti-murine EpCAM IgG (muEpCAM IgG) molecules, in the presence of crosslinking by CT26muEpCAM cells, as determined by analysis for CD25 expression.
Figure 6B:
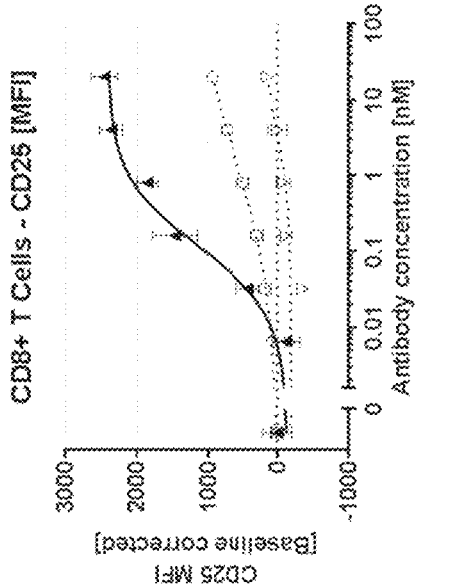
Figure 6C:
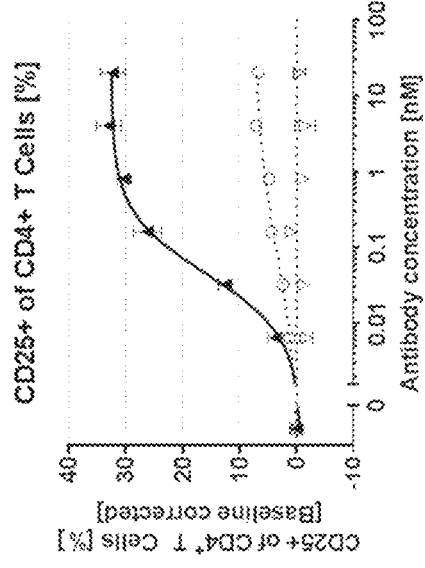
Figure 6D:
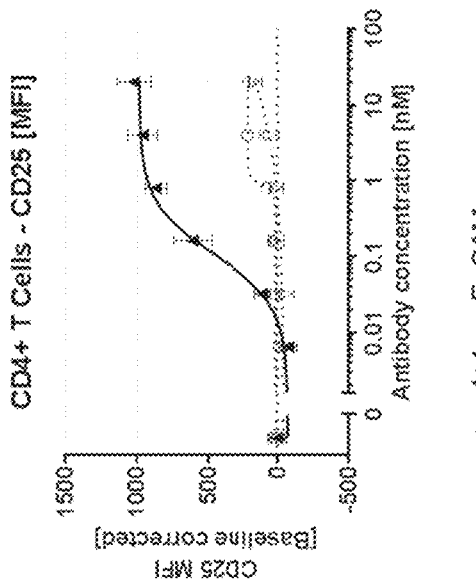
Figure 7A:
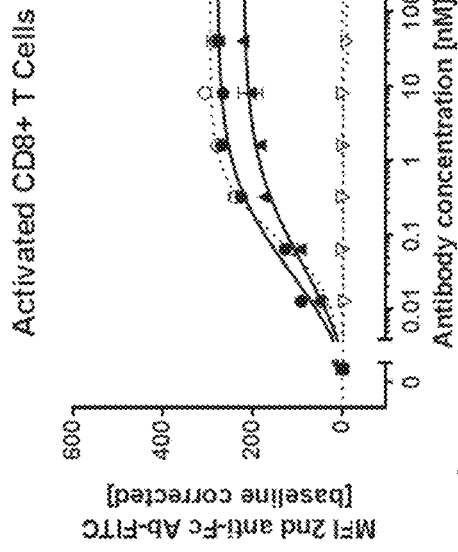
FIGS. 7A to 7D show the binding of the bispecific, tetravalent anti-human OX40, bivalent or monovalent anti-human EpCAM (i.e. 4+2 or 4+1 format); monospecific, tetravalent anti-human OX40, non-targeted (4+1 control); or monospecific, bivalent anti-human EpCAM IgG (huEpCAM IgG) molecules to resting and activated human CD4+ and CD8+ T cells.
Figure 7B:
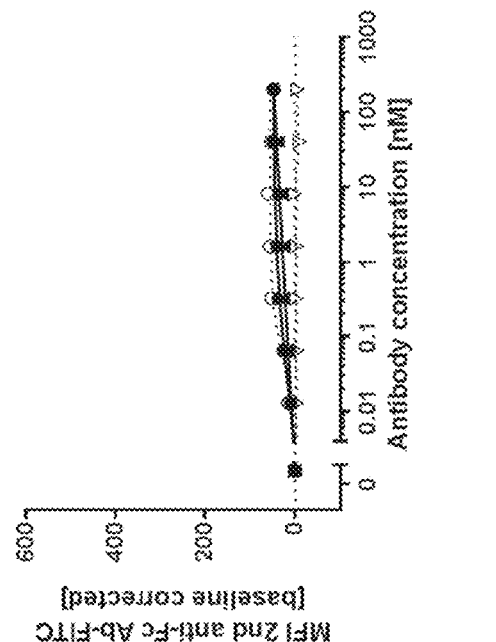
Figure 7C:
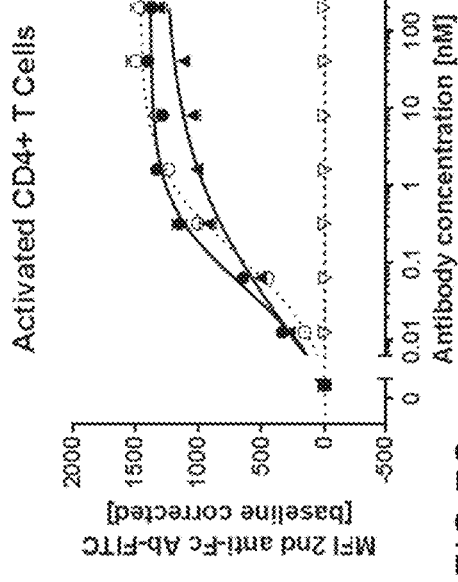
Figure 7D:
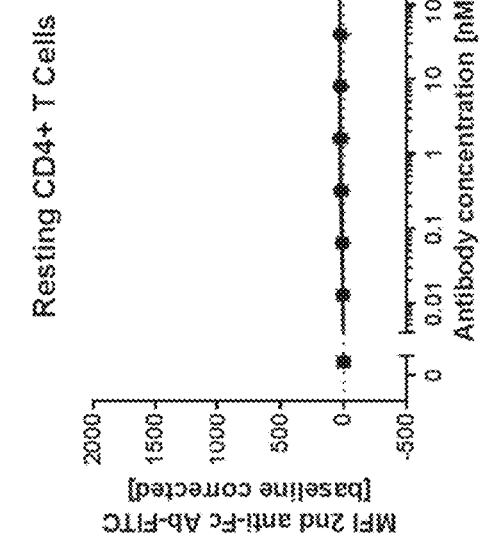

As shown in FIGS. 4A and 4B, the murine EpCAM-targeted antigen binding molecules did not display binding to muEpCAM-negative CT26muFAP cells, whereas the molecules comprising a murine EpCAM binding domain displayed binding to CT26muEpCAM cells. The parental bivalent anti-muEpCAM antibody (muEpCAM IgG; open triangle) showed strong binding to muEpCAM on CT26muEpCAM cells, and the 4+1 molecule with monovalent binding for murine EpCAM (filled triangle) showed comparatively reduced binding capacity as compared to the bivalent IgG. However, the VH/VL fusion did not hinder the binding.

$EC_{50}$ values of binding to activated murine CD4+ T and CD8+ T cells as well as to muEpCAM positive tumor cells are summarized in Table 21.

TABLE 21

EC50 values for binding of anti-murine OX40, anti-murine EpCAM antigen binding molecules to cells expressing murine OX40 or murine EpCAM.

| $EC_{50}$ (nM) | 4 + 1 anti-muOX40, anti-muEpCAM | 4 + 2 anti-muOX40, untargeted control | muEpCAM IgG |
|---|---|---|---|
| OX40+ CD4+ cells | 1.47 | 0.58 | n.a. |
| OX40+ CD8+ cells | 0.82 | 0.31 | n.a. |
| muEpCAM+ cells | 82.49 | n.a. | 2.87 | n.a. = not applicable (EC50 not calculated).

Example 4

Biological Activity of Bispecific Antigen Binding Molecules Targeting Murine OX40 and Murine EpCAM 4.1 OX40 Mediated Costimulation of Suboptimally TCR Triggered Murine Splenocytes and Hypercrosslinking by Cell Surface Murine EpCAM The ability of the murine EpCAM targeted tetravalent anti-OX40 antigen binding molecule to rescue suboptimal TCR stimulation of resting murine splenocytes was analysed. CT26muEpCAM cl25 cells were used in assays to cross-link the antibody.

Freshly isolated murine splenocytes contain (1) resting OX40 negative CD4+ and CD8+ T cells and (2) antigen presenting cells with various Fc-γ receptor molecules on their cell surface e.g. B cells and monocytes. Anti-mouse CD3 antibody (clone 145-2C11, BD Bioscience, Cat. No. 553057) can bind with its Fc part to the present Fc-γ receptor molecules and mediate a prolonged TCR activation on resting OX40-negative CD4+ and CD8+ T cells. These cells then start to express OX40 within several hours. Functional agonistic compounds against OX40 can signal via the OX40 receptor present on activated CD8+ and CD4+ T cells and support TCR-mediated stimulation.

Resting CFSE-labeled murine splenocytes were stimulated for three days with a suboptimal concentration of anti-CD3 antibody in the presence of irradiated CT26muEpCAM cl25 cells, and titrated OX40 antigen binding molecules. The effects on T-cell survival and proliferation were analyzed by monitoring FSC-area, total cell counts and CFSE dilution in living cells by flow cytometry. Additionally, cells were co-stained with fluorescently-labeled antibodies against the T-cell activation marker CD25.

CT26muEpCAM cl25 cells were harvested using cell dissociation buffer (Invitrogen, Cat.-No. 13151-014) for 10 minutes at 37° C. Cells were washed once with DPBS and irradiated in an xRay irradiator at a dose of 4,500 RAD to prevent later overgrowth of splenocytes by the tumor cell line. Irradiated cells were cultured at a density of $0.2*10^5$ cells per well in X-Vivo 15 medium in wells of a sterile 96-well round bottomed adhesion tissue culture plate (TPP, Cat. No. 92097) overnight at 37° C. and 5% $CO_2$ in an incubator (STERI-CYCLE® i160).

Murine splenocytes were isolated as described above and labeled with CFSE as follows. Freshly isolated PBMCs were washed with pre-warmed (37° C.) DPBS and adjusted to a cell density of $2\times10^6$ cells/mL in DPBS. CELLTRACE® CFSE proliferation dye (ThermoFisher, Cat. No. C34554) was added to the suspension of splenocytes at a final concentration of 0.2 μM and a final cell density of $1\times10^6$ cells/mL in DPBS. Cells were then incubated for 10 min at 37° C./5% $CO_2$ in the dark. To stop the labeling reaction, 20 mL heat inactivated FBS was added, cells were washed three times with T cell medium and finally re-suspended in X-Vivo 15 medium. All antibody dilutions were performed in X-Vivo 15 medium because it was selected as optimal assay medium for splenocytes proliferation and maintaining their viability.

CFSE-labeled splenocytes were then added to wells at a density of $1*10^5$ cells per well. Anti-mouse CD3 antibody (clone 145-2C11) was added at a final concentration of 0.5 μg/ml, and anti-OX40 molecules were added at the indicated concentrations. Cells were activated for three days at 37° C. in a 5% $CO_2$ atmosphere in an incubator (STERI-CYCLE® i160).

For discrimination between live and dead cells, samples were stained with ZOMBIE AQUA™ Viability Dye (BIOLEGEND®, Cat. No 423102) in PBS for 10 minutes at room temperature. Cells were then washed once with FACS buffer and subsequently surface-stained with fluorescent dye-conjugated antibodies anti-mouse CD4 (clone GK1.5, Rat IgG2b, κ, BIOLEGEND®, Cat. No. 100438), anti-mouse CD8 (clone 53-6.7, Rat IgG2a, κ, BIOLEGEND®, Cat.-No. 100748) and anti-mouse CD25 (clone 3C7, Rat IgG2b, κ BIOLEGEND®, Cat. No 101912) for 20 min at 4° C. Cell pellets were washed once with FACS buffer, re-suspended in 85 μL/well FACS-buffer and acquired the same day using 4-laser LSR-II cytometer (BD Bioscience with DIVA software).

The results are shown in FIGS. 5A to 5D and FIGS. 6A to 6D. Hyper-crosslinking of the antigen binding molecules bound to OX40 by culture in the presence of CT26muEpCAM cells strongly promoted maturation (as evidenced by an increase in the size of CD4+ and CD8+ cells) (FIGS. 5A and 5B), and cell proliferation (FIGS. 5C and 5D), and induced an enhanced activated (CD25+) phenotype (FIGS. 6A to 6D) in murine CD4+ and CD8+ T cells. The non-targeted 4+1 control molecule only showed minimal activity, demonstrating the importance of cross-linking. Control muEpCAM IgG showed no additional activity as compared to anti-CD3 stimulus only.

The results suggest that cell surface immobilization of OX40 receptor oligomers is important for obtaining optimal agonist activity of tetravalent anti-mouse OX40 antigen binding molecules.

Example 5

Binding of Bispecific Antibodies Targeting Human OX40 and Human Epithelial Cell Adhesion Molecule (EpCAM)

5.1 Analysis of Binding to Human OX40 Expressing Cells: Naïve and Activated PBMCs Buffy coats were obtained from the Zurich blood donation center. To isolate fresh peripheral blood mononuclear cells (PBMCs) buffy coats were diluted with an equal volume of DPBS (Gibco by Life Technologies, Cat. No. 14190 326). 50 mL polypropylene centrifuge tubes (TPP, Cat. No. 91050) were supplied with 15 mL HISTOPAQUE® 1077 (SIGMA Life Science, Cat. No. 10771, polysucrose and sodium diatrizoate, adjusted to a density of 1.077 g/mL) and the buffy coat solution was layered above the HISTOPAQUE® 1077. The tubes were centrifuged for 30 min at 400×g, at room temperature, with low acceleration and no break. Subsequently the PBMCs were collected from the interphase, washed three times with DPBS and resuspended in T cell medium consisting of RPMI 1640 medium (Gibco by Life Technology, Cat. No. 42401-042) supplemented with 10% Fetal Bovine Serum (FBS, Gibco by Life Technology, Cat. No. 16000-044, Lot 941273, gamma-irradiated, *mycoplasma*-free and heat inactivated at 56° C. for 35 min), 1% (v/v) GLUTAMAX® I (GIBCO by Life Technologies, Cat. No. 35050 038), 1 mM Sodium-Pyruvat (SIGMA, Cat. No. S8636), 1% (v/v) MEM non-essential amino acids (SIGMA, Cat.-No. M7145) and 50 µM P-Mercaptoethanol (SIGMA, M3148).

PBMCs were used in experiments either directly after isolation (for analysis of binding to resting human PBMCs) or following stimulation to provide for high expression of human OX40 on the cell surface of T cells (for analysis of binding to activated human PBMCs). For stimulations, naïve PBMCs were cultured for two days in T cell medium supplied with 400 U/mL Proleukin (Novartis) and 2 µg/mL PHA-L (Sigma-Aldrich, L2769-10) in wells of a 6-well tissue culture plate at 37° C. and 5% $CO_2$.

For detection of OX40, naïve human PBMCs and activated human PBMCs were mixed. To enable discrimination of naïve from activated human PBMCs, naïve cells were labeled prior to the binding assay using the EFLUOR® 670 cell proliferation dye (eBioscience, Cat.-No. 65-0840-85).

For labelling, cells were harvested, washed with pre-warmed (37° C.) DPBS and adjusted to a cell density of $1\times10^7$ cells/mL in DPBS. EFLUOR® 670 cell proliferation dye (eBioscience, Cat.-No. 65-0840-85) was added to the suspension of naïve human PBMCs at a final concentration of 2.5 µM, and a final cell density of 0.5×10 cells/mL in DPBS. Cells were then incubated for 10 min at room temperature in the dark. To stop labeling reaction, 4 mL heat-inactivated FBS was added and cells were washed three times with T cell medium. A mixture of $1\times10^5$ resting EFLUOR® 670 labeled human PBMCs and $1\times10^5$ unlabeled activated human PBMCs was then added to each well of a round-bottom suspension 96-well plates (greiner bio-one, cellstar, Cat. No. 650185).

For discrimination of live and dead cells, samples were stained with ZOMBIE AQUA™ Viability Dye (BIOLEGEND®, Cat. No. 423102) in DPBS for 10 minutes at room temperature. Cells were then washed once with FACS buffer and subsequently stained for 90 minutes at 4° C. in the dark in 50 µL/well 4° C. cold FACS buffer containing titrated anti-OX40 antigen binding molecules. After three washes with excess FACS buffer, cells were stained for 30 minutes at 4° C. in the dark in 25 µL/well 4° C. FACS buffer containing a mixture of fluorescently labeled anti-human CD4 (clone RPA-T4, mouse IgG1k, BIOLEGEND®, Cat. No. 300532), anti-human CD8 (clone RPa-T8, mouse IgG1 k, BIOLEGEND®, Cat.-No. 3010441) and Fluorescein isothiocyanate (FITC)-conjugated AffiniPure anti-human IgG Fcγ-fragment-specific goat IgG F(ab')2 fragment (Jackson ImmunoResearch, Cat. No. 109 096 098).

Cells were then resuspended in 85 µL/well FACS-buffer and acquired the same day using 4-laser LSR-II cytometer (BD Bioscience with DIVA software).

As shown in FIGS. 7A to 7D, none of the antigen binding molecules specific for OX40 bound to resting human $CD4^+$ T-cells or $CD8^+$ T-cells, which do not express OX40 at the cell surface. By contrast, all of the bispecific anti-OX40, anti-EpCAM molecules displayed binding to activated $CD8^+$ or $CD4^+$ T-cells, which express OX40. Binding to CD4+ T-cells was much stronger than that to CD8+ T cells. Activated human $CD8^+$ T cells express OX40 at a much lower level than the level of expression by activated $CD4^+$ T cells. Expression levels for OX40 are depended on the kinetics and strength of stimulation and conditions were here optimized for OX40 expression on $CD4^+$ T cells but not for $CD8^+$ T cells. The tetravalent, bispecific anti-OX40 antigen binding molecules in 4+1 and 4+2 formats displayed comparable binding strength to OX40-expressing cells (as shown by their EC50 values, see Table 22). The presence of a huEpCAM binding moiety had no impact on OX40 binding for the 4+1 OX40 binders (as compared to the monospecific, tetravalent, anti-OX40 untargeted control).

5.2 Binding to Human EpCAM-Expressing and EpCAM-Negative Tumor Cells

The ability of the bispecific anti-human OX40, anti-human EpCAM antigen binding molecules to bind to human EpCAM expressed at the cell surface was analysed using huEpCAM positive KATO-III cells (ATCC HTB-103). The specificity of binding was determined by analysing binding to the human EpCAM-negative cell line A549 NUCLIGHT® Red (Essen Bioscience Cat. No. 4491). A549 cells express a red protein which allowed the KATO-III and A549 NLR cells to be distinguished.

Figure 8:
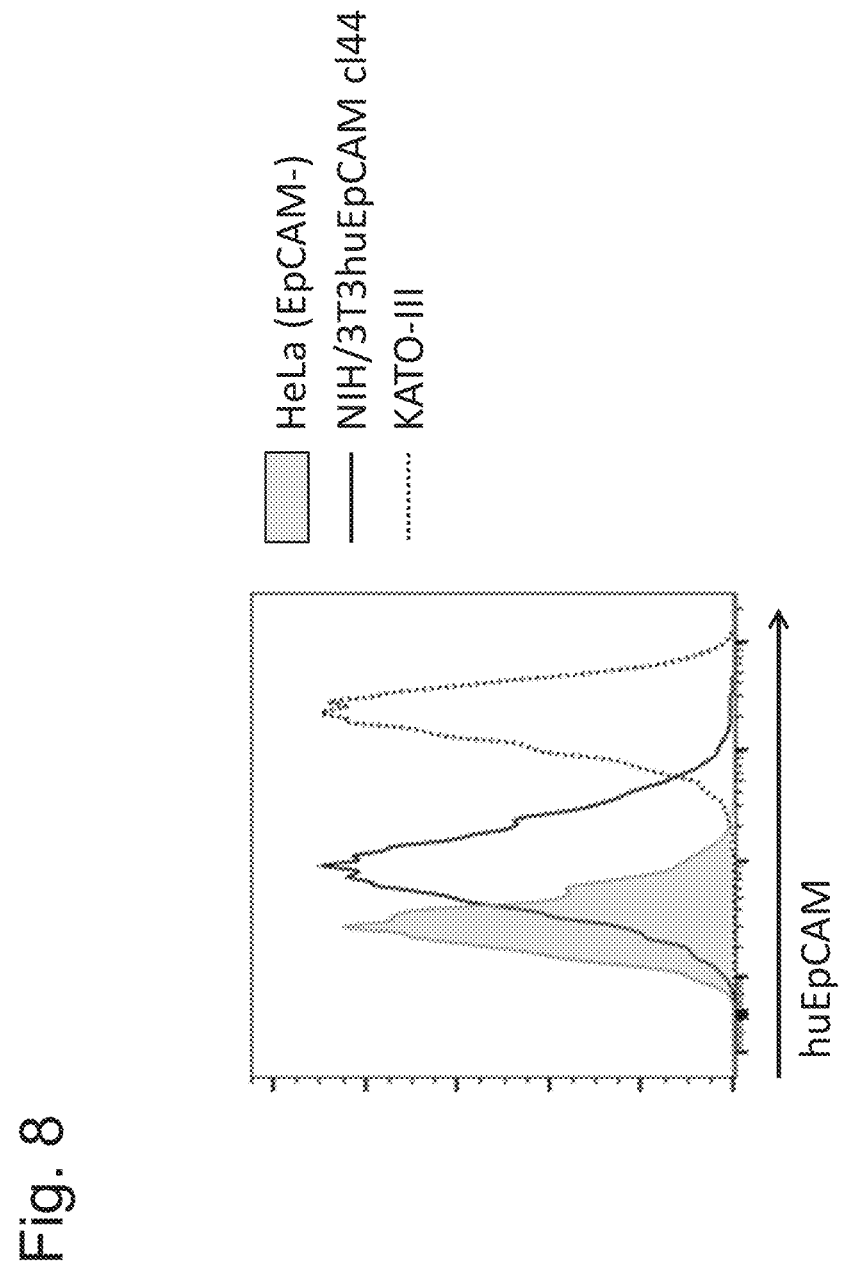

Expression of huEpCAM on tumor cells was analysed using an anti-human EpCAM antibody (clone EBA-1, BD Cat. No. 347198). Human EpCAM was expressed at a high level on KATO-III cells, to lesser extent on NIH/3T3 huEpCAM clone 44 cells (which stably express human EpCAM at the cell surface), but not on HeLa_huOX40_NFkB_Luc1 cells (FIG. 8).

To determine binding of the antigen binding molecules to the human EpCAM-positive and human EpCAM-negative cells, $0.5\times10^5$ KATO-III and $0.5\times10^5$ A549 NLR cells were added to wells of round-bottomed suspension cell 96-well plates (greiner bio-one, cellstar, Cat. No. 650185). For discrimination of live and dead cells, samples were stained with ZOMBIE AQUA™ Viability Dye (BIOLEGEND®, Cat. No 423102) in PBS for 10 minutes at room temperature. Cells were then washed once with FACS buffer and subsequently stained for 90 minutes at 4° C. in the dark in 50 µL/well 4° C. FACS buffer (DPBS (Gibco by Life Technologies, Cat. No. 14190 326) w/BSA (0.1% v/w, Sigma-Aldrich, Cat. No. A9418) containing titrated anti-OX40 antigen binding molecules. After three washes with excess FACS buffer, cells were stained for 30 minutes at 4° C. in the dark in 25 µL/well 4° C. FACS buffer containing Fluorescein isothiocyanate (FITC)-conjugated AffiniPure anti-human IgG Fcγ-fragment-specific goat IgG F(ab')2 fragment (Jackson ImmunoResearch, Cat. No. 109 096 098).

Cells were then resuspended in 85 µL/well FACS-buffer and acquired the same day using 4-laser LSR-II cytometer (BD Bioscience with DIVA software).

Figure 9B:
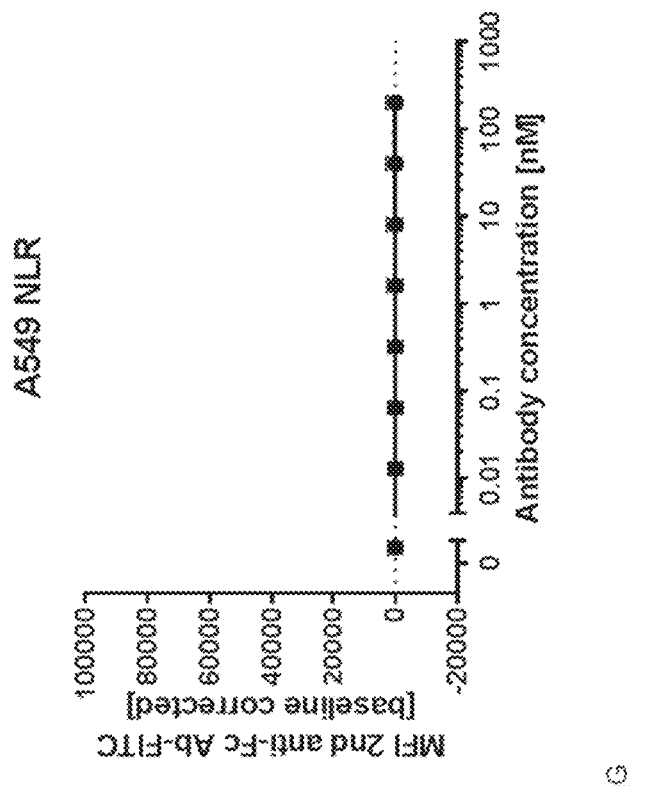
FIGS. 9A and 9B show the binding of the bispecific, tetravalent anti-human OX40, monovalent anti-human EpCAM (4+1 huEpCAM); bispecific, tetravalent anti-human OX40, bivalent anti-human EpCAM (4+2 huEpCAM); monospecific, tetravalent anti-murine OX40, non-targeted (4+1 control); and monospecific, bivalent anti-human EpCAM IgG (huEpCAM IgG) molecules to KATO-II cells and A549 NLR cells.
Figure 9A:
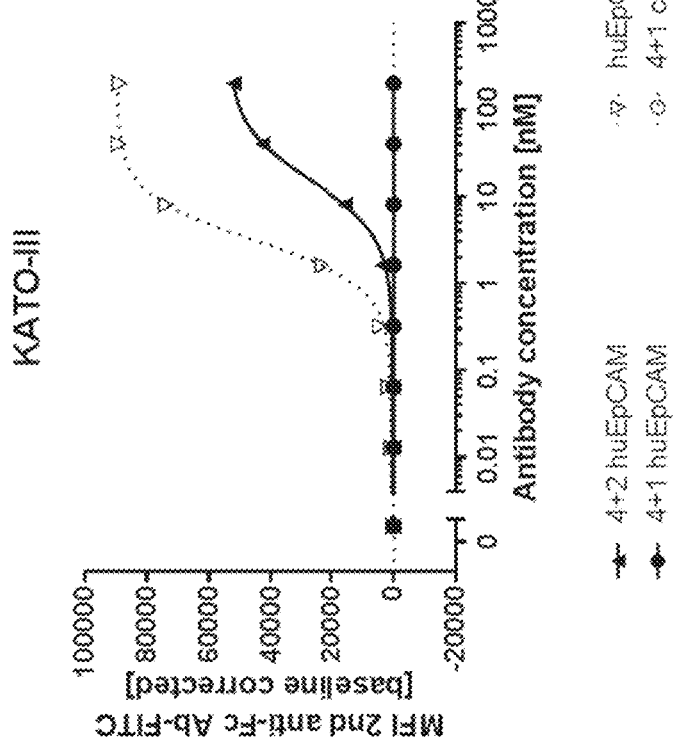

The results are shown in FIGS. 9A and 9B. No binding of the human EpCAM-targeted molecules to huEpCAM-negative A549 NLR cells was observed (FIG. 9B). The parental bivalent anti-human EpCAM antibody (clone 3-171, Affitech) displayed strong binding to human EpCAM expressed on KATO-III cells (FIG. 9A; open triangle). Bispecific tetravalent anti-human OX40, bivalent anti-human EpCAM 4+2 molecule showed a reduced level of binding to KATO-III cells as compared to the parental bivalent anti-human EpCAM antibody (FIG. 9A; compare closed triangle with open triangle). No binding of the bispecific tetravalent anti-human OX40, monovalent anti-human EpCAM 4+1 molecule to KATO-III cells was observed, suggesting a format restriction of the VH/VL fusion for this target.

$EC_{50}$ values of binding to activated human CD4 T and CD8 T cells as well as to huEpCAM positive tumor cells are summarized in Table 22.

TABLE 22

$EC_{50}$ values for binding of anti-human OX40, anti-human EpCAM antigen binding molecules to cells expressing human OX40 or human EpCAM.

| $EC_{50}$ (nM) | 4 + 2 anti-huOX40, anti-huEpCAM | 4 + 1 anti-huOX40, anti-huEpCAM | 4 + 1 anti-huOX40, untargeted control | huEp-CAM IgG |
|---|---|---|---|---|
| OX40$^+$ CD4$^+$ cells | 0.01 | 0.05 | 0.13 | n.a. |
| OX40$^+$ CD8$^+$ cells | 0.04 | 0.03 | 0.10 | n.a. |
| huEpCAM$^+$ cells | 15.21 | n.c. | n.a. | 3.11 | n.a. = not applicable (EC50 not calculated).
n.c. = curve was not to fit, no EC50 calculation possible Example 6

Biological Activity of Bispecific Antigen Binding Molecules Targeting Human OX40 and Human EpCAM 6.1 HeLa Cells Expressing Human OX40 and Reporter Gene NF-κB-Luciferase Agnostic binding of Ox40 to its ligand induces downstream signaling via activation of nuclear factor kappa B (NFκB) (A. D. Weinberg et al., J. Leukoc. Biol. 2004, 75(6), 962-972). The recombinant reporter cell line HeLa_huOX40_NFκB_Luc1 expressing human OX40 on its surface was generated. This cell line harbors a reporter plasmid containing the luciferase gene under the control of an NFκB-sensitive enhancer segment. Binding and activation of OX40 induces dose-dependent activation of NFκB, which then translocates to the nucleus, where it binds to the NFκB-sensitive enhancer of the reporter plasmid to increase expression of the luciferase protein. Luciferase catalyzes luciferin-oxidation resulting in oxyluciferin, which emits light. This can be detected and quantified using a luminometer. Thus, the HeLa_huOX40_NFκB_Luc1 reporter cells can be used to analyse the ability of anti-OX40 molecules to induce NFκB activation as a measure for bioactivity.

Adherent HeLa_huOX40_NFκB_Luc1 cells were harvested using cell dissociation buffer (Invitrogen, Cat.-No. 13151-014) for 10 minutes at 37° C. Cells were washed once with DPBS and were adjusted to a cell density of 2×10$^5$ in assay media comprising of MEM (Invitrogen, Cat.-No. 22561-021), 10% (v/v) heat-inactivated FBS, 1 mM Sodium-Pyruvate and 1% (v/v) non-essential amino acids. Cells were seeded at a density of 0.3×10$^5$ cells per well in a sterile, white 96-well flat-bottomed tissue culture plate with lid (greiner bio-one, Cat. No. 655083) and incubated overnight at 37° C. in a 5% CO$_2$ atmosphere, in an incubator (HERACELL® 150).

The next day, HeLa_huOX40_NFκB_Luc1 cells were stimulated for 5 hours by adding assay medium containing various titrated bispecific antigen binding molecules targeting OX40. To analyse the effect of hyper-crosslinking on bioactivity, 25 μL/well of medium containing secondary antibody anti-human IgG Fcγ-fragment-specific goat IgG F(ab')$_2$ fragment (Jackson ImmunoResearch, 109-006-098) was added in a or 1:2 ratio (2 times more secondary antibody than the primary anti-OX40 antigen binding molecule). Hyper-crosslinking of the constructs by cell surface human EpCAM$^+$ cells was tested by adding 25 L/well of medium containing NIH/3T3huEpCAM cl44 cells in a 3:1 ratio (three times as many EpCAM$^+$ tumor cells as reporter cells, per well).

After incubation, assay supernatant was aspirated and plates washed two times with DPBS. Quantification of light emission was performed using the luciferase 100 assay system and the reporter lysis buffer (both Promega, Cat.-No. E4550 and Cat-No: E3971) according to manufacturer's instructions. Briefly, cells were lysed for 10 minutes at −20° C. by addition of 30 μL per well 1× lysis buffer. Cells were thawed for 20 minutes at 37° C. before 90 uL luciferase assay reagent was added per well. Light emission was quantified immediately with a TECAN SPARK 10M Plate reader using 500 ms integration time, without any filter to collect all wavelengths. Emitted relative light units (RLU) were corrected by basal luminescence of HeLa_huOX40_NFkB_Luc1 cells and were plotted against the logarithmic primary antibody concentration using Prism6 (GraphPad Software, USA). Curves were fitted to the data using the inbuilt sigmoidal dose response. For a better comparison of all formats the area under the curve (AUC) of the respective dose-response curves was quantified as a marker for the agonistic capacity of each construct (FIG. 10D).

Figure 10A:
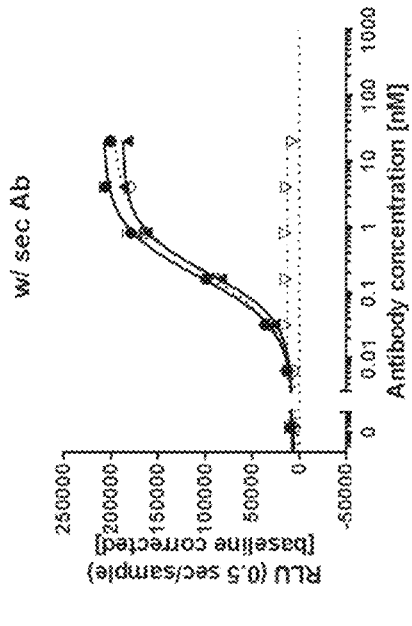
FIGS. 10A to 10D show activation of NFκB by the bispecific, tetravalent anti-human OX40, monovalent anti-human EpCAM (4+1 huEpCAM); bispecific, tetravalent anti-human OX40, bivalent anti-human EpCAM (4+2 huEpCAM); monospecific, tetravalent anti-murine OX40, non-targeted (4+1 control); and monospecific, bivalent anti-human EpCAM IgG (huEpCAM IgG) molecules.
Figure 10B:
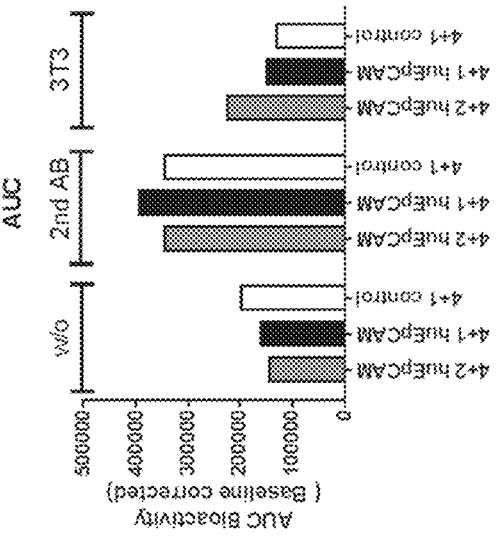
Figure 10C:
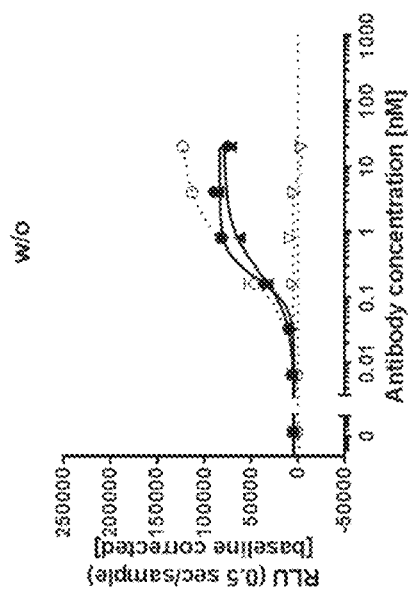
Figure 10D:
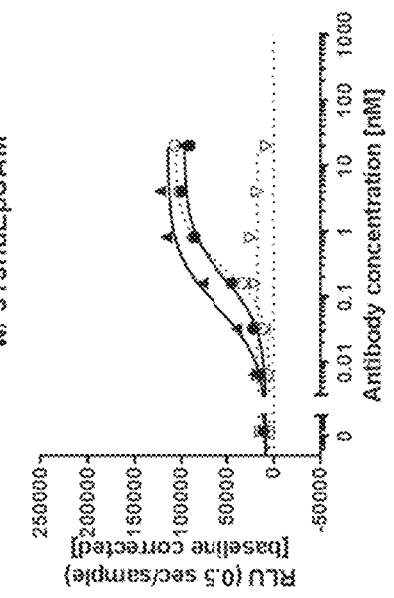
Figure 11A:
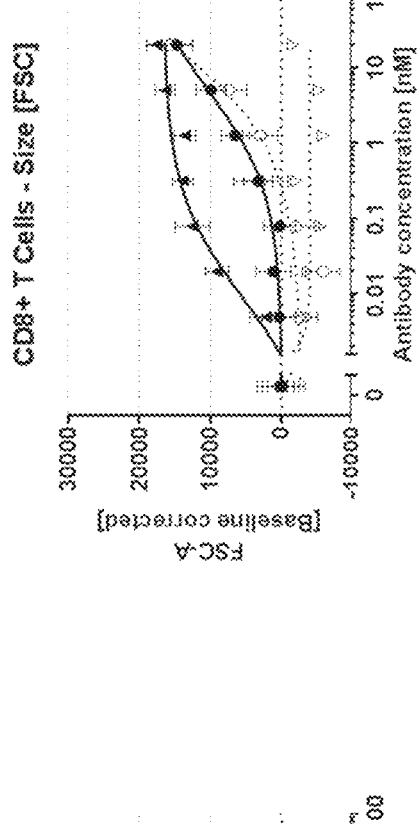
FIGS. 11A to 11D show rescue of suboptimal TCR restihulation of preactivated human CD4+ and CD8+ T cells with the bispecific, tetravalent anti-human OX40, monovalent anti-human EpCAM (4+1 huEpCAM); bispecific, tetravalent anti-human OX40, bivalent anti-human EpCAM (4+2 huEpCAM); monospecific, tetravalent anti-human OX40, non-targeted (4+1 control); or monospecific, bivalent anti-human EpCAM IgG (huEpCAM IgG), in the presence of crosslinking by human EpCAM-expressing KATO-III cells, as determined by analysis of cell size and cell number.
Figure 11C:
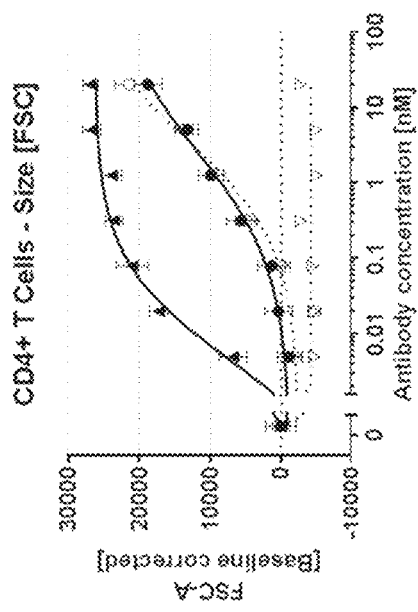
Figure 11B:
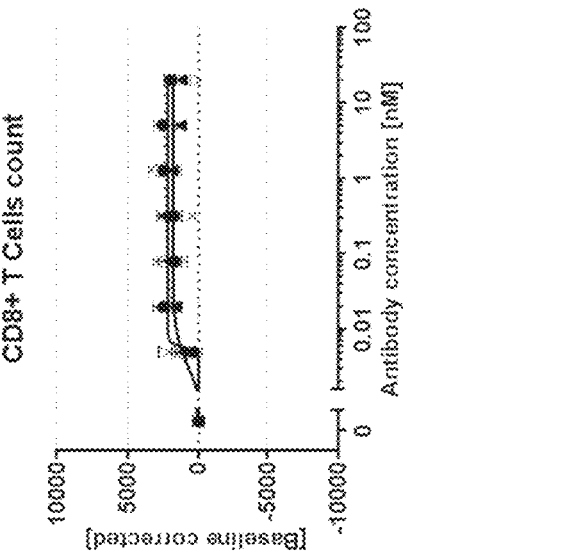
Figure 11D:
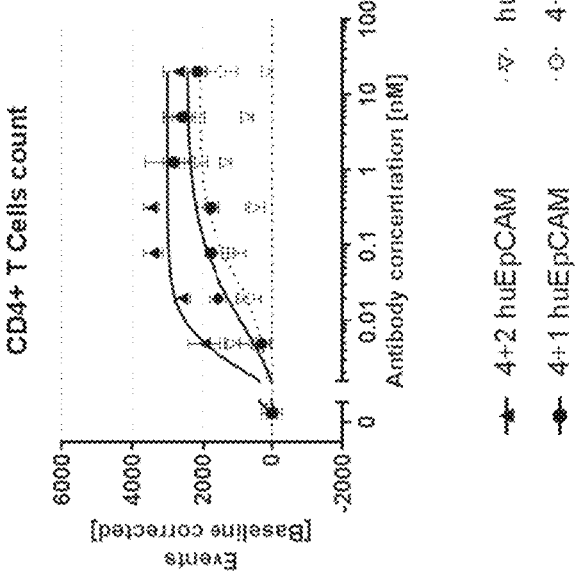
Figure 12B:
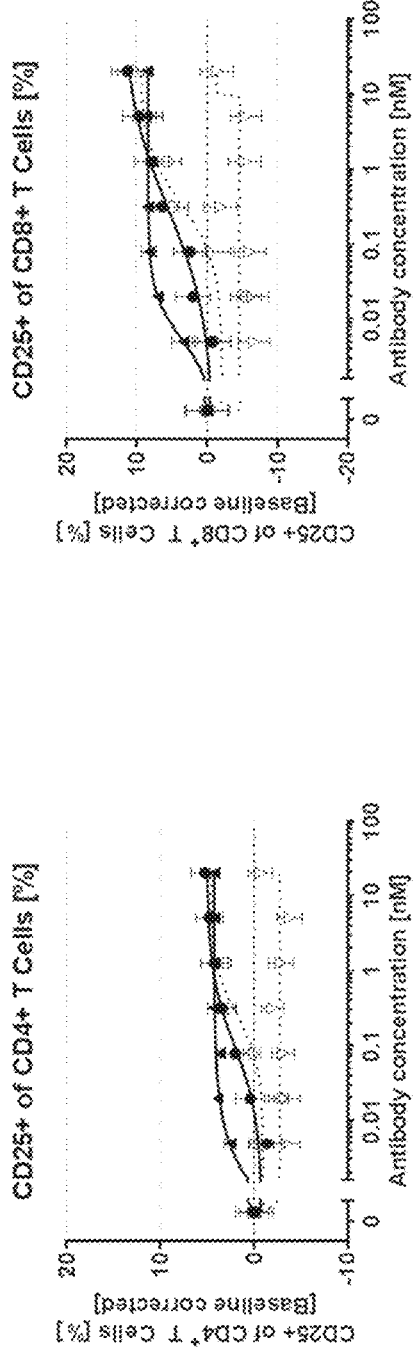
Figure 12B:
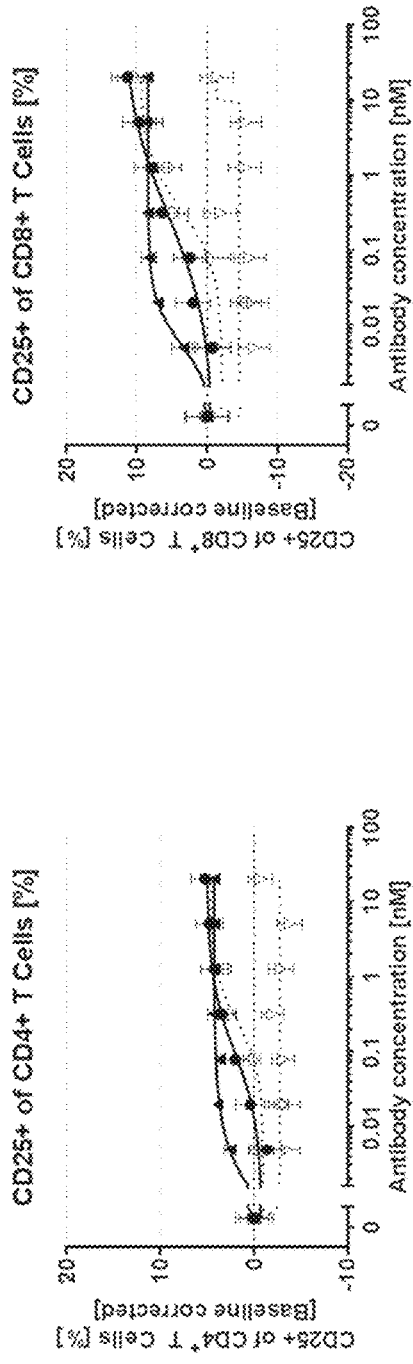
Figure 12D:
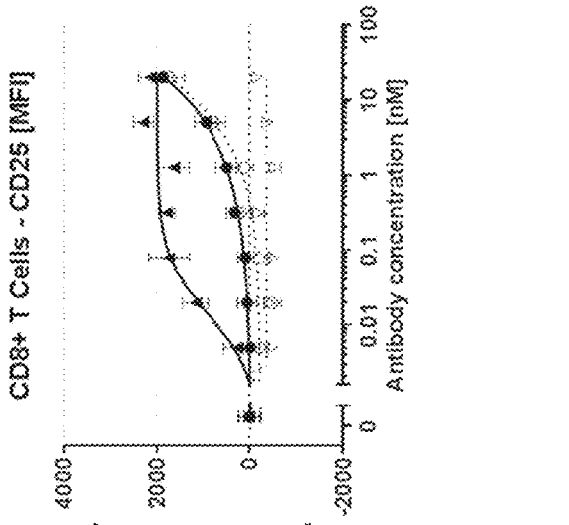
Figure 12C:
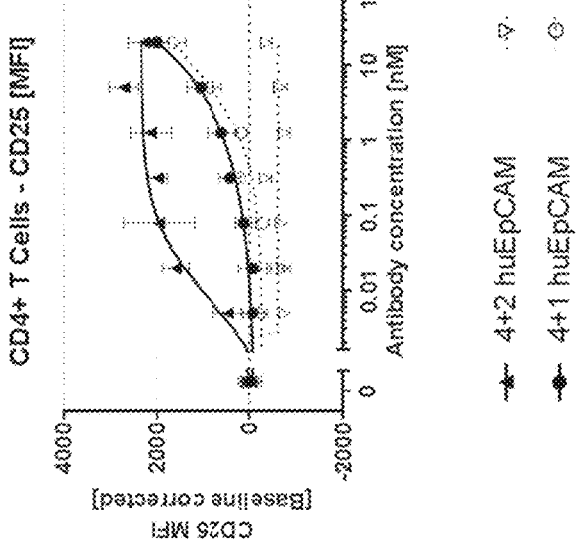
Figure 13A:
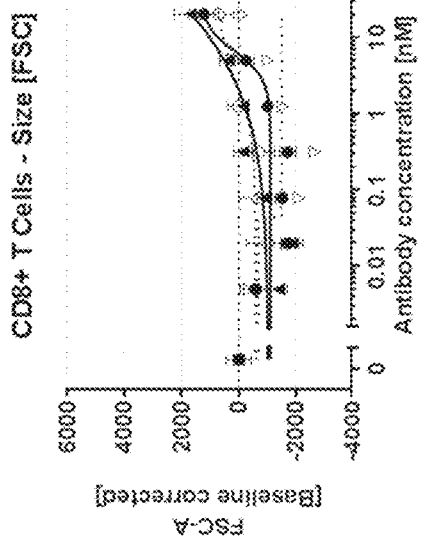
FIGS. 13A to 13D show rescue of suboptimal TCR restihulation of preactivated human CD4+ and CD8+ T cells with the bispecific, tetravalent anti-human OX40, monovalent anti-human EpCAM (4+1 huEpCAM); bispecific, tetravalent anti-human OX40, bivalent anti-human EpCAM (4+2 huEpCAM); monospecific, tetravalent anti-human OX40, non-targeted (4+1 control); or monospecific, bivalent anti-human EpCAM IgG (huEpCAM IgG), in the presence of crosslinking by human EpCAM-expressing 3T3huEpCAM cells, as determined by analysis of cell size and cell number.
Figure 13B:
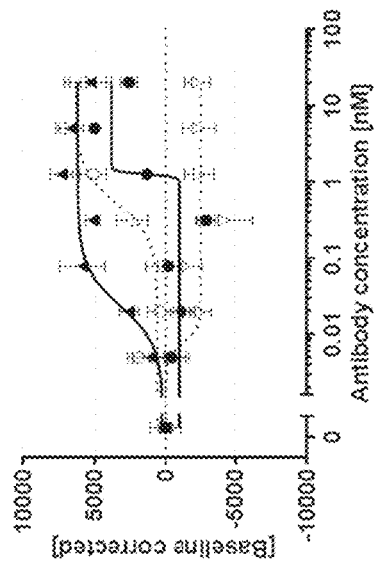
Figure 13C:
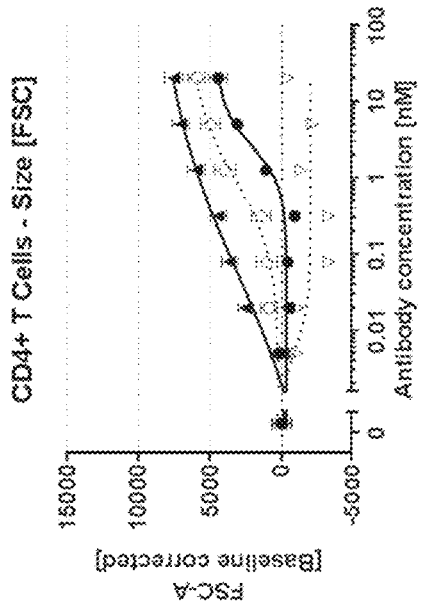
Figure 13D:
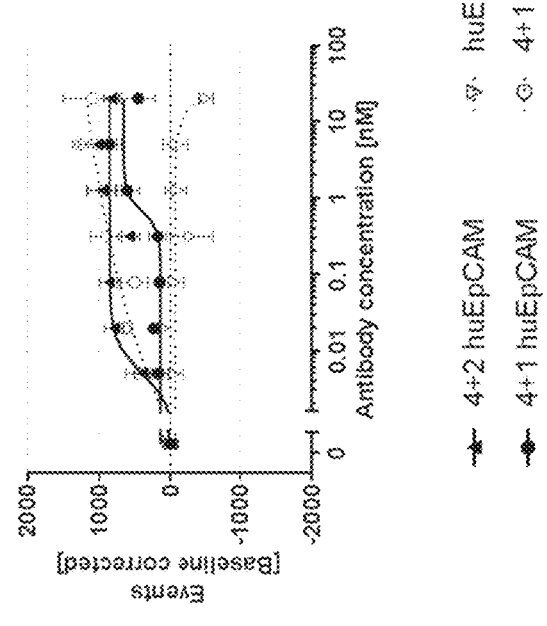
Figure 14A:
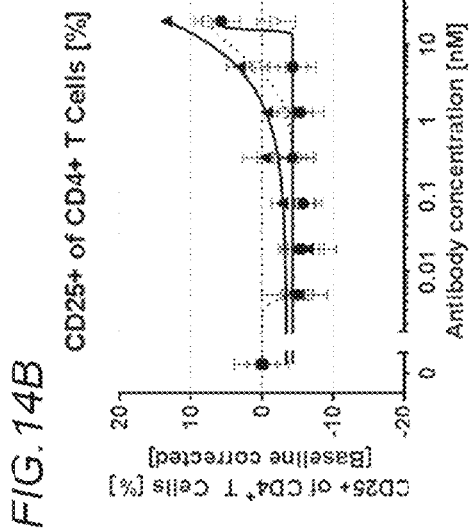
FIGS. 14A to 14D show rescue of suboptimal TCR restihulation of preactivated human CD4+ and CD8+ T cells with the bispecific, tetravalent anti-human OX40, monovalent anti-human EpCAM (4+1 huEpCAM); monospecific, tetravalent anti-human OX40, non-targeted (4+1 control); or monospecific, bivalent anti-human EpCAM IgG (huEpCAM IgG), in the presence of crosslinking by human EpCAM-expressing 3T3huEpCAM cells, as determined by analysis of CD25 expression.
Figure 14B:
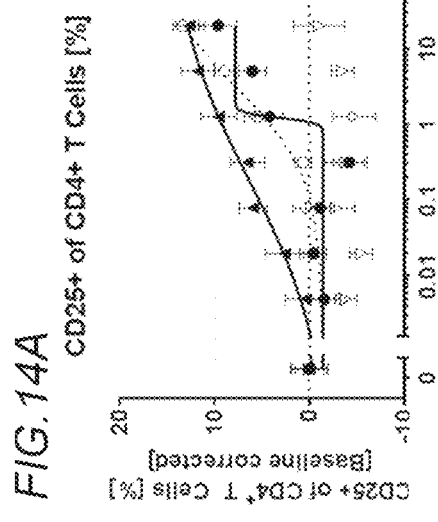
Figure 14C:
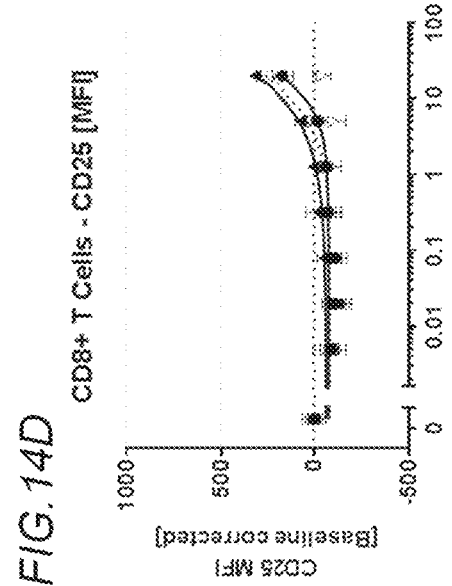
Figure 14D:
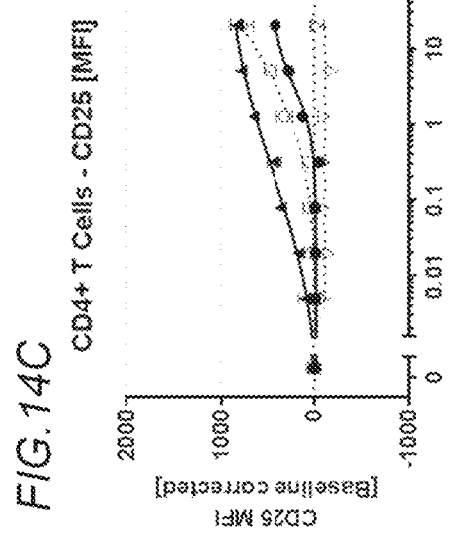

As shown in FIG. 10, all of the anti-OX40 antigen binding molecules induced limited NFkB activation (FIG. 10A). Crosslinking by anti-human Fc specific secondary antibody strongly enhanced bioactivity independently of the targeting moiety (FIG. 10B). Human EpCAM-expressing tumor cells increased induction of NFkB-mediated luciferase-activation only when the bispecific, tetravalent anti-human OX40, bivalent anti-human EpCAM 4+2 molecules were used, and not when the bispecific, tetravalent anti-human OX40, monovalent anti-human EpCAM 4+1 molecules were used (see FIGS. 10C and 10D); this is consistent with the finding that the bispecific, tetravalent anti-human OX40, monovalent anti-human EpCAM 4+1 molecules do not display binding to human EpCAM-expressing cells (see FIG. 9A).

The results indicate that hypercrosslinking by EpCAM and high valency for OX40 are important determinants for OX40 agonist activity.

6.2 OX40 Mediated Costimulation of Suboptimally TCR Triggered Resting Human PBMCs and Hypercrosslinking by Cell Surface Human EpCAM As shown in Example 6.1 and FIG. 10, addition of huEpCAM+ tumor cells can strongly increase the NFκB activation in human OX40 positive reporter cell lines by huEpCAM-targeted tetravalent anti-OX40 antigen binding molecules, by providing for strong oligomerization of OX40 receptors. The EpCAM-targeted tetravalent anti-OX40 antigen binding molecules were analysed for their ability to rescue suboptimal TCR stimulation of resting human PBMCs, in the presence of human EpCAM-expressing KATO-III or NIH/3T3huEpCAM clone 44 cells.

Human PBMC preparations contain (1) resting, OX40-negative CD4$^+$ and CD8$^+$ T cells and (2) antigen presenting cells with various Fc-receptor molecules on their cell surface e.g. B cells and monocytes. Anti-human CD3 antibody of human IgG1 isotype binds through its Fc to the Fc-γ receptor molecules and trigger a prolonged TCR activation on resting OX40-negative CD4+ and CD8+ T cells. These cells then start to express OX40 within several hours. Functional agonistic compounds against OX40 can signal via the OX40 receptor present on activated CD8+ and CD4+ T cells and support TCR-mediated stimulation.

Resting CFSE-labelled human PBMCs were stimulated for five days with a suboptimal concentration of anti-CD3 antibody in the presence of irradiated KATO-III or NIH/3T3huEpCAM cl44 cells and titrated anti-OX40 antigen binding molecules. The effects on T-cell survival and proliferation were analysed by monitoring total cell counts and CFSE dilution in living cells by flow cytometry. Additionally, cells were co-stained with fluorescently-labeled antibodies against T-cell activation marker CD25.

KATO-III and NIH/3T3huEpCAM cl44 cells were harvested using cell dissociation buffer (Invitrogen, Cat.-No. 13151-014) for 10 minutes at 37° C. Cells were washed once with DPBS. KATO-III and NIH/3T3huEpCAM cl44 cells were irradiated in an xRay irradiator using a dose of 4,500 RAD, to prevent later overgrowth of human PBMCs by the tumor cell line. Irradiated cells were cultured at a density of $0.2*10^5$ cells per well in T cell media, in sterile 96-well round-bottomed adhesion tissue culture plates (TPP, Cat. No. 92097) overnight at 37° C. and 5% $CO_2$ in an incubator (STERI-CYCLE® i160).

Human PBMCs were isolated by ficoll density centrifugation and were labeled with CFSE as follows. Freshly isolated PBMCs were washed with pre-warmed (37° C.) DPBS and adjusted to a cell density of $2\times10^6$ cells/mL in DPBS. CELLTRACE® CFSE proliferation dye (ThermoFisher, Cat.-No. C34554) was added to the suspension of resting human PBMCs at a final concentration of 0.2 µM, and a final cell density of $1\times10^6$ cells/mL in DPBS. Cells were then incubated for 10 min at 37° C. and 5% $CO_2$ in the dark. To stop labeling reaction 20 mL heat inactivated FBS were added and cells were washed three times with T cell medium. The cells were then added to each well at a density of $0.6*10^5$ cells per well. Anti-human CD3 antibody (clone V9, human IgG1) at a final concentration of 10 nM, and the indicated anti-OX40 antigen binding molecules were added at the indicated concentrations. Cells were activated for five days at 37° C. and 5% $CO_2$ in an incubator (STERI-CYCLE® i160). For discrimination between live and dead cells, samples were stained with ZOMBIE AQUA™ Viability Dye (BIOLEGEND®, Cat. No 423102) in PBS for 10 minutes at room temperature. Cells were then washed once with FACS buffer and subsequently surface-stained with fluorescent dye-conjugated antibodies anti-human CD4 (clone RPA-T4, BIOLEGEND®, Cat.-No. 300532), anti-CD8 (clone RPA-T8, BIOLEGEND®, Cat.-No. 3010441) and anti-CD25 for 20 min at 4° C. Cells were subsequently washed once with FACS buffer, re-suspended in 85 µL/well FACS-buffer, and acquired the same day using 4-laser LSR-II cytometer (BD Bioscience with DIVA software).

The results of the experiments are shown in FIGS. 11 to 14.

Hyper-crosslinking by KATO-II cells of the bispecific, tetravalent anti-human OX40, bivalent anti-human EpCAM (4+2) molecules strongly promoted proliferation and maturation of human CD4+ and CD8+ T cells (FIG. 11; filled triangle), and induced an enhanced the activated (CD25+) phenotype (FIG. 12; filled triangle). On the other hand, bispecific, tetravalent anti-human OX40, monovalent anti-human EpCAM (4+1) molecules showed similar activity to that of the monospecific, tetravalent anti-human OX40, non-targeted (4+1) control molecules (FIGS. 11 and 12; filled circles compared with open circles). This finding was consistent with the finding that the bispecific, tetravalent anti-human OX40, monovalent anti-human EpCAM 4+1 molecules do not display binding to human EpCAM-expressing cells (see FIG. 9A).

Similar findings were obtained when the bispecific, tetravalent anti-human OX40, bivalent anti-human EpCAM (4+2) molecules were cross-linked using the NIH/3T3huEpCAM cl44 cells. The bispecific, tetravalent anti-human OX40, bivalent anti-human EpCAM (4+2) molecules strongly promoted proliferation and maturation of human CD4+ and CD8+ T cells (FIG. 13; filled triangle) and induced an enhanced the activated (CD25+) phenotype (FIG. 14; filled triangle). In these experiments, the CD4+ and CD8− T cells had proliferated more rapidly after five days, which made it more difficult to see robust additional effects due to the antigen binding molecules.

The results suggest that for optimal OX40 agonism in T cells, not only sufficient oligomerization of the OX40 is required, but additionally, cell surface immobilization of OX40 oligomers is necessary.

The invention claimed is:

1. A bispecific antigen binding molecule, comprising
   (a) at least one moiety that specifically binds to OX40 comprising an antibody light chain variable region (VL) comprising: (i) a CDR-L1 comprising the amino acid sequence of SEQ ID NO:15, (ii) a CDR-L2 comprising the amino acid sequence of SEQ ID NO:18, and (iii) a CDR-L3 comprising the amino acid sequence of SEQ ID NO:22; and an antibody heavy chain variable region (VH) comprising: (iv) a CDR-H1 comprising the amino acid sequence of SEQ ID NO:4, (v) a CDR-H2 comprising the amino acid sequence of SEQ ID NO:6, and (vi) a CDR-H3 comprising the amino acid sequence of SEQ ID NO:9, and
   (b) at least one moiety that specifically binds to epithelial cell adhesion molecule (EpCAM) comprising an antibody light chain variable region (VL) comprising: (i) a CDR-L1 comprising the amino acid sequence of SEQ ID NO:54, (ii) a CDR-L2 comprising the amino acid sequence of SEQ ID NO:55, and (iii) a CDR-L3 comprising the amino acid sequence of SEQ ID NO: 56; and an antibody heavy chain variable region (VH) comprising: (iv) a CDR-H1 comprising the amino acid sequence of SEQ ID NO:51, (v) a CDR-H2 comprising the amino acid sequence of SEQ ID NO:52, and (vi) a CDR-H3 comprising the amino acid sequence of SEQ ID NO:53.

2. The bispecific antigen binding molecule of claim 1, additionally comprising (c) a Fc region composed of a first subunit and a second subunit that form stable association.

3. The bispecific antigen binding molecule of claim 2, wherein the Fc region is of human IgG1 subclass with the amino acid mutations L234A, L235A and P329G, wherein the amino acid numbering is according to Kabat EU index.

4. The bispecific antibody of claim 2, wherein
   (i) the first subunit of the Fc region comprises the amino acid substitutions S354C and T366W and the second subunit of the Fc region comprises the amino acid substitutions Y349C, T366S and Y407V, wherein the amino acid numbering is according to Kabat EU index, or
   (ii) the first subunit of the Fc region comprises the amino acid substitutions K392D and K409D and the second subunit of the Fc region comprises the amino acid substitutions E356K and D399K, wherein the amino acid numbering is according to Kabat EU index.

5. The bispecific antigen binding molecule of claim 1, wherein the moiety that specifically binds to OX40 binds to a polypeptide comprising, the amino acid sequence of SEQ ID NO:1, and wherein the moiety that specifically binds to EpCAM binds to a polypeptide comprising, the amino acid sequence of SEQ ID NO:49.

6. The bispecific antigen binding molecule of claim 1, wherein the moiety that specifically binds to OX40 comprises
   a VH comprising the amino acid sequence of SEQ ID NO:35 and a VL comprising the amino acid sequence of SEQ ID NO:36.

7. The bispecific antigen binding molecule of claim 1, comprising
   (i) at least one moiety that specifically binds to OX40, comprising a VH comprising the amino acid sequence of SEQ ID NO: 35 and a VL comprising the amino acid sequence of SEQ ID NO: 36, and
   (ii) at least one moiety that specifically binds to EpCAM, comprising a VH comprising the amino acid sequence of SEQ ID NO:63 and a VL comprising the amino acid sequence of SEQ ID NO: 64.

8. A pharmaceutical composition comprising the bispecific antigen binding molecule of claim 1, and at least one pharmaceutically acceptable excipient.

9. A bispecific antigen binding molecule that specifically binds to OX40 and EpCAM comprising:
   a first heavy chain comprising the amino acid sequence of SEQ ID NO:183,
   a second heavy chain comprising the amino acid sequence of SEQ ID NO:184, and
   four light chains, each comprising the amino acid sequence of SEQ ID NO:182.

* * * * *